United States Patent
Oehlenschlaeger et al.

(10) Patent No.: US 11,959,111 B2
(45) Date of Patent: Apr. 16, 2024

(54) POLYPEPTIDES HAVING PEPTIDOGLYCAN DEGRADING ACTIVITY AND POLYNUCLEOTIDES ENCODING SAME

(71) Applicant: Novozymes A/S, Bagsvaerd (DK)

(72) Inventors: Christian Berg Oehlenschlaeger, Valby (DK); Dorotea Raventos Segura, Runsted (DK); Jesper Salomon, Holte (DK); Fabian Barrientos Garcia, Birkerod (DK); Lillian Eva Tang Baltsen, Bagsvaerd (DK); Christian Bech Rosen, Copenhagen (DK)

(73) Assignee: Novozymes A/S, Bagsvaerd (DK)

( * ) Notice: Subject to any disclaimer, the term of this patent is extended or adjusted under 35 U.S.C. 154(b) by 494 days.

(21) Appl. No.: 17/298,836

(22) PCT Filed: Dec. 19, 2019

(86) PCT No.: PCT/EP2019/086399
§ 371 (c)(1),
(2) Date: Jun. 1, 2021

(87) PCT Pub. No.: WO2020/127796
PCT Pub. Date: Jun. 25, 2020

(65) Prior Publication Data
US 2022/0033799 A1   Feb. 3, 2022

(30) Foreign Application Priority Data
Dec. 21, 2018   (EP) .................................... 18215408

(51) Int. Cl.
*C12N 9/80* (2006.01)
*C11D 3/386* (2006.01)

(52) U.S. Cl.
CPC ............ *C12N 9/80* (2013.01); *C11D 3/38636* (2013.01); *C12Y 305/01028* (2013.01)

(58) Field of Classification Search
None
See application file for complete search history.

(56) References Cited

U.S. PATENT DOCUMENTS

| 10,081,782 B2 * | 9/2018 | Brooker ............... C11D 3/3418 |
| 2012/0171188 A1 | 7/2012 | Loessner |
| 2012/0266329 A1 | 10/2012 | Mathur |
| 2016/0017307 A1 | 1/2016 | Mayer et al. |
| 2017/0106058 A1 | 4/2017 | Miller |

FOREIGN PATENT DOCUMENTS

| CN | 101437532 A | 5/2009 |
| CN | 102186878 A | 9/2011 |
| CN | 103957929 A | 7/2014 |
| WO | 2007/130655 A2 | 11/2007 |
| WO | 2010/020657 A1 | 2/2010 |
| WO | 2013/076253 A1 | 5/2013 |
| WO | 2013/076259 A2 | 5/2013 |

OTHER PUBLICATIONS

Anonymous, UniProt Accession No. UPI0003F952BF (2015).
Anonymous, UniProt Accession No. UPI0009084F52 (2016).
Anonymous, 2016, NCBI Reference Sequence WP_051366340.1.

* cited by examiner

*Primary Examiner* — Suzanne M Noakes
*Assistant Examiner* — Jae W Lee
(74) *Attorney, Agent, or Firm* — Elias Lambiris

(57) ABSTRACT

The present invention relates to cleaning compositions comprising polypeptides having peptidoglycan degradation activity, as well as use of the cleaning compositions for cleaning of an item such as a textile or a surface.

20 Claims, No Drawings
Specification includes a Sequence Listing.

POLYPEPTIDES HAVING PEPTIDOGLYCAN DEGRADING ACTIVITY AND POLYNUCLEOTIDES ENCODING SAME

CROSS-REFERENCE TO RELATED APPLICATIONS

This application is a 35 U.S.C. 371 national application of international application no. PCT/EP2019/086399 filed Dec. 19, 2019, which claims priority or the benefit under 35 U.S.C. 119 of European application no. EP 18215408.8 filed Dec. 21, 2018. The content of each application is fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to polypeptides having peptidoglycan degrading activity, polynucleotides encoding the polypeptides and catalytic domains belonging to peptidoglycan degrading enzyme families. The invention further relates to compositions comprising such polypeptides, in particular cleaning compositions, use of polypeptides having peptidoglycan degrading activity in cleaning processes and/or for removal or reduction of bacterial-derived peptidoglycan, and methods for removal or reduction of peptidoglycan. The invention further relates to nucleic acid constructs, vectors, and host cells comprising polynucleotides encoding the polypeptides as well as methods of producing and using the polypeptides and catalytic domains.

Description of the Related Art

Enzymes have been used in detergents for decades. Usually a cocktail of various enzymes is added to detergent compositions. The enzyme cocktail often comprises various enzymes, wherein each enzyme targets a specific substrate, e.g. amylases are active towards starch stains, proteases on protein stains and so forth. Textiles and surfaces such as laundry and dishes become soiled with many different types of soiling. The soiling may be composed of proteins, grease, starch etc. Complex stains composed of different organic materials such as food stains, sebum, dead cell material, EPS (extracellular polymeric matrix) from e.g. biofilm are difficult to remove completely with traditional ADW (automatic dishwashing) and laundry detergent compositions. Contributing to the organic matter is peptidoglycan, originating from the bacterial cell wall. Bacteria are present in high numbers in laundry items. When the bacteria lyse, the destroyed cells leave a high amount of cell wall-derived peptidoglycan in the textile or on hard surfaces such as the inner surfaces of a washing machine. This peptidoglycan substrate may be sticky or gluing, which when present on textile attracts soils and may cause redeposition or back-staining of soil, resulting in a greying of the textile. Also, malodors from e.g. sweat, cigarette smoke and pollution are particularly difficult to remove from e.g. textiles. Malodor is a growing problem, particularly in laundry, with the changed habits of lower temperature washing, front loading wash machines that save water but leave behind residual water between loads, thus allowing bacterial biofilms to flourish, line drying clothes to save energy rather than appliance drying, and the increased popularity of synthetic fabrics, such as athletic wear, that appear to retain odors more than natural fabrics. In conventional detergent compositions such as laundry detergents the above problems are often solved by adding perfumes. This solution is not completely effective, however, as it is short term and furthermore only serves to mask malodor rather than dealing with the underlying cause of malodor. There is thus a need in the art for new solutions for overcoming the problems of malodor and redeposition.

SUMMARY OF THE INVENTION

The invention relates to a cleaning composition comprising a peptidoglycan degradation enzyme, at least one surfactant and at least one additional cleaning component selected from builders and bleach components. The cleaning composition may e.g. comprise a peptidoglycan degradation enzyme, at least 5 wt % anionic surfactants, and at least one additional cleaning component selected from at least one builder and at least one bleach component.

The invention further relates to the use of such a composition for cleaning of an item such as a textile or a surface. The invention further relates to a method of cleaning on an item, comprising the steps of:
 a) contacting the item with a solution comprising a peptidoglycan degradation enzyme having peptidoglycan lyase activity and preferably N-acetylmuramyl-L-alanine amidase activity; and a cleaning component, wherein the cleaning component is selected from 5 to 60 wt % of at least one surfactant; 5 to 50 wt % of at least one builder; and 1 to 20 wt % of at least one bleach component; and optionally
 b) rinsing the item,
wherein the item is preferably a textile.

OVERVIEW OF SEQUENCES

SEQ ID NO: 1 DNA encoding full length polypeptide from *Hamadaea tsunoensis*
SEQ ID NO: 2 polypeptide derived from SEQ ID NO: 1
SEQ ID NO: 3 mature polypeptide obtained from *Hamadaea tsunoensis*
SEQ ID NO: 4 DNA encoding full length polypeptide from *Micromonospora maritima*
SEQ ID NO: 5 polypeptide derived from SEQ ID NO: 4
SEQ ID NO: 6 mature polypeptide obtained from *Micromonospora maritima*
SEQ ID NO: 7 DNA encoding full length polypeptide from *Paenibacillus* sp.
SEQ ID NO: 8 polypeptide derived from SEQ ID NO: 7
SEQ ID NO: 9 mature polypeptide obtained from *Paenibacillus* sp.
SEQ ID NO: 10 DNA encoding full length polypeptide from *Nonomuraea* sp.
SEQ ID NO: 11 polypeptide derived from SEQ ID NO: 10
SEQ ID NO: 12 mature polypeptide obtained from *Nonomuraea* sp.
SEQ ID NO: 13 DNA encoding full length polypeptide from *Lysobacter antibioticus*
SEQ ID NO: 14 polypeptide derived from SEQ ID NO: 13
SEQ ID NO: 15 mature polypeptide obtained from *Lysobacter antibioticus*
SEQ ID NO: 16 DNA encoding full length polypeptide from *Micromonospora* sp.
SEQ ID NO: 17 polypeptide derived from SEQ ID NO: 16

SEQ ID NO: 18 mature polypeptide obtained from *Micromonospora* sp.
SEQ ID NO: 19 DNA encoding full length polypeptide from *Nonomuraea coxensis*
SEQ ID NO: 20 polypeptide derived from SEQ ID NO: 19
SEQ ID NO: 21 mature polypeptide obtained from *Nonomuraea coxensis*
SEQ ID NO: 22 DNA encoding full length polypeptide from *Micromonospora fulvopurpurea*
SEQ ID NO: 23 polypeptide derived from SEQ ID NO: 22
SEQ ID NO: 24 mature polypeptide obtained from *Micromonospora fulvopurpurea*
SEQ ID NO: 25 DNA encoding full length polypeptide from *Alicyclobacillus* sp.
SEQ ID NO: 26 polypeptide derived from SEQ ID NO: 25
SEQ ID NO: 27 mature polypeptide obtained from *Alicyclobacillus* sp.
SEQ ID NO: 28 DNA encoding full length polypeptide from *Halomonas* sp.
SEQ ID NO: 29 polypeptide derived from SEQ ID NO: 28
SEQ ID NO: 30 mature polypeptide obtained from *Halomonas* sp.
SEQ ID NO: 31 DNA encoding full length polypeptide from *Pseudomonas peli*
SEQ ID NO: 32 polypeptide derived from SEQ ID NO: 31
SEQ ID NO: 33 mature polypeptide obtained from *Pseudomonas peli*
SEQ ID NO: 34 DNA encoding full length polypeptide from *Halomonas* sp.
SEQ ID NO: 35 polypeptide derived from SEQ ID NO: 34
SEQ ID NO: 36 mature polypeptide obtained from *Halomonas* sp.
SEQ ID NO: 37 DNA encoding full length polypeptide from *Pseudomonas pseudoalcaligenes*
SEQ ID NO: 38 polypeptide derived from SEQ ID NO: 37
SEQ ID NO: 39 mature polypeptide obtained from *Pseudomonas pseudoalcaligenes*
SEQ ID NO: 40 DNA encoding full length polypeptide from *Tumebacillus* sp.
SEQ ID NO: 41 polypeptide derived from SEQ ID NO: 40
SEQ ID NO: 42 mature polypeptide obtained from *Tumebacillus* sp.
SEQ ID NO: 43 DNA encoding full length polypeptide from *Nonomuraea dietziae*
SEQ ID NO: 44 polypeptide derived from SEQ ID NO: 43
SEQ ID NO: 45 mature polypeptide obtained from *Nonomuraea dietziae*
SEQ ID NO: 46 DNA encoding full length polypeptide from *Laceyella sacchari*
SEQ ID NO: 47 polypeptide derived from SEQ ID NO: 46
SEQ ID NO: 48 mature polypeptide obtained from *Laceyella sacchari*
SEQ ID NO: 49 DNA encoding full length polypeptide from *Thermostaphylospora chromogena*
SEQ ID NO: 50 polypeptide derived from SEQ ID NO: 49
SEQ ID NO: 51 mature polypeptide obtained from *Thermostaphylospora chromogena*
SEQ ID NO: 52 DNA encoding full length polypeptide from *Kribbella aluminosa*
SEQ ID NO: 53 polypeptide derived from SEQ ID NO: 52
SEQ ID NO: 54 mature polypeptide obtained from *Kribbella aluminosa*
SEQ ID NO: 55 DNA encoding full length polypeptide from *Streptomyces griseus*
SEQ ID NO: 56 polypeptide derived from SEQ ID NO: 55
SEQ ID NO: 57 mature polypeptide obtained from *Streptomyces griseus*
SEQ ID NO: 58 DNA encoding full length polypeptide from *Micromonospora peucetia*
SEQ ID NO: 59 polypeptide derived from SEQ ID NO: 58
SEQ ID NO: 60 mature polypeptide obtained from *Micromonospora peucetia*
SEQ ID NO: 61 DNA encoding full length polypeptide from *Bacillus* sp.
SEQ ID NO: 62 polypeptide derived from SEQ ID NO: 61
SEQ ID NO: 63 mature polypeptide obtained from *Bacillus* sp.
SEQ ID NO: 64 DNA encoding full length polypeptide from *Bacillus sporothermodurans*
SEQ ID NO: 65 polypeptide derived from SEQ ID NO: 64
SEQ ID NO: 66 mature polypeptide obtained from *Bacillus sporothermodurans*
SEQ ID NO: 67 DNA encoding full length polypeptide from *Paenibacillus pini*
SEQ ID NO: 68 polypeptide derived from SEQ ID NO: 67
SEQ ID NO: 69 mature polypeptide obtained from *Paenibacillus pini*
SEQ ID NO: 70 DNA encoding full length polypeptide from *Bacillus cohnii*
SEQ ID NO: 71 polypeptide derived from SEQ ID NO: 70
SEQ ID NO: 72 mature polypeptide obtained from *Bacillus cohnii*
SEQ ID NO: 73 DNA encoding full length polypeptide from *Kribbella* sp.
SEQ ID NO: 74 polypeptide derived from SEQ ID NO: 73
SEQ ID NO: 75 mature polypeptide obtained from *Kribbella* sp.
SEQ ID NO: 76 DNA encoding full length polypeptide from *Bacillus* sp.
SEQ ID NO: 77 polypeptide derived from SEQ ID NO: 76
SEQ ID NO: 78 mature polypeptide obtained from *Bacillus* sp.
SEQ ID NO: 79 DNA encoding full length polypeptide from *Bacillus* sp.
SEQ ID NO: 80 polypeptide derived from SEQ ID NO: 79
SEQ ID NO: 81 mature polypeptide obtained from *Bacillus* sp.
SEQ ID NO: 82 DNA encoding full length polypeptide from *Bacillus* sp.
SEQ ID NO: 83 polypeptide derived from SEQ ID NO: 82
SEQ ID NO: 84 mature polypeptide obtained from *Bacillus* sp.
SEQ ID NO: 85 DNA encoding full length polypeptide from *Streptomyces* sp.
SEQ ID NO: 86 polypeptide derived from SEQ ID NO: 85
SEQ ID NO: 87 mature polypeptide obtained from *Streptomyces* sp.
SEQ ID NO: 88 DNA encoding full length polypeptide from *Bacillus* sp.
SEQ ID NO: 89 polypeptide derived from SEQ ID NO: 88
SEQ ID NO: 90 mature polypeptide obtained from *Bacillus* sp.
SEQ ID NO: 91 DNA encoding full length polypeptide from *Bacillus* sp.
SEQ ID NO: 92 polypeptide derived from SEQ ID NO: 91
SEQ ID NO: 93 mature polypeptide obtained from *Bacillus* sp.
SEQ ID NO: 94 DNA encoding full length polypeptide from *Nonomuraea guangzhouensis*
SEQ ID NO: 95 polypeptide derived from SEQ ID NO: 94
SEQ ID NO: 96 mature polypeptide obtained from *Nonomuraea guangzhouensis*
SEQ ID NO: 97 DNA encoding full length polypeptide from *Nonomuraea guangzhouensis*

SEQ ID NO: 98 polypeptide derived from SEQ ID NO: 97
SEQ ID NO: 99 mature polypeptide obtained from *Nonomuraea guangzhouensis*
SEQ ID NO: 100 DNA encoding full length polypeptide from *Bacillus cohnii*
SEQ ID NO: 101 polypeptide derived from SEQ ID NO: 100
SEQ ID NO: 102 mature polypeptide obtained from *Bacillus cohnii*
SEQ ID NO: 103 DNA encoding full length polypeptide from *Halomonas* sp.
SEQ ID NO: 104 polypeptide derived from SEQ ID NO: 103
SEQ ID NO: 105 mature polypeptide obtained from *Halomonas* sp.
SEQ ID NO: 106 DNA encoding full length polypeptide from *Lysobacter capsici*
SEQ ID NO: 107 polypeptide derived from SEQ ID NO: 106
SEQ ID NO: 108 mature polypeptide obtained from *Lysobacter capsica*
SEQ ID NO: 109 MKKPLGKIVASTALLISVAFSSSIASA (signal peptide)
SEQ ID NO: 110 HHHHHHPR (His-tag)
SEQ ID NO: 111 Motif Definitions Peptidoglycan degrading enzymes: The term "peptidoglycan degrading enzyme" means an enzyme having activity towards peptidoglycan. Peptidoglycan (PGN) is a major component of the bacterial cell envelope in both Gram-positive and Gram-negative bacteria (Jessica Human and Laurel L. Lenz, J Innate Immun. 2009; 1: 88-97). The peptidoglycan structure of both Gram-positive and Gram-negative bacteria comprises repeating disaccharide backbones of N-acetylglucosamine (NAG) and β-(1-4)-N-acetylmuramic acid (NAM) that are cross-linked by peptide stem chains attached to the NAM residues (Bourhis L L, Werts C Microbes Infect. 2007 April; 9(5):629-36). The peptide and glycopeptide fragments of PGN are commonly referred to as "muropeptides." PGN hydrolases are defined by their catalytic specificities. Two classes of these enzymes digest the PGN glycan backbone, N-acetylmuramidases which cleave PGN between the NAG-NAM bond upstream of NAM and N-acetylglucosaminidases which cleave the NAM-NAG bond. In contrast, N-acetylmuramyl-L-alanine amidases cleave between NAM and the first alanine of the peptide chain. Thus, catalysis by N-acetylmuramyl-L-alanine amidases separate the PGN sugar backbones from the stem peptide chain (Fournier B, Philpott D J, Clin. Microbiol. Rev. 2005 July; 18(3):521-40). The enzymes of the invention comprise an N-acetylmuramyl-L-alanine amidase (EC 3.5.1.28) domain. In the context of the present invention N-acetylmuramyl-L-alanine amidases may also be termed peptidoglycan amidohydrolases. The enzymes of the invention comprise in addition to the amidase domain also a peptidoglycan lyase domain (GH23-like). The GH 23 family comprises lysozyme type G (EC 3.2.1.17), peptidoglycan lyase (EC 4.2.2.n1, peptidoglycan lytic exotransglycosylase, and 4.2.2.n2, peptidoglycan lytic endotransglycosylase) and chitinases (EC 3.2.1.14). The domain comprised by the enzymes of the invention is a peptidoglycan lyase domain (EC 4.2.2.n1 or 4.2.2.n2). Peptidoglycan lyases are also termed lytic transglycosylases. Peptidoglycan lyases of GH23 constitute Family 1 of the organizational scheme of Blackburn and Clarke (Blackburn NT1, Clarke A J. J Mol Evol. 2001 January; 52(1):78-84). The enzymes of this family cleave the β-1,4-linkage between N-acetylmuramyl and N-acetylglucosaminyl residues in peptidoglycan. However, unlike lysozyme, peptidoglycan lyases are not hydrolases but rather catalyse an intramolecular transglycosylation to the C-6 hydroxyl group of the muramyl residue, leading to the generation of a terminal 1,6-anhydromuramic acid product that is an acetal, and not a hemiacetal (Höltje J. V. J Bacteriol. 1975 December; 124(3):1067-76. The enzymes of the invention are thus distinct from lysozymes.

The enzymes of the invention preferably comprise an N-acetylmuramyl-L-alanine amidase (EC 3.5.1.28) domain as well as a peptidoglycan lyase domain (EC 4.2.2.n1 or 4.2.2.n2). Thus, in the present invention peptidoglycan degrading enzymes are preferably N-acetylmuramyl-L-alanine amidases (EC 3.5.1.28) and peptidoglycan lyases (EC 4.2.2.n1 or 4.2.2.n2) having amidase and lyase activity towards peptidoglycan.

For purposes of the present invention, peptidoglycan lyase activity and N-acetylmuramyl-L-alanine amidase activity may be determined according to the procedures described below in the example section.

The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

A biofilm is organic matter produced by any group of microorganisms in which cells stick to each other or stick to a surface, such as a textile, dishware or hard surface or another kind of surface. These adherent cells are frequently embedded within a self-produced matrix of extracellular polymeric substance (EPS). Biofilm EPS is a polymeric conglomeration generally composed of extracellular DNA, proteins, and polysaccharides. Biofilms may form on living or non-living surfaces. The microbial cells growing in a biofilm are physiologically distinct from planktonic cells of the same organism, which, by contrast, are single-cells that may float or swim in a liquid medium. Bacteria living in a biofilm usually have significantly different properties from planktonic bacteria of the same species, as the dense and protected environment of the film allows them to cooperate and interact in various ways. One benefit of this environment for the microorganisms is increased resistance to detergents and antibiotics, as the dense extracellular matrix and the outer layer of cells protect the interior of the community. The biofilm living bacteria do not lose their ability to live as planktonic cells if the biofilm matrix is compromised. On laundry, biofilm- or EPS-producing bacteria can be found among the following species: *Acinetobacter* sp., *Aeromicrobium* sp., *Brevundimonas* sp., *Microbacterium* sp., *Micrococcus luteus*, *Pseudomonas* sp., *Staphylococcus epidermidis*, and *Stenotrophomonas* sp. In one aspect, the biofilm- or EPS-producing strain is *Pseudomonas*, for example *Pseudomonas aeruginosa*, *Pseudomonas alcaliphila* or *Pseudomonas fluorescens*.

The term "catalytic domain" means the region of an enzyme containing the catalytic machinery of the enzyme.

The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

The term "Clade" means a group of polypeptides clustered together on the basis of homologous features traced to a common ancestor. Polypeptide clades can be visualized as phylogenetic trees and a Clade is a group of polypeptides that consists of a common ancestor and all its lineal descendants. Example 6 describes generation of phylogenetic trees.

The term "coding sequence" means a polynucleotide which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

The term "cleaning component" means e.g. a detergent adjunct ingredient that is different from the polypeptides of this invention. The precise nature of these additional cleaning or adjunct components, and levels of incorporation thereof, will depend on the physical form of the composition and the nature of the operation for which it is to be used. Suitable cleaning components include, but are not limited to the components described below, such as surfactants, builders and co-builders, flocculating aid, chelating agents, dye transfer inhibitors, enzymes (other than the enzymes of the invention), enzyme stabilizers, enzyme inhibitors, catalytic materials, bleach activators, hydrogen peroxide, sources of hydrogen peroxide, preformed peracids, polymeric agents, clay soil removal/anti-redeposition agents, brighteners, suds suppressors, dyes, perfumes, structure elasticizing agents, fabric softeners, carriers, hydrotropes, fabric hueing agents, anti-foaming agents, dispersants, processing aids, and/or pigments.

The term "cleaning composition" includes "detergent composition" and refers to compositions that find use in the removal of undesired compounds from items to be cleaned, such as textiles. The detergent composition may be used to e.g. clean textiles for both household cleaning and industrial cleaning. The term encompasses any materials/compounds selected for the particular type of cleaning composition desired and the form of the product (e.g., liquid, gel, powder, granulate, paste, or spray compositions) and includes, but is not limited to, detergent compositions such as liquid and/or solid laundry detergents and fine fabric detergents; fabric fresheners; fabric softeners; and textile and laundry pre-spotters/pretreatment. In addition to containing the enzyme of the invention, the detergent formulation may contain one or more additional enzymes (such as proteases, amylases, lipases, cutinases, cellulases, endoglucanases, xyloglucanases, pectinases, pectin lyases, xanthanases, peroxidases, haloperoxygenases, catalases, mannanases, nucleases or any mixture thereof), and/or detergent adjunct ingredients such as surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anti-corrosion agents, enzyme inhibitors or stabilizers, enzyme activators, transferase(s), hydrolytic enzymes, oxido reductases, bluing agents and fluorescent dyes, antioxidants, and solubilizers.

The term "expression" includes any step involved in the production of a polypeptide including, but not limited to, transcription, post-transcriptional modification, translation, post-translational modification, and secretion.

The term "expression vector" means a linear or circular DNA molecule that comprises a polynucleotide encoding a polypeptide and is operably linked to control sequences that provide for its expression.

The term "fragment" means a polypeptide having one or more amino acids absent from the amino and/or carboxyl terminus of a mature polypeptide or domain; wherein the fragment has peptidoglycan degradation activity.

The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance). An isolated substance may be present in a fermentation broth sample; e.g. a host cell may be genetically modified to express the polypeptide of the invention. The fermentation broth from that host cell will comprise the isolated polypeptide. It will be apparent to persons skilled in the art that the polypeptides disclosed herein are preferably in isolated form.

The term "laundering" relates to both household laundering and industrial laundering and means the process of treating textiles with a solution containing a cleaning or detergent composition of the present invention. The laundering process can for example be carried out using e.g. a household or an industrial washing machine or can be carried out by hand.

The term "malodor" means an odor which is not desired on clean items. The cleaned item should smell fresh and clean without malodors adhered to the item. One example of malodor is compounds with an unpleasant smell, which may be produced by microorganisms. Another example is unpleasant smells which can be sweat or body odor adhered to an item which has been in contact with human or animal.

Another example of malodor can be the odor from spices, which sticks to items for example curry or other spices which smell strongly.

The term "mature polypeptide" means a polypeptide in its mature form following N terminal processing (e.g., removal of signal peptide).

In one aspect, the mature polypeptide is amino acids 1 to 431 of SEQ ID NO: 2. Amino acids −29 to −1 of SEQ ID NO: 2 are a signal peptide. In one aspect, the mature polypeptide is amino acids 1 to 485 of SEQ ID NO: 5. Amino acids −30 to −1 of SEQ ID NO: 5 are a signal peptide. In one aspect, the mature polypeptide is amino acids 1 to 483 of SEQ ID NO: 8. Amino acids −26 to −1 of SEQ ID NO: 8 are a signal peptide. In one aspect, the mature polypeptide is amino acids 1 to 471 of SEQ ID NO: 11. Amino acids −22 to −1 of SEQ ID NO: 11 are a signal peptide. In one aspect, the mature polypeptide is amino acids 1 to 639 of SEQ ID NO: 14. In one aspect, the mature polypeptide is amino acids 1 to 484 of SEQ ID NO: 17. Amino acids −31 to −1 of SEQ ID NO: 17 are a signal peptide. In one aspect, the mature polypeptide is amino acids 1 to 480 of SEQ ID NO: 20. Amino acids −30 to −1 of SEQ ID NO: 20 are a signal peptide. In one aspect, the mature polypeptide is amino acids 1 to 485 of SEQ ID NO: 23. Amino acids −31 to −1 of SEQ ID NO: 23 are a signal peptide. In one aspect, the mature polypeptide is amino acids 1 to 491 of SEQ ID NO: 26. Amino acids −28 to −1 of SEQ ID NO: 26 are a signal peptide. In one aspect, the mature polypeptide is amino acids 1 to 289 of SEQ ID NO: 29. Amino acids −19 to −1 of SEQ ID NO: 29 are a signal peptide. In one aspect, the mature polypeptide is amino acids 1 to 245 of SEQ ID NO: 32. Amino acids −15 to −1 of SEQ ID NO: 32 are a signal peptide. In one aspect, the mature polypeptide is amino acids 1 to 280 of SEQ ID NO: 35. Amino acids −19 to −1 of SEQ ID NO: 35 are a signal peptide. In one aspect, the mature polypeptide is amino acids 1 to 238 of SEQ ID NO: 38. Amino acids −22 to −1 of SEQ ID NO: 38 are a signal peptide. In one aspect, the mature polypeptide is amino acids 1 to 498 of SEQ ID NO: 41. Amino acids −23 to −1 of SEQ ID NO: 41 are a signal peptide. In one aspect, the mature polypeptide is amino acids 1 to 476 of SEQ ID NO: 44. Amino acids −25 to −1 of SEQ ID NO: 44 are a signal peptide. In one aspect, the mature polypeptide is amino acids 1 to 474 of SEQ ID NO: 47. Amino acids −28 to −1 of SEQ ID NO: 47 are a signal peptide. In one aspect, the mature polypeptide is amino acids 1 to 473 of SEQ ID NO: 50. Amino acids −29 to −1 of SEQ ID NO: 50 are a signal peptide. In one aspect, the mature polypeptide is amino acids 1 to 414 of SEQ ID NO: 53. Amino acids −25 to −1 of SEQ ID NO: 53 are a signal peptide. In one aspect, the mature polypeptide is amino acids 1 to 412 of SEQ ID NO: 56. Amino acids −31 to −1 of SEQ ID NO: 56 are a signal peptide. In one aspect, the mature polypeptide is amino acids 1 to 637 of SEQ ID NO: 59. Amino acids −35 to −1 of SEQ ID NO: 59 are a signal peptide. In one aspect, the mature polypeptide is amino acids 1 to 599 of SEQ ID NO: 62. Amino acids −33 to −1 of SEQ ID NO: 62 are a signal peptide. In one aspect, the mature polypeptide is amino acids 1 to 605 of SEQ ID NO: 65. Amino acids −31 to −1 of SEQ ID NO: 65 are a signal peptide. In one aspect, the mature polypeptide is amino acids 1 to 610 of SEQ ID NO: 68. Amino acids −36 to −1 of SEQ ID NO: 68 are a signal peptide. In one aspect, the mature polypeptide is amino acids 1 to 216 of SEQ ID NO: 71. Amino acids −20 to −1 of SEQ ID NO: 71 are a signal peptide. In one aspect, the mature polypeptide is amino acids 1 to 425 of SEQ ID NO: 74. Amino acids −26 to −1 of SEQ ID NO: 74 are a signal peptide. In one aspect, the mature polypeptide is amino acids 1 to 304 of SEQ ID NO: 77. Amino acids −25 to −1 of SEQ ID NO: 77 are a signal peptide. In one aspect, the mature polypeptide is amino acids 1 to 306 of SEQ ID NO: 80. Amino acids −29 to −1 of SEQ ID NO: 80 are a signal peptide. In one aspect, the mature polypeptide is amino acids 1 to 306 of SEQ ID NO: 83. Amino acids −23 to −1 of SEQ ID NO: 83 are a signal peptide. In one aspect, the mature polypeptide is amino acids 1 to 632 of SEQ ID NO: 86. Amino acids −35 to −1 of SEQ ID NO: 86 are a signal peptide. In one aspect, the mature polypeptide is amino acids 1 to 216 of SEQ ID NO: 89. Amino acids −24 to −1 of SEQ ID NO: 89 are a signal peptide. In one aspect, the mature polypeptide is amino acids 1 to 306 of SEQ ID NO: 92. Amino acids −27 to −1 of SEQ ID NO: 92 are a signal peptide. In one aspect, the mature polypeptide is amino acids 1 to 453 of SEQ ID NO: 95. Amino acids −29 to −1 of SEQ ID NO: 95 are a signal peptide. In one aspect, the mature polypeptide is amino acids 1 to 473 of SEQ ID NO: 98. Amino acids −29 to −1 of SEQ ID NO: 98 are a signal peptide. In one aspect, the mature polypeptide is amino acids 1 to 209 of SEQ ID NO: 101. Amino acids −27 to −1 of SEQ ID NO: 101 are a signal peptide. In one aspect, the mature polypeptide is amino acids 1 to 281 of SEQ ID NO: 104. Amino acids −24 to −1 of SEQ ID NO: 104 are a signal peptide. In one aspect, the mature polypeptide is amino acids 1 to 582 of SEQ ID NO: 107. Amino acids −57 to −1 of SEQ ID NO: 107 are a signal peptide.

It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

The term "mature polypeptide coding sequence" means a polynucleotide that encodes a mature polypeptide having peptidoglycan degrading activity.

In one aspect, the mature polypeptide coding sequence is nucleotides 88 to 1380 of SEQ ID NO: 1 and nucleotides 1 to 87 of SEQ ID NO: 1 encode a signal peptide. In one aspect, the mature polypeptide coding sequence is nucleotides 91 to 1545 of SEQ ID NO: 4 and nucleotides 1 to 90 of SEQ ID NO: 4 encode a signal peptide. In one aspect, the mature polypeptide coding sequence is nucleotides 79 to 1527 of SEQ ID NO: 7 and nucleotides 1 to 78 of SEQ ID NO: 7 encode a signal peptide. In one aspect, the mature polypeptide coding sequence is nucleotides 67 to 1479 of SEQ ID NO: 10 and nucleotides 1 to 66 of SEQ ID NO: 10 encode a signal peptide. In one aspect, the mature polypeptide coding sequence is nucleotides 1 to 1917 of SEQ ID NO: 13. In one aspect, the mature polypeptide coding sequence is nucleotides 94 to 1545 of SEQ ID NO: 16 and nucleotides 1 to 93 of SEQ ID NO: 16 encode a signal peptide. In one aspect, the mature polypeptide coding sequence is nucleotides 91 to 1530 of SEQ ID NO: 19 and nucleotides 1 to 90 of SEQ ID NO: 19 encode a signal peptide. In one aspect, the mature polypeptide coding sequence is nucleotides 94 to 1548 of SEQ ID NO: 22 and nucleotides 1 to 93 of SEQ ID NO: 22 encode a signal peptide. In one aspect, the mature polypeptide coding sequence is nucleotides 85 to 1557 of SEQ ID NO: 25 and nucleotides 1 to 84 of SEQ ID NO: 25 encode a signal peptide. In one aspect, the mature polypeptide coding sequence is nucleotides 58 to 924 of SEQ ID NO: 28 and nucleotides 1 to 57 of SEQ ID NO: 28 encode a signal peptide. In one aspect, the mature polypeptide coding sequence is nucleotides 46 to 780 of SEQ ID NO: 31 and nucleotides 1 to 45 of SEQ ID NO: 31 encode a signal peptide. In one aspect, the mature polypeptide coding sequence is nucleotides 58 to 897 of SEQ ID NO: 34 and nucleotides 1 to 57 of SEQ ID NO: 34 encode a signal peptide. In one aspect, the mature polypeptide coding sequence is nucleotides 67 to 780 of SEQ ID NO: 37 and nucleotides 1 to 66 of SEQ ID NO: 37 encode a signal peptide. In one aspect, the mature polypeptide coding sequence is nucleotides 70 to 1563 of SEQ ID NO: 40 and nucleotides 1 to 69 of SEQ ID NO: 40 encode a signal peptide. In one aspect, the mature polypeptide coding sequence is nucleotides 76 to 1503 of SEQ ID NO: 43 and nucleotides 1 to 75 of SEQ ID NO: 43 encode a signal peptide. In one aspect, the mature polypeptide coding sequence is nucleotides 85 to 1506 of SEQ ID NO: 46 and nucleotides 1 to 84 of SEQ ID NO: 46 encode a signal peptide. In one aspect, the mature polypeptide coding sequence is nucleotides 88 to 1506 of SEQ ID NO: 49 and nucleotides 1 to 87 of SEQ ID NO: 49 encode a signal peptide. In one aspect, the mature polypeptide coding sequence is nucleotides 76 to 1317 of SEQ ID NO: 52 and nucleotides 1 to 75 of SEQ ID NO: 52 encode a signal peptide. In one aspect, the mature polypeptide coding sequence is nucleotides 94 to 1329 of SEQ ID NO: 55 and nucleotides 1 to 93 of SEQ ID NO: 55 encode a signal peptide. In one aspect, the mature polypeptide coding sequence is nucleotides 106 to 2016 of SEQ ID NO: 58 and nucleotides 1 to 105 of SEQ ID NO: 58 encode a signal peptide. In one aspect, the mature polypeptide coding sequence is nucleotides 100 to 1896 of SEQ ID NO: 61 and nucleotides 1 to 99 of SEQ ID NO: 61 encode a signal peptide. In one aspect, the mature polypeptide coding sequence is nucleotides 94 to 1908 of SEQ ID NO: 64 and nucleotides 1 to 93 of SEQ ID NO: 64 encode a signal peptide. In one aspect, the mature polypeptide coding sequence is nucleotides 109 to 1938 of SEQ ID NO: 67 and nucleotides 1 to 108 of SEQ ID NO: 67 encode a signal peptide. In one aspect, the mature polypeptide coding sequence is nucleotides 61 to 708 of SEQ ID NO: 70 and nucleotides 1 to 60 of SEQ ID NO: 70 encode a signal peptide. In one aspect, the mature polypeptide coding sequence is nucleotides 79 to 1353 of SEQ ID NO: 73 and nucleotides 1 to 78 of SEQ ID NO: 73 encode a signal peptide. In one aspect, the mature polypeptide coding sequence is nucleotides 76 to 987 of SEQ ID NO: 76 and nucleotides 1 to 75 of SEQ ID NO: 76 encode a signal peptide. In one aspect, the mature polypeptide coding sequence is nucleotides 73 to 990 of SEQ ID NO: 79 and nucleotides 1 to 72 of SEQ ID NO: 79 encode a signal peptide. In one aspect, the mature polypeptide coding sequence is nucleotides 70 to 987 of SEQ ID NO: 82 and nucleotides 1 to 69 of SEQ ID NO: 82 encode a signal peptide. In one aspect, the mature polypeptide coding sequence is nucleotides 106 to 2001 of SEQ ID NO: 85 and nucleotides 1 to 105 of SEQ ID NO: 85 encode a signal peptide. In one aspect, the mature polypeptide coding sequence is nucleotides 73 to 720 of SEQ ID NO: 88 and nucleotides 1 to 72 of SEQ ID NO: 88 encode a signal peptide. In one aspect, the mature polypeptide coding sequence is nucleotides 82 to 999 of SEQ ID NO: 91 and nucleotides 1 to 81 of SEQ ID NO: 91 encode a signal peptide. In one aspect, the mature polypeptide coding sequence is nucleotides 88 to 1446 of SEQ ID NO: 94 and nucleotides 1 to 87 of SEQ ID NO: 94 encode a signal peptide. In one aspect, the mature polypeptide coding sequence is nucleotides 88 to 1506 of SEQ ID NO: 97 and nucleotides 1 to 87 of SEQ ID NO: 97 encode a signal peptide. In one aspect, the mature polypeptide coding sequence is nucleotides 82 to 708 of SEQ ID NO: 100 and nucleotides 1 to 81 of SEQ ID NO: 100 encode a signal peptide. In one aspect, the mature polypeptide coding sequence is nucleotides 73 to 915 of SEQ ID NO: 103 and nucleotides 1 to 72 of SEQ ID NO: 103 encode a signal peptide. In one aspect, the mature polypeptide coding sequence is nucleotides 172 to 1917 of SEQ ID NO: 106 and nucleotides 1 to 171 of SEQ ID NO: 106 encode a signal peptide.

The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

The term "operably linked" means a configuration in which a control sequence is placed at an appropriate position relative to the coding sequence of a polynucleotide such that the control sequence directs expression of the coding sequence.

The relatedness between two amino acid sequences or between two nucleotide sequences is described by the parameter "sequence identity". For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the nobrief option) is used as the percent identity and is calculated as follows:

(Identical Residues×100)/(Length of Alignment Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the nobrief option) is used as the percent identity and is calculated as follows:

(Identical Deoxyribonucleotides×100)/(Length of Alignment Total Number of Gaps in Alignment)

The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.]

The term "variant" means a polypeptide having peptidoglycan degrading activity comprising an alteration, i.e., a substitution, insertion, and/or deletion, at one or more positions. A substitution means replacement of the amino acid occupying a position with a different amino acid; a deletion means removal of the amino acid occupying a position; and an insertion means adding an amino acid adjacent to and immediately following the amino acid occupying a position.

Nomenclature: For purposes of the present invention, the nomenclature [E/Q] or [EQ] means that the amino acid at this position may be a glutamic acid (Glu, E) or a glutamine (Gln, Q). Likewise, the nomenclature [V/G/A/I] or [VGAI] means that the amino acid at this position may be a valine (Val, V), glycine (Gly, G), alanine (Ala, A) or isoleucine (Ile, I), and so forth for other combinations as described herein. Unless otherwise limited further, the amino acid X is defined such that it may be any of the 20 natural amino acids.

DETAILED DESCRIPTION OF THE INVENTION

As mentioned in the background section above, textiles and surfaces such as laundry and dishes may become soiled with many different types of soiling. A single complex stain such as a food stain, sebum, dead cells debris, EPS or biofilm related stains is often composed of different organic material such as proteins, polysaccharides, grease etc., which are often difficult to remove completely with traditional detergent compositions. Further, such stains may give rise to disadvantages such as redeposition or malodor. The polypeptides of the invention address this problem, providing good cleaning effects on complex stains such as biofilm and EPS as well as reduced redeposition and malodor from e.g. textiles and tableware. The polypeptides of the invention are peptidoglycan degrading enzymes having hydrolase activity and preferably N-acetylmuramyl-L-alanine amidase activity. The polypeptides of the invention comprise an amidase domain, preferably an Amidase_2 domain as defined in PFAM (PF01510, Pfam version 31.0 Finn (2016). Nucleic Acids Research, Database Issue 44: D279-D285). Also, clusters or clades are described herein, defined by specific motifs shared by the polypeptides of the specific clades. A phylogenetic tree was constructed of polypeptide sequences containing an Amidase_2 domain. The phylogenetic tree was constructed from a multiple alignment of mature polypeptide sequences containing at least one Amidase_2 domain as described in Example 6.

One embodiment of the invention relates to a peptidoglycan degrading enzyme having hydrolase activity and preferably N-acetylmuramyl-L-alanine amidase activity. One embodiment of the invention relates to a peptidoglycan degrading enzyme having hydrolase activity and preferably N-acetylmuramyl-L-alanine amidase activity, wherein the polypeptide comprises the motif N[IV]X[AG][GAS]A[AY][LV]L (SEQ ID NO: 111), where X can be any naturally occurring amino acid, situated in positions corresponding to positions 85 to 93 in *Micromonospora maritima* (SEQ ID NO: 6).

The polypeptides containing an Amidase_2 domain can be separated into distinct sub-clusters. The sub-clusters are defined by one or more short sequence motifs, as well as containing an Amidase_2 domain as defined in PFAM (PF01510, Pfam version 31.0). We denoted one sub-cluster comprising the motif N[IV]X[AG][GAS]A[AY][LV]L (SEQ ID NO: 111) as the PGL Glade. All polypeptide sequences containing an Amidase_2 domain as well as the motif will be denoted as belonging to the PGL Glade.

In an embodiment, the present invention relates to polypeptides having a sequence identity to the mature polypeptide of SEQ ID NO: 2 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 2.

In a particular embodiment the invention relates to polypeptides having a sequence identity to the mature polypeptide of SEQ ID NO: 2 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the peptidoglycan degrading activity of the mature polypeptide of SEQ ID NO: 2.

In an embodiment, the present invention relates to polypeptides having a sequence identity to the mature polypeptide of SEQ ID NO: 5 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 5.

In a particular embodiment the invention relates to polypeptides having a sequence identity to the mature polypeptide of SEQ ID NO: 5 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the peptidoglycan degrading activity of the mature polypeptide of SEQ ID NO: 5.

In an embodiment, the present invention relates to polypeptides having a sequence identity to the mature polypeptide of SEQ ID NO: 8 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 8.

In a particular embodiment the invention relates to polypeptides having a sequence identity to the mature polypeptide of SEQ ID NO: 8 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the peptidoglycan degrading activity of the mature polypeptide of SEQ ID NO: 8.

In an embodiment, the present invention relates to polypeptides having a sequence identity to the mature polypeptide of SEQ ID NO: 11 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 11.

In a particular embodiment the invention relates to polypeptides having a sequence identity to the mature polypeptide of SEQ ID NO: 11 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the peptidoglycan degrading activity of the mature polypeptide of SEQ ID NO: 11.

In an embodiment, the present invention relates to polypeptides having a sequence identity to the mature polypeptide of SEQ ID NO: 14 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 14. In a particular embodiment the invention relates to polypeptides having a sequence identity to the mature polypeptide of SEQ ID NO: 14 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the peptidoglycan degrading activity of the mature polypeptide of SEQ ID NO: 14.

In an embodiment, the present invention relates to polypeptides having a sequence identity to the mature polypeptide of SEQ ID NO: 17 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 17.

In a particular embodiment the invention relates to polypeptides having a sequence identity to the mature polypeptide of SEQ ID NO: 17 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the peptidoglycan degrading activity of the mature polypeptide of SEQ ID NO: 17.

In an embodiment, the present invention relates to polypeptides having a sequence identity to the mature polypeptide of SEQ ID NO: 20 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 20.

In a particular embodiment the invention relates to polypeptides having a sequence identity to the mature polypeptide of SEQ ID NO: 20 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the peptidoglycan degrading activity of the mature polypeptide of SEQ ID NO: 20.

In an embodiment, the present invention relates to polypeptides having a sequence identity to the mature polypeptide of SEQ ID NO: 23 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 23.

In a particular embodiment the invention relates to polypeptides having a sequence identity to the mature polypeptide of SEQ ID NO: 23 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the peptidoglycan degrading activity of the mature polypeptide of SEQ ID NO: 23.

In an embodiment, the present invention relates to polypeptides having a sequence identity to the mature polypeptide of SEQ ID NO: 26 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 26.

In a particular embodiment the invention relates to polypeptides having a sequence identity to the mature polypeptide of SEQ ID NO: 26 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the peptidoglycan degrading activity of the mature polypeptide of SEQ ID NO: 26.

In an embodiment, the present invention relates to polypeptides having a sequence identity to the mature polypeptide of SEQ ID NO: 29 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 29.

In a particular embodiment the invention relates to polypeptides having a sequence identity to the mature polypeptide of SEQ ID NO: 29 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the peptidoglycan degrading activity of the mature polypeptide of SEQ ID NO: 29.

In an embodiment, the present invention relates to polypeptides having a sequence identity to the mature polypeptide of SEQ ID NO: 32 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 32.

In a particular embodiment the invention relates to polypeptides having a sequence identity to the mature polypeptide of SEQ ID NO: 32 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the peptidoglycan degrading activity of the mature polypeptide of SEQ ID NO: 32.

In an embodiment, the present invention relates to polypeptides having a sequence identity to the mature polypeptide of SEQ ID NO: 35 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 35.

In a particular embodiment the invention relates to polypeptides having a sequence identity to the mature polypeptide of SEQ ID NO: 35 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the peptidoglycan degrading activity of the mature polypeptide of SEQ ID NO: 35.

In an embodiment, the present invention relates to polypeptides having a sequence identity to the mature polypeptide of SEQ ID NO: 38 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 38.

In a particular embodiment the invention relates to polypeptides having a sequence identity to the mature polypeptide of SEQ ID NO: 38 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the peptidoglycan degrading activity of the mature polypeptide of SEQ ID NO: 38.

In an embodiment, the present invention relates to polypeptides having a sequence identity to the mature polypeptide of SEQ ID NO: 41 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 41.

In a particular embodiment the invention relates to polypeptides having a sequence identity to the mature polypeptide of SEQ ID NO: 41 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the peptidoglycan degrading activity of the mature polypeptide of SEQ ID NO: 41.

In an embodiment, the present invention relates to polypeptides having a sequence identity to the mature polypeptide of SEQ ID NO: 44 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 44. In a particular embodiment the invention relates to polypeptides having a sequence identity to the mature polypeptide of SEQ ID NO: 44 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the peptidoglycan degrading activity of the mature polypeptide of SEQ ID NO: 44.

In an embodiment, the present invention relates to polypeptides having a sequence identity to the mature polypeptide of SEQ ID NO: 47 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 47.

In a particular embodiment the invention relates to polypeptides having a sequence identity to the mature polypeptide of SEQ ID NO: 47 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the peptidoglycan degrading activity of the mature polypeptide of SEQ ID NO: 47.

In an embodiment, the present invention relates to polypeptides having a sequence identity to the mature polypeptide of SEQ ID NO: 50 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 50.

In a particular embodiment the invention relates to polypeptides having a sequence identity to the mature polypeptide of SEQ ID NO: 50 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the peptidoglycan degrading activity of the mature polypeptide of SEQ ID NO: 50.

In an embodiment, the present invention relates to polypeptides having a sequence identity to the mature polypeptide of SEQ ID NO: 53 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 53.

In a particular embodiment the invention relates to polypeptides having a sequence identity to the mature polypeptide of SEQ ID NO: 53 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the peptidoglycan degrading activity of the mature polypeptide of SEQ ID NO: 53.

In an embodiment, the present invention relates to polypeptides having a sequence identity to the mature polypeptide of SEQ ID NO: 56 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 56.

In a particular embodiment the invention relates to polypeptides having a sequence identity to the mature polypeptide of SEQ ID NO: 56 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the peptidoglycan degrading activity of the mature polypeptide of SEQ ID NO: 56.

In an embodiment, the present invention relates to polypeptides having a sequence identity to the mature polypeptide of SEQ ID NO: 59 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 59.

In a particular embodiment the invention relates to polypeptides having a sequence identity to the mature polypeptide of SEQ ID NO: 59 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the peptidoglycan degrading activity of the mature polypeptide of SEQ ID NO: 59.

In an embodiment, the present invention relates to polypeptides having a sequence identity to the mature polypeptide of SEQ ID NO: 62 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 62.

In a particular embodiment the invention relates to polypeptides having a sequence identity to the mature polypeptide of SEQ ID NO: 62 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the peptidoglycan degrading activity of the mature polypeptide of SEQ ID NO: 62.

In an embodiment, the present invention relates to polypeptides having a sequence identity to the mature polypeptide of SEQ ID NO: 65 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 65.

In a particular embodiment the invention relates to polypeptides having a sequence identity to the mature polypeptide of SEQ ID NO: 65 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the peptidoglycan degrading activity of the mature polypeptide of SEQ ID NO: 65.

In an embodiment, the present invention relates to polypeptides having a sequence identity to the mature polypeptide of SEQ ID NO: 68 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 68.

In a particular embodiment the invention relates to polypeptides having a sequence identity to the mature polypeptide of SEQ ID NO: 68 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the peptidoglycan degrading activity of the mature polypeptide of SEQ ID NO: 68.

In an embodiment, the present invention relates to polypeptides having a sequence identity to the mature polypeptide of SEQ ID NO: 71 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 71.

In a particular embodiment the invention relates to polypeptides having a sequence identity to the mature polypeptide of SEQ ID NO: 71 of at least 80%, at least 85%, 90%, at least 91%, at least 92%, at least 93%, at least 94%, at least 95%, at least 96%, at least 97%, at least 98%, at least 99%, or 100%, and wherein the polypeptide has at least at least 70% of the peptidoglycan degrading activity of the mature polypeptide of SEQ ID NO: 71.

In an embodiment, the present invention relates to polypeptides having a sequence identity to the mature polypeptide of SEQ ID NO: 74 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 74.

In a particular embodiment the invention relates to polypeptides having a sequence identity to the mature polypeptide of SEQ ID NO: 74 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the peptidoglycan degrading activity of the mature polypeptide of SEQ ID NO: 74.

In an embodiment, the present invention relates to polypeptides having a sequence identity to the mature polypeptide of SEQ ID NO: 77 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 77.

In a particular embodiment the invention relates to polypeptides having a sequence identity to the mature polypeptide of SEQ ID NO: 77 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the peptidoglycan degrading activity of the mature polypeptide of SEQ ID NO: 77.

In an embodiment, the present invention relates to polypeptides having a sequence identity to the mature polypeptide of SEQ ID NO: 80 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 80.

In a particular embodiment the invention relates to polypeptides having a sequence identity to the mature polypeptide of SEQ ID NO: 80 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the peptidoglycan degrading activity of the mature polypeptide of SEQ ID NO: 80.

In an embodiment, the present invention relates to polypeptides having a sequence identity to the mature polypeptide of SEQ ID NO: 83 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 83.

In a particular embodiment the invention relates to polypeptides having a sequence identity to the mature polypeptide of SEQ ID NO: 83 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the peptidoglycan degrading activity of the mature polypeptide of SEQ ID NO: 83.

In an embodiment, the present invention relates to polypeptides having a sequence identity to the mature polypeptide of SEQ ID NO: 86 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 86.

In a particular embodiment the invention relates to polypeptides having a sequence identity to the mature polypeptide of SEQ ID NO: 86 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the peptidoglycan degrading activity of the mature polypeptide of SEQ ID NO: 86.

In an embodiment, the present invention relates to polypeptides having a sequence identity to the mature polypeptide of SEQ ID NO: 89 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 89.

In a particular embodiment the invention relates to polypeptides having a sequence identity to the mature polypeptide of SEQ ID NO: 89 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the peptidoglycan degrading activity of the mature polypeptide of SEQ ID NO: 89.

In an embodiment, the present invention relates to polypeptides having a sequence identity to the mature polypeptide of SEQ ID NO: 92 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 92.

In a particular embodiment the invention relates to polypeptides having a sequence identity to the mature polypeptide of SEQ ID NO: 92 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the peptidoglycan degrading activity of the mature polypeptide of SEQ ID NO: 92.

In an embodiment, the present invention relates to polypeptides having a sequence identity to the mature polypeptide of SEQ ID NO: 95 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 95.

In a particular embodiment the invention relates to polypeptides having a sequence identity to the mature polypeptide of SEQ ID NO: 95 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the peptidoglycan degrading activity of the mature polypeptide of SEQ ID NO: 95.

In an embodiment, the present invention relates to polypeptides having a sequence identity to the mature polypeptide of SEQ ID NO: 98 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 98.

In a particular embodiment the invention relates to polypeptides having a sequence identity to the mature polypeptide of SEQ ID NO: 98 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the peptidoglycan degrading activity of the mature polypeptide of SEQ ID NO: 98.

In an embodiment, the present invention relates to polypeptides having a sequence identity to the mature polypeptide of SEQ ID NO: 101 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 101.

In a particular embodiment the invention relates to polypeptides having a sequence identity to the mature polypeptide of SEQ ID NO: 101 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the peptidoglycan degrading activity of the mature polypeptide of SEQ ID NO: 101.

In an embodiment, the present invention relates to polypeptides having a sequence identity to the mature polypeptide of SEQ ID NO: 104 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 104.

In a particular embodiment the invention relates to polypeptides having a sequence identity to the mature polypeptide of SEQ ID NO: 104 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the peptidoglycan degrading activity of the mature polypeptide of SEQ ID NO: 104.

In an embodiment, the present invention relates to polypeptides having a sequence identity to the mature polypeptide of SEQ ID NO: 107 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peptidoglycan degrading activity. In one aspect, the polypeptides differ by up to 10 amino acids, e.g., 1, 2, 3, 4, 5, 6, 7, 8, 9, or 10, from the mature polypeptide of SEQ ID NO: 107.

In a particular embodiment the invention relates to polypeptides having a sequence identity to the mature polypeptide of SEQ ID NO: 107 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the peptidoglycan degrading activity of the mature polypeptide of SEQ ID NO: 107.

In a particular embodiment the invention relates to polypeptides having a sequence identity to the polypeptide of SEQ ID NO: 3 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment the invention relates to polypeptides having a sequence identity to the polypeptide of SEQ ID NO: 6 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment the invention relates to polypeptides having a sequence identity to the polypeptide of SEQ ID NO: 9 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment the invention relates to polypeptides having a sequence identity to the polypeptide of SEQ ID NO: 12 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment the invention relates to polypeptides having a sequence identity to the polypeptide of SEQ ID NO: 15 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment the invention relates to polypeptides having a sequence identity to the polypeptide of SEQ ID NO: 18 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment the invention relates to polypeptides having a sequence identity to the polypeptide of SEQ ID NO: 21 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment the invention relates to polypeptides having a sequence identity to the polypeptide of SEQ ID NO: 24 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment the invention relates to polypeptides having a sequence identity to the polypeptide of SEQ ID NO: 27 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment the invention relates to polypeptides having a sequence identity to the polypeptide of SEQ ID NO: 30 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment the invention relates to polypeptides having a sequence identity to the polypeptide of SEQ ID NO: 33 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment the invention relates to polypeptides having a sequence identity to the polypeptide of SEQ ID NO: 36 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment the invention relates to polypeptides having a sequence identity to the polypeptide of SEQ ID NO: 39 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment the invention relates to polypeptides having a sequence identity to the polypeptide of SEQ ID NO: 42 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment the invention relates to polypeptides having a sequence identity to the polypeptide of SEQ ID NO: 45 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment the invention relates to polypeptides having a sequence identity to the polypeptide of SEQ ID NO: 48 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment the invention relates to polypeptides having a sequence identity to the polypeptide of SEQ ID NO: 51 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment the invention relates to polypeptides having a sequence identity to the polypeptide of SEQ ID NO: 54 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment the invention relates to polypeptides having a sequence identity to the polypeptide of SEQ ID NO: 57 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment the invention relates to polypeptides having a sequence identity to the polypeptide of SEQ ID NO: 60 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment the invention relates to polypeptides having a sequence identity to the polypeptide of SEQ ID NO: 63 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment the invention relates to polypeptides having a sequence identity to the polypeptide of SEQ ID NO: 66 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment the invention relates to polypeptides having a sequence identity to the polypeptide of SEQ ID NO: 69 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment the invention relates to polypeptides having a sequence identity to the polypeptide of SEQ ID NO: 72 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment the invention relates to polypeptides having a sequence identity to the polypeptide of SEQ ID NO: 75 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment the invention relates to polypeptides having a sequence identity to the polypeptide of SEQ ID NO: 78 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment the invention relates to polypeptides having a sequence identity to the polypeptide of SEQ ID NO: 81 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment the invention relates to polypeptides having a sequence identity to the polypeptide of SEQ ID NO: 84 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment the invention relates to polypeptides having a sequence identity to the polypeptide of SEQ ID NO: 87 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment the invention relates to polypeptides having a sequence identity to the polypeptide of SEQ ID NO: 90 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment the invention relates to polypeptides having a sequence identity to the polypeptide of SEQ ID NO: 93 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment the invention relates to polypeptides having a sequence identity to the polypeptide of SEQ ID NO: 96 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment the invention relates to polypeptides having a sequence identity to the polypeptide of SEQ ID NO: 99 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment the invention relates to polypeptides having a sequence identity to the polypeptide of SEQ ID NO: 102 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment the invention relates to polypeptides having a sequence identity to the polypeptide of SEQ ID NO: 105 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

In a particular embodiment the invention relates to polypeptides having a sequence identity to the polypeptide of SEQ ID NO: 108 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has peptidoglycan degradation activity.

One embodiment of the invention relates to a polypeptide wherein the polypeptide comprises the motif N[IV]X[AG][GAS]A[AY][LV]L (SEQ ID NO: 111), wherein the polypeptide is selected from the group consisting of: SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 42, SEQ ID NO: 45, SEQ ID NO: 48, SEQ ID NO: 51, SEQ ID NO: 54, SEQ ID NO: 60, SEQ ID NO: 63, SEQ ID NO: 66, SEQ ID NO: 69, SEQ ID NO: 75, SEQ ID NO: 87, SEQ ID NO: 96, SEQ ID NO: 99 and SEQ ID NO: 108 and polypeptides having at least at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity hereto, and wherein the polypeptide has peptidoglycan degradation activity.

One embodiment of the invention relates to a polypeptide wherein the polypeptide comprises the motif N[IV]X[AG][GAS]A[AY][LV]L (SEQ ID NO: 111), wherein the polypeptide is selected from the group consisting of: SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 42, SEQ ID NO: 45, SEQ ID NO: 48, SEQ ID NO: 51, SEQ ID NO: 54, SEQ ID NO: 60, SEQ ID NO: 63, SEQ ID NO: 66, SEQ ID NO: 69, SEQ ID NO: 75, SEQ ID NO: 87, SEQ ID NO: 96, SEQ ID NO: 99 and SEQ ID NO: 108 and polypeptides having at least at least 60% sequence identity hereto, and wherein the polypeptide has peptidoglycan degradation activity.

One embodiment of the invention relates to a polypeptide wherein the polypeptide comprises the motif N[IV]X[AG][GAS]A[AY][LV]L (SEQ ID NO: 111), wherein the polypeptide is selected from the group consisting of: SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 42, SEQ ID NO: 45, SEQ ID NO: 48, SEQ ID NO: 51, SEQ ID NO: 54, SEQ ID NO: 60, SEQ ID NO: 63, SEQ ID NO: 66, SEQ ID NO: 69, SEQ ID NO: 75, SEQ ID NO: 87, SEQ ID NO: 96, SEQ ID NO: 99 and SEQ ID NO: 108 and polypeptides having at least at least 70% sequence identity hereto, and wherein the polypeptide has peptidoglycan degradation activity.

One embodiment of the invention relates to a polypeptide wherein the polypeptide comprises the motif N[IV]X[AG][GAS]A[AY][LV]L (SEQ ID NO: 111), wherein the polypeptide is selected from the group consisting of: SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 42, SEQ ID NO: 45, SEQ ID NO: 48, SEQ ID NO: 51, SEQ ID NO: 54, SEQ ID NO: 60, SEQ ID NO: 63, SEQ ID NO: 66, SEQ ID NO: 69, SEQ ID NO: 75, SEQ ID NO: 87, SEQ ID NO: 96, SEQ ID NO: 99 and SEQ ID NO: 108 and polypeptides having at least at least 80% sequence identity hereto, and wherein the polypeptide has peptidoglycan degradation activity.

One embodiment of the invention relates to a polypeptide wherein the polypeptide comprises the motif N[IV]X[AG][GAS]A[AY][LV]L (SEQ ID NO: 111), wherein the polypeptide is selected from the group consisting of: SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 42, SEQ ID NO: 45, SEQ ID NO: 48, SEQ ID NO: 51, SEQ ID NO: 54, SEQ ID NO: 60, SEQ ID NO: 63, SEQ ID NO: 66, SEQ ID NO: 69, SEQ ID NO: 75, SEQ ID NO: 87, SEQ ID NO: 96, SEQ ID NO: 99 and SEQ ID NO: 108 and polypeptides having at least at least 90% sequence identity hereto, and wherein the polypeptide has peptidoglycan degradation activity.

One embodiment of the invention relates to a polypeptide wherein the polypeptide comprises the motif N[IV]X[AG][GAS]A[AY][LV]L (SEQ ID NO: 111), wherein the polypeptide is selected from the group consisting of: SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 42, SEQ ID NO: 45, SEQ ID NO: 48, SEQ ID NO: 51, SEQ ID NO: 54, SEQ ID NO: 60, SEQ ID NO: 63, SEQ ID NO: 66, SEQ ID NO: 69, SEQ ID NO: 75, SEQ ID NO: 87, SEQ ID NO: 96, SEQ ID NO: 99 and SEQ ID NO: 108 and polypeptides having at least at least 95% sequence identity hereto, and wherein the polypeptide has peptidoglycan degradation activity.

One embodiment of the invention relates to a polypeptide wherein the polypeptide comprises the motif N[IV]X[AG][GAS]A[AY][LV]L (SEQ ID NO: 111), wherein the polypeptide is selected from the group consisting of: SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 42, SEQ ID NO: 45, SEQ ID NO: 48, SEQ ID NO: 51, SEQ ID NO: 54, SEQ ID NO: 60, SEQ ID NO: 63, SEQ ID NO: 66, SEQ ID NO: 69, SEQ ID NO: 75, SEQ ID NO: 87, SEQ ID NO: 96, SEQ ID NO: 99 and SEQ ID NO: 108 and polypeptides having at least at least 98% sequence identity hereto, and wherein the polypeptide has peptidoglycan degradation activity.

One embodiment of the invention relates to a polypeptide wherein the polypeptide comprises the motif N[IV]X[AG][GAS]A[AY][LV]L (SEQ ID NO: 111), wherein the polypeptide is selected from the group consisting of: SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 42, SEQ ID NO: 45, SEQ ID NO: 48, SEQ ID NO: 51, SEQ ID NO: 54, SEQ ID NO: 60, SEQ ID NO: 63, SEQ ID NO: 66, SEQ ID NO: 69, SEQ ID NO: 75, SEQ ID NO: 87, SEQ ID NO: 96, SEQ ID NO: 99 and SEQ ID NO: 108 and polypeptides having at least at least 99% sequence identity hereto, and wherein the polypeptide has peptidoglycan degradation activity.

In any of the embodiments disclosed herein, the polypeptide has preferably been isolated, i.e. the polypeptide is in an "isolated" form or environment as defined above.

One polypeptide of the present invention preferably comprises or consists of the amino acid sequence of SEQ ID NO: 2 or an allelic variant thereof; or is a fragment thereof having peptidoglycan degradation activity. In another aspect, the polypeptide comprises or consists of the mature polypeptide shown in SEQ ID NO: 3. In another aspect, the polypeptide comprises or consists of amino acids 1 to 431 of SEQ ID NO: 2.

A polypeptide of the present invention preferably comprises or consists of the amino acid sequence of SEQ ID NO: 5 or an allelic variant thereof; or is a fragment thereof having peptidoglycan degradation activity. In another aspect, the polypeptide comprises or consists of the mature polypeptide shown in SEQ ID NO: 6. In another aspect, the polypeptide comprises or consists of amino acids 1 to 485 of SEQ ID NO: 5.

A polypeptide of the present invention preferably comprises or consists of the amino acid sequence of SEQ ID NO: 8 or an allelic variant thereof; or is a fragment thereof having peptidoglycan degradation activity. In another aspect, the polypeptide comprises or consists of the mature polypeptide shown in SEQ ID NO: 9. In another aspect, the polypeptide comprises or consists of amino acids 1 to 483 of SEQ ID NO: 8.

A polypeptide of the present invention preferably comprises or consists of the amino acid sequence of SEQ ID NO: 11 or an allelic variant thereof; or is a fragment thereof having peptidoglycan degradation activity. In another aspect, the polypeptide comprises or consists of the mature polypeptide shown in SEQ ID NO: 12. In another aspect, the polypeptide comprises or consists of amino acids 1 to 471 of SEQ ID NO: 11.

A polypeptide of the present invention preferably comprises or consists of the amino acid sequence of SEQ ID NO: 14 or an allelic variant thereof; or is a fragment thereof having peptidoglycan degradation activity. In another aspect, the polypeptide comprises or consists of the mature polypeptide shown in SEQ ID NO: 15. In another aspect, the polypeptide comprises or consists of amino acids 1 to 639 of SEQ ID NO: 14.

A polypeptide of the present invention preferably comprises or consists of the amino acid sequence of SEQ ID NO: 17 or an allelic variant thereof; or is a fragment thereof having peptidoglycan degradation activity. In another aspect, the polypeptide comprises or consists of the mature polypeptide shown in SEQ ID NO: 18. In another aspect, the polypeptide comprises or consists of amino acids 1 to 484 of SEQ ID NO: 17.

A polypeptide of the present invention preferably comprises or consists of the amino acid sequence of SEQ ID NO: 20 or an allelic variant thereof; or is a fragment thereof having peptidoglycan degradation activity. In another aspect, the polypeptide comprises or consists of the mature polypeptide shown in SEQ ID NO: 21. In another aspect, the polypeptide comprises or consists of amino acids 1 to 480 of SEQ ID NO: 20.

A polypeptide of the present invention preferably comprises or consists of the amino acid sequence of SEQ ID NO: 23 or an allelic variant thereof; or is a fragment thereof having peptidoglycan degradation activity. In another aspect, the polypeptide comprises or consists of the mature polypeptide shown in SEQ ID NO: 24. In another aspect, the polypeptide comprises or consists of amino acids 1 to 485 of SEQ ID NO: 23.

A polypeptide of the present invention preferably comprises or consists of the amino acid sequence of SEQ ID NO: 26 or an allelic variant thereof; or is a fragment thereof having peptidoglycan degradation activity. In another aspect, the polypeptide comprises or consists of the mature polypeptide shown in SEQ ID NO: 27. In another aspect, the polypeptide comprises or consists of amino acids 1 to 491 of SEQ ID NO: 26.

A polypeptide of the present invention preferably comprises or consists of the amino acid sequence of SEQ ID NO: 29 or an allelic variant thereof; or is a fragment thereof having peptidoglycan degradation activity. In another aspect, the polypeptide comprises or consists of the mature polypeptide shown in SEQ ID NO: 30. In another aspect, the polypeptide comprises or consists of amino acids 1 to 289 of SEQ ID NO: 29.

A polypeptide of the present invention preferably comprises or consists of the amino acid sequence of SEQ ID NO: 32 or an allelic variant thereof; or is a fragment thereof having peptidoglycan degradation activity. In another aspect, the polypeptide comprises or consists of the mature polypeptide shown in SEQ ID NO: 33. In another aspect, the polypeptide comprises or consists of amino acids 1 to 245 of SEQ ID NO: 32.

A polypeptide of the present invention preferably comprises or consists of the amino acid sequence of SEQ ID NO: 35 or an allelic variant thereof; or is a fragment thereof having peptidoglycan degradation activity. In another aspect, the polypeptide comprises or consists of the mature polypeptide shown in SEQ ID NO: 36. In another aspect, the polypeptide comprises or consists of amino acids 1 to 280 of SEQ ID NO: 35.

A polypeptide of the present invention preferably comprises or consists of the amino acid sequence of SEQ ID NO: 38 or an allelic variant thereof; or is a fragment thereof having peptidoglycan degradation activity. In another aspect, the polypeptide comprises or consists of the mature polypeptide shown in SEQ ID NO: 39. In another aspect, the polypeptide comprises or consists of amino acids 1 to 238 of SEQ ID NO: 38.

A polypeptide of the present invention preferably comprises or consists of the amino acid sequence of SEQ ID NO: 41 or an allelic variant thereof; or is a fragment thereof having peptidoglycan degradation activity. In another aspect, the polypeptide comprises or consists of the mature polypeptide shown in SEQ ID NO: 42. In another aspect, the polypeptide comprises or consists of amino acids 1 to 498 of SEQ ID NO: 41.

A polypeptide of the present invention preferably comprises or consists of the amino acid sequence of SEQ ID NO: 44 or an allelic variant thereof; or is a fragment thereof having peptidoglycan degradation activity. In another aspect, the polypeptide comprises or consists of the mature polypeptide shown in SEQ ID NO: 45. In another aspect, the polypeptide comprises or consists of amino acids 1 to 476 of SEQ ID NO: 44.

A polypeptide of the present invention preferably comprises or consists of the amino acid sequence of SEQ ID NO: 47 or an allelic variant thereof; or is a fragment thereof having peptidoglycan degradation activity. In another aspect, the polypeptide comprises or consists of the mature polypeptide shown in SEQ ID NO: 48. In another aspect, the polypeptide comprises or consists of amino acids 1 to 474 of SEQ ID NO: 47.

A polypeptide of the present invention preferably comprises or consists of the amino acid sequence of SEQ ID NO: 50 or an allelic variant thereof; or is a fragment thereof having peptidoglycan degradation activity. In another aspect, the polypeptide comprises or consists of the mature polypeptide shown in SEQ ID NO: 51. In another aspect, the polypeptide comprises or consists of amino acids 1 to 473 of SEQ ID NO: 50.

A polypeptide of the present invention preferably comprises or consists of the amino acid sequence of SEQ ID NO: 53 or an allelic variant thereof; or is a fragment thereof having peptidoglycan degradation activity. In another aspect, the polypeptide comprises or consists of the mature polypeptide shown in SEQ ID NO: 54. In another aspect, the polypeptide comprises or consists of amino acids 1 to 414 of SEQ ID NO: 53.

A polypeptide of the present invention preferably comprises or consists of the amino acid sequence of SEQ ID NO: 56 or an allelic variant thereof; or is a fragment thereof having peptidoglycan degradation activity. In another aspect, the polypeptide comprises or consists of the mature polypeptide shown in SEQ ID NO: 57. In another aspect, the polypeptide comprises or consists of amino acids 1 to 412 of SEQ ID NO: 56.

A polypeptide of the present invention preferably comprises or consists of the amino acid sequence of SEQ ID NO: 59 or an allelic variant thereof; or is a fragment thereof having peptidoglycan degradation activity. In another aspect, the polypeptide comprises or consists of the mature polypeptide shown in SEQ ID NO: 60. In another aspect, the polypeptide comprises or consists of amino acids 1 to 637 of SEQ ID NO: 59.

A polypeptide of the present invention preferably comprises or consists of the amino acid sequence of SEQ ID NO: 62 or an allelic variant thereof; or is a fragment thereof having peptidoglycan degradation activity. In another aspect, the polypeptide comprises or consists of the mature polypeptide shown in SEQ ID NO: 63. In another aspect, the polypeptide comprises or consists of amino acids 1 to 599 of SEQ ID NO: 62.

A polypeptide of the present invention preferably comprises or consists of the amino acid sequence of SEQ ID NO: 65 or an allelic variant thereof; or is a fragment thereof having peptidoglycan degradation activity. In another aspect, the polypeptide comprises or consists of the mature polypeptide shown in SEQ ID NO: 66. In another aspect, the polypeptide comprises or consists of amino acids 1 to 605 of SEQ ID NO: 65.

A polypeptide of the present invention preferably comprises or consists of the amino acid sequence of SEQ ID NO: 68 or an allelic variant thereof; or is a fragment thereof having peptidoglycan degradation activity. In another aspect, the polypeptide comprises or consists of the mature polypeptide shown in SEQ ID NO: 69. In another aspect, the polypeptide comprises or consists of amino acids 1 to 610 of SEQ ID NO: 68.

A polypeptide of the present invention preferably comprises or consists of the amino acid sequence of SEQ ID NO: 71 or an allelic variant thereof; or is a fragment thereof having peptidoglycan degradation activity. In another aspect, the polypeptide comprises or consists of the mature polypeptide shown in SEQ ID NO: 72. In another aspect, the polypeptide comprises or consists of amino acids 1 to 216 of SEQ ID NO: 71.

A polypeptide of the present invention preferably comprises or consists of the amino acid sequence of SEQ ID NO: 74 or an allelic variant thereof; or is a fragment thereof having peptidoglycan degradation activity. In another aspect, the polypeptide comprises or consists of the mature polypeptide shown in SEQ ID NO: 75. In another aspect, the polypeptide comprises or consists of amino acids 1 to 425 of SEQ ID NO: 74.

A polypeptide of the present invention preferably comprises or consists of the amino acid sequence of SEQ ID NO: 77 or an allelic variant thereof; or is a fragment thereof having peptidoglycan degradation activity. In another aspect, the polypeptide comprises or consists of the mature polypeptide shown in SEQ ID NO: 78. In another aspect, the polypeptide comprises or consists of amino acids 1 to 304 of SEQ ID NO: 77.

A polypeptide of the present invention preferably comprises or consists of the amino acid sequence of SEQ ID NO: 80 or an allelic variant thereof; or is a fragment thereof having peptidoglycan degradation activity. In another aspect, the polypeptide comprises or consists of the mature polypeptide shown in SEQ ID NO: 81. In another aspect, the polypeptide comprises or consists of amino acids 1 to 306 of SEQ ID NO: 80.

A polypeptide of the present invention preferably comprises or consists of the amino acid sequence of SEQ ID NO: 83 or an allelic variant thereof; or is a fragment thereof having peptidoglycan degradation activity. In another aspect, the polypeptide comprises or consists of the mature polypeptide shown in SEQ ID NO: 84. In another aspect, the polypeptide comprises or consists of amino acids 1 to 306 of SEQ ID NO: 83.

A polypeptide of the present invention preferably comprises or consists of the amino acid sequence of SEQ ID NO: 86 or an allelic variant thereof; or is a fragment thereof having peptidoglycan degradation activity. In another aspect, the polypeptide comprises or consists of the mature polypeptide shown in SEQ ID NO: 87. In another aspect, the polypeptide comprises or consists of amino acids 1 to 632 of SEQ ID NO: 86.

A polypeptide of the present invention preferably comprises or consists of the amino acid sequence of SEQ ID NO: 89 or an allelic variant thereof; or is a fragment thereof having peptidoglycan degradation activity. In another aspect, the polypeptide comprises or consists of the mature polypeptide shown in SEQ ID NO: 90. In another aspect, the polypeptide comprises or consists of amino acids 1 to 216 of SEQ ID NO: 89.

A polypeptide of the present invention preferably comprises or consists of the amino acid sequence of SEQ ID NO: 92 or an allelic variant thereof; or is a fragment thereof having peptidoglycan degradation activity. In another aspect, the polypeptide comprises or consists of the mature polypeptide shown in SEQ ID NO: 93. In another aspect, the polypeptide comprises or consists of amino acids 1 to 306 of SEQ ID NO: 92.

A polypeptide of the present invention preferably comprises or consists of the amino acid sequence of SEQ ID NO: 95 or an allelic variant thereof; or is a fragment thereof having peptidoglycan degradation activity. In another aspect, the polypeptide comprises or consists of the mature polypeptide shown in SEQ ID NO: 96. In another aspect, the polypeptide comprises or consists of amino acids 1 to 453 of SEQ ID NO: 95.

A polypeptide of the present invention preferably comprises or consists of the amino acid sequence of SEQ ID NO: 98 or an allelic variant thereof; or is a fragment thereof having peptidoglycan degradation activity. In another aspect, the polypeptide comprises or consists of the mature polypeptide shown in SEQ ID NO: 99. In another aspect, the polypeptide comprises or consists of amino acids 1 to 473 of SEQ ID NO: 98.

A polypeptide of the present invention preferably comprises or consists of the amino acid sequence of SEQ ID NO: 101 or an allelic variant thereof; or is a fragment thereof having peptidoglycan degradation activity. In another aspect, the polypeptide comprises or consists of the mature polypeptide shown in SEQ ID NO: 102. In another aspect, the polypeptide comprises or consists of amino acids 1 to 209 of SEQ ID NO: 101.

A polypeptide of the present invention preferably comprises or consists of the amino acid sequence of SEQ ID NO: 104 or an allelic variant thereof; or is a fragment thereof having peptidoglycan degradation activity. In another aspect, the polypeptide comprises or consists of the mature polypeptide shown in SEQ ID NO: 105. In another aspect, the polypeptide comprises or consists of amino acids 1 to 281 of SEQ ID NO: 104.

A polypeptide of the present invention preferably comprises or consists of the amino acid sequence of SEQ ID NO: 107 or an allelic variant thereof; or is a fragment thereof having peptidoglycan degradation activity. In another aspect, the polypeptide comprises or consists of the mature polypeptide shown in SEQ ID NO: 108. In another aspect, the polypeptide comprises or consists of amino acids 1 to 582 of SEQ ID NO: 107.

In another embodiment, the present invention relates to a polypeptide having peptidoglycan degradation activity encoded by a polynucleotide that hybridizes under very low stringency conditions, low stringency conditions, medium stringency conditions, medium-high stringency conditions, high stringency conditions, or very high stringency conditions with (i) SEQ ID NO: 1, SEQ ID NO: 4, SEQ ID NO: 7, SEQ ID NO: 10, SEQ ID NO: 13, SEQ ID NO: 16, SEQ ID NO: 19, SEQ ID NO: 22, SEQ ID NO: 25, SEQ ID NO: 28, SEQ ID NO: 31, SEQ ID NO: 34, SEQ ID NO: 37, SEQ ID NO: 40, SEQ ID NO: 43, SEQ ID NO: 46, SEQ ID NO: 49, SEQ ID NO: 52, SEQ ID NO: 55, SEQ ID NO: 58, SEQ ID NO: 61, SEQ ID NO: 64, SEQ ID NO: 67, SEQ ID NO: 70, SEQ ID NO: 73, SEQ ID NO: 76, SEQ ID NO: 79, SEQ ID NO: 82, SEQ ID NO: 85, SEQ ID NO: 88, SEQ ID NO: 91, SEQ ID NO: 94, SEQ ID NO: 97, SEQ ID NO: 100, SEQ ID NO: 103 or SEQ ID NO: 106, (ii) the mature polypeptide coding sequence of SEQ ID NO: 1, SEQ ID NO: 4, SEQ ID NO: 7, SEQ ID NO: 10, SEQ ID NO: 13, SEQ ID NO: 16, SEQ ID NO: 19, SEQ ID NO: 22, SEQ ID NO: 25, SEQ ID NO: 28, SEQ ID NO: 31, SEQ ID NO: 34, SEQ ID NO: 37, SEQ ID NO: 40, SEQ ID NO: 43, SEQ ID NO: 46, SEQ ID NO: 49, SEQ ID NO: 52, SEQ ID NO: 55, SEQ ID NO: 58, SEQ ID NO: 61, SEQ ID NO: 64, SEQ ID NO: 67, SEQ ID NO: 70, SEQ ID NO: 73, SEQ ID NO: 76, SEQ ID NO: 79, SEQ ID NO: 82, SEQ ID NO: 85, SEQ ID NO: 88, SEQ ID NO: 91, SEQ ID NO: 94, SEQ ID NO: 97, SEQ ID NO: 100, SEQ ID NO: 103 or SEQ ID NO: 106; or (iii) the full-length complement of (i) or (ii) (Sambrook et al., 1989, *Molecular Cloning, A Laboratory Manual*, 2d edition, Cold Spring Harbor, New York). Such polypeptides have preferably been isolated.

The polynucleotide of SEQ ID NO: 1, SEQ ID NO: 4, SEQ ID NO: 7, SEQ ID NO: 10, SEQ ID NO: 13, SEQ ID NO: 16, SEQ ID NO: 19, SEQ ID NO: 22, SEQ ID NO: 25, SEQ ID NO: 28, SEQ ID NO: 31, SEQ ID NO: 34, SEQ ID NO: 37, SEQ ID NO: 40, SEQ ID NO: 43, SEQ ID NO: 46, SEQ ID NO: 49, SEQ ID NO: 52, SEQ ID NO: 55, SEQ ID NO: 58, SEQ ID NO: 61, SEQ ID NO: 64, SEQ ID NO: 67, SEQ ID NO: 70, SEQ ID NO: 73, SEQ ID NO: 76, SEQ ID NO: 79, SEQ ID NO: 82, SEQ ID NO: 85, SEQ ID NO: 88, SEQ ID NO: 91, SEQ ID NO: 94, SEQ ID NO: 97, SEQ ID NO: 100, SEQ ID NO: 103, SEQ ID NO: 106 or a subsequence thereof, as well as a fragment thereof may be used to design nucleic acid probes to identify and clone DNA encoding polypeptides having peptidoglycan degradation activity from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

A genomic DNA or cDNA library prepared from such other strains may be screened for DNA that hybridizes with the probes described above and encodes a polypeptide having peptidoglycan degradation activity. Genomic or other DNA from such other strains may be separated by agarose or polyacrylamide gel electrophoresis, or other separation techniques. DNA from the libraries or the separated DNA may be transferred to and immobilized on nitrocellulose or another suitable carrier material. In order to identify a clone or DNA that hybridizes with SEQ ID NO: 1, SEQ ID NO: 4, SEQ ID NO: 7, SEQ ID NO: 10, SEQ ID NO: 13, SEQ ID NO: 16, SEQ ID NO: 19, SEQ ID NO: 22, SEQ ID NO: 25, SEQ ID NO: 28, SEQ ID NO: 31, SEQ ID NO: 34, SEQ ID NO: 37, SEQ ID NO: 40, SEQ ID NO: 43, SEQ ID NO: 46, SEQ ID NO: 49, SEQ ID NO: 52, SEQ ID NO: 55, SEQ ID NO: 58, SEQ ID NO: 61, SEQ ID NO: 64, SEQ ID NO: 67, SEQ ID NO: 70, SEQ ID NO: 73, SEQ ID NO: 76, SEQ ID NO: 79, SEQ ID NO: 82, SEQ ID NO: 85, SEQ ID NO: 88, SEQ ID NO: 91, SEQ ID NO: 94, SEQ ID NO: 97, SEQ ID NO: 100, SEQ ID NO: 103, SEQ ID NO: 106 or a subsequence thereof, the carrier material is used in a Southern blot.

For purposes of the present invention, hybridization indicates that the polynucleotide hybridizes to a labeled nucleic acid probe corresponding to (i) SEQ ID NO: 1, SEQ ID NO: 4, SEQ ID NO: 7, SEQ ID NO: 10, SEQ ID NO: 13, SEQ ID NO: 16, SEQ ID NO: 19, SEQ ID NO: 22, SEQ ID NO: 25, SEQ ID NO: 28, SEQ ID NO: 31, SEQ ID NO: 34, SEQ ID NO: 37, SEQ ID NO: 40, SEQ ID NO: 43, SEQ ID NO: 46, SEQ ID NO: 49, SEQ ID NO: 52, SEQ ID NO: 55, SEQ ID NO: 58, SEQ ID NO: 61, SEQ ID NO: 64, SEQ ID NO: 67, SEQ ID NO: 70, SEQ ID NO: 73, SEQ ID NO: 76, SEQ ID NO: 79, SEQ ID NO: 82, SEQ ID NO: 85, SEQ ID NO: 88, SEQ ID NO: 91, SEQ ID NO: 94, SEQ ID NO: 97, SEQ ID NO: 100, SEQ ID NO: 103 or SEQ ID NO: 106; (ii) the mature polypeptide coding sequence of SEQ ID NO: 1, SEQ ID NO: 4, SEQ ID NO: 7, SEQ ID NO: 10, SEQ ID NO: 13, SEQ ID NO: 16, SEQ ID NO: 19, SEQ ID NO: 22, SEQ ID NO: 25, SEQ ID NO: 28, SEQ ID NO: 31, SEQ ID NO: 34, SEQ ID NO: 37, SEQ ID NO: 40, SEQ ID NO: 43, SEQ ID NO: 46, SEQ ID NO: 49, SEQ ID NO: 52, SEQ ID NO: 55, SEQ ID NO: 58, SEQ ID NO: 61, SEQ ID NO: 64, SEQ ID NO: 67, SEQ ID NO: 70, SEQ ID NO: 73, SEQ ID NO: 76, SEQ ID NO: 79, SEQ ID NO: 82, SEQ ID NO: 85, SEQ ID NO: 88, SEQ ID NO: 91, SEQ ID NO: 94, SEQ ID NO: 97, SEQ ID NO: 100, SEQ ID NO: 103 or SEQ ID NO: 106; (iii) the full-length complement thereof; or (iv) a subsequence thereof; under very low to very high stringency conditions. Molecules to which the nucleic acid probe hybridizes under these conditions can be detected using, for example, X-ray film or any other detection means known in the art.

In another embodiment, the present invention relates to a polypeptide having peptidoglycan degradation activity encoded by a polynucleotide having a sequence identity to the mature polypeptide coding sequence of SEQ ID NO: 1 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 4 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 7 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 10 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 13 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 16 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 19 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 22 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 25 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 28 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 31 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 34 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 37 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 40 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 43 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 46 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 49 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 52 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 55 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 58 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 61 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 64 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 67 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 70 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 73 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 76 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 79 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 82 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 85 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 88 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 91 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 94 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 97 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 100 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 103 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to a polypeptide having peptidoglycan degradation activity encoded by a polynucleotide having a sequence identity to the mature polypeptide coding sequence of SEQ ID NO: 106 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to variants of the polypeptide shown in SEQ ID NO: 3 comprising a substitution, deletion, and/or insertion at one or more positions. In an embodiment, the number of amino acid substitutions, deletions and/or insertions introduced into the polypeptide shown SEQ ID NO: 3 is up to 10, e.g., 1, 2, 3, 4, 5, 6, 7, 8, 9, or 10.

In another embodiment, the present invention relates to variants of the polypeptide shown in SEQ ID NO: 6 comprising a substitution, deletion, and/or insertion at one or more positions. In an embodiment, the number of amino acid substitutions, deletions and/or insertions introduced into the polypeptide shown SEQ ID NO: 6 is up to 10, e.g., 1, 2, 3, 4, 5, 6, 7, 8, 9, or 10.

In another embodiment, the present invention relates to variants of the polypeptide shown in SEQ ID NO: 9 comprising a substitution, deletion, and/or insertion at one or more positions. In an embodiment, the number of amino acid substitutions, deletions and/or insertions introduced into the polypeptide shown SEQ ID NO: 9 is up to 10, e.g., 1, 2, 3, 4, 5, 6, 7, 8, 9, or 10.

In another embodiment, the present invention relates to variants of the polypeptide shown in SEQ ID NO: 12 comprising a substitution, deletion, and/or insertion at one or more positions. In an embodiment, the number of amino acid substitutions, deletions and/or insertions introduced into the polypeptide shown SEQ ID NO: 12 is up to 10, e.g., 1, 2, 3, 4, 5, 6, 7, 8, 9, or 10.

In another embodiment, the present invention relates to variants of the polypeptide shown in SEQ ID NO: 15 comprising a substitution, deletion, and/or insertion at one or more positions. In an embodiment, the number of amino acid substitutions, deletions and/or insertions introduced into the polypeptide shown SEQ ID NO: 15 is up to 10, e.g., 1, 2, 3, 4, 5, 6, 7, 8, 9, or 10.

In another embodiment, the present invention relates to variants of the polypeptide shown in SEQ ID NO: 18 comprising a substitution, deletion, and/or insertion at one or more positions. In an embodiment, the number of amino acid substitutions, deletions and/or insertions introduced into the polypeptide shown SEQ ID NO: 18 is up to 10, e.g., 1, 2, 3, 4, 5, 6, 7, 8, 9, or 10.

In another embodiment, the present invention relates to variants of the polypeptide shown in SEQ ID NO: 21 comprising a substitution, deletion, and/or insertion at one or more positions. In an embodiment, the number of amino acid substitutions, deletions and/or insertions introduced into the polypeptide shown SEQ ID NO: 21 is up to 10, e.g., 1, 2, 3, 4, 5, 6, 7, 8, 9, or 10.

In another embodiment, the present invention relates to variants of the polypeptide shown in SEQ ID NO: 24 comprising a substitution, deletion, and/or insertion at one or more positions. In an embodiment, the number of amino acid substitutions, deletions and/or insertions introduced into the polypeptide shown SEQ ID NO: 24 is up to 10, e.g., 1, 2, 3, 4, 5, 6, 7, 8, 9, or 10.

In another embodiment, the present invention relates to variants of the polypeptide shown in SEQ ID NO: 27 comprising a substitution, deletion, and/or insertion at one or more positions. In an embodiment, the number of amino acid substitutions, deletions and/or insertions introduced into the polypeptide shown SEQ ID NO: 27 is up to 10, e.g., 1, 2, 3, 4, 5, 6, 7, 8, 9, or 10.

In another embodiment, the present invention relates to variants of the polypeptide shown in SEQ ID NO: 30 comprising a substitution, deletion, and/or insertion at one or more positions. In an embodiment, the number of amino acid substitutions, deletions and/or insertions introduced into the polypeptide shown SEQ ID NO: 30 is up to 10, e.g., 1, 2, 3, 4, 5, 6, 7, 8, 9, or 10.

In another embodiment, the present invention relates to variants of the polypeptide shown in SEQ ID NO: 33 comprising a substitution, deletion, and/or insertion at one or more positions. In an embodiment, the number of amino acid substitutions, deletions and/or insertions introduced into the polypeptide shown SEQ ID NO: 33 is up to 10, e.g., 1, 2, 3, 4, 5, 6, 7, 8, 9, or 10.

In another embodiment, the present invention relates to variants of the polypeptide shown in SEQ ID NO: 36 comprising a substitution, deletion, and/or insertion at one or more positions. In an embodiment, the number of amino acid substitutions, deletions and/or insertions introduced into the polypeptide shown SEQ ID NO: 36 is up to 10, e.g., 1, 2, 3, 4, 5, 6, 7, 8, 9, or 10.

In another embodiment, the present invention relates to variants of the polypeptide shown in SEQ ID NO: 39 comprising a substitution, deletion, and/or insertion at one or more positions. In an embodiment, the number of amino acid substitutions, deletions and/or insertions introduced into the polypeptide shown SEQ ID NO: 39 is up to 10, e.g., 1, 2, 3, 4, 5, 6, 7, 8, 9, or 10.

In another embodiment, the present invention relates to variants of the polypeptide shown in SEQ ID NO: 42 comprising a substitution, deletion, and/or insertion at one or more positions. In an embodiment, the number of amino acid substitutions, deletions and/or insertions introduced into the polypeptide shown SEQ ID NO: 42 is up to 10, e.g., 1, 2, 3, 4, 5, 6, 7, 8, 9, or 10.

In another embodiment, the present invention relates to variants of the polypeptide shown in SEQ ID NO: 45 comprising a substitution, deletion, and/or insertion at one or more positions. In an embodiment, the number of amino acid substitutions, deletions and/or insertions introduced into the polypeptide shown SEQ ID NO: 45 is up to 10, e.g., 1, 2, 3, 4, 5, 6, 7, 8, 9, or 10.

In another embodiment, the present invention relates to variants of the polypeptide shown in SEQ ID NO: 48 comprising a substitution, deletion, and/or insertion at one or more positions. In an embodiment, the number of amino acid substitutions, deletions and/or insertions introduced into the polypeptide shown SEQ ID NO: 48 is up to 10, e.g., 1, 2, 3, 4, 5, 6, 7, 8, 9, or 10.

In another embodiment, the present invention relates to variants of the polypeptide shown in SEQ ID NO: 51 comprising a substitution, deletion, and/or insertion at one or more positions. In an embodiment, the number of amino acid substitutions, deletions and/or insertions introduced into the polypeptide shown SEQ ID NO: 51 is up to 10, e.g., 1, 2, 3, 4, 5, 6, 7, 8, 9, or 10.

In another embodiment, the present invention relates to variants of the polypeptide shown in SEQ ID NO: 54 comprising a substitution, deletion, and/or insertion at one or more positions. In an embodiment, the number of amino acid substitutions, deletions and/or insertions introduced into the polypeptide shown SEQ ID NO: 54 is up to 10, e.g., 1, 2, 3, 4, 5, 6, 7, 8, 9, or 10.

In another embodiment, the present invention relates to variants of the polypeptide shown in SEQ ID NO: 57 comprising a substitution, deletion, and/or insertion at one or more positions. In an embodiment, the number of amino acid substitutions, deletions and/or insertions introduced into the polypeptide shown SEQ ID NO: 57 is up to 10, e.g., 1, 2, 3, 4, 5, 6, 7, 8, 9, or 10.

In another embodiment, the present invention relates to variants of the polypeptide shown in SEQ ID NO: 60 comprising a substitution, deletion, and/or insertion at one or more positions. In an embodiment, the number of amino acid substitutions, deletions and/or insertions introduced into the polypeptide shown SEQ ID NO: 60 is up to 10, e.g., 1, 2, 3, 4, 5, 6, 7, 8, 9, or 10.

In another embodiment, the present invention relates to variants of the polypeptide shown in SEQ ID NO: 63 comprising a substitution, deletion, and/or insertion at one or more positions. In an embodiment, the number of amino acid substitutions, deletions and/or insertions introduced into the polypeptide shown SEQ ID NO: 63 is up to 10, e.g., 1, 2, 3, 4, 5, 6, 7, 8, 9, or 10.

In another embodiment, the present invention relates to variants of the polypeptide shown in SEQ ID NO: 66 comprising a substitution, deletion, and/or insertion at one or more positions. In an embodiment, the number of amino acid substitutions, deletions and/or insertions introduced into the polypeptide shown SEQ ID NO: 66 is up to 10, e.g., 1, 2, 3, 4, 5, 6, 7, 8, 9, or 10.

In another embodiment, the present invention relates to variants of the polypeptide shown in SEQ ID NO: 69 comprising a substitution, deletion, and/or insertion at one or more positions. In an embodiment, the number of amino acid substitutions, deletions and/or insertions introduced into the polypeptide shown SEQ ID NO: 69 is up to 10, e.g., 1, 2, 3, 4, 5, 6, 7, 8, 9, or 10.

In another embodiment, the present invention relates to variants of the polypeptide shown in SEQ ID NO: 72 comprising a substitution, deletion, and/or insertion at one or more positions. In an embodiment, the number of amino acid substitutions, deletions and/or insertions introduced into the polypeptide shown SEQ ID NO: 72 is up to 10, e.g., 1, 2, 3, 4, 5, 6, 7, 8, 9, or 10.

In another embodiment, the present invention relates to variants of the polypeptide shown in SEQ ID NO: 75 comprising a substitution, deletion, and/or insertion at one or more positions. In an embodiment, the number of amino acid substitutions, deletions and/or insertions introduced into the polypeptide shown SEQ ID NO: 75 is up to 10, e.g., 1, 2, 3, 4, 5, 6, 7, 8, 9, or 10.

In another embodiment, the present invention relates to variants of the polypeptide shown in SEQ ID NO: 78 comprising a substitution, deletion, and/or insertion at one or more positions. In an embodiment, the number of amino acid substitutions, deletions and/or insertions introduced into the polypeptide shown SEQ ID NO: 78 is up to 10, e.g., 1, 2, 3, 4, 5, 6, 7, 8, 9, or 10.

In another embodiment, the present invention relates to variants of the polypeptide shown in SEQ ID NO: 81 comprising a substitution, deletion, and/or insertion at one or more positions. In an embodiment, the number of amino acid substitutions, deletions and/or insertions introduced into the polypeptide shown SEQ ID NO: 81 is up to 10, e.g., 1, 2, 3, 4, 5, 6, 7, 8, 9, or 10.

In another embodiment, the present invention relates to variants of the polypeptide shown in SEQ ID NO: 84 comprising a substitution, deletion, and/or insertion at one or more positions. In an embodiment, the number of amino acid substitutions, deletions and/or insertions introduced into the polypeptide shown SEQ ID NO: 84 is up to 10, e.g., 1, 2, 3, 4, 5, 6, 7, 8, 9, or 10.

In another embodiment, the present invention relates to variants of the polypeptide shown in SEQ ID NO: 87 comprising a substitution, deletion, and/or insertion at one or more positions. In an embodiment, the number of amino acid substitutions, deletions and/or insertions introduced into the polypeptide shown SEQ ID NO: 87 is up to 10, e.g., 1, 2, 3, 4, 5, 6, 7, 8, 9, or 10.

In another embodiment, the present invention relates to variants of the polypeptide shown in SEQ ID NO: 90 comprising a substitution, deletion, and/or insertion at one or more positions. In an embodiment, the number of amino acid substitutions, deletions and/or insertions introduced into the polypeptide shown SEQ ID NO: 90 is up to 10, e.g., 1, 2, 3, 4, 5, 6, 7, 8, 9, or 10.

In another embodiment, the present invention relates to variants of the polypeptide shown in SEQ ID NO: 93 comprising a substitution, deletion, and/or insertion at one or more positions. In an embodiment, the number of amino acid substitutions, deletions and/or insertions introduced into the polypeptide shown SEQ ID NO: 93 is up to 10, e.g., 1, 2, 3, 4, 5, 6, 7, 8, 9, or 10.

In another embodiment, the present invention relates to variants of the polypeptide shown in SEQ ID NO: 96 comprising a substitution, deletion, and/or insertion at one or more positions. In an embodiment, the number of amino acid substitutions, deletions and/or insertions introduced into the polypeptide shown SEQ ID NO: 96 is up to 10, e.g., 1, 2, 3, 4, 5, 6, 7, 8, 9, or 10.

In another embodiment, the present invention relates to variants of the polypeptide shown in SEQ ID NO: 99 comprising a substitution, deletion, and/or insertion at one or more positions. In an embodiment, the number of amino acid substitutions, deletions and/or insertions introduced into the polypeptide shown SEQ ID NO: 99 is up to 10, e.g., 1, 2, 3, 4, 5, 6, 7, 8, 9, or 10.

In another embodiment, the present invention relates to variants of the polypeptide shown in SEQ ID NO: 102 comprising a substitution, deletion, and/or insertion at one or more positions. In an embodiment, the number of amino acid substitutions, deletions and/or insertions introduced into the polypeptide shown SEQ ID NO: 102 is up to 10, e.g., 1, 2, 3, 4, 5, 6, 7, 8, 9, or 10.

In another embodiment, the present invention relates to variants of the polypeptide shown in SEQ ID NO: 105 comprising a substitution, deletion, and/or insertion at one or more positions. In an embodiment, the number of amino acid substitutions, deletions and/or insertions introduced into the polypeptide shown SEQ ID NO: 105 is up to 10, e.g., 1, 2, 3, 4, 5, 6, 7, 8, 9, or 10.

In another embodiment, the present invention relates to variants of the polypeptide shown in SEQ ID NO: 108 comprising a substitution, deletion, and/or insertion at one or more positions. In an embodiment, the number of amino acid substitutions, deletions and/or insertions introduced into the polypeptide shown SEQ ID NO: 108 is up to 10, e.g., 1, 2, 3, 4, 5, 6, 7, 8, 9, or 10.

The amino acid changes in any of the embodiments above or elsewhere herein may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tag, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant molecules are tested for peptidoglycan degradation activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Sources of Polypeptides Having Peptidoglycan Degradation Activity

A polypeptide having peptidoglycan degradation activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly. In one aspect, the polypeptide is an *Alicyclobacillus* polypeptide. In one aspect, the polypeptide is a *Tumebacillus* polypeptide. In one aspect, the polypeptide is a *Halomonas* polypeptide. In one aspect, the polypeptide is a *Kribbella* polypeptide, e.g., a polypeptide obtained from *Kribbella aluminosa*. In one aspect, the polypeptide is a *Streptomyces* polypeptide, e.g., a polypeptide obtained from *Streptomyces griseus*. In one aspect, the polypeptide is a *Nonomuraea* polypeptide, e.g., a polypeptide obtained from *Nonomuraea coxensis*, *Nonomuraea dietziae* or *Nonomuraea guangzhouensis*. In one aspect, the polypeptide is a *Micromonospora* polypeptide, e.g., a polypeptide obtained from *Micromonospora peucetia*, *Micromonospora fulvopurpurea* or *Micromonospora maritima*. In one aspect, the polypeptide is a *Laceyella* polypeptide, e.g., a polypeptide obtained from *Laceyella sacchari*. In one aspect, the polypeptide is a *Bacillus* polypeptide, e.g., a polypeptide obtained from *Bacillus sporothermodurans* or *Bacillus cohnii*. In one aspect, the polypeptide is a *Lysobacter* polypeptide, e.g., a polypeptide obtained from *Lysobacter antibioticus* or *Lysobacter capsica*. In one aspect, the polypeptide is a *Hamadaea* polypeptide, e.g., a polypeptide obtained from *Hamadaea tsunoensis*. In one aspect, the polypeptide is a *Paenibacillus* polypeptide, e.g., a polypeptide obtained from *Paenibacillus pini*. In one aspect, the polypeptide is a *Thermostaphylospora* polypeptide, e.g., a polypeptide obtained from *Thermostaphylospora chromogena*. In one aspect, the polypeptide is a *Pseudomonas* polypeptide, e.g., a polypeptide obtained from *Pseudomonas peli* or *Pseudomonas pseudoalcaligenes*.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including variant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the Bacillus amyloliquefaciens alpha-amylase gene (amyQ), Bacillus licheniformis alpha-amylase gene (amyL), Bacillus licheniformis penicillinase gene (penP), Bacillus stearothermophilus maltogenic amylase gene (amyM), Bacillus subtilis levansucrase gene (sacB), Bacillus subtilis xylA and xylB genes, Bacillus thuringiensis cryIIIA gene (Agaisse and Lereclus, 1994, Molecular Microbiology 13: 97-107), E. coli lac operon, E. coli trc promoter (Egon et al., 1988, Gene 69: 301-315), Streptomyces coelicolor agarase gene (dagA), and prokaryotic beta-lactamase gene (Villa-Kamaroff et al., 1978, Proc. Natl. Acad. Sci. USA 75: 3727-3731), as well as the tac promoter (DeBoer et al., 1983, Proc. Natl. Acad. Sci. USA 80: 21-25). Further promoters are described in "Useful proteins from recombinant bacteria" in Gilbert et al., 1980, Scientific American 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for Aspergillus nidulans acetamidase, Aspergillus niger neutral alpha-amylase, Aspergillus niger acid stable alpha-amylase, Aspergillus niger or Aspergillus awamori glucoamylase (glaA), Aspergillus oryzae TAKA amylase, Aspergillus oryzae alkaline protease, Aspergillus oryzae triose phosphate isomerase, Fusarium oxysporum trypsin-like protease (WO 96/00787), Fusarium venenatum amyloglucosidase (WO 00/56900), Fusarium venenatum Daria (WO 00/56900), Fusarium venenatum Quinn (WO 00/56900), Rhizomucor miehei lipase, Rhizomucor miehei aspartic proteinase, Trichoderma reesei beta-glucosidase, Trichoderma reesei cellobiohydrolase I, Trichoderma reesei cellobiohydrolase II, Trichoderma reesei endoglucanase I, Trichoderma reesei endoglucanase II, Trichoderma reesei endoglucanase III, Trichoderma reesei endoglucanase V, Trichoderma reesei xylanase I, Trichoderma reesei xylanase II, Trichoderma reesei xylanase III, Trichoderma reesei beta-xylosidase, and Trichoderma reesei translation elongation factor, as well as the NA2-tpi promoter (a modified promoter from an Aspergillus neutral alpha-amylase gene in which the untranslated leader has been replaced by an untranslated leader from an Aspergillus triose phosphate isomerase gene; non-limiting examples include modified promoters from an Aspergillus niger neutral alpha-amylase gene in which the untranslated leader has been replaced by an untranslated leader from an Aspergillus nidulans or Aspergillus oryzae triose phosphate isomerase gene); and variant, truncated, and hybrid promoters thereof. Other promoters are described in U.S. Pat. No. 6,011,147.

In a yeast host, useful promoters are obtained from the genes for Saccharomyces cerevisiae enolase (ENO-1), Saccharomyces cerevisiae galactokinase (GAL1), Saccharomyces cerevisiae alcohol dehydrogenase/glyceraldehyde-3-phosphate dehydrogenase (ADH1, ADH2/GAP), Saccharomyces cerevisiae triose phosphate isomerase (TPI), Saccharomyces cerevisiae metallothionein (CUP1), and Saccharomyces cerevisiae 3-phosphoglycerate kinase. Other useful promoters for yeast host cells are described by Romanos et al., 1992, Yeast 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for Bacillus clausii alkaline protease (aprH), Bacillus licheniformis alpha-amylase (amyL), and Escherichia coli ribosomal RNA (rrnB).

Preferred terminators for filamentous fungal host cells are obtained from the genes for Aspergillus nidulans acetamidase, Aspergillus nidulans anthranilate synthase, Aspergillus niger glucoamylase, Aspergillus niger alpha-glucosidase, Aspergillus oryzae TAKA amylase, Fusarium oxysporum trypsin-like protease, Trichoderma reesei beta-glucosidase, Trichoderma reesei cellobiohydrolase I, Trichoderma reesei cellobiohydrolase II, Trichoderma reesei endoglucanase I, Trichoderma reesei endoglucanase II, Trichoderma reesei endoglucanase III, Trichoderma reesei endoglucanase V, Trichoderma reesei xylanase I, Trichoderma reesei xylanase II, Trichoderma reesei xylanase III, Trichoderma reesei beta-xylosidase, and Trichoderma reesei translation elongation factor.

Preferred terminators for yeast host cells are obtained from the genes for Saccharomyces cerevisiae enolase, Saccharomyces cerevisiae cytochrome C (CYC1), and Saccharomyces cerevisiae glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a Bacillus thuringiensis cryIIIA gene (WO 94/25612) and a Bacillus subtilis SP82 gene (Hue et al., 1995, Journal of Bacteriology 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for Aspergillus oryzae TAKA amylase and Aspergillus nidulans triose phosphate isomerase.

Suitable leaders for yeast host cells are obtained from the genes for Saccharomyces cerevisiae enolase (ENO-1), Saccharomyces cerevisiae 3-phosphoglycerate kinase, Saccharomyces cerevisiae alpha-factor, and Saccharomyces cerevisiae alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosyl-aminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is an hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus altitudinis, Bacillus amyloliquefaciens, B. amyloliquefaciens* subsp. *plantarum, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus methylotrophicus, Bacillus pumilus, Bacillus safensis, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the *Fungi imperfecti* (Blastomycetes). Since the classification of yeast may change in the future, for the purposes of this invention, yeast shall be defined as described in Biology and Activities of Yeast (Skinner, Passmore, and Davenport, editors, *Soc. App. Bacteriol. Symposium Series* No. 9, 1980).

The yeast host cell may be a *Candida, Hansenula, Kluyveromyces, Pichia, Saccharomyces, Schizosaccharomyces,* or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis,* or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a cell, which in its wild-type form produces the polypeptide, under conditions conducive for production of the polypeptide; and optionally, (b) recovering the polypeptide.

The present invention also relates to recombinant methods of producing a polypeptide of the present invention, comprising (a) cultivating a recombinant host cell of the present invention capable of expressing the polypeptide under conditions conducive for production of the polypeptide; and optionally, (b) recovering the polypeptide.

One embodiment of the invention relates to a method of producing a polypeptide, wherein the polypeptide is selected from the group consisting of: SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72, SEQ ID NO: 75, SEQ ID NO: 78, SEQ ID NO: 81, SEQ ID NO: 84, SEQ ID NO: 87, SEQ ID NO: 90, SEQ ID NO: 93, SEQ ID NO: 96, SEQ ID NO: 99, SEQ ID NO: 102, SEQ ID NO: 105, SEQ ID NO: 108, and polypeptides having at least at least at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% hereto, comprising (a) cultivating a recombinant host cell of the present invention capable of expressing one of the polypeptides under conditions conducive for production of the polypeptide; and optionally, (b) recovering the polypeptide.

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid-state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, a fermentation broth comprising the polypeptide is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide. Another option is to use a supernatant in which the polypeptide has been expressed as a source of the polypeptide.

Formulation of Enzyme in Granules

Non-dusting granulates may be produced, e.g. as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono-, di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The composition(s) of the invention may be formulated as a granule, for example as a co-granule that combines one or more enzymes. Each enzyme will then be present in more granules, securing a more uniform distribution of enzymes in the detergent. This also reduces the physical segregation of different enzymes due to different particle sizes. Methods for producing multi-enzyme co-granulates for the detergent industry are disclosed in the IP.com disclosure IPCOM000200739D.

Another example of formulation of enzymes by the use of co-granulates is disclosed in WO 2013/188331, which relates to a detergent composition comprising (a) a multi-enzyme co-granule; (b) less than 10 wt % zeolite (anhydrous basis); and (c) less than 10 wt % phosphate salt (anhydrous basis), wherein said enzyme co-granule comprises from 10 to 98 wt % moisture sink component and the composition additionally comprises from 20 to 80 wt % detergent moisture sink component. WO 2013/188331 also relates to a method of treating and/or cleaning a surface, preferably a fabric surface comprising the steps of (i) contacting said surface with the detergent composition in aqueous wash liquor, (ii) rinsing and/or drying the surface.

A multi-enzyme co-granule may comprise an enzyme of the invention and one or more enzymes selected from the group consisting of proteases, lipases, cellulases, xyloglucanases, perhydrolases, peroxidases, lipoxygenases, laccases, hemicellulases, proteases, cellulases, cellobiose dehydrogenases, xylanases, phospho lipases, esterases, cutinases, pectinases, mannanases, pectate lyases, keratinases, reductases, oxidases, phenoloxidases, ligninases, pullulanases, tannases, pentosanases, lichenases glucanases, arabinosidases, hyaluronidase, chondroitinase, amylases, nucleases, hexosaminidases and mixtures thereof.

An embodiment of the invention relates to an enzyme granule/particle comprising the enzyme of the invention. The granule is composed of a core, and optionally one or more coatings (outer layers) surrounding the core. Typically, the granule/particle size, measured as equivalent spherical diameter (volume based average particle size), of the granule is 20-2000 μm, particularly 50-1500 μm, 100-1500 μm or 250-1200 μm.

The core may include additional materials such as fillers, fibre materials (cellulose or synthetic fibres), stabilizing agents, solubilising agents, suspension agents, viscosity regulating agents, light spheres, plasticizers, salts, lubricants and fragrances.

The core may include binders, such as synthetic polymer, wax, fat, or carbohydrate.

The core may comprise a salt of a multivalent cation, a reducing agent, an antioxidant, a peroxide decomposing catalyst and/or an acidic buffer component, typically as a homogenous blend.

The core may consist of an inert particle with the enzyme absorbed into it, or applied onto the surface, e.g., by fluid bed coating.

The core may have a diameter of 20-2000 μm, particularly 50-1500 μm, 100-1500 μm or 250-1200 μm.

The core can be prepared by granulating a blend of the ingredients, e.g., by a method comprising granulation techniques such as crystallization, precipitation, pan-coating, fluid bed coating, fluid bed agglomeration, rotary atomization, extrusion, prilling, spheronization, size reduction methods, drum granulation, and/or high shear granulation.

Methods for preparing the core can be found in Handbook of Powder Technology; Particle size enlargement by C. E. Capes; Volume 1; 1980; Elsevier.

The core of the enzyme granule/particle may be surrounded by at least one coating, e.g., to improve the storage stability, to reduce dust formation during handling, or for coloring the granule. The optional coating(s) may include a salt coating, or other suitable coating materials, such as polyethylene glycol (PEG), methyl hydroxy-propyl cellulose (MHPC) and polyvinyl alcohol (PVA). Examples of enzyme granules with multiple coatings are shown in WO 93/07263 and WO 97/23606.

The coating may be applied in an amount of at least 0.1% by weight of the core, e.g., at least 0.5%, 1% or 5%. The amount may be at most 100%, 70%, 50%, 40% or 30%.

The coating is preferably at least 0.1 µm thick, particularly at least 0.5 µm, at least 1 µm or at least 5 µm. In a particular embodiment, the thickness of the coating is below 100 µm. In a more particular embodiment the thickness of the coating is below 60 µm. In an even more particular embodiment the total thickness of the coating is below 40 µm.

The coating should encapsulate the core unit by forming a substantially continuous layer. A substantially continuous layer is to be understood as a coating having few or no holes, so that the core unit it is encapsulating/enclosing has few or none uncoated areas. The layer or coating should be homogeneous in thickness.

The coating can further contain other materials as known in the art, e.g., fillers, antisticking agents, pigments, dyes, plasticizers and/or binders, such as titanium dioxide, kaolin, calcium carbonate or talc.

A salt coating may comprise at least 60% by weight w/w of a salt, e.g., at least 65%, at least 70%, at least 75%, at least 80%, at least 85%, at least 90%, at least 95% or at least 99% by weight w/w.

The salt may be added from a salt solution where the salt is completely dissolved or from a salt suspension wherein the fine particles is less than 50 µm, such as less than 10 µm or less than 5 µm.

The salt coating may comprise a single salt or a mixture of two or more salts. The salt may be water soluble, in particular having a solubility at least 0.1 grams in 100 g of water at 20° C., preferably at least 0.5 g per 100 g water, e.g., at least 1 g per 100 g water, e.g., at least 5 g per 100 g water.

The salt may be an inorganic salt, e.g., salts of sulfate, sulfite, phosphate, phosphonate, nitrate, chloride or carbonate or salts of simple organic acids (less than 10 carbon atoms, e.g., 6 or less carbon atoms) such as citrate, malonate or acetate. Examples of cations in these salts are alkali or earth alkali metal ions, the ammonium ion or metal ions of the first transition series, such as sodium, potassium, magnesium, calcium, zinc or aluminium. Examples of anions include chloride, bromide, iodide, sulfate, sulfite, bisulfite, thiosulfate, phosphate, monobasic phosphate, dibasic phosphate, hypophosphite, dihydrogen pyrophosphate, tetraborate, borate, carbonate, bicarbonate, metasilicate, citrate, malate, maleate, malonate, succinate, lactate, formate, acetate, butyrate, propionate, benzoate, tartrate, ascorbate or gluconate. In particular alkali- or earth alkali metal salts of sulfate, sulfite, phosphate, phosphonate, nitrate, chloride or carbonate or salts of simple organic acids such as citrate, malonate or acetate may be used.

The salt in the coating may have a constant humidity at 20° C. above 60%, particularly above 70%, above 80% or above 85%, or it may be another hydrate form of such a salt (e.g., anhydrate). The salt coating may be as described in WO 00/01793 or WO 2006/034710.

Specific examples of suitable salts are NaCl ($CH_{20°\ C.}$=76%), $Na_2CO_3$ ($CH_{20°\ C.}$=92%), $NaNO_3$ ($CH_{20°\ C.}$=73%), $Na_2H\ PO_4$ ($CH_{20°\ C.}$=95%), $Na_3PO_4$ ($CH_{25°\ C.}$=92%), $NH_4Cl$ ($CH_{20°\ C.}$=79.5%), $(NH_4)_2HPO_4$ ($CH_{20°\ C.}$=93.0%), $NH_4H_2PO_4$ ($CH_{20°\ C.}$=93.1%), $(NH_4)_2SO_4$ ($CH_{20°\ C.}$=81.1%), KCl ($CH_{20°\ C.}$=85%), $K_2H\ PO_4$ ($CH_{20°\ C.}$=92%), $KH_2PO_4$ ($CH_{20°\ C.}$=96.5%), $KNO_3$ ($CH_{20°\ C.}$=93.5%), $Na_2SO_4$ ($CH_{20°\ C.}$=93%), $K_2SO_4$ ($CH_{20°\ C.}$=98%), $KHSO_4$ ($CH_{20°\ C.}$=86%), $MgSO_4$ ($CH_{20°\ C.}$=90%), $ZnSO_4$ ($CH_{20°\ C.}$=90%) and sodium citrate ($CH_{25°\ C.}$=86%). Other examples include $NaH_2PO_4$, $(NH_4)H_2PO_4$, $CuSO_4$, $Mg(NO_3)_2$ and magnesium acetate.

The salt may be in anhydrous form, or it may be a hydrated salt, i.e. a crystalline salt hydrate with bound water(s) of crystallization, such as described in WO 99/32595. Specific examples include anhydrous sodium sulfate ($Na_2SO_4$), anhydrous magnesium sulfate ($MgSO_4$), magnesium sulfate heptahydrate ($MgSO_4 \cdot 7H_2O$), zinc sulfate heptahydrate ($ZnSO_4 \cdot 7H_2O$), sodium phosphate dibasic heptahydrate ($Na_2HPO_4 \cdot 7H_2O$), magnesium nitrate hexahydrate ($Mg(NO_3)_2$ ($6H_2O$)), sodium citrate dihydrate and magnesium acetate tetrahydrate. Preferably the salt is applied as a solution of the salt, e.g., using a fluid bed.

Thus, in a further aspect, the present invention provides a granule, which comprises:
(a) a core comprising an enzyme according to the invention,
(b) optionally a coating consisting of one or more layer(s) surrounding the core; and
(c) preferably the granule is a co-granulate comprising one or more additional enzyme, preferably selected from proteases, amylases, cellulases.

In one embodiment, the present invention provides a granule, which comprises:
(a) a core comprising a polypeptide having peptidoglycan removal activity, wherein the polypeptide comprises the motif N[IV]X[AG][GAS]A[AY][LV]L (SEQ ID NO: 111),
(b) optionally a coating consisting of one or more layer(s) surrounding the core; and
(c) preferably the granule is a co-granulate comprising one or more additional enzyme, preferably selected from proteases, amylases, cellulases.

In one embodiment, the present invention provides a granule, which comprises:
(a) a core comprising a polypeptide having peptidoglycan removal activity, wherein the polypeptide is selected from the group consisting of: SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72, SEQ ID NO: 75, SEQ ID NO: 78, SEQ ID NO: 81, SEQ ID NO: 84, SEQ ID NO: 87, SEQ ID NO: 90, SEQ ID NO: 93, SEQ ID NO: 96, SEQ ID NO: 99, SEQ ID NO: 102, SEQ ID NO: 105, SEQ ID NO: 108 and polypeptides having at least at least at least 60%, e.g., at least 65%, at least 70%, at least 75%, at least 80%, at least 85%, at least 90%, at at least 91%, at least 92%, at least 93%, at least 94%, at least 95%, at least 96%, at least 97%, at least 98%, at least 99%, or 100% hereto,
(b) optionally a coating consisting of one or more layer(s) surrounding the core; and
(c) preferably the granule is a co-granulate comprising one or more additional enzyme, preferably selected from proteases, amylases, cellulases.

Fermentation Broth Formulations or Cell Compositions

The present invention also relates to a fermentation broth formulation or a cell composition comprising a polypeptide of the present invention. The fermentation broth product further comprises additional ingredients used in the fermentation process, such as, for example, cells (including the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains at least one organic acid, and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis. In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Compositions

The present invention also relates to compositions comprising a polypeptide of the present invention. Preferably, the compositions are enriched in such a polypeptide. The term "enriched" indicates that the peptidoglycan degradation activity of the composition has been increased, e.g., with an enrichment factor of at least 1.1.

The compositions may comprise a polypeptide of the present invention as the major enzymatic component, e.g., a mono-component composition. Alternatively, the compositions may comprise multiple enzymatic activities, such as one or more enzymes selected from the group consisting of hydrolase, isomerase, ligase, lyase, oxidoreductase, or transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

The invention relates to cleaning compositions e.g. detergent compositions comprising peptidoglycan degradation enzyme in combination with one or more additional cleaning composition components. The choice of additional components is within the skill of the artisan and includes conventional ingredients, including the exemplary non-limiting components set forth below.

One aspect of the invention relates to a cleaning composition comprising a polypeptide having peptidoglycan degradation activity, wherein the polypeptide comprises the motif N[IV]X[AG][GAS]A[AY][LV]L (SEQ ID NO: 111), and at least one cleaning component.

One aspect of the invention relates to a cleaning composition comprising;
  a) a polypeptide having peptidoglycan degradation activity, wherein the polypeptide is selected from the group consisting of;
    i. a polypeptide having at least at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 3,
    ii. a polypeptide having at least at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 6,
    iii. a polypeptide having at least at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 9, iv. a polypeptide having at least at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 12, v. a polypeptide having at least at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 15, vi. a polypeptide having at least at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 18, vii. a polypeptide having at least at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 21, viii. a polypeptide having at least at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 24, ix. a polypeptide having at least at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 27, x. a polypeptide having at least at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 30, xi. a polypeptide having at least at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 33, xii. a polypeptide having at least at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 36, xiii. a polypeptide having at least at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 39, xiv. a polypeptide having at least at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 42, xv. a polypeptide having at least at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 45, xvi. a polypeptide having at least at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 48, xvii. a polypeptide having at least at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 51, xviii. a polypeptide having at least at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 54, xix. a polypeptide having at least at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 57, xx. a polypeptide having at least at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 60, xxi. a polypeptide having at least at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 63, xxii. a polypeptide having at least at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 66, xxiii. a polypeptide having at least at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 69, xxiv. a polypeptide having at least at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 72, xxv. a polypeptide having at least at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 75, xxvi. a polypeptide having at least at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 78, xxvii. a polypeptide having at least at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 81, xxviii. a polypeptide having at least at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 84, xxix. a polypeptide having at least at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 87)

xxx. a polypeptide having at least at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 90, xxxi. a polypeptide having at least at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 93, xxxii. a polypeptide having at least at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 96, xxxiii. a polypeptide having at least at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 99, xxxiv. a polypeptide having at least at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 102, xxxv. a polypeptide having at least at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 105, and xxxvi. a polypeptide having at least at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 108, and b) at least one cleaning component, preferably selected from surfactants, builders, bleach components, polymers, dispersing agents and additional enzymes.

One embodiment relates to a cleaning composition comprising;
a) a polypeptide having peptidoglycan removal activity and which comprises the motif N[IV]X[AG][GAS]A[AY][LV]L (SEQ ID NO: 111), wherein the polypeptide is selected from the group consisting of: SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72, SEQ ID NO: 75, SEQ ID NO: 78, SEQ ID NO: 81, SEQ ID NO: 84, SEQ ID NO: 87, SEQ ID NO: 90, SEQ ID NO: 93, SEQ ID NO: 96, SEQ ID NO: 99, SEQ ID NO: 102, SEQ ID NO: 105, SEQ ID NO: 108 and polypeptides having at least at least at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% hereto; and b) at least one cleaning component, preferably selected from surfactants, builders, bleach components, polymers, dispersing agents and additional enzymes.

The peptidoglycan degradation enzyme may be included in the cleaning composition of the present invention at a level of at least 0.0001 to at least 100, at least 0.001 to at least 100, at least 0.01 to at least 100, at least 0.02 to at least 100, at least 0.01 to at least 100, at least 0.1 to at least 100, at least 0.2 to at least 100, at least 0.5 to at least 100 mg/mL, preferably, the concentration of peptidoglycan degradation enzyme in the cleaning composition e.g. detergent is in the range 0.01 to 100, 0.1 to 50 or 1 to 10 mg/ml. Thus, the detergent composition may comprise at least 0.00008%, preferably at least 0.002%, 0.003%, 0.004%, 0.005%, 0.006%, 0.008%, 0.01%, 0.02%, 0.03%, 0.05%, 0.1%, 0.2%, 0.3%, 0.4%, 0.6%, 0.7%, 0.8%, 0.9% or 1.0% of peptidoglycan degradation enzyme protein.

The choice of cleaning components may include, for textile care, the consideration of the type of textile to be cleaned, the type and/or degree of soiling, the temperature at which cleaning is to take place, and the formulation of the detergent product. Although components mentioned below are categorized by general header according to a particular functionality, this is not to be construed as a limitation, as a component may comprise additional functionalities as will be appreciated by the skilled artisan.

Surfactants

The cleaning composition may comprise one or more surfactants, which may be anionic and/or cationic and/or non-ionic and/or semi-polar and/or zwitterionic, or a mixture thereof. In a particular embodiment, the detergent composition includes a mixture of one or more nonionic surfactants and one or more anionic surfactants. The surfactant(s) is typically present at a level of from about 1% to 70% by weight, such as about 1 wt % to about 40 wt %, or about 3 wt % to about 20 wt %, or about 3 wt % to about 10 wt %.

The surfactant(s) is chosen based on the desired cleaning application, and may include any conventional surfactant(s) known in the art.

When included therein the detergent will usually contain from about 1% to about 70% by weight of an anionic surfactant, such as from about 5 wt % to about 50 wt %, including from about 5 wt % to about 20 wt %, or from about 15 wt % to about 20 wt %, or from about 20 wt % to about 25 wt % or at least 30 wt %, at least 40 wt % or at least 50 wt % of an anionic surfactant. Non-limiting examples of anionic surfactants include sulfates and sulfonates, in particular, alkylbenzenesulfonates, such as linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salt of fatty acids (soap), and combinations thereof.

When included therein the detergent will usually contain from about 1% to about 40% by weigh of a cationic surfactant, for example from about 0.5% to about 30%, in particular from about 1% to about 20%, from about 3% to about 10%, such as from about 3% to about 5%, from about 8% to about 12% or from about 10% to about 12%. Non-limiting examples of cationic surfactants include alkyldimethylethanolamine quat (ADMEAQ), cetyltrimethylammonium bromide (CTAB), dimethyldistearylammonium chloride (DSDMAC), and alkylbenzyldimethylammonium, alkyl quaternary ammonium compounds, alkoxylated quaternary ammonium (AQA) compounds, ester quats, and combinations thereof.

When included therein the detergent will usually contain from about 0.2% to about 40% by weight of a nonionic surfactant, for example from about 0.5 wt % to about 30 wt %, in particular from about 1 wt % to about 20 wt %, from about 3 wt % to about 10 wt %, such as from about 3% wt to about 5 wt %, from about 8 wt % to about 12 wt %, or from about 10 wt % to about 12 wt %. Non-limiting examples of nonionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA), as well as products available under the trade names SPAN and TWEEN, and combinations thereof.

When included therein the detergent will usually contain from about 0.01% to about 10% by weight of a semipolar surfactant. Non-limiting examples of semipolar surfactants include amine oxides (AO) such as alkyldimethylamineoxide, N-(coco alkyl)-N,N-dimethylamine oxide and N-(tallow-alkyl)-N,N-bis(2-hydroxyethyl)amine oxide, and combinations thereof.

When included therein the detergent will usually contain from about 0.01% to about 10% by weight of a zwitterionic surfactant. Non-limiting examples of zwitterionic surfactants include betaines such as alkyldimethylbetaines, sulfobetaines, and combinations thereof.

Typically, more than one surfactant is present in the cleaning composition e.g. at least one anionic and at least one non-ionic surfactant. Preferably the amount of all surfactant present (total amount) i.e. the amount of anionic, non-ionic, zwitterionic and cationic surfactant present is preferably from about 1 wt % to 80 wt % by weight, such as about 1 wt % to 70 wt %, such as about 1 wt % to 50 wt % such as about 1 wt % to about 40 wt %, or about 5 wt % to about 40 wt %, or about 10 wt % to about 60 wt %. The ratio between the surfactants present depends on the specific composition but the weight ratios may be when an anionic and non-ionic surfactant is included in the composition a weight ratio of the anionic to nonionic surfactant from; 30:1 to 10:1, 20:1 to 1:10, 25:1 to 1:2, 20:1 to 1:5.

One embodiment relates to a cleaning composition comprising a peptidoglycan degrading enzyme, preferably having N-acetylmuramyl-L-alanine amidase and peptidoglycan lyase activity and wherein the cleaning component is at least one surfactant, preferably anionic and/or nonionic, preferably wherein the composition comprises from 1 to 70 wt %, preferably from 5 to 40 wt % surfactant, wherein the surfactant preferably is selected from alkylbenzenesulfonates e.g. LAS, alkyl sulfates (AS) and mixtures thereof, preferably the cleaning composition comprises at least 20 wt % alkylbenzenesulfonate surfactant.

One embodiment relates to a cleaning composition comprising a peptidoglycan degrading enzyme, preferably having N-acetylmuramyl-L-alanine amidase and peptidoglycan lyase activity, wherein the cleaning composition comprises at least one anionic surfactant and wherein the cleaning composition additionally comprises a nonionic surfactant, and preferably wherein the weight ratio of the anionic to nonionic surfactant is from 25:1 to 1:2 or from 1.5:1 to 1:10.

Builders and Co-Builders

The cleaning composition may contain about 0-65% by weight, such as about 5% to about 50%, such as about 0.5% to about 20% of a detergent builder or co-builder, or a mixture thereof. In a dish wash detergent, the level of builder is typically 40-65%, particularly 50-65%. The builder and/or co-builder may particularly be a chelating agent that forms water-soluble complexes with Ca and Mg. Any builder and/or co-builder known in the art for use in cleaning detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), ethanolamines such as 2-aminoethan-1-ol (MEA), diethanolamine (DEA, also known as 2,2'-iminodiethan-1-ol), triethanolamine (TEA, also known as 2,2',2''-nitrilotriethan-1-ol), and (carboxymethyl)inulin (CMI), and combinations thereof.

The detergent composition may also contain 0-50% by weight, such as about 5% to about 30%, of a detergent co-builder. The detergent composition may include a co-builder alone, or in combination with a builder, for example a zeolite builder. Non-limiting examples of co-builders include homopolymers of polyacrylates or copolymers thereof, such as poly(acrylic acid) (PAA) or copoly(acrylic acid/maleic acid) (PAA/PMA). Further non-limiting examples include citrate, chelators such as aminocarboxylates, aminopolycarboxylates and phosphonates, and alkyl- or alkenylsuccinic acid. Additional specific examples include 2,2',2"-nitrilotriacetic acid (NTA), ethylenediaminetetraacetic acid (EDTA), diethylenetriaminepentaacetic acid (DTPA), iminodisuccinic acid (IDS), ethylenediamine-N,N'-disuccinic acid (EDDS), methylglycinediacetic acid (MGDA), glutamic acid-N,N-diacetic acid (GLDA), 1-hydroxyethane-1,1-diphosphonic acid (HEDP), ethylenediaminetetra(methylenephosphonic acid) (EDTMPA), diethylenetriaminepentakis-(methylenephosphonic acid) (DTMPA or DTPMPA), N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl)-aspartic acid (SMAS), N-(2-sulfoethyl)-aspartic acid (SEAS), N-(2-sulfomethyl)-glutamic acid (SMGL), N-(2-sulfoethyl)-glutamic acid (SEGL), N-methyliminodiacetic acid (MIDA), α-alanine-N,N-diacetic acid (α-ALDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and sulfomethyl-N,N-diacetic acid (SMDA), N-(2-hydroxyethyl)ethylenediamine-N,N',N"-triacetic acid (HEDTA), diethanolglycine (DEG), diethylenetriamine penta(methylenephosphonic acid) (DTPMP), aminotris(methylenephosphonic acid) (ATMP), and combinations and salts thereof. Further exemplary builders and/or co-builders are described in, e.g., WO 09/102854, U.S. Pat. No. 5,977,053

Bleaching Systems

The cleaning composition may contain 0-30% by weight, such as about 1% to about 20%, such as about 0.01% to about 10% of a bleaching system. Any bleaching system comprising components known in the art for use in cleaning detergents may be utilized. Suitable bleaching system components include sources of hydrogen peroxide; sources of peracids; and bleach catalysts or boosters.

Sources of Hydrogen Peroxide:

Suitable sources of hydrogen peroxide are inorganic persalts, including alkali metal salts such as sodium percarbonate and sodium perborates (usually mono- or tetrahydrate), and hydrogen peroxide-urea (1/1).

Sources of Peracids:

Peracids may be (a) incorporated directly as preformed peracids or (b) formed in situ in the wash liquor from hydrogen peroxide and a bleach activator (perhydrolysis) or (c) formed in situ in the wash liquor from hydrogen peroxide and a perhydrolase and a suitable substrate for the latter, e.g., an ester.

a) Suitable preformed peracids include, but are not limited to, peroxycarboxylic acids such as peroxybenzoic acid and its ring-substituted derivatives, peroxy-α-naphthoic acid, peroxyphthalic acid, peroxylauric acid, peroxystearic acid, ε-phthalimidoperoxycaproic acid [phthalimidoperoxyhexanoic acid (PAP)], and o-carboxybenzamidoperoxycaproic acid; aliphatic and aromatic diperoxydicarboxylic acids such as diperoxydodecanedioic acid, diperoxyazelaic acid, diperoxysebacic acid, diperoxybrassylic acid, 2-decyldiperoxybutanedioic acid, and diperoxyphthalic, -isophthalic and -terephthalic acids; perimidic acids; peroxymonosulfuric acid; peroxydisulfuric acid; peroxyphosphoric acid; peroxysilicic acid; and mixtures of said compounds. It is understood that the peracids mentioned may in some cases be best added as suitable salts, such as alkali metal salts (e.g., Oxone®) or alkaline earth-metal salts.

b) Suitable bleach activators include those belonging to the class of esters, amides, imides, nitriles or anhydrides and, where applicable, salts thereof. Suitable examples are tetraacetylethylenediamine (TAED), sodium 4-[(3,5,5-trimethylhexanoyl)oxy]benzene-1-sulfonate (ISONOBS), sodium 4-(dodecanoyloxy)benzene-1-sulfonate (LOBS), sodium 4-(decanoyloxy) benzene-1-sulfonate, 4-(decanoyloxy)benzoic acid (DOBA), sodium 4-(nonanoyloxy)benzene-1-sulfonate (NOBS), and/or those disclosed in WO98/17767. A particular family of bleach activators of interest was disclosed in EP624154 and particularly preferred in that family is acetyl triethyl citrate (ATC). ATC or a short chain triglyceride like triacetin has the advantage that they are environmentally friendly. Furthermore, acetyl triethyl citrate and triacetin have good hydrolytical stability in the product upon storage and are efficient bleach activators. Finally, ATC is multifunctional, as the citrate released in the perhydrolysis reaction may function as a builder.

Bleach Catalysts and Boosters

The bleaching system may also include a bleach catalyst or booster. Some non-limiting examples of bleach catalysts that may be used in the compositions of the present invention include manganese oxalate, manganese acetate, manganese-collagen, cobalt-amine catalysts and manganese triazacyclononane (MnTACN) catalysts; particularly preferred are complexes of manganese with 1,4,7-trimethyl-1,4,7-triazacyclononane (Me3-TACN) or 1,2,4,7-tetramethyl-1,4,7-triazacyclononane (Me4-TACN), in particular Me3-TACN, such as the dinuclear manganese complex [(Me3-TACN)Mn(O)3Mn(Me3-TACN)](PF6)2, and [2,2',2"-nitrilotris(ethane-1,2-diylazanylylidene-κN-methanylylidene)triphenolato-κ3O]manganese(III). The bleach catalysts may also be other metal compounds; such as iron or cobalt complexes.

In some embodiments, where a source of a peracid is included, an organic bleach catalyst or bleach booster may be used having one of the following formulae:

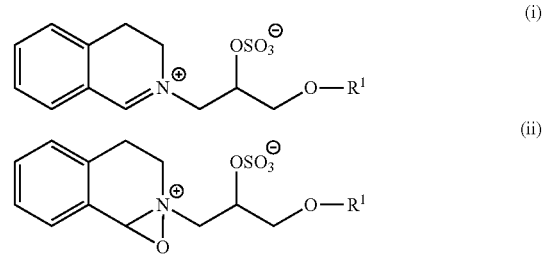

(iii) and mixtures thereof; wherein each R1 is independently a branched alkyl group containing from 9 to 24 carbons or linear alkyl group containing from 11 to 24 carbons, preferably each R1 is independently a branched alkyl group containing from 9 to 18 carbons or linear alkyl group containing from 11 to 18 carbons, more preferably each R1 is independently selected from the group consisting of 2-propylheptyl, 2-butyloctyl, 2-pentylnonyl, 2-hexyldecyl, dodecyl, tetradecyl, hexadecyl, octadecyl, isononyl, isodecyl, isotridecyl and isopentadecyl.

Other exemplary bleaching systems are described e.g. in WO2007/087258, WO2007/087244, WO2007/087259, EP1867708 (Vitamin K) and WO2007/087242. Suitable photobleaches may for example be sulfonated zinc or aluminium phthalocyanines.

Metal Care Agents

Metal care agents may prevent or reduce the tarnishing, corrosion or oxidation of metals, including aluminium, stainless steel and non-ferrous metals, such as silver and copper. Suitable examples include one or more of the following:

(a) benzatriazoles, including benzotriazole or bis-benzotriazole and substituted derivatives thereof. Benzotriazole derivatives are those compounds in which the available substitution sites on the aromatic ring are partially or completely substituted. Suitable substituents include linear or branch-chain Ci-C20-alkyl groups (e.g., C1-C20-alkyl groups) and hydroxyl, thio, phenyl or halogen such as fluorine, chlorine, bromine and iodine.

(b) metal salts and complexes chosen from the group consisting of zinc, manganese, titanium, zirconium, hafnium, vanadium, cobalt, gallium and cerium salts and/or complexes, the metals being in one of the oxidation states II, III, IV, V or VI. In one aspect, suitable metal salts and/or metal complexes may be chosen from the group consisting of Mn(II) sulphate, Mn(II) citrate, Mn(II) stearate, Mn(II) acetylacetonate, K^TiF6 (e.g., K2TiF6), K^ZrF6 (e.g., K2ZrF6), CoSO4, Co(NOs)2 and Ce(NOs)3, zinc salts, for example zinc sulphate, hydrozincite or zinc acetate;

(c) silicates, including sodium or potassium silicate, sodium disilicate, sodium metasilicate, crystalline phyllosilicate and mixtures thereof.

Further suitable organic and inorganic redox-active substances that act as silver/copper corrosion inhibitors are disclosed in WO 94/26860 and WO 94/26859. Preferably the composition of the invention comprises from 0.1 to 5% by weight of the composition of a metal care agent, preferably the metal care agent is a zinc salt.

Hydrotropes

The cleaning composition may contain 0-10% by weight, for example 0-5% by weight, such as about 0.5 to about 5%, or about 3% to about 5%, of a hydrotrope. Any hydrotrope known in the art for use in detergents may be utilized. Non-limiting examples of hydrotropes include sodium benzenesulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

Polymers

The cleaning composition may contain 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fiber protection, soil release, dye transfer inhibition, grease cleaning and/or anti-foaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly(ethylene oxide) (PEG), ethoxylated poly(ethyleneimine), carboxymethyl inulin (CMI), and polycarboxylates such as PAA, PAA/PMA, poly-aspartic acid, and lauryl methacrylate/acrylic acid copolymers, hydrophobically modified CMC (HM-CMC) and silicones, copolymers of terephthalic acid and oligomeric glycols, copolymers of poly(ethylene terephthalate) and poly(oxyethene terephthalate) (PET-POET), PVP, poly (vinylimidazole) (PVI), poly(vinylpyridine-N-oxide) (PVPO or PVPNO) and polyvinylpyrrolidone-vinylimidazole (PVPVI). Suitable examples include PVP-K15, PVP-K30, ChromaBond S-400, ChromaBond S-403E and Chromabond S-100 from Ashland Aqualon, and Sokalan® HP 165, Sokalan® HP 50 (Dispersing agent), Sokalan® HP 53 (Dispersing agent), Sokalan® HP 59 (Dispersing agent), Sokalan® HP 56 (dye transfer inhibitor), Sokalan® HP 66 K (dye transfer inhibitor) from BASF. Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130575. Salts of the above-mentioned polymers are also contemplated. Particularly preferred polymer is ethoxylated homopolymer Sokalan® HP 20 from BASF, which helps to prevent redeposition of soil in the wash liquor.

Fabric Hueing Agents

The cleaning compositions of the present invention may also include fabric hueing agents such as dyes or pigments, which when formulated in detergent compositions can deposit onto a fabric when said fabric is contacted with a wash liquor comprising said detergent compositions and thus altering the tint of said fabric through absorption/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO2005/03274, WO2005/03275, WO2005/03276 and EP1876226 (hereby incorporated by reference). The detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch. Suitable hueing agents are also disclosed in, e.g. WO 2007/087257 and WO2007/087243.

Dispersants

The cleaning compositions of the present invention can also contain dispersants. In particular, powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker, Inc.

Dye Transfer Inhibiting Agents

The cleaning compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Fluorescent Whitening Agent

The cleaning compositions of the present invention will preferably also contain additional components that may tint articles being cleaned, such as fluorescent whitening agents or optical brighteners. Where present the brightener is preferably at a level of about 0.01% to about 0.5%. Any fluorescent whitening agent suitable for use in a laundry detergent composition may be used in the composition of the present invention. The most commonly used fluorescent whitening agents are those belonging to the classes of diaminostilbene-sulfonic acid derivatives, diarylpyrazoline derivatives and bisphenyl-distyryl derivatives. Examples of the diaminostilbene-sulfonic acid derivative type of fluorescent whitening agents include the sodium salts of: 4,4'-bis-(2-diethanolamino-4-anilino-s-triazin-6-ylamino) stilbene-2,2'-disulfonate, 4,4'-bis-(2,4-dianilino-s-triazin-6-ylamino) stilbene-2,2'-disulfonate, 4,4'-bis-(2-anilino-4-(N-methyl-N-2-hydroxy-ethylamino)-s-triazin-6-ylamino) stilbene-2, 2'-disulfonate, disulfonate and sodium 5-(2H-naphtho[1,2-d][1,2,3]triazol-2-yl)-2-[(E)-2-phenylvinyl]-benzenesulfonate. Preferred fluorescent whitening agents are Tinopal DMS and Tinopal CBS available from Ciba-Geigy AG, Basel, Switzerland. Tinopal DMS is the disodium salt of 4,4'-bis-(2-morpholino-4-anilino-s-triazin-6-ylamino) stilbene-2,2'-disulfonate. Tinopal CBS is the disodium salt of 2,2'-bis-(phenyl-styryl)-disulfonate. Also preferred are fluorescent whitening agents is the commercially available Parawhite KX, supplied by Paramount Minerals and Chemicals, Mumbai, India. Other fluorescers suitable for use in the invention include the 1-3-diaryl pyrazolines and the 7-alkylaminocoumarins. Suitable fluorescent brightener levels include lower levels of from about 0.01, from 0.05, from about 0.1 or even from about 0.2 wt % to upper levels of 0.5 or even 0.75 wt %.

Soil Release Polymers

The cleaning compositions of the present invention may also include one or more soil release polymers which aid the removal of soils from fabrics such as cotton and polyester based fabrics, in particular the removal of hydrophobic soils from polyester based fabrics. The soil release polymers may for example be nonionic or anionic terephthalte based polymers, polyvinyl caprolactam and related copolymers, vinyl graft copolymers, polyester polyamides see for example Chapter 7 in Powdered Detergents, Surfactant science series volume 71, Marcel Dekker, Inc. Another type of soil release polymers is amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523 (hereby incorporated by reference). Furthermore, random graft co-polymers are suitable soil release polymers. Suitable graft co-polymers are described in more detail in WO 2007/138054, WO 2006/108856 and WO 2006/113314 (hereby incorporated by reference). Suitable polyethylene glycol polymers include random graft co-polymers comprising: (i) hydrophilic backbone comprising polyethylene glycol; and (ii) side chain(s) selected from the group consisting of: C4-C25 alkyl group, polypropylene, polybutylene, vinyl ester of a saturated C1-C6 mono-carboxylic acid, C1—C6 alkyl ester of acrylic or methacrylic acid, and mixtures thereof. Suitable polyethylene glycol polymers have a polyethylene glycol backbone with random grafted polyvinyl acetate side chains. The average molecular weight of the polyethylene glycol backbone can be in the range of from 2,000 Da to 20,000 Da, or from 4,000 Da to 8,000 Da. The molecular weight ratio of the polyethylene glycol backbone to the polyvinyl acetate side chains can be in the range of from 1:1 to 1:5, or from 1:1.2 to 1:2. The average number of graft sites per ethylene oxide units can be less than 1, or less than 0.8, the average number of graft sites per ethylene oxide units can be in the range of from 0.5 to 0.9, or the average number of graft sites per ethylene oxide units can be in the range of from 0.1 to 0.5, or from 0.2 to 0.4. A suitable polyethylene glycol polymer is Sokalan HP22. Other soil release polymers are substituted polysaccharide structures especially substituted cellulosic structures such as modified cellulose deriviatives such as those described in EP 1867808 or WO 2003/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

Anti-Redeposition Agents

The cleaning compositions of the present invention may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Rheology Modifiers

The cleaning compositions of the present invention may also include one or more rheology modifiers, structurants or thickeners, as distinct from viscosity reducing agents. The rheology modifiers are selected from the group consisting of non-polymeric crystalline, hydroxy-functional materials, polymeric rheology modifiers which impart shear thinning characteristics to the aqueous liquid matrix of a liquid detergent composition. The rheology and viscosity of the detergent can be modified and adjusted by methods known in the art, for example as shown in EP 2169040.

Other suitable cleaning composition components include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, and structurants for liquid detergents and/or structure elasticizing agents.

Polymers

The cleaning composition may contain 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fiber protection, soil release, dye transfer inhibition, grease cleaning and/or anti-foaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly(ethylene oxide) (PEG), ethoxylated poly(ethyleneimine), carboxymethyl inulin (CMI), and polycarboxylates such as PAA, PAA/PMA, poly-aspartic acid, and lauryl methacrylate/acrylic acid copolymers, hydrophobically modified CMC (HM-CMC) and silicones, copolymers of terephthalic acid and oligomeric glycols, copolymers of poly(ethylene terephthalate) and poly(oxyethene terephthalate) (PET-POET), PVP, poly(vinylimidazole) (PVI), poly(vinylpyridine-N-oxide) (PVPO or PVPNO) and polyvinylpyrrolidone-vinylimidazole (PVPVI). Suitable examples include PVP-K15, PVP-K30, ChromaBond S-400, ChromaBond S-403E and Chromabond S-100 from Ashland Aqualon, and Sokalan® HP 165, Sokalan® HP 50 (Dispersing agent), Sokalan® HP 53 (Dispersing agent), Sokalan® HP 59 (Dispersing agent), Sokalan® HP 56 (dye transfer inhibitor), Sokalan® HP 66 K (dye transfer inhibitor) from BASF. Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130575. Salts of the above-mentioned polymers are also contemplated. Particularly preferred polymer is ethoxylated homopolymer Sokalan® HP 20 from BASF, which helps to prevent redeposition of soil in the wash liquor.

Enzymes

The cleaning composition may comprise one or more additional enzymes such as one or more lipase, cutinase, an amylase, carbohydrase, cellulase, pectinase, mannanase, arabinase, galactanase, xylanase, oxidase, e.g., a laccase, and/or peroxidase. In general, the properties of the selected enzyme(s) should be compatible with the selected detergent, (i.e., pH-optimum, compatibility with other enzymatic and non-enzymatic ingredients, etc.), and the enzyme(s) should be present in effective amounts.

Mannanases

Suitable mannanases include those of bacterial or fungal origin. Chemically or genetically modified mutants are included. The mannanase may be an alkaline mannanase of Family 5 or 26. It may be a wild-type from *Bacillus* or *Humicola*, particularly *B. agaradhaerens*, *B. licheniformis*, *B. halodurans*, *B. clausii*, or *H. insolens*. Suitable mannanases are described in WO 1999/064619. A commercially available mannanase is Mannaway (Novozymes A/S).

Cellulases

Suitable cellulases include complete cellulases or mono-component endoglucanases of bacterial or fungal origin. Chemically or genetically modified mutants are included. The cellulase may for example be a mono-component or a mixture of mono-component endo-1,4-beta-glucanase often just termed endoglucanases. Suitable cellulases include a fungal cellulase from *Humicola insolens* (U.S. Pat. No. 4,435,307) or from *Trichoderma*, e.g. *T. reesei* or *T. viride*. Examples of cellulases are described in EP 0 495 257. Other suitable cellulases are from *Thielavia* e.g. *Thielavia terrestris* as described in WO 96/29397 or *Fusarium oxysporum* as described in WO 91/17244 or from *Bacillus* as described in, WO 02/099091 and JP 2000210081. Other examples are cellulase variants such as those described in WO 94/07998, EP 0 531 315, U.S. Pat. Nos. 5,457,046, 5,686,593, 5,763,254, WO 95/24471, WO 98/12307 Commercially available cellulases include Carezyme®, Celluzyme®, Celluclean®, Celluclast® and Endolase®; Renozyme®; Whitezyme® (Novozymes A/S) Puradax®, Puradax HA, and Puradax EG (available from Genencor).

Proteases

Suitable proteases may be of any origin, but are preferably of bacterial or fungal origin, optionally in the form of protein engineered or chemically modified mutants. The protease may be an alkaline protease, such as a serine protease or a metalloprotease. A serine protease may for example be of the S1 family, such as trypsin, or the S8 family such as a subtilisin. A metalloprotease may for example be a thermolysin, e.g. from the M4 family, or another metalloprotease such as those from the M5, M7 or M35 families.

The term "subtilases" refers to a sub-group of serine proteases according to Siezen et al., *Protein Eng.* 4 (1991) 719-737 and Siezen et al., *Protein Sci.* 6 (1997) 501-523. Serine proteases are a subgroup of proteases characterized by having a serine in the active site, which forms a covalent adduct with the substrate. The subtilases may be divided into six subdivisions, the Subtilisin family, the Thermitase family, the Proteinase K family, the Lantibiotic peptidase family, the Kexin family and the Pyrolysin family.

Although proteases suitable for detergent use may be obtained from a variety of organisms, including fungi such as *Aspergillus*, detergent proteases have generally been obtained from bacteria and in particular from *Bacillus*. Examples of *Bacillus* species from which subtilases have been derived include *Bacillus lentus*, *Bacillus alkalophilus*, *Bacillus subtilis*, *Bacillus amyloliquefaciens*, *Bacillus licheniformis*, *Bacillus pumilus* and *Bacillus gibsonii*. Particular subtilisins include subtilisin *lentus*, subtilisin Novo, subtilisin Carlsberg, subtilisin BPN', subtilisin 309, subtilisin 147 and subtilisin 168 and e.g. protease PD138 (described in WO 93/18140). Other useful proteases are e.g. those described in WO 01/16285 and WO 02/16547.

Examples of trypsin-like proteases include the *Fusarium* protease described in WO 94/25583 and WO 2005/040372, and the chymotrypsin proteases derived from *Cellumonas* described in WO 2005/052161 and WO 2005/052146.

Examples of metalloproteases include the neutral metalloproteases described in WO 2007/044993 such as those derived from *Bacillus amyloliquefaciens*, as well as e.g. the metalloproteases described in WO 2015/158723 and WO 2016/075078.

Examples of useful proteases are the protease variants described in WO 89/06279 WO 92/19729, WO 96/34946, WO 98/20115, WO 98/20116, WO 99/11768, WO 01/44452, WO 03/006602, WO 2004/003186, WO 2004/041979, WO 2007/006305, WO 2011/036263, WO 2014/207227, WO 2016/087617 and WO 2016/174234. Preferred protease variants may, for example, comprise one or more of the mutations selected from the group consisting of: S3T, V41, S9R, S9E, A15T, S24G, S24R, K27R, N42R, S55P, G59E, G59D, N60D, N60E, V66A, N74D, S85R, A96S, S97G, S97D, S97A, S97SD, S99E, S99D, S99G, S99M, S99N, S99R, S99H, S101A, V102I, V102Y, V102N, S104A, G116V, G116R, H118D, H118N, A120S, S126L, P127Q, S128A, S154D, A156E, G157D, G157P, S158E, Y161A, R164S, Q176E, N179E, S182E, Q185N, A188P, G189E, V193M, N198D, V199I, Q200L, Y203W, S206G, L211Q, L211D, N212D, N212S, M216S, A226V, K229L, Q230H, Q239R, N246K, S253D, N255W, N255D, N255E, L256E, L256D T268A and R269H, wherein position numbers correspond to positions of the *Bacillus lentus* protease shown in SEQ ID NO: 1 of WO 2016/001449. Protease variants having one or more of these mutations are preferably variants of the *Bacillus lentus* protease (Savinase®, also known as subtilisin 309) shown in SEQ ID NO: 1 of WO 2016/001449 or of the *Bacillus amyloliquefaciens* protease (BPN') shown in SEQ ID NO: 2 of WO 2016/001449.

Such protease variants preferably have at least 80% sequence identity to SEQ ID NO: 1 or to SEQ ID NO: 2 of WO 2016/001449.

Another protease of interest is the alkaline protease from *Bacillus lentus* DSM 5483, as described for example in WO 91/02792, and variants thereof which are described for example in WO 92/21760, WO 95/23221, EP 1921147, EP 1921148 and WO 2016/096711.

The protease may alternatively be a variant of the TY145 protease having SEQ ID NO: 1 of WO 2004/067737, for example a variant comprising a substitution at one or more positions corresponding to positions 27, 109, 111, 171, 173, 174, 175, 180, 182, 184, 198, 199 and 297 of SEQ ID NO: 1 of WO 2004/067737, wherein said protease variant has a sequence identity of at least 75% but less than 100% to SEQ ID NO: 1 of WO 2004/067737. TY145 variants of interest are described in e.g. WO 2015/014790, WO 2015/014803, WO 2015/014804, WO 2016/097350, WO 2016/097352, WO 2016/097357 and WO 2016/097354.

Examples of Preferred Proteases Include:
(a) variants of SEQ ID NO: 1 of WO 2016/001449 comprising two or more substitutions selected from the group consisting of S9E, N43R, N76D, Q206L, Y209W, S259D and L262E, for example a variant with the substitutions S9E, N43R, N76D, V205I, Q206L, Y209W, S259D, N261W and L262E, or with the substitutions S9E, N43R, N76D, N185E, S188E, Q191N, A194P, Q206L, Y209W, S259D and L262E, wherein position numbers are based on the numbering of SEQ ID NO: 2 of WO 2016/001449;
(b) a variant of the polypeptide of SEQ ID NO: 1 of WO 2016/001449 with the mutation S99SE, wherein position numbers are based on the numbering of SEQ ID NO: 2 of WO 2016/001449;
(c) a variant of the polypeptide of SEQ ID NO: 1 of WO 2016/001449 with the mutation S99AD, wherein position numbers are based on the numbering of SEQ ID NO: 2 of WO 2016/001449;
(d) a variant of the polypeptide of SEQ ID NO: 1 of WO 2016/001449 with the substitutions Y167A+R170S+A194P, wherein position numbers are based on the numbering of SEQ ID NO: 2 of WO 2016/001449;
(e) a variant of the polypeptide of SEQ ID NO: 1 of WO 2016/001449 with the substitutions S9R+A15T+V68A+N218D+Q245R, wherein position numbers are based on the numbering of SEQ ID NO: 2 of WO 2016/001449;
(f) a variant of the polypeptide of SEQ ID NO: 1 of WO 2016/001449 with the substitutions S9R+A15T+G61E+V68A+A194P+V205I+Q245R+N261D, wherein position numbers are based on the numbering of SEQ ID NO: 2 of WO 2016/001449;
(g) a variant of the polypeptide of SEQ ID NO: 1 of WO 2016/001449 with the substitutions S99D+S101R/E+S103A+V104I+G160S; for example a variant of SEQ ID NO: 1 of WO 2016/001449 with the substitutions S3T+V4I+S99D+S101E+S103A+V104I+G160S+V205I, wherein position numbers are based on the numbering of SEQ ID NO: 2 of WO 2016/001449;
(h) a variant of the polypeptide of SEQ ID NO: 2 of WO 2016/001449 with the substitutions S24G+S53G+S78N+S101N+G128A/S+Y217Q, wherein position numbers are based on the numbering of SEQ ID NO: 2 of WO 2016/001449;
(i) the polypeptide disclosed in GENESEQP under accession number BER84782, corresponding to SEQ ID NO: 302 in WO 2017/210295;
(j) a variant of the polypeptide of SEQ ID NO: 1 of WO 2016/001449 with the substitutions S99D+S101E+S103A+V104I+S156D+G160S+L262E, wherein position numbers are based on the numbering of SEQ ID NO: 2 of WO 2016/001449;
(k) a variant of the polypeptide of SEQ ID NO: 1 of WO 2016/001449 with the substitutions S9R+A15T+G61E+V68A+N76D+S99G+N218D+Q245R, wherein position numbers are based on the numbering of SEQ ID NO: 2 of WO 2016/001449;
(l) a variant of the polypeptide of SEQ ID NO: 1 of WO 2016/001449 with the substitutions V68A+S106A, wherein position numbers are based on the numbering of SEQ ID NO: 2 of WO 2016/001449; and
(m) a variant of the polypeptide of SEQ ID NO: 1 of WO 2004/067737 with the substitutions S27K+N109K+S111E+S171E+S173P+G174K+S175P+F180Y+G182A+L184F+Q198E+N199+T297P, wherein position numbers are based on the numbering of SEQ ID NO: 1 of WO 2004/067737.

Suitable commercially available protease enzymes include those sold under the trade names Alcalase®, Duralase™, Durazym™, Relase®, Relase® Ultra, Savinase®, Savinase® Ultra, Primase™, Polarzyme®, Kannase®, Liquanase®, Liquanase® Ultra, Ovozyme®, Coronase®, Coronase® Ultra, Blaze®, Blaze Evity® 100T, Blaze Evity® 125T, Blaze Evity® 150T, Blaze Evity® 200T, Neutrase®, Everlase®, Esperase®, Progress® Uno, Progress® In and Progress® Excel (Novozymes A/S), those sold under the tradename Maxatase™, Maxacal™ Maxapem®, Purafect® Ox, Purafect® OxP, Puramax®, FN2™, FN3™, FN4$^{ex}$™ Excellase®, Excellenz™ P1000, Excellenz™ P1250, Eraser™, Preferenz® P100, Purafect Prime, Preferenz P110™, Effectenz P1000™, Purafect®, Effectenz P1050™, Purafect® Ox, Effectenz™ P2000, Purafast™, Properase®, Opticlean™ and Optimase® (Danisco/DuPont), BLAP (sequence shown in FIG. 29 of U.S. Pat. No. 5,352,604) and variants hereof (Henkel AG), and KAP (*Bacillus alkalophilus* subtilisin) from Kao.

Lipases and Cutinases

Suitable lipases and cutinases include those of bacterial or fungal origin. Chemically modified or protein engineered mutant enzymes are included. Examples include lipase from *Thermomyces*, e.g. from *T. lanuginosus* (previously named *Humicola lanuginosa*) as described in EP258068 and EP305216, cutinase from *Humicola*, e.g. *H. insolens* (WO96/13580), lipase from strains of *Pseudomonas* (some of these now renamed to *Burkholderia*), e.g. *P. alcaligenes* or *P. pseudoalcaligenes* (EP218272), *P. cepacia* (EP331376), *P.* sp. strain SD705 (WO95/06720 & WO96/27002), *P. wisconsinensis* (WO96/12012), GDSL-type *Streptomyces* lipases (WO10/065455), cutinase from *Magnaporthe grisea* (WO10/107560), cutinase from *Pseudomonas mendocina* (U.S. Pat. No. 5,389,536), lipase from *Thermobifida fusca* (WO11/084412), *Geobacillus stearothermophilus* lipase (WO11/084417), lipase from *Bacillus subtilis* (WO11/084599), and lipase from *Streptomyces griseus* (WO11/150157) and *S. pristinaespiralis* (WO12/137147).

Other examples are lipase variants such as those described in EP407225, WO92/05249, WO94/01541, WO94/25578, WO95/14783, WO95/30744, WO95/35381, WO95/22615, WO96/00292, WO97/04079, WO97/07202, WO00/34450, WO00/60063, WO01/92502, WO07/87508 and WO09/109500.

Preferred commercial lipase products include Lipolase™, Lipex™; Lipolex™ and Lipoclean™ (Novozymes A/S), Lumafast (originally from Genencor) and Lipomax (originally from Gist-Brocades). Still other examples are lipases sometimes referred to as acyltransferases or perhydrolases, e.g. acyltransferases with homology to Candida antarctica lipase A (WO10/111143), acyltransferase from Mycobacterium smegmatis (WO05/56782), perhydrolases from the CE 7 family (WO09/67279), and variants of the M. smegmatis perhydrolase in particular the S54V variant used in the commercial product Gentle Power Bleach from Huntsman Textile Effects Pte Ltd (WO10/100028).

Amylases

Suitable amylases may be an alpha-amylase or a glucoamylase and may be of bacterial or fungal origin. Chemically modified or protein engineered mutants are included. Amylases include, for example, alpha-amylases obtained from Bacillus, e.g., a special strain of Bacillus licheniformis, described in more detail in GB 1,296,839.

Suitable amylases include amylases having SEQ ID NO: 2 in WO 95/10603 or variants having 90% sequence identity to SEQ ID NO: 3 thereof. Preferred variants are described in WO 94/02597, WO 94/18314, WO 97/43424 and SEQ ID NO: 4 of WO 99/019467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444.

Different suitable amylases include amylases having SEQ ID NO: 6 in WO 02/010355 or variants thereof having 90% sequence identity to SEQ ID NO: 6. Preferred variants of SEQ ID NO: 6 are those having a deletion in positions 181 and 182 and a substitution in position 193.

Other amylases which are suitable are hybrid alpha-amylase comprising residues 1-33 of the alpha-amylase derived from B. amyloliquefaciens shown in SEQ ID NO: 6 of WO 2006/066594 and residues 36-483 of the B. licheniformis alpha-amylase shown in SEQ ID NO: 4 of WO 2006/066594 or variants having 90% sequence identity thereof. Preferred variants of this hybrid alpha-amylase are those having a substitution, a deletion or an insertion in one of more of the following positions: G48, T49, G107, H156, A181, N190, M197, I201, A209 and Q264. Most preferred variants of the hybrid alpha-amylase comprising residues 1-33 of the alpha-amylase derived from B. amyloliquefaciens shown in SEQ ID NO: 6 of WO 2006/066594 and residues 36-483 of SEQ ID NO: 4 are those having the substitutions:

M197T;
H156Y+A181T+N190F+A209V+Q264S; or
G48A+T49I+G107A+H156Y+A181T+N190F+I201F+A209V+Q264S.

Further amylases which are suitable are amylases having SEQ ID NO: 6 in WO 99/019467 or variants thereof having 90% sequence identity to SEQ ID NO: 6. Preferred variants of SEQ ID NO: 6 are those having a substitution, a deletion or an insertion in one or more of the following positions: R181, G182, H183, G184, N195, I206, E212, E216 and K269. Particularly preferred amylases are those having deletion in positions R181 and G182, or positions H183 and G184.

Additional amylases which can be used are those having SEQ ID NO: 1, SEQ ID NO: 3, SEQ ID NO: 2 or SEQ ID NO: 7 of WO 96/023873 or variants thereof having 90% sequence identity to SEQ ID NO: 1, SEQ ID NO: 2, SEQ ID NO: 3 or SEQ ID NO: 7. Preferred variants of SEQ ID NO: 1, SEQ ID NO: 2, SEQ ID NO: 3 or SEQ ID NO: 7 are those having a substitution, a deletion or an insertion in one or more of the following positions: 140, 181, 182, 183, 184, 195, 206, 212, 243, 260, 269, 304 and 476, using SEQ ID 2 of WO 96/023873 for numbering. More preferred variants are those having a deletion in two positions selected from 181, 182, 183 and 184, such as 181 and 182, 182 and 183, or positions 183 and 184. Most preferred amylase variants of SEQ ID NO: 1, SEQ ID NO: 2 or SEQ ID NO: 7 are those having a deletion in positions 183 and 184 and a substitution in one or more of positions 140, 195, 206, 243, 260, 304 and 476.

Other amylases which can be used are amylases having SEQ ID NO: 2 of WO 08/153815, SEQ ID NO: 10 in WO 01/66712 or variants thereof having 90% sequence identity to SEQ ID NO: 2 of WO 08/153815 or 90% sequence identity to SEQ ID NO: 10 in WO 01/66712. Preferred variants of SEQ ID NO: 10 in WO 01/66712 are those having a substitution, a deletion or an insertion in one of more of the following positions: 176, 177, 178, 179, 190, 201, 207, 211 and 264.

Further suitable amylases are amylases having SEQ ID NO: 2 of WO 09/061380 or variants having 90% sequence identity to SEQ ID NO: 2 thereof. Preferred variants of SEQ ID NO: 2 are those having a truncation of the C-terminus and/or a substitution, a deletion or an insertion in one of more of the following positions: Q87, Q98, S125, N128, T131, T165, K178, R180, S181, T182, G183, M201, F202, N225, S243, N272, N282, Y305, R309, D319, Q320, Q359, K444 and G475. More preferred variants of SEQ ID NO: 2 are those having the substitution in one of more of the following positions: Q87E,R, Q98R, S125A, N128C, T131I, T165I, K178L, T182G, M201L, F202Y, N225E,R, N272E, R, S243Q,A,E,D, Y305R, R309A, Q320R, Q359E, K444E and G475K and/or deletion in position R180 and/or S181 or of T182 and/or G183. Most preferred amylase variants of SEQ ID NO: 2 are those having the substitutions:

N128C+K178L+T182G+Y305R+G475K;
N128C+K178L+T182G+F202Y+Y305R+D319T+G475K;
S125A+N128C+K178L+T182G+Y305R+G475K; or
S125A+N128C+T131I+T165I+K178L+T182G+Y305R+G475K wherein the variants are C-terminally truncated and optionally further comprises a substitution at position 243 and/or a deletion at position 180 and/or position 181.

Further suitable amylases are amylases having SEQ ID NO: 1 of WO13184577 or variants having 90% sequence identity to SEQ ID NO: 1 thereof. Preferred variants of SEQ ID NO: 1 are those having a substitution, a deletion or an insertion in one of more of the following positions: K176, R178, G179, T180, G181, E187, N192, M199, I203, S241, R458, T459, D460, G476 and G477. More preferred variants of SEQ ID NO: 1 are those having the substitution in one of more of the following positions: K176L, E187P, N192FYH, M199L, I203YF, S241QADN, R458N, T459S, D460T, G476K and G477K and/or deletion in position R178 and/or S179 or of T180 and/or G181. Most preferred amylase variants of SEQ ID NO: 1 are those having the substitutions:

E187P+I203Y+G476K
E187P+I203Y+R458N+T459S+D460T+G476K
wherein the variants optionally further comprise a substitution at position 241 and/or a deletion at position 178 and/or position 179.

Further suitable amylases are amylases having SEQ ID NO: 1 of WO10104675 or variants having 90% sequence identity to SEQ ID NO: 1 thereof. Preferred variants of SEQ ID NO: 1 are those having a substitution, a deletion or an insertion in one of more of the following positions: N21, D97, V128 K177, R179, S180, I181, G182, M200, L204, E242, G477 and G478. More preferred variants of SEQ ID NO: 1 are those having the substitution in one or more of the following positions: N21D, D97N, V128I K177L, M200L, L204YF, E242QA, G477K and G478K and/or deletion in position R179 and/or S180 or of I181 and/or G182. Most preferred amylase variants of SEQ ID NO: 1 are those having the substitutions:

N21D+D97N+V128I,
wherein the variants optionally further comprise a substitution at position 200 and/or a deletion at position 180 and/or position 181.

Other suitable amylases are the alpha-amylase having SEQ ID NO: 12 in WO01/66712 or a variant having at least 90% sequence identity to SEQ ID NO: 12. Preferred amylase variants are those having a substitution, a deletion or an insertion in one of more of the following positions of SEQ ID NO: 12 in WO01/66712: R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, N484. Particular preferred amylases include variants having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions.

Other examples are amylase variants such as those described in WO2011/098531, WO2013/001078 and WO2013/001087.

Commercially available amylases are Duramyl™, Termamyl™, Fungamyl™, Stainzyme™ Stainzyme Plus™, Natalase™, Liquozyme X and BAN™ (from Novozymes A/S), and Rapidase™ Purastar™/Effectenz™, Powerase, Preferenz™ S1000, Preferenz™ S100, Preferenz™ S110 and Preferenz™ S210 (from Genencor International Inc./DuPont).

Peroxidases/Oxidases

A peroxidase may be an enzyme comprised by the enzyme classification EC 1.11.1.7, as set out by the Nomenclature Committee of the International Union of Biochemistry and Molecular Biology (IUBMB), or any fragment derived therefrom, exhibiting peroxidase activity. Suitable peroxidases include those of plant, bacterial or fungal origin. Chemically modified or protein engineered mutants are included. Examples of useful peroxidases include peroxidases from *Coprinopsis*, e.g., from *C. cinerea* (EP 179,486), and variants thereof as those described in WO 93/24618, WO 95/10602, and WO 98/15257. A peroxidase may also include a haloperoxidase enzyme, such as chloroperoxidase, bromoperoxidase and compounds exhibiting chloroperoxidase or bromoperoxidase activity. Haloperoxidases are classified according to their specificity for halide ions. Chloroperoxidases (E.C. 1.11.1.10) catalyze formation of hypochlorite from chloride ions. The haloperoxidase may be a chloroperoxidase. Preferably, the haloperoxidase is a vanadium haloperoxidase, i.e., a vanadate-containing haloperoxidase. In a preferred method the vanadate-containing haloperoxidase is combined with a source of chloride ion. Haloperoxidases have been isolated from many different fungi, in particular from the fungus group dematiaceous hyphomycetes, such as *Caldariomyces*, e.g., *C. fumago, Alternaria, Curvularia*, e.g., *C. verruculosa* and *C. inaequalis, Drechslera, Ulocladium* and *Botrytis*. Haloperoxidases have also been isolated from bacteria such as *Pseudomonas*, e.g., *P. pyrrocinia* and *Streptomyces*, e.g., *S. aureofaciens*.

The haloperoxidase may be derivable from *Curvularia* sp., in particular *Curvularia verruculosa* or *Curvularia inaequalis*, such as *C. inaequalis* CBS 102.42 as described in WO 95/27046; or *C. verruculosa* CBS 147.63 or *C. verruculosa* CBS 444.70 as described in WO 97/04102; or from *Drechslera hartlebii* as described in WO 01/79459, *Dendryphiella salina* as described in WO 01/79458, *Phaeotrichoconis crotalarie* as described in WO 01/79461, or *Geniculosporium* sp. as described in WO 01/79460.

Oxidases include any laccase enzyme comprised by the enzyme classification EC 1.10.3.2, or any fragment derived therefrom exhibiting laccase activity, or a compound exhibiting a similar activity, such as a catechol oxidase (EC 1.10.3.1), an o-aminophenol oxidase (EC 1.10.3.4), or a bilirubin oxidase (EC 1.3.3.5). Preferred laccase enzymes are enzymes of microbial origin. The enzymes may be derived from plants, bacteria or fungi (including filamentous fungi and yeasts). Suitable examples from fungi include a laccase derivable from a strain of *Aspergillus, Neurospora*, e.g., *N. crassa, Podospora, Botrytis, Collybia, Fomes, Lentinus, Pleurotus, Trametes*, e.g., *T. villosa* and *T. versicolor, Rhizoctonia*, e.g., *R. solani, Coprinopsis*, e.g., *C. cinerea, C. comatus, C. friesii*, and *C. plicatilis, Psathyrella*, e.g., *P. condelleana, Panaeolus*, e.g., *P. papilionaceus, Myceliophthora*, e.g., *M. thermophila, Schytalidium*, e.g., *S. thermophilum, Polyporus*, e.g., *P. pinsitus, Phlebia*, e.g., *P. radiata* (WO 92/01046), or *Coriolus*, e.g., *C. hirsutus* (JP 2238885). Suitable examples from bacteria include a laccase derivable from a strain of *Bacillus*. A laccase derived from *Coprinopsis* or *Myceliophthora* is preferred; in particular a laccase derived from *Coprinopsis cinerea*, as disclosed in WO 97/08325; or from *Myceliophthora thermophila*, as disclosed in WO 95/33836.

Microorganisms

The detergent additive as well as the detergent composition may also comprise one or more microorganisms, such as one or more fungi, yeast, or bacteria. In an embodiment, the one or more microorganisms are dehydrated (for example by lyophilization) bacteria or yeast, such as a strain of *Lactobacillus*. In another embodiment, the microorganisms are one or more microbial spores (as opposed to vegetative cells), such as bacterial spores; or fungal spores, conidia, hypha. Preferably, the one or more spores are *Bacillus* endospores; even more preferably the one or more spores are endospores of *Bacillus subtilis, Bacillus licheniformis, Bacillus amyloliquefaciens*, or *Bacillus megaterium*. The microorganisms may be included in the detergent composition or additive in the same way as enzymes (see above).

Formulation of Detergent Products

The cleaning composition of the present invention may be formulated, for example, as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations. In a specific aspect, the present invention provides a detergent additive comprising one or more enzymes as described herein. The cleaning composition of the invention may be in any convenient form, e.g., a bar, a homogenous tablet, a tablet having two or more layers, a pouch having one or more compartments, a regular or compact powder, a granule, a paste, a gel, or a regular, compact or concentrated liquid.

Pouches can be configured as single or multicompartments. It can be of any form, shape and material which is suitable for hold the composition, e.g. without allowing the release of the composition to release of the composition from the pouch prior to water contact. The pouch is made from water soluble film which encloses an inner volume. Said inner volume can be divided into compartments of the pouch. Preferred films are polymeric materials preferably polymers which are formed into a film or sheet. Preferred polymers, copolymers or derivates thereof are selected polyacrylates, and water-soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxypropyl methyl cellulose (HPMC). Preferably the level of polymer in the film for example PVA is at least about 60%. Preferred average molecular weight will typically be about 20,000 to about 150,000. Films can also be of blended compositions comprising hydrolytically degradable and water-soluble polymer blends such as polylactide and polyvinyl alcohol (known under the Trade reference M8630 as sold by Mono-Sol LLC, Indiana, USA) plus plasticisers like glycerol, ethylene glycerol, propylene glycol, sorbitol and mixtures thereof. The pouches can comprise a solid laundry cleaning composition or part components and/or a liquid cleaning composition or part components separated by the water-soluble film. The compartment for liquid components can be different in composition than compartments containing solids: US2009/0011970 A1.

Detergent ingredients can be separated physically from each other by compartments in water dissolvable pouches or in different layers of tablets. Thereby negative storage interaction between components can be avoided. Different dissolution profiles of each of the compartments can also give rise to delayed dissolution of selected components in the wash solution.

A liquid or gel detergent, which is not unit dosed, may be aqueous, typically containing at least 20% by weight and up to 95% water, such as up to about 70% water, up to about 65% water, up to about 55% water, up to about 45% water, up to about 35% water. Other types of liquids, including without limitation, alkanols, amines, diols, ethers and polyols may be included in an aqueous liquid or gel. An aqueous liquid or gel detergent may contain from 0-30% organic solvent. A liquid or gel detergent may be non-aqueous.

Uses

The present invention is also directed to methods for using the compositions thereof. Laundry/textile/fabric (House hold laundry washing, Industrial laundry washing). Hard surface cleaning (ADW, car wash, Industrial surface)

Use of Cleaning Composition

The detergent composition of the present invention may be formulated, for example, as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations. In a specific aspect, the present invention provides a detergent additive comprising one or more enzymes as described herein.

Methods

The invention further relates to a method of treating a method of treating a fabric comprising;
 (a) contacting the fabric with an aqueous solution of peptidoglycan degradation enzyme, preferably having N-acetylmuramyl-L-alanine amidase and peptidoglycan lyase activity; and optionally
 (b) rinsing and drying the textile.

The invention further relates to a method for cleaning or laundering an item comprising the steps of:
 a. exposing an item to a wash liquor comprising at least one peptidoglycan degradation enzyme, preferably having N-acetylmuramyl-L-alanine amidase and/or peptidoglycan lyase activity or a detergent composition comprising such enzyme;
 b. completing at least one wash cycle; and optionally
 c. rinsing the item,
wherein the item is a fabric.

The invention further relates to a method for cleaning or laundering an item comprising the steps of:
 a. exposing an item to a wash liquor comprising a polypeptide or a detergent composition comprising a polypeptide, preferably wherein the polypeptide has N-acetylmuramyl-L-alanine amidase and/or peptidoglycan lyase activity;
 b. completing at least one wash cycle; and optionally
 c. rinsing the item,
wherein the item is a fabric.

The invention further relates to a method for cleaning or laundering an item comprising the steps of:
 a. exposing an item to a wash liquor comprising a polypeptide or a detergent composition comprising a polypeptide, preferably wherein the polypeptide has N-acetylmuramyl-L-alanine amidase and/or peptidoglycan lyase activity and wherein the polypeptide comprises the motif N[IV]X[AG][GAS]A[AY][LV]L (SEQ ID NO: 111);
 b. completing at least one wash cycle; and optionally
 c. rinsing the item,
wherein the item is a fabric.

The invention further relates to a method for cleaning or laundering an item comprising the steps of:
 a. exposing an item to a wash liquor comprising a polypeptide or a detergent composition comprising a polypeptide, preferably wherein the is selected from the group consisting of: SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72, SEQ ID NO: 75, SEQ ID NO: 78, SEQ ID NO: 81, SEQ ID NO: 84, SEQ ID NO: 87, SEQ ID NO: 90, SEQ ID NO: 93, SEQ ID NO: 96, SEQ ID NO: 99, SEQ ID NO: 102, SEQ ID NO: 105, SEQ ID NO: 108 and polypeptides having at least at least at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% hereto;
 b. completing at least one wash cycle; and optionally
 c. rinsing the item,
wherein the item is a fabric.

The pH of the liquid solution is in the range of 1 to 11, such as in the range 5.5 to 11, such as in the range of 7 to 9, in the range of 7 to 8 or in the range of 7 to 8.5.

The wash liquor may have a temperature in the range of 5° C. to 95° C., or in the range of 10° C. to 80° C., in the range of 10° C. to 70° C., in the range of 10° C. to 60° C., in the range of 10° C. to 50° C., in the range of 15° C. to 40° C. or in the range of 20° C. to 30° C. In one aspect, the temperature of the wash liquor is 30° C.

The concentration of the peptidoglycan degradation enzyme in the wash liquor is typically in the range of at least 0.00001 ppm to at least 10 ppm, at least 0.00002 ppm to at least 10 ppm, at least 0.0001 ppm to at least 10 ppm, at least 0.0002 ppm to at least 10 ppm, at least 0.001 ppm to at least 10 ppm, at least 0.002 ppm to at least 10 ppm, at least 0.01 ppm to at least 10 ppm, at least 0.02 ppm to at least 10 ppm, at least 0.1 ppm to at least 10 ppm, at least 0.2 ppm to at least 10 ppm, at least 0.5 ppm to at least 5 ppm.

The present invention is further described by the following examples that should not be construed as limiting the scope of the invention.

EXAMPLES

Media and Solutions

Model detergent A: 12 wt % LAS, 1.1 wt % AEO Biosoft N25-7 (NI), 7 wt % AEOS (SLES), 6 wt % MPG, 3 wt % ethanol, 3 wt % TEA (triethanolamine), 2.75 wt % cocoa soap, 2.75 wt % soya soap, 2 wt % glycerol, 2 wt % sodium hydroxide, 2 wt % sodium citrate, 1 wt % sodium formiate, 0.2 wt % DTMPA, 0.2 wt % PCA.

Model detergent 0:4 wt % sodium dodecylbenezenesulfonate (LAS), 8 wt % sodium lauryl ether sulfate (SLES/AEOS), 1 wt % soap (soy fatty acid), 4 wt % alcohol ethoxylate (AEO), 0.4 wt % triethanolamine (TEA), 2 wt % sodium citrate, 0.02 wt % calcium chloride dihydrate.

For Example 4, a wash liquor of model detergent A was prepared by dissolving 3.33 g/l of the detergent in water with a hardness of 15° dH.

For Example 5, 2.67 g/l model O and 0.44 g/l model A, respectively, were dissolved in tap water.

Assays

Peptidoglycan-Degrading Activity Measurement

The peptidoglycan-degrading activity was estimated using the Invitrogen™ EnzChek™ Lysozyme Assay Kit (ThermoFisher, E22013) as recommended by the manufacturer. The DQ™ substrate supplied with the kit was dissolved in miliQ-$H_2O$ to yield a 1.0 mg/ml substrate stock solution. This solution was further diluted to 50 μg/ml by mixing 50 μl stock substrate solution with 950 μl 1× Reaction buffer supplied with the kit. Concentrated enzyme solution was diluted to 2 μg/ml in the 1× Reaction buffer. 50 μl of the 50 μg/ml substrate solution was mixed with either 50 μl 1× Reaction buffer or 50 μl 2 μg/ml enzyme solution to yield a final enzyme concentration in the reaction of 1 μg/ml. The sample was incubated at 37° C. and fluorescence development was measured using a POLARstar Omega plate reader spectrophotometer (BMG LABTECH) with an excitation wavelength of 485 nm emission wavelength of 520 nm and a gain of 1500.

Fluorescence units were plotted against time and the initial slope was estimated. The results are given in the table below. Clear peptidoglycan-degrading enzyme activity is observed for the enzyme.

| Enzyme | Initial slope (fluorescence units/min) |
| --- | --- |
| No enzyme | −189.64 |
| SEQ ID NO: 6 | 13228 |

Example 1: Cloning and Expression of Polypeptides: Strains and DNA

DNA encoding the genes of SEQ ID NO: 1, SEQ ID NO: 4, SEQ ID NO: 7, SEQ ID NO: 10, SEQ ID NO: 13, SEQ ID NO: 16, SEQ ID NO: 19, SEQ ID NO: 22, SEQ ID NO: 25, SEQ ID NO: 28, SEQ ID NO: 31, SEQ ID NO: 34, SEQ ID NO: 37, SEQ ID NO: 40, SEQ ID NO: 43, SEQ ID NO: 46, SEQ ID NO: 49, SEQ ID NO: 52, SEQ ID NO: 55, SEQ ID NO: 58, SEQ ID NO: 61, SEQ ID NO: 64, SEQ ID NO: 67, SEQ ID NO: 70, SEQ ID NO: 73, SEQ ID NO: 76, SEQ ID NO: 79, SEQ ID NO: 82, SEQ ID NO: 85, SEQ ID NO: 88, SEQ ID NO: 91, SEQ ID NO: 94, SEQ ID NO: 97, SEQ ID NO: 100, SEQ ID NO: 103 and SEQ ID NO: 106 was isolated from bacterial strains and environmental bacterial communities isolated from soil samples collected in different countries (see Table 1). Chromosomal DNA from the different strains and bacterial communities was subjected to full genome sequencing using Illumina technology. The genome sequences were analysed for protein sequences that contained an Amidase_2 domain, as defined in PFAM (PF01510, Pfam version 31.0 Finn (2016). Nucleic Acids Research, Database Issue 44: D279-D285).

TABLE 1

| Enzyme | Donor | Country of origin |
| --- | --- | --- |
| SEQ ID NO: | | |
| 3 | Hamadaea tsunoensis | Japan |
| 6 | Micromonospora maritima | United States |
| 9 | Paenibacillus sp. | United States |
| 12 | Nonomuraea sp. | United Kingdom |
| 15 | Lysobacter antibioticus | China |
| 18 | Micromonospora sp. | United Kingdom |
| 21 | Nonomuraea coxensis | Philippines 1990 |
| 24 | Micromonospora fulvopurpurea | unknown strain isolated 1970 |
| 27 | Alicyclobacillus sp. | Denmark |
| 30 | Halomonas sp. | United States |
| 33 | Pseudomonas peli | United States |
| 36 | Halomonas sp. | United States |
| 39 | Pseudomonas pseudoalcaligenes | United States |
| 42 | Tumebacillus sp. | United States |
| 45 | Nonomuraea dietziae | United Kingdom |
| 48 | Laceyella sacchari | Denmark |
| 51 | Thermostaphylospora chromogena | Unknown, date of sampling 22 Aug. 1990 |
| 54 | Kribbella aluminosa | China |
| 57 | Streptomyces griseus | United States |
| 60 | Micromonospora peucetia | United Kingdom |
| 63 | Bacillus sp. | Japan |
| 66 | Bacillus sporothermodurans | Denmark |
| 69 | Paenibacillus pini | Sweden |
| 72 | Bacillus cohnii | United States |
| 75 | Kribbella sp. | United Kingdom |
| 78 | Bacillus sp. | United States |
| 81 | Bacillus sp. | United States |
| 84 | Bacillus sp. | United States |
| 87 | Streptomyces sp. | China |
| 90 | Bacillus sp. | United States |
| 93 | Bacillus sp. | United States |
| 96 | Nonomuraea guangzhouensis | United Kingdom |
| 99 | Nonomuraea guangzhouensis | United Kingdom |
| 102 | Bacillus cohnii | Denmark |
| 105 | Halomonas sp. | United States |
| 108 | Lysobacter capsica | United States |

Example 2: Cloning and Expression of Polypeptides of the Invention

DNA encoding the mature peptides of peptidoglycan degradation enzyme genes SEQ ID NO: 1, SEQ ID NO: 4, SEQ ID NO: 7, SEQ ID NO: 10, SEQ ID NO: 13, SEQ ID NO: 16, SEQ ID NO: 19, SEQ ID NO: 22, SEQ ID NO: 25, SEQ ID NO: 28, SEQ ID NO: 31, SEQ ID NO: 34, SEQ ID NO: 37, SEQ ID NO: 40, SEQ ID NO: 43, SEQ ID NO: 46, SEQ ID NO: 49, SEQ ID NO: 52, SEQ ID NO: 55, SEQ ID NO: 58, SEQ ID NO: 61, SEQ ID NO: 64, SEQ ID NO: 67, SEQ ID NO: 70, SEQ ID NO: 73, SEQ ID NO: 76, SEQ ID NO: 79, SEQ ID NO: 82, SEQ ID NO: 85, SEQ ID NO: 88, SEQ ID NO: 91, SEQ ID NO: 94, SEQ ID NO: 97, SEQ ID NO: 100, SEQ ID NO: 103 and SEQ ID NO: 106 was amplified from the genomic DNA of the corresponding bacterial strains by standard PCR techniques using specific primers containing an overhang to cloning vector. The amplified PCR fragments were inserted into a *Bacillus* expression vector as described in WO 2012/025577. Briefly, the DNA encoding the mature peptide of the gene was cloned in frame to a *Bacillus clausii* secretion signal (BcSP; with the following amino acid sequence: MKKPLGKIVAS-TALLISVAFSSSIASA (SEQ ID NO: 109). BcSP replaced the native secretion signal in the gene. Downstream of the BcSP sequence, an affinity tag sequence was introduced to ease the purification process (His-tag; with the following amino acid sequence: HHHHHHPR (SEQ ID NO: 110) The gene that was expressed therefore comprised the BcSP sequence followed by the His-tag sequence followed by the mature wild type gene sequence. The final expression plasmid (BcSP-His-tag-PGLGene) was transformed into a *Bacillus subtilis* expression host. The BcSP-fusion gene was integrated by homologous recombination into the *Bacillus subtilis* host cell genome upon transformation. The gene construct was expressed under the control of a triple promoter system (as described in WO 99/43835). The gene coding for chloramphenicol acetyltransferase was used as maker (as described in (Diderichsen et al., 1993, *Plasmid* 30: 312-315)). Transformants were selected on LB media agar supplemented with 6 microgram of chloramphenicol per ml. One recombinant *Bacillus subtilis* clone containing the PGL expression construct was selected and was cultivated on a rotary shaking table in 500 ml baffled Erlenmeyer flasks each containing 100 ml yeast extract-based media. After 3-5 days' cultivation time at 30° C. to 37° C., the enzyme-containing supernatant was harvested by centrifugation and the enzymes were purified by His-tag purification.

Example 3: His Tag Purification Method

The His-tagged enzymes were purified by immobilized metal chromatography (IMAC) using $Ni^{2+}$ as the metal ion on 5 mL HisTrap Excel columns (GE Healthcare Life Sciences). The purification took place at pH 7 and the bound protein was eluted with imidazole. The purity of the purified enzymes was checked by SDS-PAGE and the concentration of the enzyme determined by Absorbance 280 nm after a buffer exchange in 50 mM HEPES, 100 mM NaCl pH7.0

Example 4: Attachment of *Micrococcus luteus*

*M. luteus* is taken from −80° C. frozen stock and grown on TSA plates for 3 days. From here one colony is inoculated per 10 ml TSB glass tube, whirl mixed and incubated over night at 30° C. with 200 rpm shaking. Then the bacteria are transferred to 50 ml Falcon tubes at 3000 rpm 20° C. for 5 min in a Sorvall centrifuge. The supernatant is removed and re-suspended in 10 ml PBS per tube. Cells are washed twice, added to a 50 ml tube and mixed. A solution of the culture is made with an OD600 of 0.5 as measured in a CLARIOstar® reader. 100 mL is prepared and kept under constant stirring throughout the test.

A detergent solution containing 3.33 g/L model A detergent is prepared by mixing 0.167 g Model A detergent with 50 mL of tap water in a 100 mL BlueCap bottle, stirring for 2-5 min before use. This solution is used for the first and last rows in the setup where no bacteria is added (see below). A detergent solution with bacteria is made by preparing a tap water solution containing *M. luteus* with an OD600 of 0.5 and 0.33 g Model A detergent, stirring for 2-5 min. This is used as a mix for wells of 48-well plates (Thermo Scientific, Nunc A/S, non-treated, PS, sterile, cat. no. 150787). A setup of blanks and enzymes is created so as to randomize the positions for repetitions in the plates to account for the systematic molding variation. An example may look like the following:

| | 1<br>No bacteria added | 2<br>bacteria added | 3<br>bacteria added | 4<br>bacteria added | 5<br>bacteria added | 6<br>bacteria added | 7<br>bacteria added | 8<br>No bacteria added |
|---|---|---|---|---|---|---|---|---|
| A | Control, no enzyme | Blank, no enzyme | Enz1 | Enz3 | Enz2 | Enz4 | Ref enzyme | Control, no enzyme |
| B | Control, no enzyme | Blank, no enzyme | Enz1 | Enz3 | Enz2 | Enz4 | Ref enzyme | Control, no enzyme |
| C | Control, no enzyme | Blank, no enzyme | Enz1 | Enz3 | Enz2 | Enz4 | Ref enzyme | Control, no enzyme |
| D | Control, no enzyme | Ref enzyme | Enz2 | Enz4 | Enz1 | Enz3 | Blank, no enzyme | Control, no enzyme |
| E | Control, no enzyme | Ref enzyme | Enz2 | Enz4 | Enz1 | Enz3 | Blank, no enzyme | Control, no enzyme |
| F | Control, no enzyme | Ref enzyme | Enz2 | Enz4 | Enz1 | Enz3 | Blank, no enzyme | Control, no enzyme |

Detergent mix+/− bacteria is added to the wells by adding 0.5 mL *M. luteus* test solution to each well. 10 µl enzyme solution with the prepared concentration is added according to the setup. The plate is allowed to incubate at 30° C. for 1.5 h. After incubation, the solution is removed from the plates by turning the plate upside down on paper towel in a zip-lock bag. The plate is turned and punched two times, then rinsed with 0.75 mL 0.9% NaCl solution. Solution is removed from the plates by turning the plate upside down on paper towel in a zip-lock bag. The plate is turned and punched two times, and the rinsing and punching step is repeated. 0.5 mL crystal violet 0.095% is added to each well. It is allowed to incubate 15 min on the table, then the supernatant is removed from the plates by turning the plate upside down on paper towel in a zip-lock bag and punching the plate hard twice to secure best removal, repeating until drops of unbound dye solution are removed, followed by gentle rinsing with 1 mL 0.9% NaCl. The rinse solution is removed and punched as described earlier. The color in the wells is dissolved with 0.5 mL 96% ethanol, giving a quick shake by hand until the liquid is clear. Absorbance 595 is measured in the CLARIOstar® reader and if it is higher than 3 the samples are diluted in new wells.

The results, measured as follows, are provided in Table 2 below:

Y % attachment inhibition from $A_{590}=(1-(A_{590control}/A_{590enzx}))*100\%$.

$A_{590control}=A_{590}$ attachment in detergent solution of *M. luteus*;

$A_{590enzx}=A_{590}$ attachment in detergent+enzyme.

TABLE 2

Inhibition of attachment of *M. luteus*

| Enzyme | Model A pH 7.0 Y % attachment inhibition | Model A pH 7.8 Y % attachment inhibition | 1x PBS pH 6.0 Y % attachment inhibition |
|---|---|---|---|
| Day 1 | | | |
| SEQ ID NO: 6 (1 ppm) | 46.9 | 43 | 30.5 |
| SEQ ID NO: 30 (10 ppm) | — | −3.5 | 39.9 |
| Day 4 | | | |
| SEQ ID NO: 6 (1 ppm) | 41.8 | 45.6 | 22.4 |
| SEQ ID NO: 12 (1 ppm) | 40.9 | 17.5 | — |
| SEQ ID NO: 12 (10 ppm) | 40.8 | 33.9 | 72.9 |
| Day 14 | | | |
| SEQ ID NO: 6 (1 ppm) | — | 52.4 | 43.2 |
| SEQ ID NO: 15 (0.01 ppm) | — | 23.5 | — |
| SEQ ID NO: 15 (0.1 ppm) | — | 51.5 | — |
| SEQ ID NO: 15 (0.5 ppm) | — | 60.1 | — |
| SEQ ID NO: 15 (1 ppm) | — | 65.2 | — |
| SEQ ID NO: 15 (2 ppm) | — | 59.1 | — |
| SEQ ID NO: 15 (5 ppm) | — | 62.6 | 17.5 |
| Day 22 | | | |
| SEQ ID NO: 6 (1 ppm) | — | 50.7 | — |
| SEQ ID NO: 21 (1 ppm) | — | 5.4 | — |
| SEQ ID NO: 21 (10 ppm) | — | 34.8 | — |
| Day 23 | | | |
| SEQ ID NO: 6 (1 ppm) | — | 57.1 | — |
| SEQ ID NO: 99 (1 ppm) | — | 42.7 | — |
| SEQ ID NO: 99 (10 ppm) | — | 47.5 | — |
| Day 25 | | | |
| SEQ ID NO: 6 (1 ppm) | — | 73.9 | — |
| SEQ ID NO: 18 (1 ppm) | — | 67.1 | — |
| SEQ ID NO: 18 (10 ppm) | — | 88.2 | — |
| Day 28 | | | |
| SEQ ID NO: 6 (1 ppm) | — | 32.5 | — |
| SEQ ID NO: 108 (1 ppm) | — | 13.3 | — |
| SEQ ID NO: 108 (2.5 ppm) | — | 17.1 | — |
| SEQ ID NO: 108 (5 ppm) | — | 21.2 | — |
| SEQ ID NO: 108 (10 ppm) | — | 24.6 | — |
| Day 29 | | | |
| SEQ ID NO: 6 (1 ppm) | — | 31.8 | — |
| SEQ ID NO: 9 (1 ppm) | — | 17.8 | — |
| SEQ ID NO: 9 (10 ppm) | — | 52 | — |
| Day 30 | | | |
| SEQ ID NO: 6 (1 ppm) | — | 34.5 | — |
| SEQ ID NO: 27 (1 ppm) | — | 1.3 | — |
| SEQ ID NO: 27 (10 ppm) | — | 4.2 | — |
| SEQ ID NO: 45 (1 ppm) | — | 20.1 | — |
| SEQ ID NO: 45 (10 ppm) | — | 27.3 | — |
| Day 31 | | | |
| SEQ ID NO: 6 (1 ppm) | — | 30.7 | — |
| SEQ ID NO: 48 (10 ppm) | — | 12 | — |
| SEQ ID NO: 69 (10 ppm) | — | 3.2 | — |
| Day 32 | | | |
| SEQ ID NO: 6 (1 ppm) | — | 34.4 | — |
| SEQ ID NO: 87 (1 ppm) | — | 4.1 | — |
| SEQ ID NO: 87 (10 ppm) | — | 10 | — |

The test results have a certain day to day variation, due to e.g. fluctuations in lab temperature and humidity as well as slight variations in day-to-day cell viability, and the attachment inhibition results should therefore be compared for the same day. Our experience with the assay and the enzymes has shown that the day-to-day fluctuations in attachment and inhibition patterns in general give the same pattern in performance between the enzymes when they are repeated another day. Some enzymes work better at pH 6.0 and 7.0 and others perform optimally at pH 7.8, which has been tested for selected enzymes. SEQ ID NO: 6 is used as a reference enzyme to control the assay and measure the day to day variation.

Conclusion: In this experiment, SEQ ID NO: 6 shows robust inhibitory effects of *M. luteus* attachment at pH 6, pH 7 and pH 7.8. 10 ppm of SEQ ID NO: 30 shows an inhibitory effect on *M. luteus* on par with the effect of SEQ ID NO: 6 at a concentration of 1 ppm at pH 6, but no performance at pH 7.8. SEQ ID NO: 12 shows good performance at pH 7 compared to the control enzyme SEQ ID NO: 6. The performance of SEQ ID NO: 12 is less prominent at pH 7.8, but there is still a significant effect. SEQ ID NO: 15 can be dosed very low (0.01 ppm) and still give robust anti-attachment benefits at pH 7.8. At 0.5 ppm and 1.0 ppm there is a tendency for the inhibitory effect of SEQ ID NO: 15 to be higher than that of SEQ ID NO: 6 at a pH of 7.8. At pH 6 performance seems to be lower for SEQ ID NO: 15 at 5 ppm compared to SEQ ID NO: 6 at 1 ppm. SEQ ID Nos: 21, 99, 108, 9, 27, 45, 48, 69 and 87 also show inhibitory attachment benefits. SEQ ID NO: 18 gives very high anti-attachment performance on *M. luteus* at pH 7.8 using 1 ppm and it increases using 10 ppm.

Example 5: Preparation of Crude Cell Wall Extracts from *Micrococcus luteus* and OD Drop Activity Assay Preparation of Cell Wall Extracts Cell wall extracts from *Micrococcus luteus* were prepared following the protocol described by Mukamolova et al., Molecular Microbiology (2006) 59 (1), 84-98. Briefly, *M. luteus* cells grown overnight in 1 L LB medium were centrifuged at 10,000 g for 30 minutes, washed with deionized water, resuspended in 200 ml 5% (w/v) SDS and boiled for 20 minutes. Following centrifugation, the pellet was resuspended in 100 ml 4% (w/v) SDS and boiled again for 20 min. The pellet was then thoroughly washed six times with 100 ml hot (65° C.) water to remove the SDS. Finally, it was washed with 10 ml acetone, air dried overnight, weighed and stored at −20° C.

OD Drop Assay Using Crude Cell Wall Extracts from *M. luteus*

0.6 g of *M. luteus* cell wall extracts prepared as described above were resuspended in 15 ml of deionized water (stock solution 40 mg/ml) and passed through a syringe needle to disrupt the large flakes. This stock solution was stored at 4° C.

A cell wall extract working solution was prepared from the stock solution at 0.75 mg/ml in 50 mM MES (2-(N-morpholino) ethanesulfonic acid) pH 6 buffer and two model detergents, model O and A (2.67 g/L model O and 0.44 g/L model A, respectively, in tap water). These working solutions were prepared fresh each time when running an OD drop assay.

Next, 150 μL aliquots of the crude cell wall extract working solution were dispensed in the wells of a 96-well microtiter plate (Thermo Scientific, Nunclon Delta Surface, cat #167008) and mixed with 50 μL of a solution containing 80 ppm of a purified enzyme (3, 6, 9, 12, 15, 18, 21, 24, 27, 30, 33, 36, 39, 42, 45, 48, 51, 54, 57, 60, 63, 66, 69, 72, 75, 78, 81, 84, 87, 90, 93, 96, 99, 102, 105 or 108) in 50 mM HEPES 100 mM NaCl pH7 buffer, or the HEPES buffer as a control, and incubated at 30° C. with shaking at 600 rpm in an Eppendorf ThermoMixer C. The absorbance of the samples was measured at 600 nm in a SpectraMax M3 instrument at time=0 and after overnight incubation with the enzyme. Enzymes were tested in duplicate. The average of the OD drop measurements (calculated by the OD obtained after overnight incubation minus OD at time 0) are listed in Table 3 below.

TABLE 3

OD drop values (OD after overnight incubation minus OD time 0)

| SEQ ID NO: | MES + HEPES | Model A | Model O |
|---|---|---|---|
| 3 | 0.27 | 0.03 | 0.00 |
| 6 | 0.42 | 0.13 | 0.21 |
| 9 | 0.20 | 0.03 | 0.00 |
| 12 | 0.35 | 0.20 | 0.46 |
| 15 | 0.65 | 0.79 | 0.54 |
| 18 | 0.71 | 0.90 | 0.82 |
| 21 | 0.10 | 0.02 | 0.00 |
| 24 | 0.12 | 0.00 | 0.00 |
| 27 | 0.08 | 0.03 | 0.00 |
| 30 | 0.15 | 0.49 | 0.50 |
| 33 | 0.36 | 0.15 | 0.32 |
| 36 | 0.12 | 0.00 | 0.00 |
| 39 | 0.36 | 0.25 | 0.36 |
| 42 | 0.21 | 0.02 | 0.00 |
| 45 | 0.30 | 0.03 | 0.00 |
| 48 | 0.10 | 0.03 | 0.00 |
| 51 | 0.23 | 0.00 | 0.00 |
| 54 | 0.03 | 0.17 | 0.23 |
| 57 | 0.23 | 0.33 | 0.58 |
| 60 | 0.11 | 0.23 | 0.30 |
| 63 | 0.18 | 0.15 | 0.30 |
| 66 | 0.47 | 0.16 | 0.40 |
| 69 | 0.46 | 0.16 | 0.23 |
| 72 | 0.45 | 0.17 | 0.29 |
| 75 | 0.53 | 0.20 | 0.55 |
| 78 | 0.29 | 0.19 | 0.32 |
| 81 | 0.64 | 0.16 | 0.27 |
| 84 | 0.60 | 0.15 | 0.35 |
| 87 | 0.35 | 0.17 | 0.30 |
| 90 | 0.18 | 0.16 | 0.23 |
| 93 | 0.78 | 0.19 | 0.10 |
| 96 | 0.36 | 0.15 | 0.14 |
| 99 | 0.27 | 0.72 | 0.66 |
| 102 | 0.25 | 0.16 | 0.21 |
| 105 | 0.10 | 0.15 | 0.25 |
| 108 | 0.60 | 0.03 | 0.16 |

The results in Table 3 show that enzymes giving an OD drop can hydrolyze cell wall extracts present in the solution.

Example 6: Construction of the PGL Domain, Clades and Phylogenetic Trees

The polypeptides of the invention have hydrolase activity and comprise the Amidase_2 domain as well as clusters such as clades. A phylogenetic tree was constructed from polypeptide sequences containing an Amidase_2 domain, as defined in PFAM (PF01510, Pfam version 31.0 Finn (2016). Nucleic Acids Research, Database Issue 44: D279-D285). The phylogenetic tree was constructed from a multiple alignment of mature polypeptide sequences containing at least one Amidase_2 domain. The sequences were aligned using the MUSCLE algorithm version 3.8.31 (Edgar, 2004. Nucleic Acids Research 32(5): 1792-1797), and a tree was constructed using FastTree version 2.1.8 (Price et al., 2010, PloS one 5(3)) and visualized using iTOL (Letunic & Bork, 2007. Bioinformatics 23(1): 127-128).

Analysis of the phylogenetic tree showed that the polypeptides containing an Amidase_2 domain may be separated into distinct sub-clusters. The sub-clusters are defined by one or more short sequence motifs, as well as by containing an Amidase_2 domain as defined in PFAM (PF01510, Pfam version 31.0). We denoted one sub-cluster comprising the motif N[IV]X[AG][GAS]A[AY][LV]L (SEQ ID NO: 111), situated in positions corresponding to positions 324 to 328 in *Micromonospora maritima* (SEQ ID NO: 6), as the PGL Glade. All polypeptide sequences containing an Amidase_2 domain as well as the motif will be denoted as belonging to the PGL Glade. Polypeptides included in the Glade are SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 42, SEQ ID NO: 45, SEQ ID NO: 48, SEQ ID NO: 51, SEQ ID NO: 54, SEQ ID NO: 60, SEQ ID NO: 63, SEQ ID NO: 66, SEQ ID NO: 69, SEQ ID NO: 75, SEQ ID NO: 87, SEQ ID NO: 96, SEQ ID NO: 99 and SEQ ID NO: 108.

Example 7: N-Acetylmuramyl-L-Alanine Amidase Assay

Substrate Synthesis

The organic syntheses of peptidoglycan fragments (1) and (2) was performed in three steps from commercially available methyl 2-acetamido-4,6-O-benzylidene-2-deoxy-α-D-glucopyranoside and the appropriate peptide sequences. Both peptides used (here named *S. aureus* peptide and *M. luteus* peptide; see below) were synthesized and provided by TAG Copenhagen A/S. In the structural formulas below, an asterisk (*) denotes D-stereochemistry.

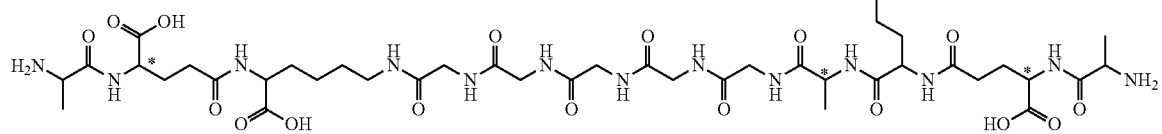

(*S. aureus* peptide)

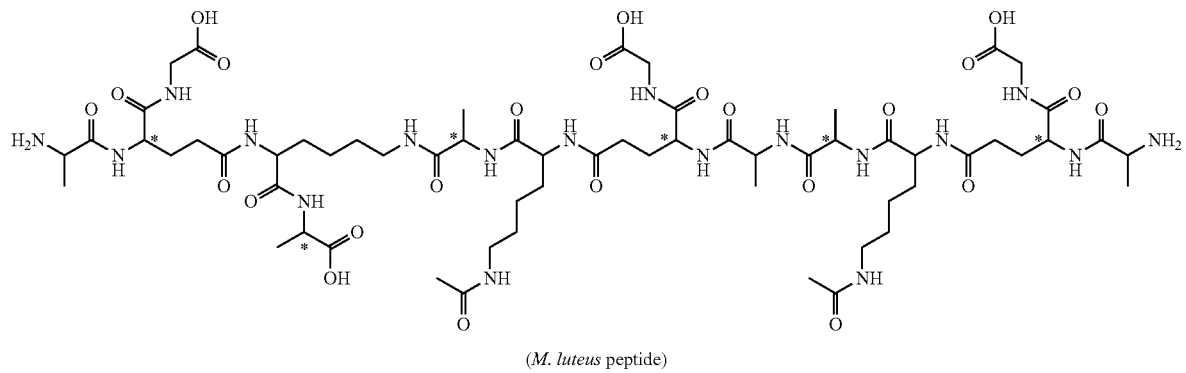

(*M. luteus* peptide)

Synthesis of the peptides modified with muramic acid derivatives was performed, cf. the schematic overview below, by initially coupling methyl 2-acetamido-4,6-O-benzylidene-2-deoxy-α-D-glucopyranoside to (S)-2-chloropropionic acid using the protocol from D. Hesek et al., *J. Org. Chem.* 2004, 69, 778-784 to result in compound (3). Then the corresponding muramic acid NHS-ester derivative (4) was synthesized by treating 200 mg of (3) with N-(3-Dimethylaminopropyl)-N-ethylcarbodiimide hydrochloride (EDC-HCl, 1.5 eq.) and N-hydroxysuccinimide (1.15 eq.) in anhydrous dichloromethane (DCM, 2 mL) at room temperature (rt) for 4 hours before the solution was diluted with DCM (10 mL), washed with 2.5% $NaHSO_4$ and brine, dried over anhydrous $NaSO_4$, filtered and concentrated in vacuo. The desired product (4) was used without further purification in 2.1 eq. to couple to a peptide (20 mg) in anhydrous dimethylformamide (DMF, 300 μL) at room temperature in the presence of triethylamine (TEA, 3.5 eq.) by overnight reaction. The desired products (*S. aureus* substrate 1, or *M. luteus* substrate 2) were used without further purification for amidase assessment.

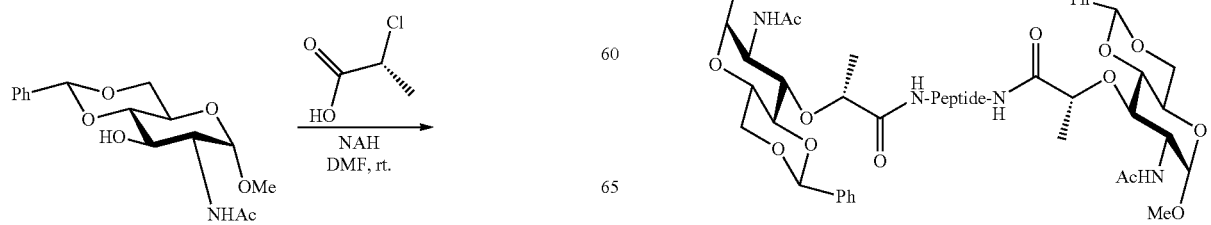

The result is the following modified peptides, *S. aureus* substrate 1 and *M. luteus* substrate 2:
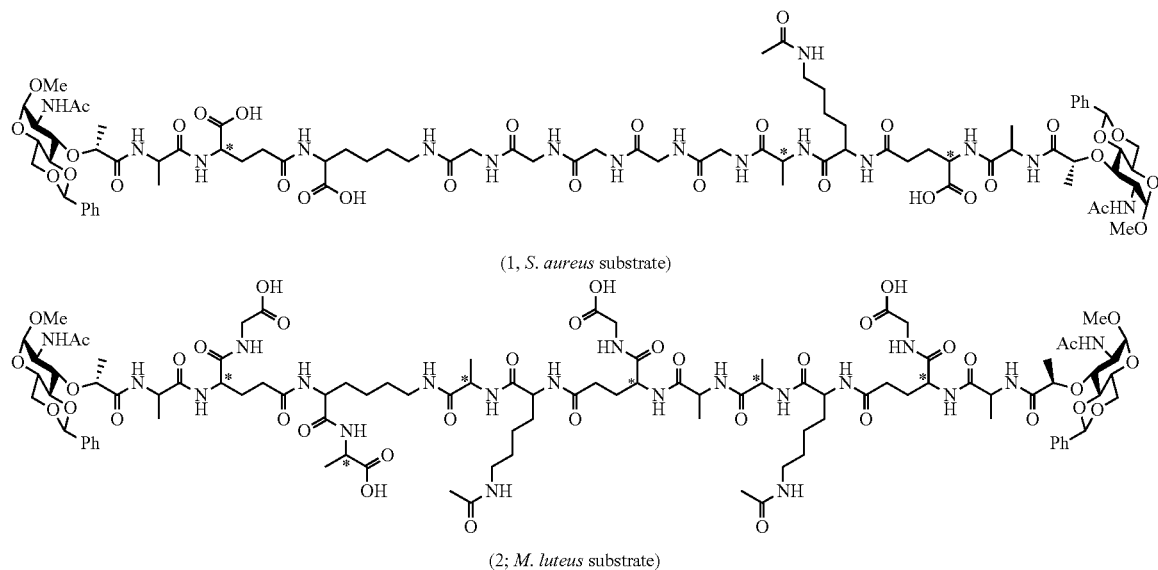
(1, *S. aureus* substrate)
(2; *M. luteus* substrate)
Amidase Assay
The amidases cleave between the peptide and the muramic acid (MurNAc) motifs to liberate one or two new N-termini, as illustrated in the following:
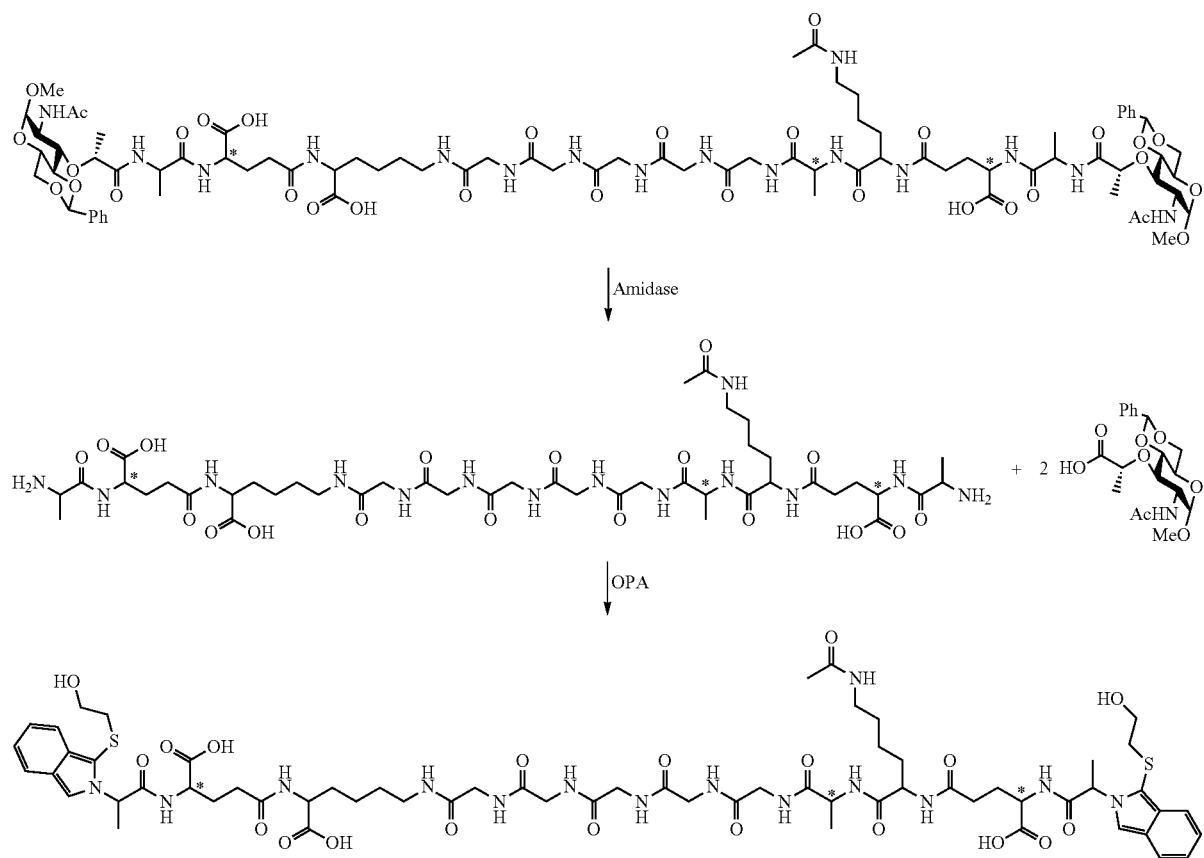

When exposed to standard o-phthaldehyde (OPA) assay conditions, the newly formed peptide amines (N-termini) react to yield a fluorescent readout (excitation=340 nm, emission=455 nm). OPA solution is prepared by dissolving 800 mg o-phthaldehyde in 10 mL 95% EtOH followed by addition of 1 L 0.5 M borate buffer (pH 9.0) containing 2 mL 2-mercaptoethanol.

Amidase reactions were performed by incubating and shaking the amidase (20 μg/mL final conc.) with the MurNAc-peptide-MurNAc substrate (substrate 1 or 2, 5 mM final conc.) in 50 mM MES buffer (pH 6.0, 100 mM NaCl) at 37° C. overnight, before the reaction products were analyzed by OPA assay and MALDI-TOF.

Amidase assessment (OPA assay) was performed by adding 100 μL OPA solution to 10 μL reaction sample. The mixture was transferred to a 96-well plate and monitored in a spectrophotometer (excitation=340 nm, emission=455 nm) after 5 min of incubation. The non-modified *S. aureus* and *M. luteus* peptides (i.e. with amino termini as shown above) were included as controls.

Results

Table 4 below shows the measured fluorescence for the *S. aureus* and *M. luteus* peptides (with amino termini) and substrates (with MurNAc termini) alone and after treatment with the amidases of SEQ ID NO: 6 or SEQ ID NO: 33, as well as for the amidases alone (negative control).

It can be seen that the MurNAc-peptide-MurNAc substrates (*S. aureus* substrate and *M. luteus* substrate) yield minimal OPA response until treated with the amidase of SEQ ID NO: 6 or SEQ ID NO: 33, where the fluorescent response increases significantly. The amidases appear to have no activity on the non-modified peptides (*S. aureus* peptide and *M. luteus* peptide), which was as expected.

MALDI-TOF MS analyses (data not shown) before and after treatment of the *S. aureus* and *M. luteus* substrates with the amidase of SEQ ID NO: 6 or SEQ ID NO: 33 confirmed that the OPA response is a result of enzymatic cleavage between the peptide and the MurNAc motifs to liberate the MurNAc motifs, yielding the free peptide N-termini.

TABLE 4

| Peptide/substrate + enzyme | Fluorescence (RFU; 340, 455 nm) |
| --- | --- |
| SEQ ID NO: 6 | 29 |
| SEQ ID NO: 33 | 27 |
| *S. aureus* peptide | 8420 |
| *S. aureus* peptide + SEQ ID NO: 6 | 8240 |
| *S. aureus* peptide + SEQ ID NO: 33 | 8547 |
| *S. aureus* substrate | 515 |
| *S. aureus* substrate + SEQ ID NO: 6 | 7077 |

TABLE 4-continued

| Peptide/substrate + enzyme | Fluorescence (RFU; 340, 455 nm) |
| --- | --- |
| *S. aureus* substrate + SEQ ID NO: 33 | 5704 |
| *M. luteus* peptide | 3447 |
| *M. luteus* peptide + SEQ ID NO: 6 | 3340 |
| *M. luteus* peptide + SEQ ID NO: 33 | 3298 |
| *M. luteus* substrate | 381 |
| *M. luteus* substrate + SEQ ID NO: 6 | 3166 |
| *M. luteus* substrate + SEQ ID NO: 33 | 1853 |

Example 8: N-Acetylmuramyl-L-Alanine Amidase Assay, Test of Additional Amidases

Several other enzymes within the same family as the amidase of SEQ ID NO: 6 were tested against the *S. aureus* substrate (substrate 1) as described in Example 7. This revealed that the amidases of SEQ ID NOs: 3, 45, 24 and 12 had comparable activity towards the *S. aureus* substrate; see the results in Table 5 below, where the individual enzymes (without peptide or substrate) are included as negative controls.

TABLE 5

| Peptide/substrate + enzyme | Fluorescence (RFU; 340, 455 nm) |
| --- | --- |
| *S. aureus* peptide | 8458 |
| *S. aureus* substrate | 735 |
| SEQ ID NO: 3 | 33 |
| SEQ ID NO: 6 | 21 |
| SEQ ID NO: 12 | 54 |
| SEQ ID NO: 24 | 108 |
| SEQ ID NO: 45 | 44 |
| *S. aureus* substrate + SEQ ID NO: 3 | 6810 |
| *S. aureus* substrate + SEQ ID NO: 6 | 7584 |
| *S. aureus* substrate + SEQ ID NO: 24 | 6903 |
| *S. aureus* substrate + SEQ ID NO: 12 | 6602 |
| *S. aureus* substrate + SEQ ID NO: 45 | 6851 |

The enzyme of SEQ ID NO: 105 was tested in a similar experiment and had comparable activity towards the *S. aureus* substrate; see Table 6.

TABLE 6

| Peptide/substrate + enzyme | Fluorescence (RFU; 340, 455 nm) |
| --- | --- |
| SEQ ID NO: 105 | 37 |
| *S. aureus* substrate | 756 |
| *S. aureus* substrate + SEQ ID NO: 105 | 6328 |

The invention claimed is:

1. A cleaning composition comprising a peptidoglycan degradation enzyme, at least one surfactant, and at least one additional cleaning component selected from builders and bleach components, wherein the peptidoglycan degradation enzyme is selected from the group consisting of:
   (1) SEQ ID NO: 12, SEQ ID NO: 30, SEQ ID NO: 84, and SEQ ID NO: 99, and polypeptides having at least 85% sequence identity thereto, and wherein the enzyme has peptidoglycan degradation activity;
   (2) SEQ ID NO: 81, and polypeptides having at least 90% sequence identity thereto, and wherein the enzyme has peptidoglycan degradation activity;
   (3) SEQ ID NO: 75, and polypeptides having at least 92% sequence identity thereto, and wherein the enzyme has peptidoglycan degradation activity;
   (4) SEQ ID NO: 18, and polypeptides having at least 95% sequence identity thereto, and wherein the enzyme has peptidoglycan degradation activity;
   (5) SEQ ID NO: 6, and polypeptides having at least 98% sequence identity thereto, and wherein the enzyme has peptidoglycan degradation activity;
   (6) SEQ ID NO: 15, and SEQ ID NO: 57.

2. The cleaning composition of claim 1, comprising a peptidoglycan degradation enzyme, at least 5 wt % anionic surfactants, and at least one additional cleaning component selected from at least one builder and at least one bleach component.

3. The cleaning composition according to claim 1, wherein the peptidoglycan degrading enzyme has N-acetyl-muramyl-L-alanine amidase activity.

4. The cleaning composition according to claim 1, wherein the peptidoglycan degrading enzyme has peptidoglycan lyase activity.

5. The cleaning composition according to claim 3, or wherein the peptidoglycan degradation enzyme has N-acetylmuramyl-L-alanine amidase activity and peptidoglycan lyase activity.

6. The cleaning composition of claim 1, wherein the peptidoglycan degradation enzyme is selected from the group consisting of: SEQ ID NO: 6, SEQ ID NO: 12, SEQ ID NO: 18, SEQ ID NO: 30, SEQ ID NO: 75, SEQ ID NO:81, SEQ ID NO: 84, and SEQ ID NO: 99.

7. A cleaning composition according to claim 1, comprising about 5 to about 60 wt % of at least one surfactant, and further comprising:
   (i) about 5 wt % to about 50 wt % of at least one builder; and/or
   (ii) about 1 wt % to about 20 wt % of at least one bleach component.

8. A cleaning composition according to claim 1, wherein the polypeptide having peptidoglycan degradation activity is selected from the group consisting of:
   a) a polypeptide having at least 90% sequence identity to SEQ ID NO: 12, SEQ ID NO: 30, SEQ ID NO: 84, or SEQ ID NO: 99;
   b) a polypeptide having at least 91% sequence identity to SEQ ID NO: 81;
   c) a polypeptide having at least 93% sequence identity to SEQ ID NO: 75;
   d) a polypeptide having at least 96% sequence identity to SEQ ID NO: 18; and
   e) a polypeptide having at least 99% sequence identity to SEQ ID NO: 6.

9. The cleaning composition according to claim 8, wherein the polypeptide has N-acetylmuramyl-L-alanine amidase and peptidoglycan lyase activity.

10. A method of cleaning an item, comprising:
    I) contacting the item with the cleaning composition of claim 1, and optionally
    II) rinsing the item;
    wherein the item is a textile.

11. The method of claim 10, wherein the cleaning composition comprises 5 to 60 wt % of at least one surfactant; and further comprises (i) 5 to 50 wt % of at least one builder, and/or (ii) 1 to 20 wt % of at least one bleach component.

12. The method of claim 10, wherein the peptidoglycan degradation enzyme has at least 98% sequence identity to SEQ ID NO: 6.

13. The method of claim 10, wherein the peptidoglycan degradation enzyme has at least 99% sequence identity to SEQ ID NO: 6.

14. The cleaning composition of claim 1, wherein the peptidoglycan degradation enzyme has at least 98% sequence identity to SEQ ID NO: 6.

15. The cleaning composition of claim 1, wherein the peptidoglycan degradation enzyme has at least 99% sequence identity to SEQ ID NO: 6.

16. The cleaning composition of claim 1, wherein the peptidoglycan degradation enzyme has at least 90% sequence identity to SEQ ID NO: 12.

17. The cleaning composition of claim 1, wherein the peptidoglycan degradation enzyme has at least 95% sequence identity to SEQ ID NO: 12.

18. The cleaning composition of claim 1, wherein the peptidoglycan degradation enzyme has at least 90% sequence identity to SEQ ID NO: 99.

19. The cleaning composition of claim 1, wherein the peptidoglycan degradation enzyme has at least 95% sequence identity to SEQ ID NO: 99.

20. The cleaning composition of claim 1, wherein the peptidoglycan degradation enzyme has at least 95% sequence identity to SEQ ID NO: 18.

* * * * *

SEQUENCE LISTING

```
<160> NUMBER OF SEQ ID NOS: 111

<210> SEQ ID NO 1
<211> LENGTH: 1380
<212> TYPE: DNA
<213> ORGANISM: Hamadaea tsunoensis
<220> FEATURE:
<221> NAME/KEY: CDS
<222> LOCATION: (1)..(1380)
<220> FEATURE:
<221> NAME/KEY: sig_peptide
<222> LOCATION: (1)..(87)
<220> FEATURE:
```

```
<221> NAME/KEY: mat_peptide
<222> LOCATION: (88)..(1380)

<400> SEQUENCE: 1 atg aca gta cca cct aca cgt cgt gct act ttc atg tta gga gcg ttg      48
Met Thr Val Pro Pro Thr Arg Arg Ala Thr Phe Met Leu Gly Ala Leu
            -25                 -20                 -15 atc tta gcc gct ggt gta gct gca ccg cca gca agc gct gct gct gct      96
Ile Leu Ala Ala Gly Val Ala Ala Pro Pro Ala Ser Ala Ala Ala Ala
        -10                 -5                  -1  1 cca gta gcg cct gac gca tta aca gta gcg tca act cca gca tca act     144
Pro Val Ala Pro Asp Ala Leu Thr Val Ala Ser Thr Pro Ala Ser Thr
      5                  10                  15 ggt agc ctt act gct gct ttt gat gct gca gca aca cgt tat gga gtt     192
Gly Ser Leu Thr Ala Ala Phe Asp Ala Ala Ala Thr Arg Tyr Gly Val
 20                  25                  30                  35 cca cgt gac tta ttg atc gct att ggt tac gct gaa aca cac ctt gat     240
Pro Arg Asp Leu Leu Ile Ala Ile Gly Tyr Ala Glu Thr His Leu Asp
                 40                  45                  50 gga cac gca ggc act cca tct gca gct ggt gga tat ggt gtt atg aat     288
Gly His Ala Gly Thr Pro Ser Ala Ala Gly Gly Tyr Gly Val Met Asn
             55                  60                  65 ctt act ggc aat ccg gct gtt cac act ctt gct gaa gct tct cgc tta     336
Leu Thr Gly Asn Pro Ala Val His Thr Leu Ala Glu Ala Ser Arg Leu
         70                  75                  80 act ggc ctt aaa gct agc acg tta gag aat aac caa gct gct aac atc     384
Thr Gly Leu Lys Ala Ser Thr Leu Glu Asn Asn Gln Ala Ala Asn Ile
 85                  90                  95 ctt ggt gcg gct gca gtt tta cgc tct tac gct gct gat ttg aaa act     432
Leu Gly Ala Ala Ala Val Leu Arg Ser Tyr Ala Ala Asp Leu Lys Thr
100                 105                 110                 115 gct caa cgt gac tct gta gac aat tgg tac gct gct gta gct cgt tat     480
Ala Gln Arg Asp Ser Val Asp Asn Trp Tyr Ala Ala Val Ala Arg Tyr
                120                 125                 130 ggt ggc gca act gat ccg tct gtt gct cgc ctt tat gct gat aca gtt     528
Gly Gly Ala Thr Asp Pro Ser Val Ala Arg Leu Tyr Ala Asp Thr Val
            135                 140                 145 tac gat ctt ctt gcg aca ggt ttc gga gtt cca gct aaa ggc gtt agc     576
Tyr Asp Leu Leu Ala Thr Gly Phe Gly Val Pro Ala Lys Gly Val Ser
        150                 155                 160 gtt aca gct cgt gct gta gca cct caa cgt ggt act ctt gct act gcg     624
Val Thr Ala Arg Ala Val Ala Pro Gln Arg Gly Thr Leu Ala Thr Ala
165                 170                 175 cgt gca tca ttg gac tct gca gac tac ggt cct gct gct tgg gct cca     672
Arg Ala Ser Leu Asp Ser Ala Asp Tyr Gly Pro Ala Ala Trp Ala Pro
180                 185                 190                 195 gca tct aca tct aac tac aca gtt gca aac cgc gaa aca gac tat aac     720
Ala Ser Thr Ser Asn Tyr Thr Val Ala Asn Arg Glu Thr Asp Tyr Asn
                200                 205                 210 atc aat tac att gtt atc cac gta act caa gga tct tac gct ggc tct     768
Ile Asn Tyr Ile Val Ile His Val Thr Gln Gly Ser Tyr Ala Gly Ser
            215                 220                 225 att tct tgg ttc caa aat cct gcg gct cag gtt tct gct cat tac gtt     816
Ile Ser Trp Phe Gln Asn Pro Ala Ala Gln Val Ser Ala His Tyr Val
        230                 235                 240 gta cgt tca tct gat ggt gcc atc acg cag tct gtt cgt gaa aaa gat     864
Val Arg Ser Ser Asp Gly Ala Ile Thr Gln Ser Val Arg Glu Lys Asp
245                 250                 255
```

```
atc gct tgg cac gca ggc aac tgg aca tac aac acg caa gct atc ggc        912
Ile Ala Trp His Ala Gly Asn Trp Thr Tyr Asn Thr Gln Ala Ile Gly
260             265                 270                 275 atc gaa cat gaa ggc tat atc gac gac cct tca tgg ttc act gac gca        960
Ile Glu His Glu Gly Tyr Ile Asp Asp Pro Ser Trp Phe Thr Asp Ala
                280                 285                 290 atg tat cgt tct tca gca gct ctt aca cgt tca ctt aca acg aaa tac       1008
Met Tyr Arg Ser Ser Ala Ala Leu Thr Arg Ser Leu Thr Thr Lys Tyr
                295                 300                 305 gct att cct cgt gac cgc agc cac atc atc ggt cat atc gaa gtt cct       1056
Ala Ile Pro Arg Asp Arg Ser His Ile Ile Gly His Ile Glu Val Pro
            310                 315                 320 tct gca acg cac acg gat cct ggt cag tat tgg aac tgg act tac tac       1104
Ser Ala Thr His Thr Asp Pro Gly Gln Tyr Trp Asn Trp Thr Tyr Tyr
325                 330                 335 atg caa ttg gta aac gga gta acg ggt atc gga aca gga acg gta aac       1152
Met Gln Leu Val Asn Gly Val Thr Gly Ile Gly Thr Gly Thr Val Asn
340                 345                 350                 355 gta tct ggc tca ttg aac att cgc tca ggt cct ggt aca ggc tac gct       1200
Val Ser Gly Ser Leu Asn Ile Arg Ser Gly Pro Gly Thr Gly Tyr Ala
                360                 365                 370 gtt gct gga tct ctt gcg aac gga gcg gga gtt tct gtt tac tgc caa       1248
Val Ala Gly Ser Leu Ala Asn Gly Ala Gly Val Ser Val Tyr Cys Gln
                375                 380                 385 gct acg ggc acg aca gta acg ggt act tac ggc act agc aac atc tgg       1296
Ala Thr Gly Thr Thr Val Thr Gly Thr Tyr Gly Thr Ser Asn Ile Trp
                390                 395                 400 gac cgt atc ggt acg aat aag tat gtt gca gat gcg tat gta ttg act       1344
Asp Arg Ile Gly Thr Asn Lys Tyr Val Ala Asp Ala Tyr Val Leu Thr
            405                 410                 415 ggt tct gac ggc ttt atc cct ggt gta cca cgt tgc                       1380
Gly Ser Asp Gly Phe Ile Pro Gly Val Pro Arg Cys
420                 425                 430

<210> SEQ ID NO 2
<211> LENGTH: 460
<212> TYPE: PRT
<213> ORGANISM: Hamadaea tsunoensis

<400> SEQUENCE: 2

Met Thr Val Pro Pro Thr Arg Arg Ala Thr Phe Met Leu Gly Ala Leu
                -25                 -20                 -15

Ile Leu Ala Ala Gly Val Ala Ala Pro Pro Ala Ser Ala Ala Ala Ala
            -10                 -5              -1  1

Pro Val Ala Pro Asp Ala Leu Thr Val Ala Ser Thr Pro Ala Ser Thr
  5                  10                 15

Gly Ser Leu Thr Ala Ala Phe Asp Ala Ala Ala Thr Arg Tyr Gly Val
 20                  25                 30                  35

Pro Arg Asp Leu Leu Ile Ala Ile Gly Tyr Ala Glu Thr His Leu Asp
                 40                 45                  50

Gly His Ala Gly Thr Pro Ser Ala Ala Gly Gly Tyr Gly Val Met Asn
             55                 60                  65

Leu Thr Gly Asn Pro Ala Val His Thr Leu Ala Glu Ala Ser Arg Leu
         70                 75                  80

Thr Gly Leu Lys Ala Ser Thr Leu Glu Asn Asn Gln Ala Ala Asn Ile
     85                 90                  95

Leu Gly Ala Ala Ala Val Leu Arg Ser Tyr Ala Ala Asp Leu Lys Thr
100                 105                 110                 115
```

```
Ala Gln Arg Asp Ser Val Asp Asn Trp Tyr Ala Val Ala Arg Tyr
                120                 125                 130

Gly Gly Ala Thr Asp Pro Ser Val Ala Arg Leu Tyr Ala Asp Thr Val
            135                 140                 145

Tyr Asp Leu Leu Ala Thr Gly Phe Gly Val Pro Ala Lys Gly Val Ser
        150                 155                 160

Val Thr Ala Arg Ala Val Ala Pro Gln Arg Gly Thr Leu Ala Thr Ala
165                 170                 175

Arg Ala Ser Leu Asp Ser Ala Asp Tyr Gly Pro Ala Ala Trp Ala Pro
180                 185                 190                 195

Ala Ser Thr Ser Asn Tyr Thr Val Ala Asn Arg Glu Thr Asp Tyr Asn
                200                 205                 210

Ile Asn Tyr Ile Val Ile His Val Thr Gln Gly Ser Tyr Ala Gly Ser
                215                 220                 225

Ile Ser Trp Phe Gln Asn Pro Ala Ala Gln Val Ser Ala His Tyr Val
            230                 235                 240

Val Arg Ser Ser Asp Gly Ala Ile Thr Gln Ser Val Arg Glu Lys Asp
        245                 250                 255

Ile Ala Trp His Ala Gly Asn Trp Thr Tyr Asn Thr Gln Ala Ile Gly
260                 265                 270                 275

Ile Glu His Glu Gly Tyr Ile Asp Asp Pro Ser Trp Phe Thr Asp Ala
                280                 285                 290

Met Tyr Arg Ser Ser Ala Ala Leu Thr Arg Ser Leu Thr Thr Lys Tyr
                295                 300                 305

Ala Ile Pro Arg Asp Arg Ser His Ile Ile Gly His Ile Glu Val Pro
            310                 315                 320

Ser Ala Thr His Thr Asp Pro Gly Gln Tyr Trp Asn Trp Thr Tyr Tyr
        325                 330                 335

Met Gln Leu Val Asn Gly Val Thr Gly Ile Gly Thr Gly Thr Val Asn
340                 345                 350                 355

Val Ser Gly Ser Leu Asn Ile Arg Ser Gly Pro Gly Thr Gly Tyr Ala
                360                 365                 370

Val Ala Gly Ser Leu Ala Asn Gly Ala Gly Val Ser Val Tyr Cys Gln
                375                 380                 385

Ala Thr Gly Thr Thr Val Thr Gly Thr Tyr Gly Thr Ser Asn Ile Trp
            390                 395                 400

Asp Arg Ile Gly Thr Asn Lys Tyr Val Ala Asp Ala Tyr Val Leu Thr
            405                 410                 415

Gly Ser Asp Gly Phe Ile Pro Gly Val Pro Arg Cys
420                 425                 430

<210> SEQ ID NO 3
<211> LENGTH: 431
<212> TYPE: PRT
<213> ORGANISM: Hamadaea tsunoensis

<400> SEQUENCE: 3

Ala Ala Ala Pro Val Ala Pro Asp Ala Leu Thr Val Ala Ser Thr Pro
1               5                   10                  15

Ala Ser Thr Gly Ser Leu Thr Ala Ala Phe Asp Ala Ala Ala Thr Arg
            20                  25                  30

Tyr Gly Val Pro Arg Asp Leu Leu Ile Ala Ile Gly Tyr Ala Glu Thr
        35                  40                  45
```

-continued

```
His Leu Asp Gly His Ala Gly Thr Pro Ser Ala Ala Gly Gly Tyr Gly
        50                  55                  60

Val Met Asn Leu Thr Gly Asn Pro Ala Val His Thr Leu Ala Glu Ala
 65                  70                  75                  80

Ser Arg Leu Thr Gly Leu Lys Ala Ser Thr Leu Glu Asn Asn Gln Ala
                 85                  90                  95

Ala Asn Ile Leu Gly Ala Ala Val Leu Arg Ser Tyr Ala Ala Asp
            100                 105                 110

Leu Lys Thr Ala Gln Arg Asp Ser Val Asp Asn Trp Tyr Ala Ala Val
            115                 120                 125

Ala Arg Tyr Gly Gly Ala Thr Asp Pro Ser Val Ala Arg Leu Tyr Ala
            130                 135                 140

Asp Thr Val Tyr Asp Leu Leu Ala Thr Gly Phe Gly Val Pro Ala Lys
145                 150                 155                 160

Gly Val Ser Val Thr Ala Arg Ala Val Ala Pro Gln Arg Gly Thr Leu
                165                 170                 175

Ala Thr Ala Arg Ala Ser Leu Asp Ser Ala Asp Tyr Gly Pro Ala Ala
            180                 185                 190

Trp Ala Pro Ala Ser Thr Ser Asn Tyr Thr Val Ala Asn Arg Glu Thr
            195                 200                 205

Asp Tyr Asn Ile Asn Tyr Ile Val Ile His Val Thr Gln Gly Ser Tyr
210                 215                 220

Ala Gly Ser Ile Ser Trp Phe Gln Asn Pro Ala Ala Gln Val Ser Ala
225                 230                 235                 240

His Tyr Val Val Arg Ser Ser Asp Gly Ala Ile Thr Gln Ser Val Arg
                245                 250                 255

Glu Lys Asp Ile Ala Trp His Ala Gly Asn Trp Thr Tyr Asn Thr Gln
            260                 265                 270

Ala Ile Gly Ile Glu His Glu Gly Tyr Ile Asp Asp Pro Ser Trp Phe
            275                 280                 285

Thr Asp Ala Met Tyr Arg Ser Ser Ala Ala Leu Thr Arg Ser Leu Thr
            290                 295                 300

Thr Lys Tyr Ala Ile Pro Arg Asp Arg Ser His Ile Ile Gly His Ile
305                 310                 315                 320

Glu Val Pro Ser Ala Thr His Thr Asp Pro Gly Gln Tyr Trp Asn Trp
                325                 330                 335

Thr Tyr Tyr Met Gln Leu Val Asn Gly Val Thr Gly Ile Gly Thr Gly
            340                 345                 350

Thr Val Asn Val Ser Gly Ser Leu Asn Ile Arg Ser Gly Pro Gly Thr
            355                 360                 365

Gly Tyr Ala Val Ala Gly Ser Leu Ala Asn Gly Ala Gly Val Ser Val
            370                 375                 380

Tyr Cys Gln Ala Thr Gly Thr Thr Val Thr Gly Thr Tyr Gly Thr Ser
385                 390                 395                 400

Asn Ile Trp Asp Arg Ile Gly Thr Asn Lys Tyr Val Ala Asp Ala Tyr
                405                 410                 415

Val Leu Thr Gly Ser Asp Gly Phe Ile Pro Gly Val Pro Arg Cys
            420                 425                 430
```

<210> SEQ ID NO 4
<211> LENGTH: 1548
<212> TYPE: DNA
<213> ORGANISM: Micromonospora maritima
<220> FEATURE:

-continued

```
<221> NAME/KEY: CDS
<222> LOCATION: (1)..(1545)
<220> FEATURE:
<221> NAME/KEY: sig_peptide
<222> LOCATION: (1)..(90)
<220> FEATURE:
<221> NAME/KEY: mat_peptide
<222> LOCATION: (91)..(1545)

<400> SEQUENCE: 4 gtg acg att cgg aga ccc tcg cgt cgg gtg agt ctg ctc ggc ggc gcc      48
Val Thr Ile Arg Arg Pro Ser Arg Arg Val Ser Leu Leu Gly Gly Ala
-30                 -25                 -20                 -15 atg atc ctc atg atc ggc ctg acc ggc cag ccg gcc cag gcc gcg cct      96
Met Ile Leu Met Ile Gly Leu Thr Gly Gln Pro Ala Gln Ala Ala Pro
            -10                  -5                  -1   1 gca cac cgc gcg cag cct ctc gcc gcg gcc ttc gcg cag gcc gcg gcc     144
Ala His Arg Ala Gln Pro Leu Ala Ala Ala Phe Ala Gln Ala Ala Ala
                5                  10                  15 gat tcc gac gtg ccg cgc gac ctg ctc gcc gcg ctc ggg tac gcc gag     192
Asp Ser Asp Val Pro Arg Asp Leu Leu Ala Ala Leu Gly Tyr Ala Glu
 20                 25                  30 acc cgc ctg gac ggc cac ggc ggc gcg ccc agc gcc tcc ggc ggg tac     240
Thr Arg Leu Asp Gly His Gly Gly Ala Pro Ser Ala Ser Gly Gly Tyr
 35                 40                  45                  50 ggc gtg atg cac ctg acc agc aac ccg aag gtg cgg acg ctc gac gag     288
Gly Val Met His Leu Thr Ser Asn Pro Lys Val Arg Thr Leu Asp Glu
                55                  60                  65 gcc gcg cgc cgg acc cgg ctg gac cgc gcc gag ctg cgt acc cgg gac     336
Ala Ala Arg Arg Thr Arg Leu Asp Arg Ala Glu Leu Arg Thr Arg Asp
                70                  75                  80 gcg gcg aac gtg gcc ggc gcg gcg gtg ctg cgt tcc tac gcc gac         384
Ala Ala Asn Val Ala Gly Ala Ala Ala Val Leu Arg Ser Tyr Ala Asp
                85                  90                  95 gag gcc ggg ctc agc gcg gcg cag cgc gac gac gtc aac cag tgg tac     432
Glu Ala Gly Leu Ser Ala Ala Gln Arg Asp Asp Val Asn Gln Trp Tyr
            100                 105                 110 ggc ccg atc gcc cgc tac ggc ggc gcg acc gac ggg gcc acc gcc cgg     480
Gly Pro Ile Ala Arg Tyr Gly Gly Ala Thr Asp Gly Ala Thr Ala Arg
115                 120                 125                 130 ctg tac gcc gac tcc gtg tac gac ctc ctc gcc cgg ggc ttc atc gcg     528
Leu Tyr Ala Asp Ser Val Tyr Asp Leu Leu Ala Arg Gly Phe Ile Ala
                135                 140                 145 acc acg gcc ggc ggc gag gtc agc gtg gac ggc cgt ccg gtc gca ccg     576
Thr Thr Ala Gly Gly Glu Val Ser Val Asp Gly Arg Pro Val Ala Pro
            150                 155                 160 cag cgg ggc cgg tac gcc gac gtg gcg ccg ctg ggc acc ggt gac ttc     624
Gln Arg Gly Arg Tyr Ala Asp Val Ala Pro Leu Gly Thr Gly Asp Phe
            165                 170                 175 ggc acc ctg agc acc gac tac ggc ccg gcg gcc tgg gtg ccg gcc aac     672
Gly Thr Leu Ser Thr Asp Tyr Gly Pro Ala Ala Trp Val Pro Ala Asn
180                 185                 190 tcg tcc aac tac acg gtc tcc agc cgc gag tcg gcg tac ccg atc aac     720
Ser Ser Asn Tyr Thr Val Ser Ser Arg Glu Ser Ala Tyr Pro Ile Asn
195                 200                 205                 210 tac atc gtc atc cac acc atg cag ggc agc tac gcc ggc tcg atc agc     768
Tyr Ile Val Ile His Thr Met Gln Gly Ser Tyr Ala Gly Ser Ile Ser
                215                 220                 225 tgg ttc cag aac gcc gcc gcc ggc acc agc gcg cac tac ctg ctc cgc     816
Trp Phe Gln Asn Ala Ala Ala Gly Thr Ser Ala His Tyr Leu Leu Arg
            230                 235                 240
```

```
tcc tcc gac ggt gcg gtg acc cag atg gtg cgg gac aag gac atc gcc    864
Ser Ser Asp Gly Ala Val Thr Gln Met Val Arg Asp Lys Asp Ile Ala
        245                 250                 255 tgg cac gcc ggc aac tgg acc tac aac acc cag tcg atc ggc atc gag    912
Trp His Ala Gly Asn Trp Thr Tyr Asn Thr Gln Ser Ile Gly Ile Glu
260                 265                 270 cac gag ggg tac gtc gac aac gcc tcc tgg tac acc gac gcg atg tac    960
His Glu Gly Tyr Val Asp Asn Ala Ser Trp Tyr Thr Asp Ala Met Tyr
275                 280                 285                 290 cgg tcg tcg gcg gcg ctg acc cgg tac ctg tgc gac aag tac ggc atc   1008
Arg Ser Ser Ala Ala Leu Thr Arg Tyr Leu Cys Asp Lys Tyr Gly Ile
                295                 300                 305 ccg aag acc cgc acc aac atc atc ggg cac aac cag gtg ccg ggc gcc   1056
Pro Lys Thr Arg Thr Asn Ile Ile Gly His Asn Gln Val Pro Gly Ala
            310                 315                 320 acg cac acc gac ccg ggt ccg aac tgg aac tgg acc tac tac atg cag   1104
Thr His Thr Asp Pro Gly Pro Asn Trp Asn Trp Thr Tyr Tyr Met Gln
        325                 330                 335 ctc gtc acc ggc ggc acc acg ccc ccg acc gac tgg tcg acg atc       1152
Leu Val Thr Gly Gly Thr Thr Pro Pro Pro Thr Asp Trp Ser Thr Ile
340                 345                 350 gtg gac aac acc acc gcc ggc cgg ttc acc gcg agc gcc aac tgg ggc   1200
Val Asp Asn Thr Thr Ala Gly Arg Phe Thr Ala Ser Ala Asn Trp Gly
355                 360                 365                 370 acc tcg acg tac tcg gcg cag cgc tac ggc gcc gac tac cgg tac gcc   1248
Thr Ser Thr Tyr Ser Ala Gln Arg Tyr Gly Ala Asp Tyr Arg Tyr Ala
                375                 380                 385 aac ccc gtc gcg gcc agc gac acc gcc tgg tac aag gtg aac atc ccg   1296
Asn Pro Val Ala Ala Ser Asp Thr Ala Trp Tyr Lys Val Asn Ile Pro
            390                 395                 400 gcg acc gcc acc tac cgg gtg gag gtc tgg tat ccg gcc gtg gcc ggc   1344
Ala Thr Ala Thr Tyr Arg Val Glu Val Trp Tyr Pro Ala Val Ala Gly
        405                 410                 415 tac aac acc tcc acg ccg tac atc gtg gcg acg acc agc ggc aac cag   1392
Tyr Asn Thr Ser Thr Pro Tyr Ile Val Ala Thr Thr Ser Gly Asn Gln
420                 425                 430 acg gtc tcg gtg aac cag acg gcg aac ggc ggc ggg tgg cgg tcg ctg   1440
Thr Val Ser Val Asn Gln Thr Ala Asn Gly Gly Gly Trp Arg Ser Leu
435                 440                 445                 450 ggc acc ttc acc ctg gcc gcc ggg gac gcc aac aag gtg ggt gtc agc   1488
Gly Thr Phe Thr Leu Ala Ala Gly Asp Ala Asn Lys Val Gly Val Ser
                455                 460                 465 agg tgg tcc ggc agc acc ggg tac gtg atc gcc gac gcc atc cgc gtc   1536
Arg Trp Ser Gly Ser Thr Gly Tyr Val Ile Ala Asp Ala Ile Arg Val
            470                 475                 480 acc cgc gtc tag                                                   1548
Thr Arg Val
        485

<210> SEQ ID NO 5
<211> LENGTH: 515
<212> TYPE: PRT
<213> ORGANISM: Micromonospora maritima

<400> SEQUENCE: 5

Val Thr Ile Arg Arg Pro Ser Arg Arg Val Ser Leu Leu Gly Gly Ala
-30                 -25                 -20                 -15

Met Ile Leu Met Ile Gly Leu Thr Gly Gln Pro Ala Gln Ala Ala Pro
                -10                 -5                  -1  1
```

```
Ala His Arg Ala Gln Pro Leu Ala Ala Phe Ala Gln Ala Ala Ala
          5                  10                 15

Asp Ser Asp Val Pro Arg Asp Leu Leu Ala Ala Leu Gly Tyr Ala Glu
         20                  25                 30

Thr Arg Leu Asp Gly His Gly Gly Ala Pro Ser Ala Ser Gly Gly Tyr
35                  40                  45                 50

Gly Val Met His Leu Thr Ser Asn Pro Lys Val Arg Thr Leu Asp Glu
                55                  60                 65

Ala Ala Arg Arg Thr Arg Leu Asp Arg Ala Glu Leu Arg Thr Arg Asp
             70                  75                 80

Ala Ala Asn Val Ala Gly Ala Ala Val Leu Arg Ser Tyr Ala Asp
             85                  90                 95

Glu Ala Gly Leu Ser Ala Ala Gln Arg Asp Asp Val Asn Gln Trp Tyr
         100                 105                110

Gly Pro Ile Ala Arg Tyr Gly Gly Ala Thr Asp Gly Ala Thr Ala Arg
115                 120                 125                130

Leu Tyr Ala Asp Ser Val Tyr Asp Leu Leu Ala Arg Gly Phe Ile Ala
                135                 140                 145

Thr Thr Ala Gly Gly Glu Val Ser Val Asp Gly Arg Pro Val Ala Pro
             150                 155                 160

Gln Arg Gly Arg Tyr Ala Asp Val Ala Pro Leu Gly Thr Gly Asp Phe
         165                 170                 175

Gly Thr Leu Ser Thr Asp Tyr Gly Pro Ala Ala Trp Val Pro Ala Asn
180                 185                 190

Ser Ser Asn Tyr Thr Val Ser Ser Arg Glu Ser Ala Tyr Pro Ile Asn
195                 200                 205                 210

Tyr Ile Val Ile His Thr Met Gln Gly Ser Tyr Ala Gly Ser Ile Ser
                215                 220                 225

Trp Phe Gln Asn Ala Ala Ala Gly Thr Ser Ala His Tyr Leu Leu Arg
             230                 235                 240

Ser Ser Asp Gly Ala Val Thr Gln Met Val Arg Asp Lys Asp Ile Ala
         245                 250                 255

Trp His Ala Gly Asn Trp Thr Tyr Asn Thr Gln Ser Ile Gly Ile Glu
         260                 265                 270

His Glu Gly Tyr Val Asp Asn Ala Ser Trp Tyr Thr Asp Ala Met Tyr
275                 280                 285                 290

Arg Ser Ser Ala Ala Leu Thr Arg Tyr Leu Cys Asp Lys Tyr Gly Ile
             295                 300                 305

Pro Lys Thr Arg Thr Asn Ile Ile Gly His Asn Gln Val Pro Gly Ala
         310                 315                 320

Thr His Thr Asp Pro Gly Pro Asn Trp Asn Trp Thr Tyr Tyr Met Gln
         325                 330                 335

Leu Val Thr Gly Gly Thr Thr Pro Pro Thr Asp Trp Ser Thr Ile
340                 345                 350

Val Asp Asn Thr Thr Ala Gly Arg Phe Thr Ala Ser Ala Asn Trp Gly
355                 360                 365                 370

Thr Ser Thr Tyr Ser Ala Gln Arg Tyr Gly Ala Asp Tyr Arg Tyr Ala
                375                 380                 385

Asn Pro Val Ala Ala Ser Asp Thr Ala Trp Tyr Lys Val Asn Ile Pro
         390                 395                 400

Ala Thr Ala Thr Tyr Arg Val Glu Val Trp Tyr Pro Ala Val Ala Gly
         405                 410                 415
```

```
Tyr Asn Thr Ser Thr Pro Tyr Ile Val Ala Thr Thr Ser Gly Asn Gln
    420                 425                 430

Thr Val Ser Val Asn Gln Thr Ala Asn Gly Gly Gly Trp Arg Ser Leu
435                 440                 445                 450

Gly Thr Phe Thr Leu Ala Ala Gly Asp Ala Asn Lys Val Gly Val Ser
            455                 460                 465

Arg Trp Ser Gly Ser Thr Gly Tyr Val Ile Ala Asp Ala Ile Arg Val
            470                 475                 480

Thr Arg Val
        485

<210> SEQ ID NO 6
<211> LENGTH: 485
<212> TYPE: PRT
<213> ORGANISM: Micromonospora maritima

<400> SEQUENCE: 6

Ala Pro Ala His Arg Ala Gln Pro Leu Ala Ala Phe Ala Gln Ala
1               5                   10                  15

Ala Ala Asp Ser Asp Val Pro Arg Asp Leu Leu Ala Ala Leu Gly Tyr
                20                  25                  30

Ala Glu Thr Arg Leu Asp Gly His Gly Gly Ala Pro Ser Ala Ser Gly
            35                  40                  45

Gly Tyr Gly Val Met His Leu Thr Ser Asn Pro Lys Val Arg Thr Leu
    50                  55                  60

Asp Glu Ala Ala Arg Arg Thr Arg Leu Asp Arg Ala Glu Leu Arg Thr
65                  70                  75                  80

Arg Asp Ala Ala Asn Val Ala Gly Ala Ala Ala Val Leu Arg Ser Tyr
                85                  90                  95

Ala Asp Glu Ala Gly Leu Ser Ala Ala Gln Arg Asp Asp Val Asn Gln
            100                 105                 110

Trp Tyr Gly Pro Ile Ala Arg Tyr Gly Gly Ala Thr Asp Gly Ala Thr
    115                 120                 125

Ala Arg Leu Tyr Ala Asp Ser Val Tyr Asp Leu Leu Ala Arg Gly Phe
130                 135                 140

Ile Ala Thr Thr Ala Gly Gly Glu Val Ser Val Asp Gly Arg Pro Val
145                 150                 155                 160

Ala Pro Gln Arg Gly Arg Tyr Ala Asp Val Ala Pro Leu Gly Thr Gly
                165                 170                 175

Asp Phe Gly Thr Leu Ser Thr Asp Tyr Gly Pro Ala Ala Trp Val Pro
            180                 185                 190

Ala Asn Ser Ser Asn Tyr Thr Val Ser Ser Arg Glu Ser Ala Tyr Pro
    195                 200                 205

Ile Asn Tyr Ile Val Ile His Thr Met Gln Gly Ser Tyr Ala Gly Ser
210                 215                 220

Ile Ser Trp Phe Gln Asn Ala Ala Ala Gly Thr Ser Ala His Tyr Leu
225                 230                 235                 240

Leu Arg Ser Ser Asp Gly Ala Val Thr Gln Met Val Arg Asp Lys Asp
                245                 250                 255

Ile Ala Trp His Ala Gly Asn Trp Thr Tyr Asn Thr Gln Ser Ile Gly
            260                 265                 270

Ile Glu His Glu Gly Tyr Val Asp Asn Ala Ser Trp Tyr Thr Asp Ala
    275                 280                 285

Met Tyr Arg Ser Ser Ala Ala Leu Thr Arg Tyr Leu Cys Asp Lys Tyr
290                 295                 300
```

-continued

```
Gly Ile Pro Lys Thr Arg Thr Asn Ile Ile Gly His Asn Gln Val Pro
305                 310                 315                 320

Gly Ala Thr His Thr Asp Pro Gly Pro Asn Trp Asn Trp Thr Tyr Tyr
                325                 330                 335

Met Gln Leu Val Thr Gly Gly Thr Thr Pro Pro Pro Thr Asp Trp Ser
            340                 345                 350

Thr Ile Val Asp Asn Thr Thr Ala Gly Arg Phe Thr Ala Ser Ala Asn
        355                 360                 365

Trp Gly Thr Ser Thr Tyr Ser Ala Gln Arg Tyr Gly Ala Asp Tyr Arg
    370                 375                 380

Tyr Ala Asn Pro Val Ala Ala Ser Asp Thr Ala Trp Tyr Lys Val Asn
385                 390                 395                 400

Ile Pro Ala Thr Ala Thr Tyr Arg Val Glu Val Trp Tyr Pro Ala Val
                405                 410                 415

Ala Gly Tyr Asn Thr Ser Thr Pro Tyr Ile Val Ala Thr Thr Ser Gly
            420                 425                 430

Asn Gln Thr Val Ser Val Asn Gln Thr Ala Asn Gly Gly Gly Trp Arg
        435                 440                 445

Ser Leu Gly Thr Phe Thr Leu Ala Ala Gly Asp Ala Asn Lys Val Gly
    450                 455                 460

Val Ser Arg Trp Ser Gly Ser Thr Gly Tyr Val Ile Ala Asp Ala Ile
465                 470                 475                 480

Arg Val Thr Arg Val
                485

<210> SEQ ID NO 7
<211> LENGTH: 1527
<212> TYPE: DNA
<213> ORGANISM: Paenibacillus sp
<220> FEATURE:
<221> NAME/KEY: CDS
<222> LOCATION: (1)..(1527)
<220> FEATURE:
<221> NAME/KEY: sig_peptide
<222> LOCATION: (1)..(78)
<220> FEATURE:
<221> NAME/KEY: mat_peptide
<222> LOCATION: (79)..(1527)

<400> SEQUENCE: 7 atg gga att cgt cgc gtt tct cgc ctt ctt agc atc tct ctt tct gcc      48
Met Gly Ile Arg Arg Val Ser Arg Leu Leu Ser Ile Ser Leu Ser Ala
    -25                 -20                 -15 atg ctt ctt ctt cca ttt aca gtt cca gct gca tca ttt gca gca gac      96
Met Leu Leu Leu Pro Phe Thr Val Pro Ala Ala Ser Phe Ala Ala Asp
-10                  -5                  -1   1               5 gac gct gcg gta tca gcg aac tct gca tct gca gga aaa ggt tct ctt     144
Asp Ala Ala Val Ser Ala Asn Ser Ala Ser Ala Gly Lys Gly Ser Leu
                10                  15                  20 caa aaa gct ttc gaa gcc gct agc caa gag ttt ggc gtt cca gta gag     192
Gln Lys Ala Phe Glu Ala Ala Ser Gln Glu Phe Gly Val Pro Val Glu
            25                  30                  35 atc ctt ctt ggc ctt agc tac gct gag act cgc tgg aac gac cac gag     240
Ile Leu Leu Gly Leu Ser Tyr Ala Glu Thr Arg Trp Asn Asp His Glu
        40                  45                  50 gga aag cct tct caa ctt aac gga tat ggc ctt atg cac ctt gct gag     288
Gly Lys Pro Ser Gln Leu Asn Gly Tyr Gly Leu Met His Leu Ala Glu
55                  60                  65                  70
```

| | | | | | | | | | | | | | | | |
|---|---|---|---|---|---|---|---|---|---|---|---|---|---|---|---|
| aac | ccg | aaa | aac | tct | tca | ctt | agc | aca | gct | gct | gag | caa | ctt | aaa | gta | 336
| Asn | Pro | Lys | Asn | Ser | Ser | Leu | Ser | Thr | Ala | Ala | Glu | Gln | Leu | Lys | Val |
| | | | | 75 | | | | 80 | | | | | 85 | | |
| gac | aaa | caa | ctt | ctt | aag | aca | gac | aaa | gca | gtt | aac | att | cgc | gga | tct | 384
| Asp | Lys | Gln | Leu | Leu | Lys | Thr | Asp | Lys | Ala | Val | Asn | Ile | Arg | Gly | Ser |
| | | | 90 | | | | 95 | | | | | 100 | | | |
| gcg | gct | gta | ctt | gca | ggc | ctt | gca | aag | gcg | aaa | aac | aac | gga | aaa | ctt | 432
| Ala | Ala | Val | Leu | Ala | Gly | Leu | Ala | Lys | Ala | Lys | Asn | Asn | Gly | Lys | Leu |
| | | | 105 | | | | 110 | | | | | 115 | | | |
| ccg | gct | tct | ctt | gct | gac | tgg | tat | acg | aca | gta | gca | gcg | tat | tct | gga | 480
| Pro | Ala | Ser | Leu | Ala | Asp | Trp | Tyr | Thr | Thr | Val | Ala | Ala | Tyr | Ser | Gly |
| | | 120 | | | | | 125 | | | | | 130 | | | |
| atc | gac | gac | ctt | ccg | ctt | gct | cgc | gtt | tac | gct | gac | gag | gtt | ttc | aaa | 528
| Ile | Asp | Asp | Leu | Pro | Leu | Ala | Arg | Val | Tyr | Ala | Asp | Glu | Val | Phe | Lys |
| 135 | | | | 140 | | | | | 145 | | | | | | 150 |
| gtt | atc | aac | gag | gga | aaa | caa | gcg | ctt | agc | ggc | aca | gag | atc | ctt | cac | 576
| Val | Ile | Asn | Glu | Gly | Lys | Gln | Ala | Leu | Ser | Gly | Thr | Glu | Ile | Leu | His |
| | | | | | 155 | | | | | 160 | | | | | 165 |
| ctt | aac | cct | acg | cca | gtt | act | ccg | aat | cgc | gct | gag | tac | acg | caa | gct | 624
| Leu | Asn | Pro | Thr | Pro | Val | Thr | Pro | Asn | Arg | Ala | Glu | Tyr | Thr | Gln | Ala |
| | | | 170 | | | | | 175 | | | | | 180 | | |
| act | ctt | gct | gcg | act | gct | atg | gac | tac | cct | ggt | gct | atc | tgg | aac | gct | 672
| Thr | Leu | Ala | Ala | Thr | Ala | Met | Asp | Tyr | Pro | Gly | Ala | Ile | Trp | Asn | Ala |
| | | 185 | | | | | 190 | | | | | 195 | | | |
| gct | tac | tct | ggc | aac | tac | tct | gta | ggc | tct | cgt | ggc | cca | gga | gac | atc | 720
| Ala | Tyr | Ser | Gly | Asn | Tyr | Ser | Val | Gly | Ser | Arg | Gly | Pro | Gly | Asp | Ile |
| | | 200 | | | | 205 | | | | | 210 | | | | |
| tct | aac | atc | gta | atc | cat | act | aca | caa | ggt | tca | tat | gct | ggc | aca | atc | 768
| Ser | Asn | Ile | Val | Ile | His | Thr | Thr | Gln | Gly | Ser | Tyr | Ala | Gly | Thr | Ile |
| 215 | | | | | 220 | | | | | 225 | | | | | 230 |
| aac | tgg | ttc | aaa | gac | cct | gct | gct | gta | gtt | tca | gcg | cat | tat | gtt | gtt | 816
| Asn | Trp | Phe | Lys | Asp | Pro | Ala | Ala | Val | Val | Ser | Ala | His | Tyr | Val | Val |
| | | | | 235 | | | | | 240 | | | | | 245 | |
| cgc | agc | tct | gac | ggc | cag | atc | aca | caa | atg | gta | cgc | gac | aaa | gac | atc | 864
| Arg | Ser | Ser | Asp | Gly | Gln | Ile | Thr | Gln | Met | Val | Arg | Asp | Lys | Asp | Ile |
| | | | 250 | | | | | 255 | | | | | 260 | | |
| gca | tac | cat | gct | cgc | tct | gca | aac | agc | aca | tca | ctt | ggc | atc | gag | cat | 912
| Ala | Tyr | His | Ala | Arg | Ser | Ala | Asn | Ser | Thr | Ser | Leu | Gly | Ile | Glu | His |
| | | 265 | | | | | 270 | | | | | 275 | | | |
| gag | ggc | tat | gta | act | gac | cct | gca | tgg | tat | act | gac | tca | atg | tat | cgc | 960
| Glu | Gly | Tyr | Val | Thr | Asp | Pro | Ala | Trp | Tyr | Thr | Asp | Ser | Met | Tyr | Arg |
| | 280 | | | | | 285 | | | | | 290 | | | | |
| tca | tct | gca | gct | ctt | act | cgc | tgg | ctt | tgc | gac | cag | tat | ggc | atc | cca | 1008
| Ser | Ser | Ala | Ala | Leu | Thr | Arg | Trp | Leu | Cys | Asp | Gln | Tyr | Gly | Ile | Pro |
| 295 | | | | | 300 | | | | | 305 | | | | | 310 |
| aaa | aca | cgc | aca | gct | atc | aaa | ggc | cat | tct | gag | atg | cct | ggt | aac | gac | 1056
| Lys | Thr | Arg | Thr | Ala | Ile | Lys | Gly | His | Ser | Glu | Met | Pro | Gly | Asn | Asp |
| | | | | 315 | | | | | 320 | | | | | 325 | |
| cac | aca | gac | cct | ggc | agc | aac | tgg | gac | tgg | act | tac | tac | atg | tca | ctt | 1104
| His | Thr | Asp | Pro | Gly | Ser | Asn | Trp | Asp | Trp | Thr | Tyr | Tyr | Met | Ser | Leu |
| | | 330 | | | | | 335 | | | | | 340 | | | |
| gtt | aac | cct | cca | gta | act | ggt | ggc | atc | atc | gta | gac | aac | gca | aca | gct | 1152
| Val | Asn | Pro | Pro | Val | Thr | Gly | Gly | Ile | Ile | Val | Asp | Asn | Ala | Thr | Ala |
| | | 345 | | | | | 350 | | | | | 355 | | | |
| ggc | gct | ttc | acg | gcg | agc | gca | aac | tgg | ggt | aca | gct | act | tgg | aac | act | 1200
| Gly | Ala | Phe | Thr | Ala | Ser | Ala | Asn | Trp | Gly | Thr | Ala | Thr | Trp | Asn | Thr |
| | 360 | | | | | 365 | | | | | 370 | | | | |

```
gag aag tat ggc tct gac tat cgc tac aca aca cct caa gct gtt tca    1248
Glu Lys Tyr Gly Ser Asp Tyr Arg Tyr Thr Thr Pro Gln Ala Val Ser
375                 380                 385                 390 gac cca gca tgg ttc caa gcg aca atc cct aca gct ggc tct tat gac    1296
Asp Pro Ala Trp Phe Gln Ala Thr Ile Pro Thr Ala Gly Ser Tyr Asp
                395                 400                 405 gtt tat gct tgg tgg cct tca aac gct gcg tat aac gac aaa acg ccg    1344
Val Tyr Ala Trp Trp Pro Ser Asn Ala Ala Tyr Asn Asp Lys Thr Pro
410                 415                 420 ttt atc atc agc aca tct act ggt aac caa aca gtt aac gtt aac cag    1392
Phe Ile Ile Ser Thr Ser Thr Gly Asn Gln Thr Val Asn Val Asn Gln
        425                 430                 435 caa gct aac ggt ggt aaa tgg atg ctt ctt ggt aag tac act ctt aac    1440
Gln Ala Asn Gly Gly Lys Trp Met Leu Leu Gly Lys Tyr Thr Leu Asn
440                 445                 450 agc ggc acg tat aac gta gtt ggc atc tct cgc tgg aca tca gga act    1488
Ser Gly Thr Tyr Asn Val Val Gly Ile Ser Arg Trp Thr Ser Gly Thr
455                 460                 465                 470 ggc aac atc ttc gcc gac gct atc cgc ctt gta atc aaa                1527
Gly Asn Ile Phe Ala Asp Ala Ile Arg Leu Val Ile Lys
                475                 480

<210> SEQ ID NO 8
<211> LENGTH: 509
<212> TYPE: PRT
<213> ORGANISM: Paenibacillus sp

<400> SEQUENCE: 8

Met Gly Ile Arg Arg Val Ser Arg Leu Leu Ser Ile Ser Leu Ser Ala
        -25                 -20                 -15

Met Leu Leu Leu Pro Phe Thr Val Pro Ala Ala Ser Phe Ala Ala Asp
-10                 -5              -1   1                   5

Asp Ala Ala Val Ser Ala Asn Ser Ala Ser Ala Gly Lys Gly Ser Leu
                10                  15                  20

Gln Lys Ala Phe Glu Ala Ala Ser Gln Glu Phe Gly Val Pro Val Glu
            25                  30                  35

Ile Leu Leu Gly Leu Ser Tyr Ala Glu Thr Arg Trp Asn Asp His Glu
        40                  45                  50

Gly Lys Pro Ser Gln Leu Asn Gly Tyr Gly Leu Met His Leu Ala Glu
55                  60                  65                  70

Asn Pro Lys Asn Ser Ser Leu Ser Thr Ala Ala Glu Gln Leu Lys Val
                75                  80                  85

Asp Lys Gln Leu Leu Lys Thr Asp Lys Ala Val Asn Ile Arg Gly Ser
            90                  95                  100

Ala Ala Val Leu Ala Gly Leu Ala Lys Ala Lys Asn Asn Gly Lys Leu
        105                 110                 115

Pro Ala Ser Leu Ala Asp Trp Tyr Thr Thr Val Ala Ala Tyr Ser Gly
120                 125                 130

Ile Asp Asp Leu Pro Leu Ala Arg Val Tyr Ala Asp Glu Val Phe Lys
135                 140                 145                 150

Val Ile Asn Glu Gly Lys Gln Ala Leu Ser Gly Thr Glu Ile Leu His
                155                 160                 165

Leu Asn Pro Thr Pro Val Thr Pro Asn Arg Ala Glu Tyr Thr Gln Ala
            170                 175                 180

Thr Leu Ala Ala Thr Ala Met Asp Tyr Pro Gly Ala Ile Trp Asn Ala
        185                 190                 195
```

Ala Tyr Ser Gly Asn Tyr Ser Val Gly Ser Arg Gly Pro Gly Asp Ile
            200                 205                 210

Ser Asn Ile Val Ile His Thr Thr Gln Gly Ser Tyr Ala Gly Thr Ile
215                 220                 225                 230

Asn Trp Phe Lys Asp Pro Ala Ala Val Val Ser Ala His Tyr Val Val
                235                 240                 245

Arg Ser Ser Asp Gly Gln Ile Thr Gln Met Val Arg Asp Lys Asp Ile
            250                 255                 260

Ala Tyr His Ala Arg Ser Ala Asn Ser Thr Ser Leu Gly Ile Glu His
            265                 270                 275

Glu Gly Tyr Val Thr Asp Pro Ala Trp Tyr Thr Asp Ser Met Tyr Arg
    280                 285                 290

Ser Ser Ala Ala Leu Thr Arg Trp Leu Cys Asp Gln Tyr Gly Ile Pro
295                 300                 305                 310

Lys Thr Arg Thr Ala Ile Lys Gly His Ser Glu Met Pro Gly Asn Asp
                315                 320                 325

His Thr Asp Pro Gly Ser Asn Trp Asp Trp Thr Tyr Tyr Met Ser Leu
            330                 335                 340

Val Asn Pro Pro Val Thr Gly Ile Ile Val Asp Asn Ala Thr Ala
            345                 350                 355

Gly Ala Phe Thr Ala Ser Ala Asn Trp Gly Thr Ala Thr Trp Asn Thr
    360                 365                 370

Glu Lys Tyr Gly Ser Asp Tyr Arg Tyr Thr Thr Pro Gln Ala Val Ser
375                 380                 385                 390

Asp Pro Ala Trp Phe Gln Ala Thr Ile Pro Thr Ala Gly Ser Tyr Asp
                395                 400                 405

Val Tyr Ala Trp Trp Pro Ser Asn Ala Ala Tyr Asn Asp Lys Thr Pro
            410                 415                 420

Phe Ile Ile Ser Thr Ser Thr Gly Asn Gln Thr Val Asn Val Asn Gln
                425                 430                 435

Gln Ala Asn Gly Gly Lys Trp Met Leu Leu Gly Lys Tyr Thr Leu Asn
    440                 445                 450

Ser Gly Thr Tyr Asn Val Val Gly Ile Ser Arg Trp Thr Ser Gly Thr
455                 460                 465                 470

Gly Asn Ile Phe Ala Asp Ala Ile Arg Leu Val Ile Lys
                475                 480

<210> SEQ ID NO 9
<211> LENGTH: 483
<212> TYPE: PRT
<213> ORGANISM: Paenibacillus sp

<400> SEQUENCE: 9

Ala Ser Phe Ala Ala Asp Ala Ala Val Ser Ala Asn Ser Ala Ser
1               5                   10                  15

Ala Gly Lys Gly Ser Leu Gln Lys Ala Phe Glu Ala Ala Ser Gln Glu
            20                  25                  30

Phe Gly Val Pro Val Glu Ile Leu Leu Gly Leu Ser Tyr Ala Glu Thr
        35                  40                  45

Arg Trp Asn Asp His Glu Gly Lys Pro Ser Gln Leu Asn Gly Tyr Gly
    50                  55                  60

Leu Met His Leu Ala Glu Asn Pro Lys Asn Ser Ser Leu Ser Thr Ala
65                  70                  75                  80

Ala Glu Gln Leu Lys Val Asp Lys Gln Leu Leu Lys Thr Asp Lys Ala
                85                  90                  95

```
Val Asn Ile Arg Gly Ser Ala Ala Val Leu Ala Gly Leu Ala Lys Ala
            100                 105                 110

Lys Asn Asn Gly Lys Leu Pro Ala Ser Leu Ala Asp Trp Tyr Thr Thr
            115                 120                 125

Val Ala Ala Tyr Ser Gly Ile Asp Asp Leu Pro Leu Ala Arg Val Tyr
130                 135                 140

Ala Asp Glu Val Phe Lys Val Ile Asn Glu Gly Lys Gln Ala Leu Ser
145                 150                 155                 160

Gly Thr Glu Ile Leu His Leu Asn Pro Thr Pro Val Thr Pro Asn Arg
                165                 170                 175

Ala Glu Tyr Thr Gln Ala Thr Leu Ala Ala Thr Ala Met Asp Tyr Pro
            180                 185                 190

Gly Ala Ile Trp Asn Ala Ala Tyr Ser Gly Asn Tyr Ser Val Gly Ser
            195                 200                 205

Arg Gly Pro Gly Asp Ile Ser Asn Ile Val Ile His Thr Thr Gln Gly
            210                 215                 220

Ser Tyr Ala Gly Thr Ile Asn Trp Phe Lys Asp Pro Ala Ala Val Val
225                 230                 235                 240

Ser Ala His Tyr Val Val Arg Ser Ser Asp Gly Gln Ile Thr Gln Met
                245                 250                 255

Val Arg Asp Lys Asp Ile Ala Tyr His Ala Arg Ser Ala Asn Ser Thr
                260                 265                 270

Ser Leu Gly Ile Glu His Glu Gly Tyr Val Thr Asp Pro Ala Trp Tyr
            275                 280                 285

Thr Asp Ser Met Tyr Arg Ser Ser Ala Ala Leu Thr Arg Trp Leu Cys
290                 295                 300

Asp Gln Tyr Gly Ile Pro Lys Thr Arg Thr Ala Ile Lys Gly His Ser
305                 310                 315                 320

Glu Met Pro Gly Asn Asp His Thr Asp Pro Gly Ser Asn Trp Asp Trp
                325                 330                 335

Thr Tyr Tyr Met Ser Leu Val Asn Pro Pro Val Thr Gly Gly Ile Ile
            340                 345                 350

Val Asp Asn Ala Thr Ala Gly Ala Phe Thr Ala Ser Ala Asn Trp Gly
            355                 360                 365

Thr Ala Thr Trp Asn Thr Glu Lys Tyr Gly Ser Asp Tyr Arg Tyr Thr
370                 375                 380

Thr Pro Gln Ala Val Ser Asp Pro Ala Trp Phe Gln Ala Thr Ile Pro
385                 390                 395                 400

Thr Ala Gly Ser Tyr Asp Val Tyr Ala Trp Pro Ser Asn Ala Ala
                405                 410                 415

Tyr Asn Asp Lys Thr Pro Phe Ile Ile Ser Thr Ser Thr Gly Asn Gln
            420                 425                 430

Thr Val Asn Val Asn Gln Gln Ala Asn Gly Gly Lys Trp Met Leu Leu
            435                 440                 445

Gly Lys Tyr Thr Leu Asn Ser Gly Thr Tyr Asn Val Val Gly Ile Ser
            450                 455                 460

Arg Trp Thr Ser Gly Thr Gly Asn Ile Phe Ala Asp Ala Ile Arg Leu
465                 470                 475                 480

Val Ile Lys

<210> SEQ ID NO 10
<211> LENGTH: 1479
<212> TYPE: DNA
```

```
<213> ORGANISM: Nonomuraea sp
<220> FEATURE:
<221> NAME/KEY: CDS
<222> LOCATION: (1)..(1479)
<220> FEATURE:
<221> NAME/KEY: sig_peptide
<222> LOCATION: (1)..(66)
<220> FEATURE:
<221> NAME/KEY: mat_peptide
<222> LOCATION: (67)..(1479)

<400> SEQUENCE: 10
```

| | | | | | | | | | | | | | | | | |
|---|---|---|---|---|---|---|---|---|---|---|---|---|---|---|---|---|
| atg | agc | cgt | ctt | gca | gca | atc | gtt | ttt | gct | gta | ctt | ctt | gct | ttc | ggt | 48 |
| Met | Ser | Arg | Leu | Ala | Ala | Ile | Val | Phe | Ala | Val | Leu | Leu | Ala | Phe | Gly | |
| | | -20 | | | | -15 | | | | -10 | | | | | | |
| ttt | tct | cct | gcg | tac | gca | gcg | gca | gac | cca | ctt | aca | gaa | gct | ttc | gac | 96 |
| Phe | Ser | Pro | Ala | Tyr | Ala | Ala | Ala | Asp | Pro | Leu | Thr | Glu | Ala | Phe | Asp | |
| | -5 | | | | -1 | 1 | | | 5 | | | | | | 10 | |
| cgt | gct | gcg | gct | gct | cac | gac | gta | cct | cgt | gac | ctt | ctt | gtt | gct | ttg | 144 |
| Arg | Ala | Ala | Ala | Ala | His | Asp | Val | Pro | Arg | Asp | Leu | Leu | Val | Ala | Leu | |
| | | | | 15 | | | | | 20 | | | | | 25 | | |
| gct | tac | gct | gaa | aca | cac | tta | aac | ggc | cac | aac | ggc | gaa | cca | tct | gca | 192 |
| Ala | Tyr | Ala | Glu | Thr | His | Leu | Asn | Gly | His | Asn | Gly | Glu | Pro | Ser | Ala | |
| | | | 30 | | | | | 35 | | | | | 40 | | | |
| tca | ggt | ggc | tat | gga | atg | atg | cac | ctt | gtt | tct | aat | cca | aca | aca | aaa | 240 |
| Ser | Gly | Gly | Tyr | Gly | Met | Met | His | Leu | Val | Ser | Asn | Pro | Thr | Thr | Lys | |
| | | 45 | | | | | 50 | | | | | 55 | | | | |
| gct | ctt | gct | aaa | gct | gcc | gaa | ctt | aca | gga | tta | cct | gca | gct | gag | tta | 288 |
| Ala | Leu | Ala | Lys | Ala | Ala | Glu | Leu | Thr | Gly | Leu | Pro | Ala | Ala | Glu | Leu | |
| | 60 | | | | | 65 | | | | | 70 | | | | | |
| cgt | gct | gac | gat | gca | gcg | aac | atc | tta | ggt | ggt | gca | gca | gta | ctt | cgt | 336 |
| Arg | Ala | Asp | Asp | Ala | Ala | Asn | Ile | Leu | Gly | Gly | Ala | Ala | Val | Leu | Arg | |
| 75 | | | | | 80 | | | | | 85 | | | | | 90 | |
| agc | cat | gct | gat | gct | ctt | ggt | ttg | gac | gaa | gca | gca | cgt | aaa | gat | gct | 384 |
| Ser | His | Ala | Asp | Ala | Leu | Gly | Leu | Asp | Glu | Ala | Ala | Arg | Lys | Asp | Ala | |
| | | | | 95 | | | | | 100 | | | | | 105 | | |
| ggc | cgt | tgg | tac | caa | gca | gtt | gcg | gaa | tac | ggt | aac | gca | tct | aca | cca | 432 |
| Gly | Arg | Trp | Tyr | Gln | Ala | Val | Ala | Glu | Tyr | Gly | Asn | Ala | Ser | Thr | Pro | |
| | | | 110 | | | | | 115 | | | | | 120 | | | |
| gag | act | gca | cgt | ctt | tat | gcg | gat | gca | gta | tac | gaa | ttc | ctt | ggc | aaa | 480 |
| Glu | Thr | Ala | Arg | Leu | Tyr | Ala | Asp | Ala | Val | Tyr | Glu | Phe | Leu | Gly | Lys | |
| | | 125 | | | | | 130 | | | | | 135 | | | | |
| ggc | ttc | gag | gct | gca | ggt | gtt | aaa | gta | gct | cca | caa | gaa | gta | act | gcc | 528 |
| Gly | Phe | Glu | Ala | Ala | Gly | Val | Lys | Val | Ala | Pro | Gln | Glu | Val | Thr | Ala | |
| | 140 | | | | | 145 | | | | | 150 | | | | | |
| gac | cgt | ggt | gcg | tac | gct | aag | aca | cgc | gag | tta | aca | gct | gcg | gct | agc | 576 |
| Asp | Arg | Gly | Ala | Tyr | Ala | Lys | Thr | Arg | Glu | Leu | Thr | Ala | Ala | Ala | Ser | |
| 155 | | | | | 160 | | | | | 165 | | | | | 170 | |
| cca | gac | tac | cct | gac | ggc | aca | tgg | gtt | gct | gct | tct | tct | tct | aac | tac | 624 |
| Pro | Asp | Tyr | Pro | Asp | Gly | Thr | Trp | Val | Ala | Ala | Ser | Ser | Ser | Asn | Tyr | |
| | | | 175 | | | | | 180 | | | | | 185 | | | |
| act | gca | tct | tct | cgc | cca | tca | agc | tac | gcg | atc | gat | cgt | gtt | gta | atc | 672 |
| Thr | Ala | Ser | Ser | Arg | Pro | Ser | Ser | Tyr | Ala | Ile | Asp | Arg | Val | Val | Ile | |
| | | 190 | | | | | 195 | | | | | 200 | | | | |
| cac | gta | act | cag | gga | tca | tat | gct | ggc | agc | atc | agc | tgg | ttt | caa | aac | 720 |
| His | Val | Thr | Gln | Gly | Ser | Tyr | Ala | Gly | Ser | Ile | Ser | Trp | Phe | Gln | Asn | |
| | 205 | | | | | 210 | | | | | 215 | | | | | |
| cct | tct | gct | ggc | gtt | tct | gca | cac | tac | gtt | att | cgt | tct | tct | gat | ggt | 768 |
| Pro | Ser | Ala | Gly | Val | Ser | Ala | His | Tyr | Val | Ile | Arg | Ser | Ser | Asp | Gly | |
| 220 | | | | | 225 | | | | | 230 | | | | | | |

```
gct gtt act caa atg gtt cgt aac aaa gat gtt gct tgg cat gca ggc      816
Ala Val Thr Gln Met Val Arg Asn Lys Asp Val Ala Trp His Ala Gly
235                 240                 245                 250 aac tgg ggc tat aac aca cgt tct atc ggc att gaa cat gaa gga tgg      864
Asn Trp Gly Tyr Asn Thr Arg Ser Ile Gly Ile Glu His Glu Gly Trp
                255                 260                 265 gta tca gat gct tct tgg ttc act gaa gct atg tat cgt agc tct ggt      912
Val Ser Asp Ala Ser Trp Phe Thr Glu Ala Met Tyr Arg Ser Ser Gly
            270                 275                 280 gca ttg act cgt tac att tgt gac aaa tac ggc atc cct aaa gat cgt      960
Ala Leu Thr Arg Tyr Ile Cys Asp Lys Tyr Gly Ile Pro Lys Asp Arg
        285                 290                 295 tca cac atc att ggt cac aac caa gta cca gga gcg act cat aca gac     1008
Ser His Ile Ile Gly His Asn Gln Val Pro Gly Ala Thr His Thr Asp
300                 305                 310 cca ggt agc cat tgg gat tgg acg aag tat atg tct tat gtt aat ggt     1056
Pro Gly Ser His Trp Asp Trp Thr Lys Tyr Met Ser Tyr Val Asn Gly
315                 320                 325                 330 gga gga gga aca cca tct tgg tct gtt act gta gac aat act aca gca     1104
Gly Gly Gly Thr Pro Ser Trp Ser Val Thr Val Asp Asn Thr Thr Ala
                335                 340                 345 ggc aaa ttc aca gct tca gca aac tgg ggt act tct gcc tat tct ggc     1152
Gly Lys Phe Thr Ala Ser Ala Asn Trp Gly Thr Ser Ala Tyr Ser Gly
            350                 355                 360 caa cgc cat ggt gct gac tac cgt ttc gca act cct ctt gca gca tct     1200
Gln Arg His Gly Ala Asp Tyr Arg Phe Ala Thr Pro Leu Ala Ala Ser
        365                 370                 375 gat cct gct tgg ttc aaa gct aac atc cct tct gca ggt tct tat cgt     1248
Asp Pro Ala Trp Phe Lys Ala Asn Ile Pro Ser Ala Gly Ser Tyr Arg
380                 385                 390 gtt gaa gtt tgg tat ccg tct gac cct ggc tat aac tct tca gct cct     1296
Val Glu Val Trp Tyr Pro Ser Asp Pro Gly Tyr Asn Ser Ser Ala Pro
395                 400                 405                 410 tac atc gta gct gct tct ggc ggt aac caa aca gtt ttc gtt gat caa     1344
Tyr Ile Val Ala Ala Ser Gly Gly Asn Gln Thr Val Phe Val Asp Gln
                415                 420                 425 cgt tca gga ggc ggt gga tgg cgc act ctt gga acg ttc tct ttg acg     1392
Arg Ser Gly Gly Gly Trp Arg Thr Leu Gly Thr Phe Ser Leu Thr
            430                 435                 440 gct ggc gaa cac gac gtt gta gga gtt agc cgc tgg aca tct ggc acg     1440
Ala Gly Glu His Asp Val Val Gly Val Ser Arg Trp Thr Ser Gly Thr
        445                 450                 455 ggc tat gta gta gca gat gct gta cgc att tca cat tta                 1479
Gly Tyr Val Val Ala Asp Ala Val Arg Ile Ser His Leu
460                 465                 470

<210> SEQ ID NO 11
<211> LENGTH: 493
<212> TYPE: PRT
<213> ORGANISM: Nonomuraea sp

<400> SEQUENCE: 11

Met Ser Arg Leu Ala Ala Ile Val Phe Ala Val Leu Leu Ala Phe Gly
        -20                 -15                 -10

Phe Ser Pro Ala Tyr Ala Ala Ala Asp Pro Leu Thr Glu Ala Phe Asp
    -5                  -1  1               5                  10

Arg Ala Ala Ala His Asp Val Pro Arg Asp Leu Leu Val Ala Leu
                15                  20                  25
```

Ala Tyr Ala Glu Thr His Leu Asn Gly His Asn Gly Glu Pro Ser Ala
                30                  35                  40

Ser Gly Gly Tyr Gly Met Met His Leu Val Ser Asn Pro Thr Thr Lys
            45                  50                  55

Ala Leu Ala Lys Ala Ala Glu Leu Thr Gly Leu Pro Ala Ala Glu Leu
        60                  65                  70

Arg Ala Asp Asp Ala Ala Asn Ile Leu Gly Ala Ala Val Leu Arg
75                  80                  85                  90

Ser His Ala Asp Ala Leu Gly Leu Asp Glu Ala Ala Arg Lys Asp Ala
                95                  100                 105

Gly Arg Trp Tyr Gln Ala Val Ala Glu Tyr Gly Asn Ala Ser Thr Pro
            110                 115                 120

Glu Thr Ala Arg Leu Tyr Ala Asp Ala Val Tyr Glu Phe Leu Gly Lys
        125                 130                 135

Gly Phe Glu Ala Ala Gly Val Lys Val Ala Pro Gln Glu Val Thr Ala
    140                 145                 150

Asp Arg Gly Ala Tyr Ala Lys Thr Arg Glu Leu Thr Ala Ala Ala Ser
155                 160                 165                 170

Pro Asp Tyr Pro Asp Gly Thr Trp Val Ala Ala Ser Ser Ser Asn Tyr
                175                 180                 185

Thr Ala Ser Ser Arg Pro Ser Ser Tyr Ala Ile Asp Arg Val Val Ile
            190                 195                 200

His Val Thr Gln Gly Ser Tyr Ala Gly Ser Ile Ser Trp Phe Gln Asn
        205                 210                 215

Pro Ser Ala Gly Val Ser Ala His Tyr Val Ile Arg Ser Ser Asp Gly
220                 225                 230

Ala Val Thr Gln Met Val Arg Asn Lys Asp Val Ala Trp His Ala Gly
235                 240                 245                 250

Asn Trp Gly Tyr Asn Thr Arg Ser Ile Gly Ile Glu His Glu Gly Trp
                255                 260                 265

Val Ser Asp Ala Ser Trp Phe Thr Glu Ala Met Tyr Arg Ser Ser Gly
            270                 275                 280

Ala Leu Thr Arg Tyr Ile Cys Asp Lys Tyr Gly Ile Pro Lys Asp Arg
        285                 290                 295

Ser His Ile Ile Gly His Asn Gln Val Pro Gly Ala Thr His Thr Asp
    300                 305                 310

Pro Gly Ser His Trp Asp Trp Thr Lys Tyr Met Ser Tyr Val Asn Gly
315                 320                 325                 330

Gly Gly Gly Thr Pro Ser Trp Ser Val Thr Val Asp Asn Thr Thr Ala
                335                 340                 345

Gly Lys Phe Thr Ala Ser Ala Asn Trp Gly Thr Ser Ala Tyr Ser Gly
            350                 355                 360

Gln Arg His Gly Ala Asp Tyr Arg Phe Ala Thr Pro Leu Ala Ala Ser
        365                 370                 375

Asp Pro Ala Trp Phe Lys Ala Asn Ile Pro Ser Ala Gly Ser Tyr Arg
    380                 385                 390

Val Glu Val Trp Tyr Pro Ser Asp Pro Gly Tyr Asn Ser Ser Ala Pro
395                 400                 405                 410

Tyr Ile Val Ala Ala Ser Gly Gly Asn Gln Thr Val Phe Val Asp Gln
                415                 420                 425

Arg Ser Gly Gly Gly Gly Trp Arg Thr Leu Gly Thr Phe Ser Leu Thr
            430                 435                 440

```
Ala Gly Glu His Asp Val Val Gly Val Ser Arg Trp Thr Ser Gly Thr
            445                 450                 455

Gly Tyr Val Val Ala Asp Ala Val Arg Ile Ser His Leu
    460                 465                 470

<210> SEQ ID NO 12
<211> LENGTH: 471
<212> TYPE: PRT
<213> ORGANISM: Nonomuraea sp

<400> SEQUENCE: 12

Ala Ala Asp Pro Leu Thr Glu Ala Phe Asp Arg Ala Ala Ala His
1               5                   10                  15

Asp Val Pro Arg Asp Leu Leu Val Ala Leu Ala Tyr Ala Glu Thr His
            20                  25                  30

Leu Asn Gly His Asn Gly Glu Pro Ser Ala Ser Gly Gly Tyr Gly Met
        35                  40                  45

Met His Leu Val Ser Asn Pro Thr Thr Lys Ala Leu Ala Lys Ala Ala
    50                  55                  60

Glu Leu Thr Gly Leu Pro Ala Ala Glu Leu Arg Ala Asp Asp Ala Ala
65                  70                  75                  80

Asn Ile Leu Gly Gly Ala Ala Val Leu Arg Ser His Ala Asp Ala Leu
                85                  90                  95

Gly Leu Asp Glu Ala Ala Arg Lys Asp Ala Gly Arg Trp Tyr Gln Ala
            100                 105                 110

Val Ala Glu Tyr Gly Asn Ala Ser Thr Pro Glu Thr Ala Arg Leu Tyr
        115                 120                 125

Ala Asp Ala Val Tyr Glu Phe Leu Gly Lys Gly Phe Glu Ala Ala Gly
    130                 135                 140

Val Lys Val Ala Pro Gln Glu Val Thr Ala Asp Arg Gly Ala Tyr Ala
145                 150                 155                 160

Lys Thr Arg Glu Leu Thr Ala Ala Ser Pro Asp Tyr Pro Asp Gly
                165                 170                 175

Thr Trp Val Ala Ala Ser Ser Ser Asn Tyr Thr Ala Ser Ser Arg Pro
            180                 185                 190

Ser Ser Tyr Ala Ile Asp Arg Val Val Ile His Val Thr Gln Gly Ser
        195                 200                 205

Tyr Ala Gly Ser Ile Ser Trp Phe Gln Asn Pro Ser Ala Gly Val Ser
    210                 215                 220

Ala His Tyr Val Ile Arg Ser Ser Asp Gly Ala Val Thr Gln Met Val
225                 230                 235                 240

Arg Asn Lys Asp Val Ala Trp His Ala Gly Asn Trp Gly Tyr Asn Thr
                245                 250                 255

Arg Ser Ile Gly Ile Glu His Glu Gly Trp Val Ser Asp Ala Ser Trp
            260                 265                 270

Phe Thr Glu Ala Met Tyr Arg Ser Ser Gly Ala Leu Thr Arg Tyr Ile
        275                 280                 285

Cys Asp Lys Tyr Gly Ile Pro Lys Asp Arg Ser His Ile Ile Gly His
    290                 295                 300

Asn Gln Val Pro Gly Ala Thr Thr Asp Pro Gly Ser His Trp Asp
305                 310                 315                 320

Trp Thr Lys Tyr Met Ser Tyr Val Asn Gly Gly Gly Thr Pro Ser
                325                 330                 335

Trp Ser Val Thr Val Asp Asn Thr Thr Ala Gly Lys Phe Thr Ala Ser
            340                 345                 350
```

```
Ala Asn Trp Gly Thr Ser Ala Tyr Ser Gly Gln Arg His Gly Ala Asp
        355                 360                 365

Tyr Arg Phe Ala Thr Pro Leu Ala Ala Ser Asp Pro Ala Trp Phe Lys
    370                 375                 380

Ala Asn Ile Pro Ser Ala Gly Ser Tyr Arg Val Glu Val Trp Tyr Pro
385                 390                 395                 400

Ser Asp Pro Gly Tyr Asn Ser Ser Ala Pro Tyr Ile Val Ala Ala Ser
                405                 410                 415

Gly Gly Asn Gln Thr Val Phe Val Asp Gln Arg Ser Gly Gly Gly
            420                 425                 430

Trp Arg Thr Leu Gly Thr Phe Ser Leu Thr Ala Gly Glu His Asp Val
        435                 440                 445

Val Gly Val Ser Arg Trp Thr Ser Gly Thr Gly Tyr Val Val Ala Asp
    450                 455                 460

Ala Val Arg Ile Ser His Leu
465                 470

<210> SEQ ID NO 13
<211> LENGTH: 1920
<212> TYPE: DNA
<213> ORGANISM: Lysobacter antibioticus
<220> FEATURE:
<221> NAME/KEY: CDS
<222> LOCATION: (1)..(1917)
<220> FEATURE:
<221> NAME/KEY: sig_peptide
<222> LOCATION: (1)..(117)
<220> FEATURE:
<221> NAME/KEY: mat_peptide
<222> LOCATION: (118)..(1917)

<400> SEQUENCE: 13 atg aac gaa tat tcc att gcg cgc cat ggg gcc ggt acc ggc gtg cgt      48
Met Asn Glu Tyr Ser Ile Ala Arg His Gly Ala Gly Thr Gly Val Arg
            -35                 -30                 -25 tcg ctg tcg tgg tcg ctg acc ctc gcc ctg ctg gcg ctc gcc gcg ccg      96
Ser Leu Ser Trp Ser Leu Thr Leu Ala Leu Leu Ala Leu Ala Ala Pro
        -20                 -15                 -10 tgg gcc gcg cag gcc cag gcc gca ccc gaa gac cgc gcc ctg gcc cag     144
Trp Ala Ala Gln Ala Gln Ala Ala Pro Glu Asp Arg Ala Leu Ala Gln
    -5                  -1  1                   5 cgc ctg cag atc gag gaa tcg ctg caa cgc gtc gac cgc gcg ctg tac     192
Arg Leu Gln Ile Glu Glu Ser Leu Gln Arg Val Asp Arg Ala Leu Tyr
10                  15                  20                  25 gcg gac tac ttc cgc cag gcc tat gcg cgt tac ccg tcg atc ccg gcc     240
Ala Asp Tyr Phe Arg Gln Ala Tyr Ala Arg Tyr Pro Ser Ile Pro Ala
                30                  35                  40 ggc acc ctg gaa tcg atc gcc tac gtg atg agc cgc tgg cag caa ctg     288
Gly Thr Leu Glu Ser Ile Ala Tyr Val Met Ser Arg Trp Gln Gln Leu
            45                  50                  55 cag ccc ggc ccg gcc gcg ggc tat ggc gaa cag cac cag cac atg ccg     336
Gln Pro Gly Pro Ala Ala Gly Tyr Gly Glu Gln His Gln His Met Pro
        60                  65                  70 cgc tcg tac ggc gtc atg ggc ctg tac cac ggc gag ggt ttc gcc gat     384
Arg Ser Tyr Gly Val Met Gly Leu Tyr His Gly Glu Gly Phe Ala Asp
    75                  80                  85 caa gtc agc gaa ggc gcg cgc ctg atc ggc gtg ccc gcg gcg cgc gtg     432
Gln Val Ser Glu Gly Ala Arg Leu Ile Gly Val Pro Ala Ala Arg Val
90                  95                  100                 105
```

```
cag cgc gat ccg ctc agc aac atc ctc gcc tcg gcg gcc ttg ctc gat     480
Gln Arg Asp Pro Leu Ser Asn Ile Leu Ala Ser Ala Ala Leu Leu Asp
            110                 115                 120 cgc gag ctg cgc gcc gac ggg gtc ggt gcc aag tcg gcg atc gaa gcc     528
Arg Glu Leu Arg Ala Asp Gly Val Gly Ala Lys Ser Ala Ile Glu Ala
            125                 130                 135 acg cgt ccg gcg ctg gag cgc tac gcc ggt ttc gcc ggc aat gcg ggc     576
Thr Arg Pro Ala Leu Glu Arg Tyr Ala Gly Phe Ala Gly Asn Ala Gly
            140                 145                 150 aag agc gcg atc cag gat cac gcc cgt tcc agt ttc gcc ttc gac gtg     624
Lys Ser Ala Ile Gln Asp His Ala Arg Ser Ser Phe Ala Phe Asp Val
    155                 160                 165 ctg ctg gcg cag gac aag ggc gtc aac gac cgc ggc atc gtc gtg ccc     672
Leu Leu Ala Gln Asp Lys Gly Val Asn Asp Arg Gly Ile Val Val Pro
170                 175                 180                 185 acg cgc gcg gtc gcc tgg gaa cgc gcc ttc gat gcg cgc aag ctg gtg     720
Thr Arg Ala Val Ala Trp Glu Arg Ala Phe Asp Ala Arg Lys Leu Val
                190                 195                 200 cag ctg cgc gcg ccg ttc gtg cgt ctg gac gtg agc cgc gat cgg gtc     768
Gln Leu Arg Ala Pro Phe Val Arg Leu Asp Val Ser Arg Asp Arg Val
            205                 210                 215 gag gcc ggc gcg ttg agg gac gac ggc gcg ttc gcg atc gat ccg ctc     816
Glu Ala Gly Ala Leu Arg Asp Asp Gly Ala Phe Ala Ile Asp Pro Leu
            220                 225                 230 agc gaa acc ctg cgc gcg cca tcg ctg acc gcg gcc gac gaa aag agc     864
Ser Glu Thr Leu Arg Ala Pro Ser Leu Thr Ala Ala Asp Glu Lys Ser
            235                 240                 245 acc gat tac ggc ccg gcg ctg tgg gtc gct tcg cct tac cac tcc acc     912
Thr Asp Tyr Gly Pro Ala Leu Trp Val Ala Ser Pro Tyr His Ser Thr
250                 255                 260                 265 cgc acg tcg tac gac tcg gtg acc atc cac acg atg cag ggc tat tac     960
Arg Thr Ser Tyr Asp Ser Val Thr Ile His Thr Met Gln Gly Tyr Tyr
            270                 275                 280 gcc ggc agc atc tcg tgg ttc cag aac aac ccc aac agc gtc agc gcg    1008
Ala Gly Ser Ile Ser Trp Phe Gln Asn Asn Pro Asn Ser Val Ser Ala
            285                 290                 295 cat tac ctg atc cgc agc tcc gac ggc cag atc acc cag atg gtg cgc    1056
His Tyr Leu Ile Arg Ser Ser Asp Gly Gln Ile Thr Gln Met Val Arg
            300                 305                 310 gag aac cgc gcg gcc cat cac gtc ggc gtg cat aac aag acc acg ctc    1104
Glu Asn Arg Ala Ala His His Val Gly Val His Asn Lys Thr Thr Leu
            315                 320                 325 ggc atc gag cac gaa ggc ttc atc aac aac gcg agt tgg tac acc gcg    1152
Gly Ile Glu His Glu Gly Phe Ile Asn Asn Ala Ser Trp Tyr Thr Ala
330                 335                 340                 345 gcg atg tac aac gcc tcg gcg gcg ttg acc cgg cac ttc tgc gcg acc    1200
Ala Met Tyr Asn Ala Ser Ala Ala Leu Thr Arg His Phe Cys Ala Thr
            350                 355                 360 tac agc gcg atc agc tgc gcg agc gcg ttc aag ggc ccg gcc ggc agc    1248
Tyr Ser Ala Ile Ser Cys Ala Ser Ala Phe Lys Gly Pro Ala Gly Ser
            365                 370                 375 ggc atc aac gtg ttg ccg gcc agc gtc aag gtc aag ggc cac cag cac    1296
Gly Ile Asn Val Leu Pro Ala Ser Val Lys Val Lys Gly His Gln His
            380                 385                 390 tac agc agc cag acc cac acc gat ccg ggc atc aac tgg gat tgg gcg    1344
Tyr Ser Ser Gln Thr His Thr Asp Pro Gly Ile Asn Trp Asp Trp Ala
            395                 400                 405
```

-continued

```
cgc tac tac aac ctg ctc aat ccg ggc aat ccg ccc ggc ggc ggc agc      1392
Arg Tyr Tyr Asn Leu Leu Asn Pro Gly Asn Pro Pro Gly Gly Gly Ser
410             415                 420                 425 gtg atc gac agt ttc gaa agc acg gtc ggg cat ttc gac acc ggc ccg      1440
Val Ile Asp Ser Phe Glu Ser Thr Val Gly His Phe Asp Thr Gly Pro
                430                 435                 440 gcg tat tcg ggc agc acc acc ggc atc gcc gcg acc tcg ctg agc gaa      1488
Ala Tyr Ser Gly Ser Thr Thr Gly Ile Ala Ala Thr Ser Leu Ser Glu
            445                 450                 455 cgc aac tgc acc acg cgc aag aac ggc gag tgc tcg ctg cgg ctg ctg      1536
Arg Asn Cys Thr Thr Arg Lys Asn Gly Glu Cys Ser Leu Arg Leu Leu
        460                 465                 470 ctg aaa gac gat gcc gcc agc gcc gat gcc tgg gcg gtg cgg ctg ttg      1584
Leu Lys Asp Asp Ala Ala Ser Ala Asp Ala Trp Ala Val Arg Leu Leu
    475                 480                 485 tcg ggc agc ggc aat ccg ggc agc aac gcg gcc ctg acg cgc gcc aac      1632
Ser Gly Ser Gly Asn Pro Gly Ser Asn Ala Ala Leu Thr Arg Ala Asn
490                 495                 500                 505 ggc aag gtc ggt ttc tgg gtc ttc acc ggc gcg acc ggg atg agc gcg      1680
Gly Lys Val Gly Phe Trp Val Phe Thr Gly Ala Thr Gly Met Ser Ala
                510                 515                 520 gcg atc ggc atc gac gac agc gac ggc acc gag cgc tcg gtg agc cgc      1728
Ala Ile Gly Ile Asp Asp Ser Asp Gly Thr Glu Arg Ser Val Ser Arg
            525                 530                 535 gcg att gcg gcc aac acc tgg acc tat ctg gag tgg agc ctg acc gac      1776
Ala Ile Ala Ala Asn Thr Trp Thr Tyr Leu Glu Trp Ser Leu Thr Asp
        540                 545                 550 gac gcg cag tgg gat gcg tgg gtc ggc ggc gcc aac ggc gcg atc acc      1824
Asp Ala Gln Trp Asp Ala Trp Val Gly Gly Ala Asn Gly Ala Ile Thr
    555                 560                 565 gcc gcg tcg gtg aag ctc gat gcg gtg tgg ttc tac cgc gat cag acc      1872
Ala Ala Ser Val Lys Leu Asp Ala Val Trp Phe Tyr Arg Asp Gln Thr
570                 575                 580                 585 tcg ttc gac gtg aac gtg tac gtc gac gat gtg cag gtg aag aac tga      1920
Ser Phe Asp Val Asn Val Tyr Val Asp Asp Val Gln Val Lys Asn
                590                 595                 600
```

<210> SEQ ID NO 14
<211> LENGTH: 639
<212> TYPE: PRT
<213> ORGANISM: Lysobacter antibioticus

<400> SEQUENCE: 14

```
Met Asn Glu Tyr Ser Ile Ala Arg His Gly Ala Gly Thr Gly Val Arg
                -35                 -30                 -25

Ser Leu Ser Trp Ser Leu Thr Leu Ala Leu Leu Ala Leu Ala Ala Pro
            -20                 -15                 -10

Trp Ala Ala Gln Ala Gln Ala Ala Pro Glu Asp Arg Ala Leu Ala Gln
        -5                  -1  1                   5

Arg Leu Gln Ile Glu Glu Ser Leu Gln Arg Val Asp Arg Ala Leu Tyr
 10                  15                  20                  25

Ala Asp Tyr Phe Arg Gln Ala Tyr Ala Arg Tyr Pro Ser Ile Pro Ala
                30                  35                  40

Gly Thr Leu Glu Ser Ile Ala Tyr Val Met Ser Arg Trp Gln Gln Leu
            45                  50                  55

Gln Pro Gly Pro Ala Ala Gly Tyr Gly Glu Gln His Gln His Met Pro
        60                  65                  70
```

-continued

```
Arg Ser Tyr Gly Val Met Gly Leu Tyr His Gly Glu Gly Phe Ala Asp
    75                  80                  85

Gln Val Ser Glu Gly Ala Arg Leu Ile Gly Val Pro Ala Ala Arg Val
90                  95                 100                 105

Gln Arg Asp Pro Leu Ser Asn Ile Leu Ala Ser Ala Ala Leu Leu Asp
                110                 115                 120

Arg Glu Leu Arg Ala Asp Gly Val Gly Ala Lys Ser Ala Ile Glu Ala
                125                 130                 135

Thr Arg Pro Ala Leu Glu Arg Tyr Ala Gly Phe Ala Gly Asn Ala Gly
                140                 145                 150

Lys Ser Ala Ile Gln Asp His Ala Arg Ser Ser Phe Ala Phe Asp Val
    155                 160                 165

Leu Leu Ala Gln Asp Lys Gly Val Asn Asp Arg Gly Ile Val Val Pro
170                 175                 180                 185

Thr Arg Ala Val Ala Trp Glu Arg Ala Phe Asp Ala Arg Lys Leu Val
                190                 195                 200

Gln Leu Arg Ala Pro Phe Val Arg Leu Asp Val Ser Arg Asp Arg Val
                205                 210                 215

Glu Ala Gly Ala Leu Arg Asp Asp Gly Ala Phe Ala Ile Asp Pro Leu
                220                 225                 230

Ser Glu Thr Leu Arg Ala Pro Ser Leu Thr Ala Ala Asp Glu Lys Ser
    235                 240                 245

Thr Asp Tyr Gly Pro Ala Leu Trp Val Ala Ser Pro Tyr His Ser Thr
250                 255                 260                 265

Arg Thr Ser Tyr Asp Ser Val Thr Ile His Thr Met Gln Gly Tyr Tyr
                270                 275                 280

Ala Gly Ser Ile Ser Trp Phe Gln Asn Asn Pro Asn Ser Val Ser Ala
                285                 290                 295

His Tyr Leu Ile Arg Ser Ser Asp Gly Gln Ile Thr Gln Met Val Arg
                300                 305                 310

Glu Asn Arg Ala Ala His His Val Gly Val His Asn Lys Thr Thr Leu
    315                 320                 325

Gly Ile Glu His Glu Gly Phe Ile Asn Asn Ala Ser Trp Tyr Thr Ala
330                 335                 340                 345

Ala Met Tyr Asn Ala Ser Ala Ala Leu Thr Arg His Phe Cys Ala Thr
                350                 355                 360

Tyr Ser Ala Ile Ser Cys Ala Ser Ala Phe Lys Gly Pro Ala Gly Ser
                365                 370                 375

Gly Ile Asn Val Leu Pro Ala Ser Val Lys Val Lys Gly His Gln His
                380                 385                 390

Tyr Ser Ser Gln Thr His Thr Asp Pro Gly Ile Asn Trp Asp Trp Ala
    395                 400                 405

Arg Tyr Tyr Asn Leu Leu Asn Pro Gly Asn Pro Pro Gly Gly Gly Ser
410                 415                 420                 425

Val Ile Asp Ser Phe Glu Ser Thr Val Gly His Phe Asp Thr Gly Pro
                430                 435                 440

Ala Tyr Ser Gly Ser Thr Thr Gly Ile Ala Ala Thr Ser Leu Ser Glu
                445                 450                 455

Arg Asn Cys Thr Thr Arg Lys Asn Gly Glu Cys Ser Leu Arg Leu Leu
                460                 465                 470

Leu Lys Asp Asp Ala Ala Ser Ala Asp Ala Trp Ala Val Arg Leu Leu
    475                 480                 485
```

```
Ser Gly Ser Gly Asn Pro Gly Ser Asn Ala Ala Leu Thr Arg Ala Asn
490                 495                 500                 505

Gly Lys Val Gly Phe Trp Val Phe Thr Gly Ala Thr Gly Met Ser Ala
            510                 515                 520

Ala Ile Gly Ile Asp Asp Ser Asp Gly Thr Glu Arg Ser Val Ser Arg
            525                 530                 535

Ala Ile Ala Ala Asn Thr Trp Thr Tyr Leu Glu Trp Ser Leu Thr Asp
            540                 545                 550

Asp Ala Gln Trp Asp Ala Trp Val Gly Gly Ala Asn Gly Ala Ile Thr
            555                 560                 565

Ala Ala Ser Val Lys Leu Asp Ala Val Trp Phe Tyr Arg Asp Gln Thr
570                 575                 580                 585

Ser Phe Asp Val Asn Val Tyr Val Asp Asp Val Gln Val Lys Asn
                590                 595                 600

<210> SEQ ID NO 15
<211> LENGTH: 600
<212> TYPE: PRT
<213> ORGANISM: Lysobacter antibioticus

<400> SEQUENCE: 15

Ala Pro Glu Asp Arg Ala Leu Ala Gln Arg Leu Gln Ile Glu Glu Ser
1               5                   10                  15

Leu Gln Arg Val Asp Arg Ala Leu Tyr Ala Asp Tyr Phe Arg Gln Ala
            20                  25                  30

Tyr Ala Arg Tyr Pro Ser Ile Pro Ala Gly Thr Leu Glu Ser Ile Ala
            35                  40                  45

Tyr Val Met Ser Arg Trp Gln Gln Leu Gln Pro Gly Pro Ala Ala Gly
50                  55                  60

Tyr Gly Glu Gln His Gln His Met Pro Arg Ser Tyr Gly Val Met Gly
65                  70                  75                  80

Leu Tyr His Gly Glu Gly Phe Ala Asp Gln Val Ser Glu Gly Ala Arg
            85                  90                  95

Leu Ile Gly Val Pro Ala Ala Arg Val Gln Arg Asp Pro Leu Ser Asn
            100                 105                 110

Ile Leu Ala Ser Ala Ala Leu Leu Asp Arg Glu Leu Arg Ala Asp Gly
            115                 120                 125

Val Gly Ala Lys Ser Ala Ile Glu Ala Thr Arg Pro Ala Leu Glu Arg
            130                 135                 140

Tyr Ala Gly Phe Ala Gly Asn Ala Gly Lys Ser Ala Ile Gln Asp His
145                 150                 155                 160

Ala Arg Ser Ser Phe Ala Phe Asp Val Leu Leu Ala Gln Asp Lys Gly
            165                 170                 175

Val Asn Asp Arg Gly Ile Val Val Pro Thr Arg Ala Val Ala Trp Glu
            180                 185                 190

Arg Ala Phe Asp Ala Arg Lys Leu Val Gln Leu Arg Ala Pro Phe Val
            195                 200                 205

Arg Leu Asp Val Ser Arg Asp Arg Val Glu Ala Gly Ala Leu Arg Asp
            210                 215                 220

Asp Gly Ala Phe Ala Ile Asp Pro Leu Ser Glu Thr Leu Arg Ala Pro
225                 230                 235                 240

Ser Leu Thr Ala Ala Asp Glu Lys Ser Thr Asp Tyr Gly Pro Ala Leu
            245                 250                 255

Trp Val Ala Ser Pro Tyr His Ser Thr Arg Thr Ser Tyr Asp Ser Val
            260                 265                 270
```

```
Thr Ile His Thr Met Gln Gly Tyr Tyr Ala Gly Ser Ile Ser Trp Phe
        275                 280                 285

Gln Asn Asn Pro Asn Ser Val Ser Ala His Tyr Leu Ile Arg Ser Ser
    290                 295                 300

Asp Gly Gln Ile Thr Gln Met Val Arg Glu Asn Arg Ala Ala His His
305                 310                 315                 320

Val Gly Val His Asn Lys Thr Thr Leu Gly Ile Glu His Glu Gly Phe
                325                 330                 335

Ile Asn Asn Ala Ser Trp Tyr Thr Ala Met Tyr Asn Ala Ser Ala
                340                 345                 350

Ala Leu Thr Arg His Phe Cys Ala Thr Tyr Ser Ala Ile Ser Cys Ala
        355                 360                 365

Ser Ala Phe Lys Gly Pro Ala Gly Ser Gly Ile Asn Val Leu Pro Ala
    370                 375                 380

Ser Val Lys Val Lys Gly His Gln His Tyr Ser Ser Gln Thr His Thr
385                 390                 395                 400

Asp Pro Gly Ile Asn Trp Asp Trp Ala Arg Tyr Tyr Asn Leu Leu Asn
                405                 410                 415

Pro Gly Asn Pro Pro Gly Gly Ser Val Ile Asp Ser Phe Glu Ser
                420                 425                 430

Thr Val Gly His Phe Asp Thr Gly Pro Ala Tyr Ser Gly Ser Thr Thr
        435                 440                 445

Gly Ile Ala Ala Thr Ser Leu Ser Glu Arg Asn Cys Thr Thr Arg Lys
    450                 455                 460

Asn Gly Glu Cys Ser Leu Arg Leu Leu Leu Lys Asp Asp Ala Ala Ser
465                 470                 475                 480

Ala Asp Ala Trp Ala Val Arg Leu Leu Ser Gly Ser Gly Asn Pro Gly
                485                 490                 495

Ser Asn Ala Ala Leu Thr Arg Ala Asn Gly Lys Val Gly Phe Trp Val
                500                 505                 510

Phe Thr Gly Ala Thr Gly Met Ser Ala Ala Ile Gly Ile Asp Asp Ser
        515                 520                 525

Asp Gly Thr Glu Arg Ser Val Ser Arg Ala Ile Ala Ala Asn Thr Trp
    530                 535                 540

Thr Tyr Leu Glu Trp Ser Leu Thr Asp Asp Ala Gln Trp Asp Ala Trp
545                 550                 555                 560

Val Gly Gly Ala Asn Gly Ala Ile Thr Ala Ala Ser Val Lys Leu Asp
                565                 570                 575

Ala Val Trp Phe Tyr Arg Asp Gln Thr Ser Phe Asp Val Asn Val Tyr
                580                 585                 590

Val Asp Asp Val Gln Val Lys Asn
        595                 600

<210> SEQ ID NO 16
<211> LENGTH: 1548
<212> TYPE: DNA
<213> ORGANISM: Micromonospora sp
<220> FEATURE:
<221> NAME/KEY: CDS
<222> LOCATION: (1)..(1545)
<220> FEATURE:
<221> NAME/KEY: sig_peptide
<222> LOCATION: (1)..(93)
<220> FEATURE:
<221> NAME/KEY: mat_peptide
<222> LOCATION: (94)..(1545)
```

<400> SEQUENCE: 16

| | | | | | | | | | | | | | | | | |
|---|---|---|---|---|---|---|---|---|---|---|---|---|---|---|---|---|
| gtg | act | gtt | cgg | aga | ccc | tcg | cgt | cgg | gtg | agc | caa | ctg | ctc | ggc | ggc | 48 |
| Val | Thr | Val | Arg | Arg | Pro | Ser | Arg | Arg | Val | Ser | Gln | Leu | Leu | Gly | Gly | |
| | -30 | | | | -25 | | | | | -20 | | | | | | |

| | | | | | | | | | | | | | | | | |
|---|---|---|---|---|---|---|---|---|---|---|---|---|---|---|---|---|
| gca | gcg | att | ttg | atg | atc | ggc | ctg | acc | agc | cag | ccg | gcc | cag | gcc | gcg | 96 |
| Ala | Ala | Ile | Leu | Met | Ile | Gly | Leu | Thr | Ser | Gln | Pro | Ala | Gln | Ala | Ala | |
| -15 | | | | -10 | | | | | -5 | | | | | -1 | 1 | |

| | | | | | | | | | | | | | | | | |
|---|---|---|---|---|---|---|---|---|---|---|---|---|---|---|---|---|
| ccg | cag | cag | ggc | gcg | gag | acg | ctc | gcc | gcc | gcc | ttc | gac | cag | gcg | gcg | 144 |
| Pro | Gln | Gln | Gly | Ala | Glu | Thr | Leu | Ala | Ala | Ala | Phe | Asp | Gln | Ala | Ala | |
| | | | 5 | | | | | 10 | | | | | 15 | | | |

| | | | | | | | | | | | | | | | | |
|---|---|---|---|---|---|---|---|---|---|---|---|---|---|---|---|---|
| gcc | cgc | tcc | gac | gtg | ccg | cgc | gac | ctg | ctc | gcc | gcg | ctc | ggg | tac | gcg | 192 |
| Ala | Arg | Ser | Asp | Val | Pro | Arg | Asp | Leu | Leu | Ala | Ala | Leu | Gly | Tyr | Ala | |
| | | 20 | | | | | 25 | | | | | 30 | | | | |

| | | | | | | | | | | | | | | | | |
|---|---|---|---|---|---|---|---|---|---|---|---|---|---|---|---|---|
| gag | acc | cgg | ctg | gac | ggt | cac | aac | ggc | gag | ccc | agc | gcc | tcc | ggc | ggg | 240 |
| Glu | Thr | Arg | Leu | Asp | Gly | His | Asn | Gly | Glu | Pro | Ser | Ala | Ser | Gly | Gly | |
| 35 | | | | | 40 | | | | | 45 | | | | | | |

| | | | | | | | | | | | | | | | | |
|---|---|---|---|---|---|---|---|---|---|---|---|---|---|---|---|---|
| tac | ggc | gtg | atg | cac | ctg | acc | agc | aac | ccg | aag | gtg | cgg | acc | ctc | gac | 288 |
| Tyr | Gly | Val | Met | His | Leu | Thr | Ser | Asn | Pro | Lys | Val | Arg | Thr | Leu | Asp | |
| 50 | | | | | 55 | | | | | 60 | | | | | 65 | |

| | | | | | | | | | | | | | | | | |
|---|---|---|---|---|---|---|---|---|---|---|---|---|---|---|---|---|
| gag | gcc | gcg | cgc | cgt | gcc | cga | ctg | gac | cgc | acc | gaa | ctg | cgc | acc | cgt | 336 |
| Glu | Ala | Ala | Arg | Arg | Ala | Arg | Leu | Asp | Arg | Thr | Glu | Leu | Arg | Thr | Arg | |
| | | | | 70 | | | | | 75 | | | | | 80 | | |

| | | | | | | | | | | | | | | | | |
|---|---|---|---|---|---|---|---|---|---|---|---|---|---|---|---|---|
| gac | gcg | gcg | aac | gtc | gcc | ggc | gcg | gcg | gcg | gtg | ctc | cgc | tcg | tac | gcc | 384 |
| Asp | Ala | Ala | Asn | Val | Ala | Gly | Ala | Ala | Ala | Val | Leu | Arg | Ser | Tyr | Ala | |
| | | 85 | | | | | 90 | | | | | 95 | | | | |

| | | | | | | | | | | | | | | | | |
|---|---|---|---|---|---|---|---|---|---|---|---|---|---|---|---|---|
| gat | cag | gcc | ggg | ctc | acc | gcg | aag | cag | cgc | gac | gac | gtc | aac | cag | tgg | 432 |
| Asp | Gln | Ala | Gly | Leu | Thr | Ala | Lys | Gln | Arg | Asp | Asp | Val | Asn | Gln | Trp | |
| | | 100 | | | | | 105 | | | | | 110 | | | | |

| | | | | | | | | | | | | | | | | |
|---|---|---|---|---|---|---|---|---|---|---|---|---|---|---|---|---|
| tac | ggc | ttg | atc | gcc | cgc | tac | ggc | ggt | tcg | tcg | gac | aag | gcc | acc | gcc | 480 |
| Tyr | Gly | Leu | Ile | Ala | Arg | Tyr | Gly | Gly | Ser | Ser | Asp | Lys | Ala | Thr | Ala | |
| 115 | | | | | 120 | | | | | 125 | | | | | | |

| | | | | | | | | | | | | | | | | |
|---|---|---|---|---|---|---|---|---|---|---|---|---|---|---|---|---|
| cgg | ctg | tac | gcc | gac | gcc | gtg | tac | gac | ctg | ctc | ggc | agc | ggc | ttc | agg | 528 |
| Arg | Leu | Tyr | Ala | Asp | Ala | Val | Tyr | Asp | Leu | Leu | Gly | Ser | Gly | Phe | Arg | |
| 130 | | | | | 135 | | | | | 140 | | | | | 145 | |

| | | | | | | | | | | | | | | | | |
|---|---|---|---|---|---|---|---|---|---|---|---|---|---|---|---|---|
| gcg | acc | acg | gcc | acc | ggc | gag | gtc | acc | gtg | gac | ggc | cgt | ccg | gtc | gcg | 576 |
| Ala | Thr | Thr | Ala | Thr | Gly | Glu | Val | Thr | Val | Asp | Gly | Arg | Pro | Val | Ala | |
| | | | | 150 | | | | | 155 | | | | | 160 | | |

| | | | | | | | | | | | | | | | | |
|---|---|---|---|---|---|---|---|---|---|---|---|---|---|---|---|---|
| ccc | cag | cgg | ggc | gac | tac | gcc | gcg | gtg | gcg | ccg | ctg | ggc | gcc | gcc | gac | 624 |
| Pro | Gln | Arg | Gly | Asp | Tyr | Ala | Ala | Val | Ala | Pro | Leu | Gly | Ala | Ala | Asp | |
| | | 165 | | | | | 170 | | | | | 175 | | | | |

| | | | | | | | | | | | | | | | | |
|---|---|---|---|---|---|---|---|---|---|---|---|---|---|---|---|---|
| atg | ggc | acc | cag | agc | acc | gac | tac | ggc | ccg | gcg | gcc | tgg | gtg | gcg | gcg | 672 |
| Met | Gly | Thr | Gln | Ser | Thr | Asp | Tyr | Gly | Pro | Ala | Ala | Trp | Val | Ala | Ala | |
| | | 180 | | | | | 185 | | | | | 190 | | | | |

| | | | | | | | | | | | | | | | | |
|---|---|---|---|---|---|---|---|---|---|---|---|---|---|---|---|---|
| aac | tcg | tcc | aac | tac | acg | gcc | tcc | agc | cgc | gag | tcg | tcg | tac | ccg | atc | 720 |
| Asn | Ser | Ser | Asn | Tyr | Thr | Ala | Ser | Ser | Arg | Glu | Ser | Ser | Tyr | Pro | Ile | |
| | 195 | | | | | 200 | | | | | 205 | | | | | |

| | | | | | | | | | | | | | | | | |
|---|---|---|---|---|---|---|---|---|---|---|---|---|---|---|---|---|
| aac | tac | atc | atc | atc | cac | acc | atg | cag | ggc | agc | tac | gcc | ggc | tcg | atc | 768 |
| Asn | Tyr | Ile | Ile | Ile | His | Thr | Met | Gln | Gly | Ser | Tyr | Ala | Gly | Ser | Ile | |
| 210 | | | | | 215 | | | | | 220 | | | | | 225 | |

| | | | | | | | | | | | | | | | | |
|---|---|---|---|---|---|---|---|---|---|---|---|---|---|---|---|---|
| agc | tgg | ttc | cag | aac | gca | gcg | gcc | ggc | acc | agc | gcg | cac | tac | ctg | ctc | 816 |
| Ser | Trp | Phe | Gln | Asn | Ala | Ala | Ala | Gly | Thr | Ser | Ala | His | Tyr | Leu | Leu | |
| | | | 230 | | | | | 235 | | | | | 240 | | | |

| | | | | | | | | | | | | | | | | |
|---|---|---|---|---|---|---|---|---|---|---|---|---|---|---|---|---|
| cgt | tcc | tcg | gac | ggc | gcg | gtg | acc | cag | atg | gtg | cgg | gac | aag | gac | gtc | 864 |
| Arg | Ser | Ser | Asp | Gly | Ala | Val | Thr | Gln | Met | Val | Arg | Asp | Lys | Asp | Val | |
| | | | 245 | | | | | 250 | | | | | 255 | | | |

| | | | | | | | | | | | | | | | | |
|---|---|---|---|---|---|---|---|---|---|---|---|---|---|---|---|---|
| gcc | tgg | cac | gcc | ggc | aac | tgg | acc | tac | aac | acc | cag | tcg | atc | ggt | atc | 912 |
| Ala | Trp | His | Ala | Gly | Asn | Trp | Thr | Tyr | Asn | Thr | Gln | Ser | Ile | Gly | Ile | |
| | | | 260 | | | | | 265 | | | | | 270 | | | |

```
gag cac gag ggc tac gtc gac aac gcc tcc tgg tac acc gac gcg atg       960
Glu His Glu Gly Tyr Val Asp Asn Ala Ser Trp Tyr Thr Asp Ala Met
275                 280                 285 tac cgg tcg tcg gcc gcg ctg acg cgg cac ctg gcc gac aag tac ggc      1008
Tyr Arg Ser Ser Ala Ala Leu Thr Arg His Leu Ala Asp Lys Tyr Gly
290                 295                 300                 305 atc ccg aag acc cgc agc aac atc atc ggt cac aac cag gtg ccg ggc      1056
Ile Pro Lys Thr Arg Ser Asn Ile Ile Gly His Asn Gln Val Pro Gly
            310                 315                 320 gcc acg cac acc gac ccg ggt ccg aac tgg aac tgg acc tac tac atg      1104
Ala Thr His Thr Asp Pro Gly Pro Asn Trp Asn Trp Thr Tyr Tyr Met
            325                 330                 335 cag ctc gtc acc ggc acc acg ccg ccg ccg acc tgg tcg acc atc          1152
Gln Leu Val Thr Gly Thr Thr Pro Pro Pro Thr Trp Ser Thr Ile
            340                 345                 350 gtg gac aac acc acc gcc ggc cgg ttc acc gcg agc gcc aac tgg agc      1200
Val Asp Asn Thr Thr Ala Gly Arg Phe Thr Ala Ser Ala Asn Trp Ser
355                 360                 365 acc tcg tcg tac tcg tcg cag cgc tac ggg gcc gac tac cgc tac gcc      1248
Thr Ser Ser Tyr Ser Ser Gln Arg Tyr Gly Ala Asp Tyr Arg Tyr Ala
370                 375                 380                 385 aac cct gtc gcg gcc agc gac gcc gcc tgg tac aag gtg aac atc ccg      1296
Asn Pro Val Ala Ala Ser Asp Ala Ala Trp Tyr Lys Val Asn Ile Pro
            390                 395                 400 gcc acc gcc acc tac cgg gtg gag gtc tgg tac ccg gcc gtc gcc ggt      1344
Ala Thr Ala Thr Tyr Arg Val Glu Val Trp Tyr Pro Ala Val Ala Gly
            405                 410                 415 tac aac gcc acc acg ccg tac atc gtg gcg acc agc agc ggc aac cag      1392
Tyr Asn Ala Thr Thr Pro Tyr Ile Val Ala Thr Ser Ser Gly Asn Gln
            420                 425                 430 acg gtc aac gtg aac cag tcg gcc aac ggt ggt ggt tgg cgc tcg ctg      1440
Thr Val Asn Val Asn Gln Ser Ala Asn Gly Gly Gly Trp Arg Ser Leu
435                 440                 445 ggc aac ttc acc ctg gcc gcc ggg gac gcc aac aag gtg ggc atc agc      1488
Gly Asn Phe Thr Leu Ala Ala Gly Asp Ala Asn Lys Val Gly Ile Ser
450                 455                 460                 465 cgt tgg tcc ggt agc acc ggc tac gtg atc gcc gac gcg atc cgc atc      1536
Arg Trp Ser Gly Ser Thr Gly Tyr Val Ile Ala Asp Ala Ile Arg Ile
            470                 475                 480 acc cgc gtc taa                                                       1548
Thr Arg Val <210> SEQ ID NO 17
<211> LENGTH: 515
<212> TYPE: PRT
<213> ORGANISM: Micromonospora sp

<400> SEQUENCE: 17

Val Thr Val Arg Arg Pro Ser Arg Arg Val Ser Gln Leu Leu Gly Gly
        -30                 -25                 -20

Ala Ala Ile Leu Met Ile Gly Leu Thr Ser Gln Pro Ala Gln Ala Ala
-15                 -10                  -5                  -1  1

Pro Gln Gln Gly Ala Glu Thr Leu Ala Ala Ala Phe Asp Gln Ala Ala
                5                  10                  15

Ala Arg Ser Asp Val Pro Arg Asp Leu Leu Ala Ala Leu Gly Tyr Ala
            20                  25                  30

Glu Thr Arg Leu Asp Gly His Asn Gly Glu Pro Ser Ala Ser Gly Gly
        35                  40                  45
```

```
Tyr Gly Val Met His Leu Thr Ser Asn Pro Lys Val Arg Thr Leu Asp
 50                  55                  60                  65

Glu Ala Ala Arg Arg Ala Arg Leu Asp Arg Thr Glu Leu Arg Thr Arg
                 70                  75                  80

Asp Ala Ala Asn Val Ala Gly Ala Ala Val Leu Arg Ser Tyr Ala
                 85                  90                  95

Asp Gln Ala Gly Leu Thr Ala Lys Gln Arg Asp Asp Val Asn Gln Trp
            100                 105                 110

Tyr Gly Leu Ile Ala Arg Tyr Gly Gly Ser Ser Asp Lys Ala Thr Ala
            115                 120                 125

Arg Leu Tyr Ala Asp Ala Val Tyr Asp Leu Leu Gly Ser Gly Phe Arg
130                 135                 140                 145

Ala Thr Thr Ala Thr Gly Glu Val Thr Val Asp Gly Arg Pro Val Ala
                150                 155                 160

Pro Gln Arg Gly Asp Tyr Ala Ala Val Ala Pro Leu Gly Ala Ala Asp
                165                 170                 175

Met Gly Thr Gln Ser Thr Asp Tyr Gly Pro Ala Ala Trp Val Ala Ala
                180                 185                 190

Asn Ser Ser Asn Tyr Thr Ala Ser Ser Arg Glu Ser Ser Tyr Pro Ile
195                 200                 205

Asn Tyr Ile Ile Ile His Thr Met Gln Gly Ser Tyr Ala Gly Ser Ile
210                 215                 220                 225

Ser Trp Phe Gln Asn Ala Ala Ala Gly Thr Ser Ala His Tyr Leu Leu
                230                 235                 240

Arg Ser Ser Asp Gly Ala Val Thr Gln Met Val Arg Asp Lys Asp Val
                245                 250                 255

Ala Trp His Ala Gly Asn Trp Thr Tyr Asn Thr Gln Ser Ile Gly Ile
                260                 265                 270

Glu His Glu Gly Tyr Val Asp Asn Ala Ser Trp Tyr Thr Asp Ala Met
                275                 280                 285

Tyr Arg Ser Ser Ala Ala Leu Thr Arg His Leu Ala Asp Lys Tyr Gly
290                 295                 300                 305

Ile Pro Lys Thr Arg Ser Asn Ile Ile Gly His Asn Gln Val Pro Gly
                310                 315                 320

Ala Thr His Thr Asp Pro Gly Pro Asn Trp Asn Trp Thr Tyr Tyr Met
                325                 330                 335

Gln Leu Val Thr Gly Thr Thr Pro Pro Thr Trp Ser Thr Ile
                340                 345                 350

Val Asp Asn Thr Thr Ala Gly Arg Phe Thr Ala Ser Ala Asn Trp Ser
355                 360                 365

Thr Ser Ser Tyr Ser Ser Gln Arg Tyr Gly Ala Asp Tyr Arg Tyr Ala
370                 375                 380                 385

Asn Pro Val Ala Ala Ser Asp Ala Ala Trp Tyr Lys Val Asn Ile Pro
                390                 395                 400

Ala Thr Ala Thr Tyr Arg Val Glu Val Trp Tyr Pro Ala Val Ala Gly
                405                 410                 415

Tyr Asn Ala Thr Pro Tyr Ile Val Ala Thr Ser Gly Asn Gln
                420                 425                 430

Thr Val Asn Val Asn Gln Ser Ala Asn Gly Gly Trp Arg Ser Leu
435                 440                 445

Gly Asn Phe Thr Leu Ala Ala Gly Asp Ala Asn Lys Val Gly Ile Ser
450                 455                 460                 465
```

Arg Trp Ser Gly Ser Thr Gly Tyr Val Ile Ala Asp Ala Ile Arg Ile
            470                 475                 480

Thr Arg Val

<210> SEQ ID NO 18
<211> LENGTH: 484
<212> TYPE: PRT
<213> ORGANISM: Micromonospora sp

<400> SEQUENCE: 18

Ala Pro Gln Gln Gly Ala Glu Thr Leu Ala Ala Phe Asp Gln Ala
1               5                   10                  15

Ala Ala Arg Ser Asp Val Pro Arg Asp Leu Leu Ala Ala Leu Gly Tyr
            20                  25                  30

Ala Glu Thr Arg Leu Asp Gly His Asn Gly Glu Pro Ser Ala Ser Gly
        35                  40                  45

Gly Tyr Gly Val Met His Leu Thr Ser Asn Pro Lys Val Arg Thr Leu
    50                  55                  60

Asp Glu Ala Ala Arg Arg Ala Arg Leu Asp Arg Thr Glu Leu Arg Thr
65                  70                  75                  80

Arg Asp Ala Ala Asn Val Ala Gly Ala Ala Val Leu Arg Ser Tyr
                85                  90                  95

Ala Asp Gln Ala Gly Leu Thr Ala Lys Gln Arg Asp Asp Val Asn Gln
            100                 105                 110

Trp Tyr Gly Leu Ile Ala Arg Tyr Gly Gly Ser Ser Asp Lys Ala Thr
        115                 120                 125

Ala Arg Leu Tyr Ala Asp Ala Val Tyr Asp Leu Leu Gly Ser Gly Phe
130                 135                 140

Arg Ala Thr Thr Ala Thr Gly Glu Val Thr Val Asp Gly Arg Pro Val
145                 150                 155                 160

Ala Pro Gln Arg Gly Asp Tyr Ala Ala Val Ala Pro Leu Gly Ala Ala
                165                 170                 175

Asp Met Gly Thr Gln Ser Thr Asp Tyr Gly Pro Ala Ala Trp Val Ala
            180                 185                 190

Ala Asn Ser Ser Asn Tyr Thr Ala Ser Ser Arg Glu Ser Ser Tyr Pro
        195                 200                 205

Ile Asn Tyr Ile Ile His Thr Met Gln Gly Ser Tyr Ala Gly Ser
    210                 215                 220

Ile Ser Trp Phe Gln Asn Ala Ala Ala Gly Thr Ser Ala His Tyr Leu
225                 230                 235                 240

Leu Arg Ser Ser Asp Gly Ala Val Thr Gln Met Val Arg Asp Lys Asp
                245                 250                 255

Val Ala Trp His Ala Gly Asn Trp Thr Tyr Asn Thr Gln Ser Ile Gly
            260                 265                 270

Ile Glu His Glu Gly Tyr Val Asp Asn Ala Ser Trp Tyr Thr Asp Ala
        275                 280                 285

Met Tyr Arg Ser Ser Ala Ala Leu Thr Arg His Leu Ala Asp Lys Tyr
    290                 295                 300

Gly Ile Pro Lys Thr Arg Ser Asn Ile Gly His Asn Gln Val Pro
305                 310                 315                 320

Gly Ala Thr His Thr Asp Pro Gly Pro Asn Trp Asn Trp Thr Tyr Tyr
                325                 330                 335

Met Gln Leu Val Thr Gly Thr Thr Pro Pro Thr Trp Ser Thr
            340                 345                 350

```
Ile Val Asp Asn Thr Thr Ala Gly Arg Phe Thr Ala Ser Ala Asn Trp
            355                 360                 365

Ser Thr Ser Ser Tyr Ser Ser Gln Arg Tyr Gly Ala Asp Tyr Arg Tyr
        370                 375                 380

Ala Asn Pro Val Ala Ala Ser Asp Ala Ala Trp Tyr Lys Val Asn Ile
385                 390                 395                 400

Pro Ala Thr Ala Thr Tyr Arg Val Glu Val Trp Tyr Pro Ala Val Ala
                405                 410                 415

Gly Tyr Asn Ala Thr Thr Pro Tyr Ile Val Ala Thr Ser Ser Gly Asn
            420                 425                 430

Gln Thr Val Asn Val Asn Gln Ser Ala Asn Gly Gly Trp Arg Ser
        435                 440                 445

Leu Gly Asn Phe Thr Leu Ala Ala Gly Asp Ala Asn Lys Val Gly Ile
    450                 455                 460

Ser Arg Trp Ser Gly Ser Thr Gly Tyr Val Ala Asp Ala Ile Arg
465                 470                 475                 480

Ile Thr Arg Val

<210> SEQ ID NO 19
<211> LENGTH: 1533
<212> TYPE: DNA
<213> ORGANISM: Nonomuraea coxensis
<220> FEATURE:
<221> NAME/KEY: CDS
<222> LOCATION: (1)..(1530)
<220> FEATURE:
<221> NAME/KEY: sig_peptide
<222> LOCATION: (1)..(90)
<220> FEATURE:
<221> NAME/KEY: mat_peptide
<222> LOCATION: (91)..(1530)

<400> SEQUENCE: 19
```

| | |
|---|---|
| atg gaa ctc gcc cgc acg cga tta aca gcc ctc gcc acc tcc ttc ctc<br>Met Glu Leu Ala Arg Thr Arg Leu Thr Ala Leu Ala Thr Ser Phe Leu<br>-30              -25                 -20                 -15 | 48 |
| gcc gtc ctc gtc ctc gtc gcc acg ggc cgc ccc gcc ctg gcc gcg ccc<br>Ala Val Leu Val Leu Val Ala Thr Gly Arg Pro Ala Leu Ala Ala Pro<br>         -10                  -5                  -1  1 | 96 |
| acg gcc gcg gac ggc acc ctc acc gcc gcc ttc gcc aag gcg gcg gcc<br>Thr Ala Ala Asp Gly Thr Leu Thr Ala Ala Phe Ala Lys Ala Ala Ala<br>             5                  10                  15 | 144 |
| gcg tac gac gtg ccc cgc gac ctg ctg gtc gcc ctc ggc tac gcc gag<br>Ala Tyr Asp Val Pro Arg Asp Leu Leu Val Ala Leu Gly Tyr Ala Glu<br>         20                  25                  30 | 192 |
| acc cac ctc gac ggt cac gac ggc aag ccc agc gcc agc ggc ggc tac<br>Thr His Leu Asp Gly His Asp Gly Lys Pro Ser Ala Ser Gly Gly Tyr<br>35                  40                  45                  50 | 240 |
| ggc gtc atg cac ctg gtc agc aac ccc acc aac cac tcc ctg gag aag<br>Gly Val Met His Leu Val Ser Asn Pro Thr Asn His Ser Leu Glu Lys<br>             55                  60                  65 | 288 |
| gcc gcc gag ctc acc ggc cgc tcc acc ggc gaa ctg cgc gcc gac gac<br>Ala Ala Glu Leu Thr Gly Arg Ser Thr Gly Glu Leu Arg Ala Asp Asp<br>         70                  75                  80 | 336 |
| gcc gcc aac gtg ctc ggc ggc gcc gcc gta ctc cgc tcc cac gcc gac<br>Ala Ala Asn Val Leu Gly Gly Ala Ala Val Leu Arg Ser His Ala Asp<br>     85                  90                  95 | 384 |
| gcc ctc ggc ctc gac gaa acg gcc agg aag gac gcc gga cgc tgg tac<br>Ala Leu Gly Leu Asp Glu Thr Ala Arg Lys Asp Ala Gly Arg Trp Tyr<br>100                 105                 110 | 432 |

```
cag gcc gtc gcc aag tac ggc aac gcc acc tcg ccc gag ctc gcc cgc      480
Gln Ala Val Ala Lys Tyr Gly Asn Ala Thr Ser Pro Glu Leu Ala Arg
115                 120                 125                 130 ctc tac gcc gac gcc gtc tac gag agc ctc ggc ctc ggc atc gac atc      528
Leu Tyr Ala Asp Ala Val Tyr Glu Ser Leu Gly Leu Gly Ile Asp Ile
                135                 140                 145 cgc ggc gtc cag gtc aag ccc cag gag gtc acc gcc gac cgc ggc gag      576
Arg Gly Val Gln Val Lys Pro Gln Glu Val Thr Ala Asp Arg Gly Glu
        150                 155                 160 tac gcc aag gcc cgc gac ctc aac gcc aag gcc gac gcc ggc gtc ctc      624
Tyr Ala Lys Ala Arg Asp Leu Asn Ala Lys Ala Asp Ala Gly Val Leu
        165                 170                 175 agc acc gac tac ggc ccc gcc gcc tgg gtc gcc gcc agc tcc agc aac      672
Ser Thr Asp Tyr Gly Pro Ala Ala Trp Val Ala Ala Ser Ser Ser Asn
180                 185                 190 tac acc gcc tcc agc cgc ccg tcg agc tac gcc atc gac cgc gtg atc      720
Tyr Thr Ala Ser Ser Arg Pro Ser Ser Tyr Ala Ile Asp Arg Val Ile
195                 200                 205                 210 atc cac gtg acg cag ggc tcg tac gcc ggc acc atc tcc tgg ttc cag      768
Ile His Val Thr Gln Gly Ser Tyr Ala Gly Thr Ile Ser Trp Phe Gln
                215                 220                 225 aac ccc tcc gcc cag gtc tcg gcc cac tac gtg gtc aag tcc tcc aac      816
Asn Pro Ser Ala Gln Val Ser Ala His Tyr Val Val Lys Ser Ser Asn
        230                 235                 240 ggc gcc atc acc cag atg gtg cgc gag aag gac gtc gcc tgg cac gcc      864
Gly Ala Ile Thr Gln Met Val Arg Glu Lys Asp Val Ala Trp His Ala
        245                 250                 255 ggc aac tgg acc tac aac acc cgg tcg atc ggc atc gag cac gag ggc      912
Gly Asn Trp Thr Tyr Asn Thr Arg Ser Ile Gly Ile Glu His Glu Gly
260                 265                 270 tac gtc aac gac gcc tcg tgg ttc acc gac gcg atg tac cgg gcg tcc      960
Tyr Val Asn Asp Ala Ser Trp Phe Thr Asp Ala Met Tyr Arg Ala Ser
275                 280                 285                 290 gcg gcc ctc acc aag aac atc tgc gag aag tac ggc atc ccc aag gac     1008
Ala Ala Leu Thr Lys Asn Ile Cys Glu Lys Tyr Gly Ile Pro Lys Asp
                295                 300                 305 cgc agc cac atc atc ggc cac aac cag gtg ccc ggc gcc acc cac acc     1056
Arg Ser His Ile Ile Gly His Asn Gln Val Pro Gly Ala Thr His Thr
        310                 315                 320 gac ccg ggc tcc aac tgg aac tgg acc acg tac atg aac tac gtg acc     1104
Asp Pro Gly Ser Asn Trp Asn Trp Thr Thr Tyr Met Asn Tyr Val Thr
        325                 330                 335 ggt ggc ggc ggc acc ccc tcg tgg acc acc acg atc gac aac gcc acc     1152
Gly Gly Gly Gly Thr Pro Ser Trp Thr Thr Thr Ile Asp Asn Ala Thr
340                 345                 350 tcc ggc cag ttc acc gcc agc gcc aac tgg ggc acc tcc acc tac tcc     1200
Ser Gly Gln Phe Thr Ala Ser Ala Asn Trp Gly Thr Ser Thr Tyr Ser
355                 360                 365                 370 agc cag cgc tac ggc tcc gac tac cgc ttc gcc gac ccg gtc tcc gcc     1248
Ser Gln Arg Tyr Gly Ser Asp Tyr Arg Phe Ala Asp Pro Val Ser Ala
                375                 380                 385 agc gac gcg gcg tgg tac tcg gcc gcc atc ccc agc gcg ggc acc tac     1296
Ser Asp Ala Ala Trp Tyr Ser Ala Ala Ile Pro Ser Ala Gly Thr Tyr
        390                 395                 400 cgc gtc gag gtc tgg tat ccg gcc gac gcg ggc tac aac agc tcg gcg     1344
Arg Val Glu Val Trp Tyr Pro Ala Asp Ala Gly Tyr Asn Ser Ser Ala
        405                 410                 415
```

```
ccg tac atc gtg gcg acg tca ggc ggc aac cag acc gtc tac gtc gac    1392
Pro Tyr Ile Val Ala Thr Ser Gly Gly Asn Gln Thr Val Tyr Val Asp
    420                 425                 430 caa cgc agc ggc ggc ggc tcc tgg aag agc atc ggc acg ttc tcg ctg    1440
Gln Arg Ser Gly Gly Gly Ser Trp Lys Ser Ile Gly Thr Phe Ser Leu
435                 440                 445                 450 aac gcg ggg acg tac aac gtg gtc gga atc agc cgg tgg acc gcc ggc    1488
Asn Ala Gly Thr Tyr Asn Val Val Gly Ile Ser Arg Trp Thr Ala Gly
                455                 460                 465 acc ggc tac gtc atc gcc gac gcc gtc cgc atc agc cgc gtc tga        1533
Thr Gly Tyr Val Ile Ala Asp Ala Val Arg Ile Ser Arg Val
            470                 475                 480

<210> SEQ ID NO 20
<211> LENGTH: 510
<212> TYPE: PRT
<213> ORGANISM: Nonomuraea coxensis

<400> SEQUENCE: 20

Met Glu Leu Ala Arg Thr Arg Leu Thr Ala Leu Ala Thr Ser Phe Leu
-30                 -25                 -20                 -15

Ala Val Leu Val Leu Val Ala Thr Gly Arg Pro Ala Leu Ala Ala Pro
            -10                  -5                  -1   1

Thr Ala Ala Asp Gly Thr Leu Thr Ala Ala Phe Ala Lys Ala Ala Ala
         5                  10                  15

Ala Tyr Asp Val Pro Arg Asp Leu Leu Val Ala Leu Gly Tyr Ala Glu
     20                  25                  30

Thr His Leu Asp Gly His Asp Gly Lys Pro Ser Ala Ser Gly Gly Tyr
 35                  40                  45                  50

Gly Val Met His Leu Val Ser Asn Pro Thr Asn His Ser Leu Glu Lys
                 55                  60                  65

Ala Ala Glu Leu Thr Gly Arg Ser Thr Gly Glu Leu Arg Ala Asp Asp
                 70                  75                  80

Ala Ala Asn Val Leu Gly Gly Ala Ala Val Leu Arg Ser His Ala Asp
                 85                  90                  95

Ala Leu Gly Leu Asp Glu Thr Ala Arg Lys Asp Ala Gly Arg Trp Tyr
            100                 105                 110

Gln Ala Val Ala Lys Tyr Gly Asn Ala Thr Ser Pro Glu Leu Ala Arg
115                 120                 125                 130

Leu Tyr Ala Asp Ala Val Tyr Glu Ser Leu Gly Leu Gly Ile Asp Ile
                135                 140                 145

Arg Gly Val Gln Val Lys Pro Gln Glu Val Thr Ala Asp Arg Gly Glu
            150                 155                 160

Tyr Ala Lys Ala Arg Asp Leu Asn Ala Lys Ala Asp Ala Gly Val Leu
            165                 170                 175

Ser Thr Asp Tyr Gly Pro Ala Ala Trp Val Ala Ala Ser Ser Ser Asn
    180                 185                 190

Tyr Thr Ala Ser Ser Arg Pro Ser Ser Tyr Ala Ile Asp Arg Val Ile
195                 200                 205                 210

Ile His Val Thr Gln Gly Ser Tyr Ala Gly Thr Ile Ser Trp Phe Gln
            215                 220                 225

Asn Pro Ser Ala Gln Val Ser Ala His Tyr Val Val Lys Ser Ser Asn
            230                 235                 240

Gly Ala Ile Thr Gln Met Val Arg Glu Lys Asp Val Ala Trp His Ala
            245                 250                 255
```

```
Gly Asn Trp Thr Tyr Asn Thr Arg Ser Ile Gly Ile Glu His Glu Gly
    260                 265                 270

Tyr Val Asn Asp Ala Ser Trp Phe Thr Asp Ala Met Tyr Arg Ala Ser
275                 280                 285                 290

Ala Ala Leu Thr Lys Asn Ile Cys Glu Lys Tyr Gly Ile Pro Lys Asp
                295                 300                 305

Arg Ser His Ile Ile Gly His Asn Gln Val Pro Gly Ala Thr His Thr
            310                 315                 320

Asp Pro Gly Ser Asn Trp Asn Trp Thr Thr Tyr Met Asn Tyr Val Thr
        325                 330                 335

Gly Gly Gly Gly Thr Pro Ser Trp Thr Thr Thr Ile Asp Asn Ala Thr
    340                 345                 350

Ser Gly Gln Phe Thr Ala Ser Ala Asn Trp Gly Thr Ser Thr Tyr Ser
355                 360                 365                 370

Ser Gln Arg Tyr Gly Ser Asp Tyr Arg Phe Ala Asp Pro Val Ser Ala
                375                 380                 385

Ser Asp Ala Ala Trp Tyr Ser Ala Ala Ile Pro Ser Ala Gly Thr Tyr
            390                 395                 400

Arg Val Glu Val Trp Tyr Pro Ala Asp Ala Gly Tyr Asn Ser Ser Ala
        405                 410                 415

Pro Tyr Ile Val Ala Thr Ser Gly Gly Asn Gln Thr Val Tyr Val Asp
    420                 425                 430

Gln Arg Ser Gly Gly Ser Trp Lys Ser Ile Gly Thr Phe Ser Leu
435                 440                 445                 450

Asn Ala Gly Thr Tyr Asn Val Val Gly Ile Ser Arg Trp Thr Ala Gly
                455                 460                 465

Thr Gly Tyr Val Ile Ala Asp Ala Val Arg Ile Ser Arg Val
            470                 475                 480

<210> SEQ ID NO 21
<211> LENGTH: 480
<212> TYPE: PRT
<213> ORGANISM: Nonomuraea coxensis

<400> SEQUENCE: 21

Ala Pro Thr Ala Ala Asp Gly Thr Leu Thr Ala Ala Phe Ala Lys Ala
1               5                   10                  15

Ala Ala Ala Tyr Asp Val Pro Arg Asp Leu Leu Val Ala Leu Gly Tyr
                20                  25                  30

Ala Glu Thr His Leu Asp Gly His Asp Gly Lys Pro Ser Ala Ser Gly
            35                  40                  45

Gly Tyr Gly Val Met His Leu Val Ser Asn Pro Thr Asn His Ser Leu
50                  55                  60

Glu Lys Ala Ala Glu Leu Thr Gly Arg Ser Thr Gly Glu Leu Arg Ala
65                  70                  75                  80

Asp Asp Ala Ala Asn Val Leu Gly Gly Ala Ala Val Leu Arg Ser His
                85                  90                  95

Ala Asp Ala Leu Gly Leu Asp Glu Thr Ala Arg Lys Asp Ala Gly Arg
            100                 105                 110

Trp Tyr Gln Ala Val Ala Lys Tyr Gly Asn Ala Thr Ser Pro Glu Leu
        115                 120                 125

Ala Arg Leu Tyr Ala Asp Ala Val Tyr Glu Ser Leu Gly Leu Gly Ile
    130                 135                 140

Asp Ile Arg Gly Val Gln Val Lys Pro Gln Glu Val Thr Ala Asp Arg
145                 150                 155                 160
```

Gly Glu Tyr Ala Lys Ala Arg Asp Leu Asn Ala Lys Ala Asp Ala Gly
            165                 170                 175

Val Leu Ser Thr Asp Tyr Gly Pro Ala Ala Trp Val Ala Ala Ser Ser
        180                 185                 190

Ser Asn Tyr Thr Ala Ser Ser Arg Pro Ser Tyr Ala Ile Asp Arg
        195                 200                 205

Val Ile Ile His Val Thr Gln Gly Ser Tyr Ala Gly Thr Ile Ser Trp
    210                 215                 220

Phe Gln Asn Pro Ser Ala Gln Val Ser Ala His Tyr Val Val Lys Ser
225                 230                 235                 240

Ser Asn Gly Ala Ile Thr Gln Met Val Arg Glu Lys Asp Val Ala Trp
            245                 250                 255

His Ala Gly Asn Trp Thr Tyr Asn Thr Arg Ser Ile Gly Ile Glu His
            260                 265                 270

Glu Gly Tyr Val Asn Asp Ala Ser Trp Phe Thr Asp Ala Met Tyr Arg
        275                 280                 285

Ala Ser Ala Ala Leu Thr Lys Asn Ile Cys Glu Lys Tyr Gly Ile Pro
        290                 295                 300

Lys Asp Arg Ser His Ile Ile Gly His Asn Gln Val Pro Gly Ala Thr
305                 310                 315                 320

His Thr Asp Pro Gly Ser Asn Trp Asn Trp Thr Thr Tyr Met Asn Tyr
            325                 330                 335

Val Thr Gly Gly Gly Gly Thr Pro Ser Trp Thr Thr Thr Ile Asp Asn
            340                 345                 350

Ala Thr Ser Gly Gln Phe Thr Ala Ser Ala Asn Trp Gly Thr Ser Thr
        355                 360                 365

Tyr Ser Ser Gln Arg Tyr Gly Ser Asp Tyr Arg Phe Ala Asp Pro Val
        370                 375                 380

Ser Ala Ser Asp Ala Ala Trp Tyr Ser Ala Ala Ile Pro Ser Ala Gly
385                 390                 395                 400

Thr Tyr Arg Val Glu Val Trp Tyr Pro Ala Asp Ala Gly Tyr Asn Ser
            405                 410                 415

Ser Ala Pro Tyr Ile Val Ala Thr Ser Gly Gly Asn Gln Thr Val Tyr
        420                 425                 430

Val Asp Gln Arg Ser Gly Gly Ser Trp Lys Ser Ile Gly Thr Phe
        435                 440                 445

Ser Leu Asn Ala Gly Thr Tyr Asn Val Val Gly Ile Ser Arg Trp Thr
450                 455                 460

Ala Gly Thr Gly Tyr Val Ile Ala Asp Ala Val Arg Ile Ser Arg Val
465                 470                 475                 480

<210> SEQ ID NO 22
<211> LENGTH: 1548
<212> TYPE: DNA
<213> ORGANISM: Micromonospora fulvopurpurea
<220> FEATURE:
<221> NAME/KEY: CDS
<222> LOCATION: (1)..(1548)
<220> FEATURE:
<221> NAME/KEY: sig_peptide
<222> LOCATION: (1)..(93)
<220> FEATURE:
<221> NAME/KEY: mat_peptide
<222> LOCATION: (94)..(1548)

<400> SEQUENCE: 22

```
atg acg atc cgt cgt cca cca cgt cgc gtt tca cac ctt tta gga gga      48
Met Thr Ile Arg Arg Pro Pro Arg Arg Val Ser His Leu Leu Gly Gly
    -30                 -25                 -20 gca atg att ctt atg att gga tta act ggt caa cct gca cag gct gcg      96
Ala Met Ile Leu Met Ile Gly Leu Thr Gly Gln Pro Ala Gln Ala Ala
    -15                 -10                  -5              -1   1 cca gct cat gga gct caa cct ttg gct gcc gca ttc gac cgt gca gct     144
Pro Ala His Gly Ala Gln Pro Leu Ala Ala Ala Phe Asp Arg Ala Ala
             5                   10                  15 gcg tca tca gat gtt cct cgt gac gtt ctt gcg gct ctt gga tac gcg     192
Ala Ser Ser Asp Val Pro Arg Asp Val Leu Ala Ala Leu Gly Tyr Ala
         20                  25                  30 gaa act cgc ttg gat ggt cat ggt ggt gag ccg tct gta tca ggt gga     240
Glu Thr Arg Leu Asp Gly His Gly Gly Glu Pro Ser Val Ser Gly Gly
     35                  40                  45 tac ggt gta atg cat ctt aca tca aac cca aaa gtt cgt act tta gat     288
Tyr Gly Val Met His Leu Thr Ser Asn Pro Lys Val Arg Thr Leu Asp
50                   55                  60                  65 gaa gct gcg cgt cgc aca cgt tta gac cgt gca gac ctt cgt act cgt     336
Glu Ala Ala Arg Arg Thr Arg Leu Asp Arg Ala Asp Leu Arg Thr Arg
                 70                  75                  80 gac gct gcg aac gta gct gga gct gct gca gta ctt cgc tct tac gcg     384
Asp Ala Ala Asn Val Ala Gly Ala Ala Ala Val Leu Arg Ser Tyr Ala
             85                  90                  95 gat gaa gcg ggt ctt acg gct gct cag cgc gac gac gta aac cag tgg     432
Asp Glu Ala Gly Leu Thr Ala Ala Gln Arg Asp Asp Val Asn Gln Trp
        100                 105                 110 tat ggc cca att gct cgt tat ggc gga agc act gat gct gca act gct     480
Tyr Gly Pro Ile Ala Arg Tyr Gly Gly Ser Thr Asp Ala Ala Thr Ala
    115                 120                 125 cgt ctt tac gca gat tct gta tat gac ttg ctt gcg cgt gga ttc atc     528
Arg Leu Tyr Ala Asp Ser Val Tyr Asp Leu Leu Ala Arg Gly Phe Ile
130                 135                 140                 145 gcg act act gca ggt ggc gaa gtt tct gta gat ggc cgt ccg gtt gcg     576
Ala Thr Thr Ala Gly Gly Glu Val Ser Val Asp Gly Arg Pro Val Ala
                150                 155                 160 cct caa cgt ggt cgt tat gct gct gta gct cca ctt ggc act ggt gat     624
Pro Gln Arg Gly Arg Tyr Ala Ala Val Ala Pro Leu Gly Thr Gly Asp
            165                 170                 175 ttc ggt act ctt tct act gat tac ggt cca gct gct tgg gtt cca gcg     672
Phe Gly Thr Leu Ser Thr Asp Tyr Gly Pro Ala Ala Trp Val Pro Ala
        180                 185                 190 aac agc tct aac tac aca gtt tca tct cgt gaa tca gca tac ccg atc     720
Asn Ser Ser Asn Tyr Thr Val Ser Ser Arg Glu Ser Ala Tyr Pro Ile
    195                 200                 205 aat tac att gtt atc cat act atg caa ggt tca tac gca ggc tca att     768
Asn Tyr Ile Val Ile His Thr Met Gln Gly Ser Tyr Ala Gly Ser Ile
210                 215                 220                 225 tct tgg ttt cag aac gct gct gct ggc aca tct gct cac tac ctt ctt     816
Ser Trp Phe Gln Asn Ala Ala Ala Gly Thr Ser Ala His Tyr Leu Leu
                230                 235                 240 cgt tct tca gat ggt gcg gtt act caa atg gta cgt gac aaa gat att     864
Arg Ser Ser Asp Gly Ala Val Thr Gln Met Val Arg Asp Lys Asp Ile
            245                 250                 255 gca tgg cac gct ggc aat tgg act tac aac act cag tct atc gga atc     912
Ala Trp His Ala Gly Asn Trp Thr Tyr Asn Thr Gln Ser Ile Gly Ile
        260                 265                 270
```

| | | | | | | | | | | | | | | | |
|---|---|---|---|---|---|---|---|---|---|---|---|---|---|---|---|
| gag | cat | gaa | gga | tat | gta | gac | aat | gcg | tct | tgg | tac | aca | gac | gca | atg | 960 |
| Glu | His | Glu | Gly | Tyr | Val | Asp | Asn | Ala | Ser | Trp | Tyr | Thr | Asp | Ala | Met | |
| | 275 | | | | 280 | | | | | 285 | | | | | | |

```
gag cat gaa gga tat gta gac aat gcg tct tgg tac aca gac gca atg      960
Glu His Glu Gly Tyr Val Asp Asn Ala Ser Trp Tyr Thr Asp Ala Met
    275                 280                 285 tat cgt tct tct gct gcg ctt aca cgc tac tta tgc gac aag tat gga     1008
Tyr Arg Ser Ser Ala Ala Leu Thr Arg Tyr Leu Cys Asp Lys Tyr Gly
290                 295                 300                 305 atc ccg aaa aca cgc act aac att atc ggt cat aat caa gtt cct gga     1056
Ile Pro Lys Thr Arg Thr Asn Ile Ile Gly His Asn Gln Val Pro Gly
                310                 315                 320 gca act cat act gat cca ggc cct aac tgg aac tgg acg tat tac atg     1104
Ala Thr His Thr Asp Pro Gly Pro Asn Trp Asn Trp Thr Tyr Tyr Met
            325                 330                 335 caa ctt gtt act ggt ggc acg acg cca ccg cct aca aca tgg tct aca     1152
Gln Leu Val Thr Gly Gly Thr Thr Pro Pro Pro Thr Thr Trp Ser Thr
    340                 345                 350 gtt gtt gat aac aca act gct ggt cgc ttc act gca tct gct aac tgg     1200
Val Val Asp Asn Thr Thr Ala Gly Arg Phe Thr Ala Ser Ala Asn Trp
355                 360                 365 tct aca tct aca tac agc gct caa cgc tat gga act gat tat cgt tac     1248
Ser Thr Ser Thr Tyr Ser Ala Gln Arg Tyr Gly Thr Asp Tyr Arg Tyr
370                 375                 380                 385 gcg aat cct gta gct gct agc gat aca gca tgg tat aag gtt aac att     1296
Ala Asn Pro Val Ala Ala Ser Asp Thr Ala Trp Tyr Lys Val Asn Ile
                390                 395                 400 cct gcc acg gcc acg tat cgt gtt gaa gta tgg tat cca gca gta gct     1344
Pro Ala Thr Ala Thr Tyr Arg Val Glu Val Trp Tyr Pro Ala Val Ala
            405                 410                 415 ggc tat aac act tct aca cca tac atc gta gct aca aca agc gga aac     1392
Gly Tyr Asn Thr Ser Thr Pro Tyr Ile Val Ala Thr Thr Ser Gly Asn
    420                 425                 430 caa acg gta tct gtt aac caa aca gct aat ggc ggt act tgg cgt tca     1440
Gln Thr Val Ser Val Asn Gln Thr Ala Asn Gly Gly Thr Trp Arg Ser
435                 440                 445 tta ggt act ttc aca ctt gcc gct ggt gat gcg aac aag gta ggt gta     1488
Leu Gly Thr Phe Thr Leu Ala Ala Gly Asp Ala Asn Lys Val Gly Val
450                 455                 460                 465 tct cgt tgg tca gga tct acg gga tac gta atc gcc gat gct att cgt     1536
Ser Arg Trp Ser Gly Ser Thr Gly Tyr Val Ile Ala Asp Ala Ile Arg
                470                 475                 480 gtt act cgc gta                                                     1548
Val Thr Arg Val
            485

<210> SEQ ID NO 23
<211> LENGTH: 516
<212> TYPE: PRT
<213> ORGANISM: Micromonospora fulvopurpurea

<400> SEQUENCE: 23

Met Thr Ile Arg Arg Pro Pro Arg Arg Val Ser His Leu Leu Gly Gly
        -30                 -25                 -20

Ala Met Ile Leu Met Ile Gly Leu Thr Gly Gln Pro Ala Gln Ala Ala
-15                 -10                  -5                  -1   1

Pro Ala His Gly Ala Gln Pro Leu Ala Ala Ala Phe Asp Arg Ala Ala
                 5                  10                  15

Ala Ser Ser Asp Val Pro Arg Asp Val Leu Ala Ala Leu Gly Tyr Ala
            20                  25                  30

Glu Thr Arg Leu Asp Gly His Gly Gly Glu Pro Ser Val Ser Gly Gly
        35                  40                  45
```

```
Tyr Gly Val Met His Leu Thr Ser Asn Pro Lys Val Arg Thr Leu Asp
 50                  55                  60                  65

Glu Ala Ala Arg Arg Thr Arg Leu Asp Arg Ala Asp Leu Arg Thr Arg
                 70                  75                  80

Asp Ala Ala Asn Val Ala Gly Ala Ala Val Leu Arg Ser Tyr Ala
                 85                  90                  95

Asp Glu Ala Gly Leu Thr Ala Ala Gln Arg Asp Val Asn Gln Trp
                100                 105                 110

Tyr Gly Pro Ile Ala Arg Tyr Gly Ser Thr Asp Ala Ala Thr Ala
                115                 120                 125

Arg Leu Tyr Ala Asp Ser Val Tyr Asp Leu Leu Ala Arg Gly Phe Ile
130                 135                 140                 145

Ala Thr Thr Ala Gly Gly Glu Val Ser Val Asp Gly Arg Pro Val Ala
                150                 155                 160

Pro Gln Arg Gly Arg Tyr Ala Ala Val Ala Pro Leu Gly Thr Gly Asp
                165                 170                 175

Phe Gly Thr Leu Ser Thr Asp Tyr Gly Pro Ala Ala Trp Val Pro Ala
                180                 185                 190

Asn Ser Ser Asn Tyr Thr Val Ser Ser Arg Glu Ser Ala Tyr Pro Ile
195                 200                 205

Asn Tyr Ile Val Ile His Thr Met Gln Gly Ser Tyr Ala Gly Ser Ile
210                 215                 220                 225

Ser Trp Phe Gln Asn Ala Ala Gly Thr Ser Ala His Tyr Leu Leu
                230                 235                 240

Arg Ser Ser Asp Gly Ala Val Thr Gln Met Val Arg Asp Lys Asp Ile
                245                 250                 255

Ala Trp His Ala Gly Asn Trp Thr Tyr Asn Thr Gln Ser Ile Gly Ile
                260                 265                 270

Glu His Glu Gly Tyr Val Asp Asn Ala Ser Trp Tyr Thr Asp Ala Met
                275                 280                 285

Tyr Arg Ser Ser Ala Ala Leu Thr Arg Tyr Leu Cys Asp Lys Tyr Gly
290                 295                 300                 305

Ile Pro Lys Thr Arg Thr Asn Ile Ile Gly His Asn Gln Val Pro Gly
                310                 315                 320

Ala Thr His Thr Asp Pro Gly Pro Asn Trp Asn Trp Thr Tyr Tyr Met
                325                 330                 335

Gln Leu Val Thr Gly Thr Thr Pro Pro Thr Thr Trp Ser Thr
                340                 345                 350

Val Val Asp Asn Thr Thr Ala Gly Arg Phe Thr Ala Ser Ala Asn Trp
                355                 360                 365

Ser Thr Ser Thr Tyr Ser Ala Gln Arg Tyr Gly Thr Asp Tyr Arg Tyr
370                 375                 380                 385

Ala Asn Pro Val Ala Ala Ser Asp Thr Ala Trp Tyr Lys Val Asn Ile
                390                 395                 400

Pro Ala Thr Ala Thr Tyr Arg Val Glu Val Trp Tyr Pro Ala Val Ala
                405                 410                 415

Gly Tyr Asn Thr Ser Thr Pro Tyr Ile Val Ala Thr Ser Gly Asn
                420                 425                 430

Gln Thr Val Ser Val Asn Gln Thr Ala Asn Gly Gly Thr Trp Arg Ser
                435                 440                 445

Leu Gly Thr Phe Thr Leu Ala Ala Gly Asp Ala Asn Lys Val Gly Val
450                 455                 460                 465
```

Ser Arg Trp Ser Gly Ser Thr Gly Tyr Val Ile Ala Asp Ala Ile Arg
                470                 475                 480

Val Thr Arg Val
            485

<210> SEQ ID NO 24
<211> LENGTH: 485
<212> TYPE: PRT
<213> ORGANISM: Micromonospora fulvopurpurea

<400> SEQUENCE: 24

Ala Pro Ala His Gly Ala Gln Pro Leu Ala Ala Phe Asp Arg Ala
1               5                   10                  15

Ala Ala Ser Ser Asp Val Pro Arg Asp Val Leu Ala Ala Leu Gly Tyr
                20                  25                  30

Ala Glu Thr Arg Leu Asp Gly His Gly Gly Glu Pro Ser Val Ser Gly
            35                  40                  45

Gly Tyr Gly Val Met His Leu Thr Ser Asn Pro Lys Val Arg Thr Leu
        50                  55                  60

Asp Glu Ala Ala Arg Arg Thr Arg Leu Asp Arg Ala Asp Leu Arg Thr
65              70                  75                  80

Arg Asp Ala Ala Asn Val Ala Gly Ala Ala Val Leu Arg Ser Tyr
                85                  90                  95

Ala Asp Glu Ala Gly Leu Thr Ala Ala Gln Arg Asp Asp Val Asn Gln
                100                 105                 110

Trp Tyr Gly Pro Ile Ala Arg Tyr Gly Gly Ser Thr Asp Ala Ala Thr
            115                 120                 125

Ala Arg Leu Tyr Ala Asp Ser Val Tyr Asp Leu Leu Ala Arg Gly Phe
        130                 135                 140

Ile Ala Thr Thr Ala Gly Gly Glu Val Ser Val Asp Gly Arg Pro Val
145             150                 155                 160

Ala Pro Gln Arg Gly Arg Tyr Ala Ala Val Ala Pro Leu Gly Thr Gly
                165                 170                 175

Asp Phe Gly Thr Leu Ser Thr Asp Tyr Gly Pro Ala Ala Trp Val Pro
            180                 185                 190

Ala Asn Ser Ser Asn Tyr Thr Val Ser Ser Arg Glu Ser Ala Tyr Pro
        195                 200                 205

Ile Asn Tyr Ile Val Ile His Thr Met Gln Gly Ser Tyr Ala Gly Ser
        210                 215                 220

Ile Ser Trp Phe Gln Asn Ala Ala Ala Gly Thr Ser Ala His Tyr Leu
225             230                 235                 240

Leu Arg Ser Ser Asp Gly Ala Val Thr Gln Met Val Arg Asp Lys Asp
                245                 250                 255

Ile Ala Trp His Ala Gly Asn Trp Thr Tyr Asn Thr Gln Ser Ile Gly
            260                 265                 270

Ile Glu His Glu Gly Tyr Val Asp Asn Ala Ser Trp Tyr Thr Asp Ala
        275                 280                 285

Met Tyr Arg Ser Ala Ala Leu Thr Arg Tyr Leu Cys Asp Lys Tyr
        290                 295                 300

Gly Ile Pro Lys Thr Arg Thr Asn Ile Ile Gly His Asn Gln Val Pro
305             310                 315                 320

Gly Ala Thr His Thr Asp Pro Gly Pro Asn Trp Asn Trp Thr Tyr Tyr
                325                 330                 335

```
Met Gln Leu Val Thr Gly Gly Thr Thr Pro Pro Thr Thr Trp Ser
            340                 345                 350

Thr Val Val Asp Asn Thr Thr Ala Gly Arg Phe Thr Ala Ser Ala Asn
                355                 360                 365

Trp Ser Thr Ser Thr Tyr Ser Ala Gln Arg Tyr Gly Thr Asp Tyr Arg
    370                 375                 380

Tyr Ala Asn Pro Val Ala Ala Ser Asp Thr Ala Trp Tyr Lys Val Asn
385                 390                 395                 400

Ile Pro Ala Thr Ala Thr Tyr Arg Val Glu Val Trp Tyr Pro Ala Val
                405                 410                 415

Ala Gly Tyr Asn Thr Ser Thr Pro Tyr Ile Val Ala Thr Thr Ser Gly
            420                 425                 430

Asn Gln Thr Val Ser Val Asn Gln Thr Ala Asn Gly Gly Thr Trp Arg
        435                 440                 445

Ser Leu Gly Thr Phe Thr Leu Ala Ala Gly Asp Ala Asn Lys Val Gly
    450                 455                 460

Val Ser Arg Trp Ser Gly Ser Thr Gly Tyr Val Ile Ala Asp Ala Ile
465                 470                 475                 480

Arg Val Thr Arg Val
                485

<210> SEQ ID NO 25
<211> LENGTH: 1560
<212> TYPE: DNA
<213> ORGANISM: Alicyclobacillus sp
<220> FEATURE:
<221> NAME/KEY: CDS
<222> LOCATION: (1)..(1557)
<220> FEATURE:
<221> NAME/KEY: sig_peptide
<222> LOCATION: (1)..(84)
<220> FEATURE:
<221> NAME/KEY: mat_peptide
<222> LOCATION: (85)..(1557)

<400> SEQUENCE: 25
```

| | | |
|---|---|---|
| atg aag aaa act tgg gtt acg gtc ctg gct acc acc gca ttg acc ttc<br>Met Lys Lys Thr Trp Val Thr Val Leu Ala Thr Thr Ala Leu Thr Phe<br>            -25               -20               -15 | 48 |
| tcc gtc ggc gca agc tac gca act ccc tcg ttt gca gcg aaa tcg gac<br>Ser Val Gly Ala Ser Tyr Ala Thr Pro Ser Phe Ala Ala Lys Ser Asp<br>     -10               -5               -1 1 | 96 |
| gcg cag tcg caa acg acc gca ccg gcg ttg gac aat gcg ttc acc gca<br>Ala Gln Ser Gln Thr Thr Ala Pro Ala Leu Asp Asn Ala Phe Thr Ala<br>5                 10               15               20 | 144 |
| gcg gcg aag gaa ttc aaa gtc ccg aaa gat ctg ctg atg gcg atc tcc<br>Ala Ala Lys Glu Phe Lys Val Pro Lys Asp Leu Leu Met Ala Ile Ser<br>             25               30               35 | 192 |
| tac gcg gaa tcc cgt tgg caa gtg ccg gct gag acg gtc gcc gat gac<br>Tyr Ala Glu Ser Arg Trp Gln Val Pro Ala Glu Thr Val Ala Asp Asp<br>            40               45               50 | 240 |
| gac cat gcg cac ggc aaa ggc ttg atg cac ttg acg gac aac tcg ttc<br>Asp His Ala His Gly Lys Gly Leu Met His Leu Thr Asp Asn Ser Phe<br>            55               60               65 | 288 |
| aaa aag aac ctg agc gac acg gcg aaa ggt ctt ggg atc acg gcg aag<br>Lys Lys Asn Leu Ser Asp Thr Ala Lys Gly Leu Gly Ile Thr Ala Lys<br>     70               75               80 | 336 |
| caa ctg gag gac aac gca ggg ctg aac atc cgc ggc ggc gcg tac ctg<br>Gln Leu Glu Asp Asn Ala Gly Leu Asn Ile Arg Gly Gly Ala Tyr Leu<br>85                 90               95              100 | 384 |

```
ctc gcc aaa gcg caa cat gag ctc ggc aaa ccg ctc tcc gac aac gtc    432
Leu Ala Lys Ala Gln His Glu Leu Gly Lys Pro Leu Ser Asp Asn Val
            105                 110                 115 aac gac tgg tac gaa gcg gtc gct tcc ttt gaa ggc gct tct gac aag    480
Asn Asp Trp Tyr Glu Ala Val Ala Ser Phe Glu Gly Ala Ser Asp Lys
            120                 125                 130 agc gac aaa gtg ctg ttc gcc gat gaa gtc tat cgc atc ctg aag gac    528
Ser Asp Lys Val Leu Phe Ala Asp Glu Val Tyr Arg Ile Leu Lys Asp
            135                 140                 145 ggg acc tcg ctt gcc atc gac ggc ggc acc ctc tcg atc ttc ccg aac    576
Gly Thr Ser Leu Ala Ile Asp Gly Gly Thr Leu Ser Ile Phe Pro Asn
            150                 155                 160 aaa acc gtc gct ccg gtc aaa gga caa ctg tcg gac gtc acc tac ggc    624
Lys Thr Val Ala Pro Val Lys Gly Gln Leu Ser Asp Val Thr Tyr Gly
165                 170                 175                 180 gtg acg acc aac ccg tcg gcg acc ccg gac tac tcc ggc gcg atc tgg    672
Val Thr Thr Asn Pro Ser Ala Thr Pro Asp Tyr Ser Gly Ala Ile Trp
                185                 190                 195 aat gcg gcg agc aca tcg aac tac caa gtg gcg agc cgt ccg act tcc    720
Asn Ala Ala Ser Thr Ser Asn Tyr Gln Val Ala Ser Arg Pro Thr Ser
                200                 205                 210 aac ccg atc acc tac gtg gtc atc cac gat acc gag ggt tcc tac tcc    768
Asn Pro Ile Thr Tyr Val Val Ile His Asp Thr Glu Gly Ser Tyr Ser
                215                 220                 225 ggc acg atc aac tgg ttc aaa gac ccg agc gcg caa gtt tcg gca cac    816
Gly Thr Ile Asn Trp Phe Lys Asp Pro Ser Ala Gln Val Ser Ala His
            230                 235                 240 tat gtc gtc cgt tct tcc gac ggc cag atc acg cag atg gtg cag gac    864
Tyr Val Val Arg Ser Ser Asp Gly Gln Ile Thr Gln Met Val Gln Asp
245                 250                 255                 260 aag gac atc gct tgg cat gcg cgt acc ttc aac acg aac ggc atc ggc    912
Lys Asp Ile Ala Trp His Ala Arg Thr Phe Asn Thr Asn Gly Ile Gly
                265                 270                 275 atc gag cat gaa gga tat gaa gcg caa acc ggt tgg tac acc gac gcg    960
Ile Glu His Glu Gly Tyr Glu Ala Gln Thr Gly Trp Tyr Thr Asp Ala
                280                 285                 290 atg tac acc caa tcg gcg gcg ttg acc cgt gcg atc tgc caa aaa tac   1008
Met Tyr Thr Gln Ser Ala Ala Leu Thr Arg Ala Ile Cys Gln Lys Tyr
                295                 300                 305 ggc att ccg atg gac cgc gac cac atc ctc ggc cac tcc gaa ctg tgg   1056
Gly Ile Pro Met Asp Arg Asp His Ile Leu Gly His Ser Glu Leu Trp
310                 315                 320 ggc aat gac cac acc gat ccg ggc gtg aac tgg gat tgg aac aaa tac   1104
Gly Asn Asp His Thr Asp Pro Gly Val Asn Trp Asp Trp Asn Lys Tyr
325                 330                 335                 340 atg acc aaa gtc acc ggc gtc tcc aag aac tgg acc gtc gtc gac gtc   1152
Met Thr Lys Val Thr Gly Val Ser Lys Asn Trp Thr Val Val Asp Val
            345                 350                 355 gat gac aaa gac acg gca tcc ggc gcc ttc acc atg tac ggc gct tcg   1200
Asp Asp Lys Asp Thr Ala Ser Gly Ala Phe Thr Met Tyr Gly Ala Ser
            360                 365                 370 caa tac tgg cac ccg gtc tcc ggc tat ggc gtg cac aac gaa atc aac   1248
Gln Tyr Trp His Pro Val Ser Gly Tyr Gly Val His Asn Glu Ile Asn
            375                 380                 385 tac acc aac ggc aac ggc gcg acg atc tac aac tac gcg atc tgg aag   1296
Tyr Thr Asn Gly Asn Gly Ala Thr Ile Tyr Asn Tyr Ala Ile Trp Lys
390                 395                 400
```

```
ccg acg atc ccg gtc gcc ggc aac tac gaa gtc aaa gtg ttc gtc ccg      1344
Pro Thr Ile Pro Val Ala Gly Asn Tyr Glu Val Lys Val Phe Val Pro
405                 410                 415                 420 tcc aac tac gcg ggc acg acc agc gcg aag tat gaa atc cac tac aac      1392
Ser Asn Tyr Ala Gly Thr Thr Ser Ala Lys Tyr Glu Ile His Tyr Asn
                425                 430                 435 ggc ggc gtc gta acc aag acc gtc tcg caa agc gcc tac tcc aac caa      1440
Gly Gly Val Val Thr Lys Thr Val Ser Gln Ser Ala Tyr Ser Asn Gln
440                 445                 450 tgg gta tcg ctt ggc acc tac aac ttc gca acc ggc acc ggc ggc tac      1488
Trp Val Ser Leu Gly Thr Tyr Asn Phe Ala Thr Gly Thr Gly Gly Tyr
        455                 460                 465 gtc aag ttg ggc gac aac acc ggc gac acc aac acg atc gcc ttc gat      1536
Val Lys Leu Gly Asp Asn Thr Gly Asp Thr Asn Thr Ile Ala Phe Asp
470                 475                 480 acg atc cgc ttc atg ggt caa taa                                      1560
Thr Ile Arg Phe Met Gly Gln
485                 490

<210> SEQ ID NO 26
<211> LENGTH: 519
<212> TYPE: PRT
<213> ORGANISM: Alicyclobacillus sp

<400> SEQUENCE: 26

Met Lys Lys Thr Trp Val Thr Val Leu Ala Thr Thr Ala Leu Thr Phe
                -25                 -20                 -15

Ser Val Gly Ala Ser Tyr Ala Thr Pro Ser Phe Ala Ala Lys Ser Asp
        -10                  -5                  -1   1

Ala Gln Ser Gln Thr Thr Ala Pro Ala Leu Asp Asn Ala Phe Thr Ala
5                   10                  15                  20

Ala Ala Lys Glu Phe Lys Val Pro Lys Asp Leu Leu Met Ala Ile Ser
                25                  30                  35

Tyr Ala Glu Ser Arg Trp Gln Val Pro Ala Glu Thr Val Ala Asp Asp
            40                  45                  50

Asp His Ala His Gly Lys Gly Leu Met His Leu Thr Asp Asn Ser Phe
        55                  60                  65

Lys Lys Asn Leu Ser Asp Thr Ala Lys Gly Leu Gly Ile Thr Ala Lys
70                  75                  80

Gln Leu Glu Asp Asn Ala Gly Leu Asn Ile Arg Gly Gly Ala Tyr Leu
                85                  90                  95                  100

Leu Ala Lys Ala Gln His Glu Leu Gly Lys Pro Leu Ser Asp Asn Val
                105                 110                 115

Asn Asp Trp Tyr Glu Ala Val Ala Ser Phe Glu Gly Ala Ser Asp Lys
            120                 125                 130

Ser Asp Lys Val Leu Phe Ala Asp Glu Val Tyr Arg Ile Leu Lys Asp
        135                 140                 145

Gly Thr Ser Leu Ala Ile Asp Gly Gly Thr Leu Ser Ile Phe Pro Asn
150                 155                 160

Lys Thr Val Ala Pro Val Lys Gly Gln Leu Ser Asp Val Thr Tyr Gly
165                 170                 175                 180

Val Thr Thr Asn Pro Ser Ala Thr Pro Asp Tyr Ser Gly Ala Ile Trp
                185                 190                 195

Asn Ala Ala Ser Thr Ser Asn Tyr Gln Val Ala Ser Arg Pro Thr Ser
            200                 205                 210
```

Asn Pro Ile Thr Tyr Val Val Ile His Asp Thr Glu Gly Ser Tyr Ser
        215                 220                 225

Gly Thr Ile Asn Trp Phe Lys Asp Pro Ser Ala Gln Val Ser Ala His
        230                 235                 240

Tyr Val Val Arg Ser Ser Asp Gly Gln Ile Thr Gln Met Val Gln Asp
245                 250                 255                 260

Lys Asp Ile Ala Trp His Ala Arg Thr Phe Asn Thr Asn Gly Ile Gly
                265                 270                 275

Ile Glu His Glu Gly Tyr Glu Ala Gln Thr Gly Trp Tyr Thr Asp Ala
        280                 285                 290

Met Tyr Thr Gln Ser Ala Ala Leu Thr Arg Ala Ile Cys Gln Lys Tyr
        295                 300                 305

Gly Ile Pro Met Asp Arg Asp His Ile Leu Gly His Ser Glu Leu Trp
        310                 315                 320

Gly Asn Asp His Thr Asp Pro Gly Val Asn Trp Asp Trp Asn Lys Tyr
325                 330                 335                 340

Met Thr Lys Val Thr Gly Val Ser Lys Asn Trp Thr Val Val Asp Val
                345                 350                 355

Asp Asp Lys Asp Thr Ala Ser Gly Ala Phe Thr Met Tyr Gly Ala Ser
        360                 365                 370

Gln Tyr Trp His Pro Val Ser Gly Tyr Gly Val His Asn Glu Ile Asn
        375                 380                 385

Tyr Thr Asn Gly Asn Gly Ala Thr Ile Tyr Asn Tyr Ala Ile Trp Lys
        390                 395                 400

Pro Thr Ile Pro Val Ala Gly Asn Tyr Glu Val Lys Val Phe Val Pro
405                 410                 415                 420

Ser Asn Tyr Ala Gly Thr Thr Ser Ala Lys Tyr Glu Ile His Tyr Asn
                425                 430                 435

Gly Gly Val Val Thr Lys Thr Val Ser Gln Ser Ala Tyr Ser Asn Gln
        440                 445                 450

Trp Val Ser Leu Gly Thr Tyr Asn Phe Ala Thr Gly Thr Gly Gly Tyr
        455                 460                 465

Val Lys Leu Gly Asp Asn Thr Gly Asp Thr Asn Thr Ile Ala Phe Asp
470                 475                 480

Thr Ile Arg Phe Met Gly Gln
485                 490

<210> SEQ ID NO 27
<211> LENGTH: 491
<212> TYPE: PRT
<213> ORGANISM: Alicyclobacillus sp

<400> SEQUENCE: 27

Ala Lys Ser Asp Ala Gln Ser Gln Thr Thr Ala Pro Ala Leu Asp Asn
1               5                   10                  15

Ala Phe Thr Ala Ala Ala Lys Glu Phe Lys Val Pro Lys Asp Leu Leu
                20                  25                  30

Met Ala Ile Ser Tyr Ala Glu Ser Arg Trp Gln Val Pro Ala Glu Thr
        35                  40                  45

Val Ala Asp Asp His Ala His Gly Lys Gly Leu Met His Leu Thr
        50                  55                  60

Asp Asn Ser Phe Lys Lys Asn Leu Ser Asp Thr Ala Lys Gly Leu Gly
65                  70                  75                  80

```
Ile Thr Ala Lys Gln Leu Glu Asp Asn Ala Gly Leu Asn Ile Arg Gly
                85                  90                  95

Gly Ala Tyr Leu Leu Ala Lys Ala Gln His Glu Leu Gly Lys Pro Leu
            100                 105                 110

Ser Asp Asn Val Asn Asp Trp Tyr Glu Ala Val Ala Ser Phe Glu Gly
        115                 120                 125

Ala Ser Asp Lys Ser Asp Lys Val Leu Phe Ala Asp Glu Val Tyr Arg
    130                 135                 140

Ile Leu Lys Asp Gly Thr Ser Leu Ala Ile Asp Gly Gly Thr Leu Ser
145                 150                 155                 160

Ile Phe Pro Asn Lys Thr Val Ala Pro Val Lys Gly Gln Leu Ser Asp
                165                 170                 175

Val Thr Tyr Gly Val Thr Thr Asn Pro Ser Ala Thr Pro Asp Tyr Ser
            180                 185                 190

Gly Ala Ile Trp Asn Ala Ala Ser Thr Ser Asn Tyr Gln Val Ala Ser
        195                 200                 205

Arg Pro Thr Ser Asn Pro Ile Thr Tyr Val Val Ile His Asp Thr Glu
    210                 215                 220

Gly Ser Tyr Ser Gly Thr Ile Asn Trp Phe Lys Asp Pro Ser Ala Gln
225                 230                 235                 240

Val Ser Ala His Tyr Val Val Arg Ser Ser Asp Gly Gln Ile Thr Gln
                245                 250                 255

Met Val Gln Asp Lys Asp Ile Ala Trp His Ala Arg Thr Phe Asn Thr
            260                 265                 270

Asn Gly Ile Gly Ile Glu His Glu Gly Tyr Glu Ala Gln Thr Gly Trp
        275                 280                 285

Tyr Thr Asp Ala Met Tyr Thr Gln Ser Ala Ala Leu Thr Arg Ala Ile
    290                 295                 300

Cys Gln Lys Tyr Gly Ile Pro Met Asp Arg Asp His Ile Leu Gly His
305                 310                 315                 320

Ser Glu Leu Trp Gly Asn Asp His Thr Asp Pro Gly Val Asn Trp Asp
                325                 330                 335

Trp Asn Lys Tyr Met Thr Lys Val Thr Gly Val Ser Lys Asn Trp Thr
            340                 345                 350

Val Val Asp Val Asp Asp Lys Asp Thr Ala Ser Gly Ala Phe Thr Met
        355                 360                 365

Tyr Gly Ala Ser Gln Tyr Trp His Pro Val Ser Gly Tyr Gly Val His
    370                 375                 380

Asn Glu Ile Asn Tyr Thr Asn Gly Asn Gly Ala Thr Ile Tyr Asn Tyr
385                 390                 395                 400

Ala Ile Trp Lys Pro Thr Ile Pro Val Ala Gly Asn Tyr Glu Val Lys
                405                 410                 415

Val Phe Val Pro Ser Asn Tyr Ala Gly Thr Thr Ser Ala Lys Tyr Glu
            420                 425                 430

Ile His Tyr Asn Gly Gly Val Val Thr Lys Thr Val Ser Gln Ser Ala
        435                 440                 445

Tyr Ser Asn Gln Trp Val Ser Leu Gly Thr Tyr Asn Phe Ala Thr Gly
    450                 455                 460

Thr Gly Gly Tyr Val Lys Leu Gly Asp Asn Thr Gly Asp Thr Asn Thr
465                 470                 475                 480

Ile Ala Phe Asp Thr Ile Arg Phe Met Gly Gln
                485                 490
```

```
<210> SEQ ID NO 28
<211> LENGTH: 927
<212> TYPE: DNA
<213> ORGANISM: Halomonas sp
<220> FEATURE:
<221> NAME/KEY: CDS
<222> LOCATION: (1)..(924)
<220> FEATURE:
<221> NAME/KEY: sig_peptide
<222> LOCATION: (1)..(57)
<220> FEATURE:
<221> NAME/KEY: mat_peptide
<222> LOCATION: (58)..(924)

<400> SEQUENCE: 28
```

| | | | | | | | | | | | | | | | | |
|---|---|---|---|---|---|---|---|---|---|---|---|---|---|---|---|---|
| gtg | ctg | cgc | cat | tgg | acc | gcc | gtg | atg | ggc | atc | gcc | atg | gca | agt | gca | 48 |
| Val | Leu | Arg | His | Trp | Thr | Ala | Val | Met | Gly | Ile | Ala | Met | Ala | Ser | Ala | |
| | | | -15 | | | | -10 | | | | -5 | | | | | |
| tgg | ctg | gcc | ggc | tgc | gcc | tcc | ccg | gaa | cac | ctg | gag | cga | cgc | gac | ggc | 96 |
| Trp | Leu | Ala | Gly | Cys | Ala | Ser | Pro | Glu | His | Leu | Glu | Arg | Arg | Asp | Gly | |
| | -1 | 1 | | | | 5 | | | | | 10 | | | | | |
| tac | gtg | gtg | gat | cac | act | cac | ctt | tcg | ccg | tcg | cac | acc | agc | cgg | gtg | 144 |
| Tyr | Val | Val | Asp | His | Thr | His | Leu | Ser | Pro | Ser | His | Thr | Ser | Arg | Val | |
| | 15 | | | | | 20 | | | | | 25 | | | | | |
| cgc | cac | ttg | gtg | atg | cac | tac | acc | gac | gtc | gac | gag | gcc | gag | tcg | ctg | 192 |
| Arg | His | Leu | Val | Met | His | Tyr | Thr | Asp | Val | Asp | Glu | Ala | Glu | Ser | Leu | |
| 30 | | | | | 35 | | | | | 40 | | | | | 45 | |
| gcc | gtg | ctc | acc | ggt | cct | cac | gtc | agc | gcc | cac | tac | gta | ctg | ccg | ttg | 240 |
| Ala | Val | Leu | Thr | Gly | Pro | His | Val | Ser | Ala | His | Tyr | Val | Leu | Pro | Leu | |
| | | | 50 | | | | | 55 | | | | | 60 | | | |
| ccg | ccc | cgg | gag | cgt | cga | ggc | ctg | ccg | ctg | gtc | tat | cag | ctc | gtc | gac | 288 |
| Pro | Pro | Arg | Glu | Arg | Arg | Gly | Leu | Pro | Leu | Val | Tyr | Gln | Leu | Val | Asp | |
| | | 65 | | | | | 70 | | | | | 75 | | | | |
| gag | gag | cgc | cgc | gcc | tgg | cac | gcc | ggc | gcc | agc | gcg | tgg | aaa | ggc | cgc | 336 |
| Glu | Glu | Arg | Arg | Ala | Trp | His | Ala | Gly | Ala | Ser | Ala | Trp | Lys | Gly | Arg | |
| | 80 | | | | | 85 | | | | | 90 | | | | | |
| ccc | cat | atc | aac | gac | act | tcg | atc | ggc | atc | gag | atc | gtc | aat | acc | ggg | 384 |
| Pro | His | Ile | Asn | Asp | Thr | Ser | Ile | Gly | Ile | Glu | Ile | Val | Asn | Thr | Gly | |
| 95 | | | | | 100 | | | | | 105 | | | | | | |
| ccc | gac | cga | ccc | tac | atc | gag | gtg | gag | cgg | ttg | ctg | gaa | ggg | cat | ccc | 432 |
| Pro | Asp | Arg | Pro | Tyr | Ile | Glu | Val | Glu | Arg | Leu | Leu | Glu | Gly | His | Pro | |
| 110 | | | | | 115 | | | | | 120 | | | | | 125 | |
| gag | gac | gcc | gtg | gaa | gtg | aac | tgg | gca | cct | tat | cca | gac | gcg | cag | atc | 480 |
| Glu | Asp | Ala | Val | Glu | Val | Asn | Trp | Ala | Pro | Tyr | Pro | Asp | Ala | Gln | Ile | |
| | | | | 130 | | | | | 135 | | | | | 140 | | |
| gag | gcg | ctg | att | gcg | ctg | tcg | cgc | gac | atc | atc | gag | cgc | cac | gac | atc | 528 |
| Glu | Ala | Leu | Ile | Ala | Leu | Ser | Arg | Asp | Ile | Ile | Glu | Arg | His | Asp | Ile | |
| | | | 145 | | | | | 150 | | | | | 155 | | | |
| cac | ccc | acc | gac | gtt | gtc | gcc | cac | tcc | gac | atc | gcg | ccg | acg | cgc | aag | 576 |
| His | Pro | Thr | Asp | Val | Val | Ala | His | Ser | Asp | Ile | Ala | Pro | Thr | Arg | Lys | |
| | | 160 | | | | | 165 | | | | | 170 | | | | |
| atc | gac | ccc | ggc | cca | cgc | ttc | ccc | tgg | cgc | aaa | ctc | tac | cag | gca | ggc | 624 |
| Ile | Asp | Pro | Gly | Pro | Arg | Phe | Pro | Trp | Arg | Lys | Leu | Tyr | Gln | Ala | Gly | |
| | 175 | | | | | 180 | | | | | 185 | | | | | |
| atc | ggc | gtc | tgg | cca | gag | gag | gaa | gcg | gta | tcg | cac | tgg | cag | gct | cgc | 672 |
| Ile | Gly | Val | Trp | Pro | Glu | Glu | Glu | Ala | Val | Ser | His | Trp | Gln | Ala | Arg | |
| 190 | | | | | 195 | | | | | 200 | | | | | 205 | |
| ttc | gag | gca | gag | cag | cta | ccg | ctc | gcc | act | ctg | cag | cag | gcg | ctt | cgc | 720 |
| Phe | Glu | Ala | Glu | Gln | Leu | Pro | Leu | Ala | Thr | Leu | Gln | Gln | Ala | Leu | Arg | |
| | | | | 210 | | | | | 215 | | | | | 220 | | |

```
gcc tgg ggc tat ccg ctg gag gcg acg ggc gag ctg gac cgc cag acc      768
Ala Trp Gly Tyr Pro Leu Glu Ala Thr Gly Glu Leu Asp Arg Gln Thr
            225                 230                 235 cgc gcg gtg cta cgc gcc ttc cag atg cgc ttc cgg cct gcc gac tac      816
Arg Ala Val Leu Arg Ala Phe Gln Met Arg Phe Arg Pro Ala Asp Tyr
        240                 245                 250 cgc ggc aag ccg gac gca gag agc gcc gcc att ctc tgg gcg ctg ctg      864
Arg Gly Lys Pro Asp Ala Glu Ser Ala Ala Ile Leu Trp Ala Leu Leu
    255                 260                 265 gaa gcg tat cgc ccc ctc gag ctg gaa cgg ctc gaa gga gcg atg acg      912
Glu Ala Tyr Arg Pro Leu Glu Leu Glu Arg Leu Glu Gly Ala Met Thr
270                 275                 280                 285 cag ccg gaa agc tag                                                   927
Gln Pro Glu Ser <210> SEQ ID NO 29
<211> LENGTH: 308
<212> TYPE: PRT
<213> ORGANISM: Halomonas sp

<400> SEQUENCE: 29

Val Leu Arg His Trp Thr Ala Val Met Gly Ile Ala Met Ala Ser Ala
            -15                 -10                 -5

Trp Leu Ala Gly Cys Ala Ser Pro Glu His Leu Glu Arg Arg Asp Gly
        -1  1                   5                   10

Tyr Val Val Asp His Thr His Leu Ser Pro Ser His Thr Ser Arg Val
    15                  20                  25

Arg His Leu Val Met His Tyr Thr Asp Val Asp Glu Ala Glu Ser Leu
30                  35                  40                  45

Ala Val Leu Thr Gly Pro His Val Ser Ala His Tyr Val Leu Pro Leu
            50                  55                  60

Pro Pro Arg Glu Arg Gly Leu Pro Leu Val Tyr Gln Leu Val Asp
        65                  70                  75

Glu Glu Arg Arg Ala Trp His Ala Gly Ala Ser Ala Trp Lys Gly Arg
    80                  85                  90

Pro His Ile Asn Asp Thr Ser Ile Gly Ile Glu Ile Val Asn Thr Gly
95                  100                 105

Pro Asp Arg Pro Tyr Ile Glu Val Glu Arg Leu Leu Glu Gly His Pro
110                 115                 120                 125

Glu Asp Ala Val Glu Val Asn Trp Ala Pro Tyr Pro Asp Ala Gln Ile
            130                 135                 140

Glu Ala Leu Ile Ala Leu Ser Arg Asp Ile Ile Glu Arg His Asp Ile
        145                 150                 155

His Pro Thr Asp Val Val Ala His Ser Asp Ile Ala Pro Thr Arg Lys
    160                 165                 170

Ile Asp Pro Gly Pro Arg Phe Pro Trp Arg Lys Leu Tyr Gln Ala Gly
175                 180                 185

Ile Gly Val Trp Pro Glu Glu Ala Val Ser His Trp Gln Ala Arg
190                 195                 200                 205

Phe Glu Ala Glu Gln Leu Pro Leu Ala Thr Leu Gln Gln Ala Leu Arg
            210                 215                 220

Ala Trp Gly Tyr Pro Leu Glu Ala Thr Gly Glu Leu Asp Arg Gln Thr
        225                 230                 235

Arg Ala Val Leu Arg Ala Phe Gln Met Arg Phe Arg Pro Ala Asp Tyr
    240                 245                 250
```

Arg Gly Lys Pro Asp Ala Glu Ser Ala Ala Ile Leu Trp Ala Leu Leu
255                 260                 265

Glu Ala Tyr Arg Pro Leu Glu Leu Glu Arg Leu Glu Gly Ala Met Thr
270                 275                 280                 285

Gln Pro Glu Ser

<210> SEQ ID NO 30
<211> LENGTH: 289
<212> TYPE: PRT
<213> ORGANISM: Halomonas sp

<400> SEQUENCE: 30

Gly Cys Ala Ser Pro Glu His Leu Glu Arg Arg Asp Gly Tyr Val Val
1               5                   10                  15

Asp His Thr His Leu Ser Pro Ser His Thr Ser Arg Val Arg His Leu
                20                  25                  30

Val Met His Tyr Thr Asp Val Asp Glu Ala Glu Ser Leu Ala Val Leu
            35                  40                  45

Thr Gly Pro His Val Ser Ala His Tyr Val Leu Pro Leu Pro Pro Arg
        50                  55                  60

Glu Arg Arg Gly Leu Pro Leu Val Tyr Gln Leu Val Asp Glu Glu Arg
65                  70                  75                  80

Arg Ala Trp His Ala Gly Ala Ser Ala Trp Lys Gly Arg Pro His Ile
                85                  90                  95

Asn Asp Thr Ser Ile Gly Ile Glu Ile Val Asn Thr Gly Pro Asp Arg
            100                 105                 110

Pro Tyr Ile Glu Val Glu Arg Leu Leu Glu Gly His Pro Glu Asp Ala
        115                 120                 125

Val Glu Val Asn Trp Ala Pro Tyr Pro Asp Ala Gln Ile Glu Ala Leu
    130                 135                 140

Ile Ala Leu Ser Arg Asp Ile Ile Glu Arg His Asp Ile His Pro Thr
145                 150                 155                 160

Asp Val Val Ala His Ser Asp Ile Ala Pro Thr Arg Lys Ile Asp Pro
                165                 170                 175

Gly Pro Arg Phe Pro Trp Arg Lys Leu Tyr Gln Ala Gly Ile Gly Val
            180                 185                 190

Trp Pro Glu Glu Glu Ala Val Ser His Trp Gln Ala Arg Phe Glu Ala
        195                 200                 205

Glu Gln Leu Pro Leu Ala Thr Leu Gln Gln Ala Leu Arg Ala Trp Gly
    210                 215                 220

Tyr Pro Leu Glu Ala Thr Gly Glu Leu Asp Arg Gln Thr Arg Ala Val
225                 230                 235                 240

Leu Arg Ala Phe Gln Met Arg Phe Arg Pro Ala Asp Tyr Arg Gly Lys
                245                 250                 255

Pro Asp Ala Glu Ser Ala Ala Ile Leu Trp Ala Leu Leu Glu Ala Tyr
            260                 265                 270

Arg Pro Leu Glu Leu Glu Arg Leu Glu Gly Ala Met Thr Gln Pro Glu
        275                 280                 285

Ser

<210> SEQ ID NO 31
<211> LENGTH: 783
<212> TYPE: DNA
<213> ORGANISM: Pseudomonas peli
<220> FEATURE:
<221> NAME/KEY: CDS

```
<222> LOCATION: (1)..(780)
<220> FEATURE:
<221> NAME/KEY: sig_peptide
<222> LOCATION: (1)..(45)
<220> FEATURE:
<221> NAME/KEY: mat_peptide
<222> LOCATION: (46)..(780)

<400> SEQUENCE: 31 atg aga att ctt gct ctt gcc ctg ctg atc acc ctg ttg act gcc tgc      48
Met Arg Ile Leu Ala Leu Ala Leu Leu Ile Thr Leu Leu Thr Ala Cys
-15             -10                 -5                  -1   1 acc agc ggc ctg ccc atc gac acc cgc tat gag gcg cta ggg cag aac      96
Thr Ser Gly Leu Pro Ile Asp Thr Arg Tyr Glu Ala Leu Gly Gln Asn
             5                  10                  15 agc cgg gtg cag tac atc atc ctg cac tac acc tcg acc aac ctg cag     144
Ser Arg Val Gln Tyr Ile Ile Leu His Tyr Thr Ser Thr Asn Leu Gln
         20                  25                  30 cac tcc ctg gag ctg ctg acc cag ggc gag gtg agc agc cat tac ctg     192
His Ser Leu Glu Leu Leu Thr Gln Gly Glu Val Ser Ser His Tyr Leu
     35                  40                  45 atc ggc gag aac ccg ccg acc atc tac cgc ctg gtg gat gag aat cgg     240
Ile Gly Glu Asn Pro Pro Thr Ile Tyr Arg Leu Val Asp Glu Asn Arg
50                  55                  60                  65 cgc gcc tgg cat gcc ggg gtc agt cag tgg cag gga cgc acc tgg ctc     288
Arg Ala Trp His Ala Gly Val Ser Gln Trp Gln Gly Arg Thr Trp Leu
                 70                  75                  80 aat ggc acc agc atc ggt atc gaa ctg gtc aac cag ggt ttc tat gat     336
Asn Gly Thr Ser Ile Gly Ile Glu Leu Val Asn Gln Gly Phe Tyr Asp
             85                  90                  95 ggc ccc aat ggg cgc tac tgg cag ccc tat gcg ccg gcg cag att gat     384
Gly Pro Asn Gly Arg Tyr Trp Gln Pro Tyr Ala Pro Ala Gln Ile Asp
         100                 105                 110 gcg ctg atc ctc ctg ctc aag gac atc atg cag cgt cat gag ctg ccc     432
Ala Leu Ile Leu Leu Leu Lys Asp Ile Met Gln Arg His Glu Leu Pro
     115                 120                 125 ctg ggc agc atc att ggt cat agc gat atc gcc ccc cag cgc aag gtc     480
Leu Gly Ser Ile Ile Gly His Ser Asp Ile Ala Pro Gln Arg Lys Val
130                 135                 140                 145 gat ccg ggc ccg tta ttc ccc tgg cag cgt ctg gcc gag gcc gga ttg     528
Asp Pro Gly Pro Leu Phe Pro Trp Gln Arg Leu Ala Glu Ala Gly Leu
                 150                 155                 160 ata ccc tgg ccg gaa gcc ggt gca gtg gcg cgc cag cag gcc gtg tac     576
Ile Pro Trp Pro Glu Ala Gly Ala Val Ala Arg Gln Gln Ala Val Tyr
             165                 170                 175 gag cag caa ctg cct gat gtg gcc tgg ttt cag cag caa ctg gcc agc     624
Glu Gln Gln Leu Pro Asp Val Ala Trp Phe Gln Gln Gln Leu Ala Ser
         180                 185                 190 cac ggc tac gag gtg ccc agc cat ggc gag ctg gat cag gcc acg cgc     672
His Gly Tyr Glu Val Pro Ser His Gly Glu Leu Asp Gln Ala Thr Arg
     195                 200                 205 aat gtg atc gcc gcc ttc cag atg aaa tac cgc cag gcc aac tat gac     720
Asn Val Ile Ala Ala Phe Gln Met Lys Tyr Arg Gln Ala Asn Tyr Asp
210                 215                 220                 225 ggc gag ccg gac agc gaa act ggc gcc ctg ctc tgg gtg cta aac aat     768
Gly Glu Pro Asp Ser Glu Thr Gly Ala Leu Leu Trp Val Leu Asn Asn
                 230                 235                 240 agc gcc agc cgc tga                                                 783
Ser Ala Ser Arg
         245
```

```
<210> SEQ ID NO 32
<211> LENGTH: 260
<212> TYPE: PRT
<213> ORGANISM: Pseudomonas peli

<400> SEQUENCE: 32

Met Arg Ile Leu Ala Leu Ala Leu Leu Ile Thr Leu Thr Ala Cys
-15                 -10                 -5                  -1  1

Thr Ser Gly Leu Pro Ile Asp Thr Arg Tyr Glu Ala Leu Gly Gln Asn
            5                   10                  15

Ser Arg Val Gln Tyr Ile Ile Leu His Tyr Thr Ser Thr Asn Leu Gln
        20                  25                  30

His Ser Leu Glu Leu Leu Thr Gln Gly Glu Val Ser Ser His Tyr Leu
    35                  40                  45

Ile Gly Glu Asn Pro Pro Thr Ile Tyr Arg Leu Val Asp Glu Asn Arg
50                  55                  60                  65

Arg Ala Trp His Ala Gly Val Ser Gln Trp Gln Gly Arg Thr Trp Leu
                70                  75                  80

Asn Gly Thr Ser Ile Gly Ile Glu Leu Val Asn Gln Gly Phe Tyr Asp
            85                  90                  95

Gly Pro Asn Gly Arg Tyr Trp Gln Pro Tyr Ala Pro Ala Gln Ile Asp
        100                 105                 110

Ala Leu Ile Leu Leu Lys Asp Ile Met Gln Arg His Glu Leu Pro
    115                 120                 125

Leu Gly Ser Ile Ile Gly His Ser Asp Ile Ala Pro Gln Arg Lys Val
130                 135                 140                 145

Asp Pro Gly Pro Leu Phe Pro Trp Gln Arg Leu Ala Glu Ala Gly Leu
                150                 155                 160

Ile Pro Trp Pro Glu Ala Gly Ala Val Ala Arg Gln Gln Ala Val Tyr
            165                 170                 175

Glu Gln Gln Leu Pro Asp Val Ala Trp Phe Gln Gln Leu Ala Ser
        180                 185                 190

His Gly Tyr Glu Val Pro Ser His Gly Glu Leu Asp Gln Ala Thr Arg
    195                 200                 205

Asn Val Ile Ala Ala Phe Gln Met Lys Tyr Arg Gln Ala Asn Tyr Asp
210                 215                 220                 225

Gly Glu Pro Asp Ser Glu Thr Gly Ala Leu Leu Trp Val Leu Asn Asn
                230                 235                 240

Ser Ala Ser Arg
            245

<210> SEQ ID NO 33
<211> LENGTH: 245
<212> TYPE: PRT
<213> ORGANISM: Pseudomonas peli

<400> SEQUENCE: 33

Cys Thr Ser Gly Leu Pro Ile Asp Thr Arg Tyr Glu Ala Leu Gly Gln
1               5                   10                  15

Asn Ser Arg Val Gln Tyr Ile Ile Leu His Tyr Thr Ser Thr Asn Leu
            20                  25                  30

Gln His Ser Leu Glu Leu Leu Thr Gln Gly Glu Val Ser Ser His Tyr
        35                  40                  45

Leu Ile Gly Glu Asn Pro Pro Thr Ile Tyr Arg Leu Val Asp Glu Asn
    50                  55                  60
```

```
Arg Arg Ala Trp His Ala Gly Val Ser Gln Trp Gln Gly Arg Thr Trp
 65                  70                  75                  80

Leu Asn Gly Thr Ser Ile Gly Ile Glu Leu Val Asn Gln Gly Phe Tyr
             85                  90                  95

Asp Gly Pro Asn Gly Arg Tyr Trp Gln Pro Tyr Ala Pro Ala Gln Ile
            100                 105                 110

Asp Ala Leu Ile Leu Leu Leu Lys Asp Ile Met Gln Arg His Glu Leu
            115                 120                 125

Pro Leu Gly Ser Ile Ile Gly His Ser Asp Ile Ala Pro Gln Arg Lys
            130                 135                 140

Val Asp Pro Gly Pro Leu Phe Pro Trp Gln Arg Leu Ala Glu Ala Gly
145                 150                 155                 160

Leu Ile Pro Trp Pro Glu Ala Gly Ala Val Ala Arg Gln Gln Ala Val
                165                 170                 175

Tyr Glu Gln Gln Leu Pro Asp Val Ala Trp Phe Gln Gln Leu Ala
                180                 185                 190

Ser His Gly Tyr Glu Val Pro Ser His Gly Glu Leu Asp Gln Ala Thr
            195                 200                 205

Arg Asn Val Ile Ala Ala Phe Gln Met Lys Tyr Arg Gln Ala Asn Tyr
210                 215                 220

Asp Gly Glu Pro Asp Ser Glu Thr Gly Ala Leu Leu Trp Val Leu Asn
225                 230                 235                 240

Asn Ser Ala Ser Arg
                245

<210> SEQ ID NO 34
<211> LENGTH: 900
<212> TYPE: DNA
<213> ORGANISM: Halomonas sp
<220> FEATURE:
<221> NAME/KEY: CDS
<222> LOCATION: (1)..(897)
<220> FEATURE:
<221> NAME/KEY: sig_peptide
<222> LOCATION: (1)..(57)
<220> FEATURE:
<221> NAME/KEY: mat_peptide
<222> LOCATION: (58)..(897)

<400> SEQUENCE: 34 atg tgg cga aag cgt gtt gtc gtt gca tcc ctg acc ctg ctg ctc act    48
Met Trp Arg Lys Arg Val Val Val Ala Ser Leu Thr Leu Leu Leu Thr
                -15                 -10                 -5 gcc tgt gcg ggg ccc ggc cac cgg gaa caa cgc aat ggt tat gtg gtg    96
Ala Cys Ala Gly Pro Gly His Arg Glu Gln Arg Asn Gly Tyr Val Val
        -1  1               5                  10 gac cac acc cat gtg gca cct tcc cac aac agc cga gta cgg cac ctg   144
Asp His Thr His Val Ala Pro Ser His Asn Ser Arg Val Arg His Leu
        15                  20                  25 gtg atg cac tac acg gat gtg gat gaa gcg gag tcg ctc gcc gtg ctc   192
Val Met His Tyr Thr Asp Val Asp Glu Ala Glu Ser Leu Ala Val Leu
 30                  35                  40                  45 acc ggc ccc cag gtc agc agc cac tac gtg ctg ccg cta ccg gca cgg   240
Thr Gly Pro Gln Val Ser Ser His Tyr Val Leu Pro Leu Pro Ala Arg
                50                  55                  60 gag cat cgc ggc cag ccg ctg gtc tac cag ctc gtc gac gag gag cgc   288
Glu His Arg Gly Gln Pro Leu Val Tyr Gln Leu Val Asp Glu Glu Arg
            65                  70                  75
```

```
cgc gcc tgg cac gcc ggg gcc agc gcc tgg aag cgc cgc acc aat atc      336
Arg Ala Trp His Ala Gly Ala Ser Ala Trp Lys Arg Arg Thr Asn Ile
        80                  85                  90 aac gat acg tcc atc ggc atc gag atc gtc aat acc ggc ccc gat cgc      384
Asn Asp Thr Ser Ile Gly Ile Glu Ile Val Asn Thr Gly Pro Asp Arg
    95                 100                 105 ccc tac gcc gag gtg gag cgg ctg ctg gag cag cac ccc gag gcg acg      432
Pro Tyr Ala Glu Val Glu Arg Leu Leu Glu Gln His Pro Glu Ala Thr
110                 115                 120                 125 gtg gag atc ggt tgg gca ccc tac ccc gag gca cag atc cag gcg ctg      480
Val Glu Ile Gly Trp Ala Pro Tyr Pro Glu Ala Gln Ile Gln Ala Leu
                130                 135                 140 atc gcc ctg tcg cgg gat atc atc gag cgc cac aat atc cat ccc acc      528
Ile Ala Leu Ser Arg Asp Ile Ile Glu Arg His Asn Ile His Pro Thr
            145                 150                 155 gac gtg gtg gcc cac tcg gat atc tcg ccg acg cgc aag atc gac ccg      576
Asp Val Val Ala His Ser Asp Ile Ser Pro Thr Arg Lys Ile Asp Pro
        160                 165                 170 ggc ccg gcg ttt ccc tgg cat gcc ctt tac gaa gcg ggt atc ggc gta      624
Gly Pro Ala Phe Pro Trp His Ala Leu Tyr Glu Ala Gly Ile Gly Val
175                 180                 185 tgg ccc gaa gag gcc acc gtg gcg cgc tat cgc gac cgc ttc gac cag      672
Trp Pro Glu Glu Ala Thr Val Ala Arg Tyr Arg Asp Arg Phe Asp Gln
190                 195                 200                 205 gcg ctg ccc gag ctc tcc acg ctg cag gcg gca ctt cat gcc tgg ggc      720
Ala Leu Pro Glu Leu Ser Thr Leu Gln Ala Ala Leu His Ala Trp Gly
                210                 215                 220 tat ccg ctg gtg gta agc gac gaa ctg gat tca cag act cgc gcg gta      768
Tyr Pro Leu Val Val Ser Asp Glu Leu Asp Ser Gln Thr Arg Ala Val
            225                 230                 235 ctt cgc gcc ttc cag atg cgc ttt cgc ccc acc gac tat cgc ggc ctg      816
Leu Arg Ala Phe Gln Met Arg Phe Arg Pro Thr Asp Tyr Arg Gly Leu
        240                 245                 250 ccc gat gcc gag acc gcc gca atc ctc tgg gca ctt ctg gca cgc tat      864
Pro Asp Ala Glu Thr Ala Ala Ile Leu Trp Ala Leu Leu Ala Arg Tyr
255                 260                 265 cga ccc gat gaa ctc acc gcg ctg gag ccc cga tag                      900
Arg Pro Asp Glu Leu Thr Ala Leu Glu Pro Arg
270                 275                 280

<210> SEQ ID NO 35
<211> LENGTH: 299
<212> TYPE: PRT
<213> ORGANISM: Halomonas sp

<400> SEQUENCE: 35

Met Trp Arg Lys Arg Val Val Ala Ser Leu Thr Leu Leu Thr
            -15                 -10                  -5

Ala Cys Ala Gly Pro Gly His Arg Glu Gln Arg Asn Gly Tyr Val Val
        -1   1                   5                  10

Asp His Thr His Val Ala Pro Ser His Asn Ser Arg Val Arg His Leu
 15                  20                  25

Val Met His Tyr Thr Asp Val Asp Glu Ala Glu Ser Leu Ala Val Leu
 30                  35                  40                  45

Thr Gly Pro Gln Val Ser Ser His Tyr Val Leu Pro Leu Pro Ala Arg
                 50                  55                  60

Glu His Arg Gly Gln Pro Leu Val Tyr Gln Leu Val Asp Glu Glu Arg
             65                  70                  75
```

```
Arg Ala Trp His Ala Gly Ala Ser Ala Trp Lys Arg Arg Thr Asn Ile
            80                  85                  90

Asn Asp Thr Ser Ile Gly Ile Glu Ile Val Asn Thr Gly Pro Asp Arg
        95                 100                 105

Pro Tyr Ala Glu Val Glu Arg Leu Leu Glu Gln His Pro Glu Ala Thr
110                 115                 120                 125

Val Glu Ile Gly Trp Ala Pro Tyr Pro Glu Ala Gln Ile Gln Ala Leu
                130                 135                 140

Ile Ala Leu Ser Arg Asp Ile Ile Glu Arg His Asn Ile His Pro Thr
            145                 150                 155

Asp Val Val Ala His Ser Asp Ile Ser Pro Thr Arg Lys Ile Asp Pro
        160                 165                 170

Gly Pro Ala Phe Pro Trp His Ala Leu Tyr Glu Ala Gly Ile Gly Val
175                 180                 185

Trp Pro Glu Glu Ala Thr Val Ala Arg Tyr Arg Asp Arg Phe Asp Gln
190                 195                 200                 205

Ala Leu Pro Glu Leu Ser Thr Leu Gln Ala Ala Leu His Ala Trp Gly
                210                 215                 220

Tyr Pro Leu Val Val Ser Asp Glu Leu Asp Ser Gln Thr Arg Ala Val
            225                 230                 235

Leu Arg Ala Phe Gln Met Arg Phe Arg Pro Thr Asp Tyr Arg Gly Leu
        240                 245                 250

Pro Asp Ala Glu Thr Ala Ala Ile Leu Trp Ala Leu Leu Ala Arg Tyr
    255                 260                 265

Arg Pro Asp Glu Leu Thr Ala Leu Glu Pro Arg
270                 275                 280

<210> SEQ ID NO 36
<211> LENGTH: 280
<212> TYPE: PRT
<213> ORGANISM: Halomonas sp

<400> SEQUENCE: 36

Gly Pro Gly His Arg Glu Gln Arg Asn Gly Tyr Val Val Asp His Thr
1               5                   10                  15

His Val Ala Pro Ser His Asn Ser Arg Val Arg His Leu Val Met His
            20                  25                  30

Tyr Thr Asp Val Asp Glu Ala Glu Ser Leu Ala Val Leu Thr Gly Pro
        35                  40                  45

Gln Val Ser Ser His Tyr Val Leu Pro Leu Pro Ala Arg Glu His Arg
    50                  55                  60

Gly Gln Pro Leu Val Tyr Gln Leu Val Asp Glu Glu Arg Arg Ala Trp
65                  70                  75                  80

His Ala Gly Ala Ser Ala Trp Lys Arg Arg Thr Asn Ile Asn Asp Thr
            85                  90                  95

Ser Ile Gly Ile Glu Ile Val Asn Thr Gly Pro Asp Arg Pro Tyr Ala
        100                 105                 110

Glu Val Glu Arg Leu Leu Glu Gln His Pro Glu Ala Thr Val Glu Ile
    115                 120                 125

Gly Trp Ala Pro Tyr Pro Glu Ala Gln Ile Gln Ala Leu Ile Ala Leu
130                 135                 140

Ser Arg Asp Ile Ile Glu Arg His Asn Ile His Pro Thr Asp Val Val
145                 150                 155                 160

Ala His Ser Asp Ile Ser Pro Thr Arg Lys Ile Asp Pro Gly Pro Ala
            165                 170                 175
```

```
Phe Pro Trp His Ala Leu Tyr Glu Ala Gly Ile Gly Val Trp Pro Glu
            180                 185                 190

Glu Ala Thr Val Ala Arg Tyr Arg Asp Arg Phe Asp Gln Ala Leu Pro
        195                 200                 205

Glu Leu Ser Thr Leu Gln Ala Ala Leu His Ala Trp Gly Tyr Pro Leu
    210                 215                 220

Val Val Ser Asp Glu Leu Asp Ser Gln Thr Arg Ala Val Leu Arg Ala
225                 230                 235                 240

Phe Gln Met Arg Phe Arg Pro Thr Asp Tyr Arg Gly Leu Pro Asp Ala
                245                 250                 255

Glu Thr Ala Ala Ile Leu Trp Ala Leu Leu Ala Arg Tyr Arg Pro Asp
            260                 265                 270

Glu Leu Thr Ala Leu Glu Pro Arg
        275                 280

<210> SEQ ID NO 37
<211> LENGTH: 783
<212> TYPE: DNA
<213> ORGANISM: Pseudomonas pseudoalcaligenes
<220> FEATURE:
<221> NAME/KEY: CDS
<222> LOCATION: (1)..(780)
<220> FEATURE:
<221> NAME/KEY: sig_peptide
<222> LOCATION: (1)..(66)
<220> FEATURE:
<221> NAME/KEY: mat_peptide
<222> LOCATION: (67)..(780)

<400> SEQUENCE: 37 atg aag tct ctt tgc ctt gcc ctc gcc ctt gtt ctg ctt gcc ggt tgc      48
Met Lys Ser Leu Cys Leu Ala Leu Ala Leu Val Leu Leu Ala Gly Cys
        -20                 -15                 -10 acc ggt ggt cta cgt atc gat gac agc cac acg gcg acc ggc cag aac      96
Thr Gly Gly Leu Arg Ile Asp Asp Ser His Thr Ala Thr Gly Gln Asn
    -5                  -1  1               5                  10 agt cgt gtg caa tac gtc gtg ctg cac tac acc tcc gct gac ctg cag      144
Ser Arg Val Gln Tyr Val Val Leu His Tyr Thr Ser Ala Asp Leu Gln
                15                  20                  25 cgc tcg ctc gac ctg ctg acg cag acc gag gtg agc agc cac tac ctg      192
Arg Ser Leu Asp Leu Leu Thr Gln Thr Glu Val Ser Ser His Tyr Leu
            30                  35                  40 atc ggg gat gca cca ccg acc gtc tac cgc ctg gtg gat gag aac cgt      240
Ile Gly Asp Ala Pro Pro Thr Val Tyr Arg Leu Val Asp Glu Asn Arg
        45                  50                  55 cgc gcc tgg cac gtg ggt gtc agc gag tgg aag ggg cgc acc tgg ctc      288
Arg Ala Trp His Val Gly Val Ser Glu Trp Lys Gly Arg Thr Trp Leu
    60                  65                  70 aac agc acc acg atc ggc atc gag ctg gtc aac cag ggc tac tac cag      336
Asn Ser Thr Thr Ile Gly Ile Glu Leu Val Asn Gln Gly Tyr Tyr Gln
75                  80                  85                  90 acg ccg gcc ggc cgc tac tgg cag cct ttc gcg ccg cag cag atc gat      384
Thr Pro Ala Gly Arg Tyr Trp Gln Pro Phe Ala Pro Gln Gln Ile Asp
                95                  100                 105 acc ctg atc gtg ctg ctc aag gac atc gtc aag cgt cac cag cta ccg      432
Thr Leu Ile Val Leu Leu Lys Asp Ile Val Lys Arg His Gln Leu Pro
            110                 115                 120 ctg ggc tcg atc atc gcg cac agc gat gtg gcg ccg cag cgc aag gtc      480
Leu Gly Ser Ile Ile Ala His Ser Asp Val Ala Pro Gln Arg Lys Val
        125                 130                 135
```

```
gat ccg ggc cct ttg ttc ccc tgg aag cgt ctg gcc gac gag ggc ctg      528
Asp Pro Gly Pro Leu Phe Pro Trp Lys Arg Leu Ala Asp Glu Gly Leu
140             145                 150 gtg ccc tgg ccg aac gag gac gcc gtg gcg cgc cag cag gcg ctg ttc      576
Val Pro Trp Pro Asn Glu Asp Ala Val Ala Arg Gln Gln Ala Leu Phe
155                 160                 165                 170 agc acc agc ctg ccc agc gtg cag tgg ttc cag gag cag ttg gcg caa      624
Ser Thr Ser Leu Pro Ser Val Gln Trp Phe Gln Glu Gln Leu Ala Gln
                175                 180                 185 aac ggc tac acg gtg ccg cag cat ggc gag ctg gat gag gca acg cgc      672
Asn Gly Tyr Thr Val Pro Gln His Gly Glu Leu Asp Glu Ala Thr Arg
            190                 195                 200 aat gtc att gcc gct ttc cag atg aaa tat cgt ccg gcc aac tac gac      720
Asn Val Ile Ala Ala Phe Gln Met Lys Tyr Arg Pro Ala Asn Tyr Asp
        205                 210                 215 ggc cag ccg gac gcc gaa act gca gcg cgg ttg ctg gtg ctc aat ctg      768
Gly Gln Pro Asp Ala Glu Thr Ala Ala Arg Leu Leu Val Leu Asn Leu
    220                 225                 230 cag gcg gca gga tag                                                  783
Gln Ala Ala Gly
235

<210> SEQ ID NO 38
<211> LENGTH: 260
<212> TYPE: PRT
<213> ORGANISM: Pseudomonas pseudoalcaligenes

<400> SEQUENCE: 38

Met Lys Ser Leu Cys Leu Ala Leu Ala Leu Val Leu Leu Ala Gly Cys
        -20                 -15                 -10

Thr Gly Gly Leu Arg Ile Asp Asp Ser His Thr Ala Thr Gly Gln Asn
    -5                  -1  1               5                   10

Ser Arg Val Gln Tyr Val Val Leu His Tyr Thr Ser Ala Asp Leu Gln
                15                  20                  25

Arg Ser Leu Asp Leu Leu Thr Gln Thr Glu Val Ser Ser His Tyr Leu
            30                  35                  40

Ile Gly Asp Ala Pro Pro Thr Val Tyr Arg Leu Val Asp Glu Asn Arg
        45                  50                  55

Arg Ala Trp His Val Gly Val Ser Glu Trp Lys Gly Arg Thr Trp Leu
    60                  65                  70

Asn Ser Thr Thr Ile Gly Ile Glu Leu Val Asn Gln Gly Tyr Tyr Gln
75                  80                  85                  90

Thr Pro Ala Gly Arg Tyr Trp Gln Pro Phe Ala Pro Gln Gln Ile Asp
                95                  100                 105

Thr Leu Ile Val Leu Leu Lys Asp Ile Val Lys Arg His Gln Leu Pro
            110                 115                 120

Leu Gly Ser Ile Ile Ala His Ser Asp Val Ala Pro Gln Arg Lys Val
        125                 130                 135

Asp Pro Gly Pro Leu Phe Pro Trp Lys Arg Leu Ala Asp Glu Gly Leu
    140                 145                 150

Val Pro Trp Pro Asn Glu Asp Ala Val Ala Arg Gln Gln Ala Leu Phe
155                 160                 165                 170

Ser Thr Ser Leu Pro Ser Val Gln Trp Phe Gln Glu Gln Leu Ala Gln
                175                 180                 185

Asn Gly Tyr Thr Val Pro Gln His Gly Glu Leu Asp Glu Ala Thr Arg
            190                 195                 200
```

Asn Val Ile Ala Ala Phe Gln Met Lys Tyr Arg Pro Ala Asn Tyr Asp
        205                 210                 215

Gly Gln Pro Asp Ala Glu Thr Ala Ala Arg Leu Leu Val Leu Asn Leu
    220                 225                 230

Gln Ala Ala Gly
235

<210> SEQ ID NO 39
<211> LENGTH: 238
<212> TYPE: PRT
<213> ORGANISM: Pseudomonas pseudoalcaligenes

<400> SEQUENCE: 39

Asp Asp Ser His Thr Ala Thr Gly Gln Asn Ser Arg Val Gln Tyr Val
1               5                   10                  15

Val Leu His Tyr Thr Ser Ala Asp Leu Gln Arg Ser Leu Asp Leu Leu
            20                  25                  30

Thr Gln Thr Glu Val Ser Ser His Tyr Leu Ile Gly Asp Ala Pro Pro
        35                  40                  45

Thr Val Tyr Arg Leu Val Asp Glu Asn Arg Arg Ala Trp His Val Gly
    50                  55                  60

Val Ser Glu Trp Lys Gly Arg Thr Trp Leu Asn Ser Thr Thr Ile Gly
65                  70                  75                  80

Ile Glu Leu Val Asn Gln Gly Tyr Tyr Gln Thr Pro Ala Gly Arg Tyr
                85                  90                  95

Trp Gln Pro Phe Ala Pro Gln Gln Ile Asp Thr Leu Ile Val Leu Leu
            100                 105                 110

Lys Asp Ile Val Lys Arg His Gln Leu Pro Leu Gly Ser Ile Ile Ala
        115                 120                 125

His Ser Asp Val Ala Pro Gln Arg Lys Val Asp Pro Gly Pro Leu Phe
    130                 135                 140

Pro Trp Lys Arg Leu Ala Asp Glu Gly Leu Val Pro Trp Pro Asn Glu
145                 150                 155                 160

Asp Ala Val Ala Arg Gln Gln Ala Leu Phe Ser Thr Ser Leu Pro Ser
                165                 170                 175

Val Gln Trp Phe Gln Glu Gln Leu Ala Gln Asn Gly Tyr Thr Val Pro
            180                 185                 190

Gln His Gly Glu Leu Asp Glu Ala Thr Arg Asn Val Ile Ala Ala Phe
        195                 200                 205

Gln Met Lys Tyr Arg Pro Ala Asn Tyr Asp Gly Gln Pro Asp Ala Glu
    210                 215                 220

Thr Ala Ala Arg Leu Leu Val Leu Asn Leu Gln Ala Ala Gly
225                 230                 235

<210> SEQ ID NO 40
<211> LENGTH: 1566
<212> TYPE: DNA
<213> ORGANISM: Tumebacillus sp
<220> FEATURE:
<221> NAME/KEY: CDS
<222> LOCATION: (1)..(1563)
<220> FEATURE:
<221> NAME/KEY: sig_peptide
<222> LOCATION: (1)..(69)
<220> FEATURE:
<221> NAME/KEY: mat_peptide
<222> LOCATION: (70)..(1563)

<400> SEQUENCE: 40

```
atg aac aaa acg tgg gta tcg gtc ctc gcg acc acc gca ctg acc ctg         48
Met Asn Lys Thr Trp Val Ser Val Leu Ala Thr Thr Ala Leu Thr Leu
        -20                 -15                 -10 tcg gtc agc agc gtg tat gcg caa cca acg cat gca gcc aaa ctc gac         96
Ser Val Ser Ser Val Tyr Ala Gln Pro Thr His Ala Ala Lys Leu Asp
    -5                  -1   1                   5 aac caa acg gtc gcg aca gca ccg gtt ttg gaa agc acc ttc agc tct        144
Asn Gln Thr Val Ala Thr Ala Pro Val Leu Glu Ser Thr Phe Ser Ser
 10                  15                  20                  25 gct gcg aag gaa ttt ggc gtt ccg aag gaa ctg ctg atg gcg atc tcc        192
Ala Ala Lys Glu Phe Gly Val Pro Lys Glu Leu Leu Met Ala Ile Ser
                 30                  35                  40 tac agc gaa tcg cgc tgg cag atc gcg cca gag gaa aca cat ctc acc        240
Tyr Ser Glu Ser Arg Trp Gln Ile Ala Pro Glu Glu Thr His Leu Thr
                     45                  50                  55 gct gag ccg gac aaa aac aac ggc aaa ggc ctg atg cac ctc aac gac        288
Ala Glu Pro Asp Lys Asn Asn Gly Lys Gly Leu Met His Leu Asn Asp
             60                  65                  70 aac tcc ttc aaa aaa ggc ctg agc gat gct gca aaa gcg ctc ggc gtc        336
Asn Ser Phe Lys Lys Gly Leu Ser Asp Ala Ala Lys Ala Leu Gly Val
 75                  80                  85 tcc aag aaa cag atg gaa gac gat gtg caa ctg aac atc cgc ggc ggt        384
Ser Lys Lys Gln Met Glu Asp Asp Val Gln Leu Asn Ile Arg Gly Gly
 90                  95                 100                 105 gct tac ctg ctc gcg aag gca caa aaa gac ctc ggc aag gcg ctt aca        432
Ala Tyr Leu Leu Ala Lys Ala Gln Lys Asp Leu Gly Lys Ala Leu Thr
                110                 115                 120 tcc aac gtc aac gat tgg tat gaa gcg gtt gct tcc ttt gaa ggt gcc        480
Ser Asn Val Asn Asp Trp Tyr Glu Ala Val Ala Ser Phe Glu Gly Ala
                    125                 130                 135 aag gac aag gac gtt gcc gcc ttg ttt gca gat gaa gtc tac cgt gtg        528
Lys Asp Lys Asp Val Ala Ala Leu Phe Ala Asp Glu Val Tyr Arg Val
                140                 145                 150 cta caa gaa gga acc gca ctg gcg atc gaa ggc ggc acg ctg acc ctc        576
Leu Gln Glu Gly Thr Ala Leu Ala Ile Glu Gly Gly Thr Leu Thr Leu
            155                 160                 165 gac ccg aac tcc aaa gtc gat ccg agc aaa ggc gtc tac gca ggc ttg        624
Asp Pro Asn Ser Lys Val Asp Pro Ser Lys Gly Val Tyr Ala Gly Leu
170                 175                 180                 185 acc aac ggc ggc acc aac tat gga ctg act ccg gac tac tcc ggc gcg        672
Thr Asn Gly Gly Thr Asn Tyr Gly Leu Thr Pro Asp Tyr Ser Gly Ala
                    190                 195                 200 atc tgg aac ccg gcg agc acg tcc aac tat gcc gtc gcc tct cgc ccg        720
Ile Trp Asn Pro Ala Ser Thr Ser Asn Tyr Ala Val Ala Ser Arg Pro
                205                 210                 215 act tcg aac ccg atc aac tcg gtc atc atc cat gac acc gag ggt tcc        768
Thr Ser Asn Pro Ile Asn Ser Val Ile Ile His Asp Thr Glu Gly Ser
                220                 225                 230 tac tcc ggt tcg atc aac tgg ttc aaa gac ccg gcg gca caa gtt tcc        816
Tyr Ser Gly Ser Ile Asn Trp Phe Lys Asp Pro Ala Ala Gln Val Ser
            235                 240                 245 gca cac tac atc gtc cgt tcc tcc gat ggc caa atc acc cag ttg gta        864
Ala His Tyr Ile Val Arg Ser Ser Asp Gly Gln Ile Thr Gln Leu Val
250                 255                 260                 265 cag gac aaa gac atc gca tgg cat gca cgc agc ttc aac acc aac gga        912
Gln Asp Lys Asp Ile Ala Trp His Ala Arg Ser Phe Asn Thr Asn Gly
                270                 275                 280
```

```
atc ggc atc gaa cac gaa ggc tat gcg gca caa acc ggc tgg tac acc      960
Ile Gly Ile Glu His Glu Gly Tyr Ala Ala Gln Thr Gly Trp Tyr Thr
            285                 290                 295 gac gcg atg tac acc gca tcg gcg gcg ctc acc cgt gct gtc tgc ctc     1008
Asp Ala Met Tyr Thr Ala Ser Ala Ala Leu Thr Arg Ala Val Cys Leu
        300                 305                 310 aaa tac aac atc ccg atg gac cgc gac cac atc ctc gct cac tcc gaa     1056
Lys Tyr Asn Ile Pro Met Asp Arg Asp His Ile Leu Ala His Ser Glu
315                 320                 325 ctg tgg ggc aat gac cac acc gat ccg ggc gtg aac tgg gat tgg aac     1104
Leu Trp Gly Asn Asp His Thr Asp Pro Gly Val Asn Trp Asp Trp Asn
330                 335                 340                 345 aaa tac atg agc aaa gtg acc ggt gtg acg aaa aac tac gcg gcg gta     1152
Lys Tyr Met Ser Lys Val Thr Gly Val Thr Lys Asn Tyr Ala Ala Val
                350                 355                 360 ctg gtc gac aac acc gac gca tcc tcc ggc ttc acg ctg ggt ggc ccg     1200
Leu Val Asp Asn Thr Asp Ala Ser Ser Gly Phe Thr Leu Gly Gly Pro
            365                 370                 375 tcc caa tac tgg cac ccg acc gca ggg tac ggc atc cac aac cag atg     1248
Ser Gln Tyr Trp His Pro Thr Ala Gly Tyr Gly Ile His Asn Gln Met
        380                 385                 390 acg tac acg atg ggc aac ggc acc aac ccg atc tcc aac tac gcg acg     1296
Thr Tyr Thr Met Gly Asn Gly Thr Asn Pro Ile Ser Asn Tyr Ala Thr
395                 400                 405 tgg aag ccg acg atc ccg act gct ggc aac tac caa gtc aaa gtc ttc     1344
Trp Lys Pro Thr Ile Pro Thr Ala Gly Asn Tyr Gln Val Lys Val Phe
410                 415                 420                 425 atc ccg tcc aac ttc gca gcg acc acc aac gcg aag tat gaa atc cac     1392
Ile Pro Ser Asn Phe Ala Ala Thr Thr Asn Ala Lys Tyr Glu Ile His
                430                 435                 440 tac aac ggt ggc gtc atc acc aaa acg atc tcc caa gca gcc tac tcc     1440
Tyr Asn Gly Gly Val Ile Thr Lys Thr Ile Ser Gln Ala Ala Tyr Ser
            445                 450                 455 aac caa tgg gtg agc ctt ggc acg tac agc ttc gca gca ggc acc gca     1488
Asn Gln Trp Val Ser Leu Gly Thr Tyr Ser Phe Ala Ala Gly Thr Ala
        460                 465                 470 ggc tac gtg aaa ctc ggt gac aac acc ggc gac acg gcg tac gtc ggc     1536
Gly Tyr Val Lys Leu Gly Asp Asn Thr Gly Asp Thr Ala Tyr Val Gly
475                 480                 485 atc gac ggc atg cgt ttc ctc gct caa taa                             1566
Ile Asp Gly Met Arg Phe Leu Ala Gln
490                 495

<210> SEQ ID NO 41
<211> LENGTH: 521
<212> TYPE: PRT
<213> ORGANISM: Tumebacillus sp

<400> SEQUENCE: 41

Met Asn Lys Thr Trp Val Ser Val Leu Ala Thr Thr Ala Leu Thr Leu
            -20                 -15                 -10

Ser Val Ser Val Tyr Ala Gln Pro Thr His Ala Ala Lys Leu Asp
        -5              -1   1               5

Asn Gln Thr Val Ala Thr Ala Pro Val Leu Glu Ser Thr Phe Ser Ser
10                  15                  20                  25

Ala Ala Lys Glu Phe Gly Val Pro Lys Glu Leu Leu Met Ala Ile Ser
                30                  35                  40

Tyr Ser Glu Ser Arg Trp Gln Ile Ala Pro Glu Glu Thr His Leu Thr
            45                  50                  55
```

```
Ala Glu Pro Asp Lys Asn Asn Gly Lys Gly Leu Met His Leu Asn Asp
         60                  65                  70

Asn Ser Phe Lys Lys Gly Leu Ser Asp Ala Ala Lys Ala Leu Gly Val
 75                  80                  85

Ser Lys Lys Gln Met Glu Asp Val Gln Leu Asn Ile Arg Gly Gly
 90                  95                 100                 105

Ala Tyr Leu Leu Ala Lys Ala Gln Lys Asp Leu Gly Lys Ala Leu Thr
            110                 115                 120

Ser Asn Val Asn Asp Trp Tyr Glu Val Ala Ser Phe Glu Gly Ala
            125                 130                 135

Lys Asp Lys Asp Val Ala Ala Leu Phe Ala Asp Glu Val Tyr Arg Val
        140                 145                 150

Leu Gln Glu Gly Thr Ala Leu Ala Ile Glu Gly Gly Thr Leu Thr Leu
    155                 160                 165

Asp Pro Asn Ser Lys Val Asp Pro Ser Lys Gly Val Tyr Ala Gly Leu
170                 175                 180                 185

Thr Asn Gly Gly Thr Asn Tyr Gly Leu Thr Pro Asp Tyr Ser Gly Ala
                190                 195                 200

Ile Trp Asn Pro Ala Ser Thr Ser Asn Tyr Ala Val Ala Ser Arg Pro
        205                 210                 215

Thr Ser Asn Pro Ile Asn Ser Val Ile His Asp Thr Glu Gly Ser
    220                 225                 230

Tyr Ser Gly Ser Ile Asn Trp Phe Lys Asp Pro Ala Ala Gln Val Ser
    235                 240                 245

Ala His Tyr Ile Val Arg Ser Ser Asp Gly Gln Ile Thr Gln Leu Val
250                 255                 260                 265

Gln Asp Lys Asp Ile Ala Trp His Ala Arg Ser Phe Asn Thr Asn Gly
            270                 275                 280

Ile Gly Ile Glu His Glu Gly Tyr Ala Ala Gln Thr Gly Trp Tyr Thr
            285                 290                 295

Asp Ala Met Tyr Thr Ala Ser Ala Ala Leu Thr Arg Ala Val Cys Leu
        300                 305                 310

Lys Tyr Asn Ile Pro Met Asp Arg Asp His Ile Leu Ala His Ser Glu
    315                 320                 325

Leu Trp Gly Asn Asp His Thr Asp Pro Gly Val Asn Trp Asp Trp Asn
330                 335                 340                 345

Lys Tyr Met Ser Lys Val Thr Gly Val Thr Lys Asn Tyr Ala Ala Val
                350                 355                 360

Leu Val Asp Asn Thr Asp Ala Ser Ser Gly Phe Thr Leu Gly Gly Pro
            365                 370                 375

Ser Gln Tyr Trp His Pro Thr Ala Gly Tyr Gly Ile His Asn Gln Met
        380                 385                 390

Thr Tyr Thr Met Gly Asn Gly Thr Asn Pro Ile Ser Asn Tyr Ala Thr
    395                 400                 405

Trp Lys Pro Thr Ile Pro Thr Ala Gly Asn Tyr Gln Val Lys Val Phe
410                 415                 420                 425

Ile Pro Ser Asn Phe Ala Ala Thr Asn Ala Lys Tyr Glu Ile His
            430                 435                 440

Tyr Asn Gly Gly Val Ile Thr Lys Thr Ile Ser Gln Ala Ala Tyr Ser
                445                 450                 455

Asn Gln Trp Val Ser Leu Gly Thr Tyr Ser Phe Ala Ala Gly Thr Ala
        460                 465                 470
```

Gly Tyr Val Lys Leu Gly Asp Asn Thr Gly Asp Thr Ala Tyr Val Gly
    475                 480                 485

Ile Asp Gly Met Arg Phe Leu Ala Gln
490                 495

<210> SEQ ID NO 42
<211> LENGTH: 498
<212> TYPE: PRT
<213> ORGANISM: Tumebacillus sp

<400> SEQUENCE: 42

Gln Pro Thr His Ala Ala Lys Leu Asp Asn Gln Thr Val Ala Thr Ala
1               5                   10                  15

Pro Val Leu Glu Ser Thr Phe Ser Ser Ala Ala Lys Glu Phe Gly Val
            20                  25                  30

Pro Lys Glu Leu Leu Met Ala Ile Ser Tyr Ser Glu Ser Arg Trp Gln
        35                  40                  45

Ile Ala Pro Glu Glu Thr His Leu Thr Ala Glu Pro Asp Lys Asn Asn
    50                  55                  60

Gly Lys Gly Leu Met His Leu Asn Asp Asn Ser Phe Lys Lys Gly Leu
65                  70                  75                  80

Ser Asp Ala Ala Lys Ala Leu Gly Val Ser Lys Lys Gln Met Glu Asp
                85                  90                  95

Asp Val Gln Leu Asn Ile Arg Gly Gly Ala Tyr Leu Leu Ala Lys Ala
            100                 105                 110

Gln Lys Asp Leu Gly Lys Ala Leu Thr Ser Asn Val Asn Asp Trp Tyr
        115                 120                 125

Glu Ala Val Ala Ser Phe Glu Gly Ala Lys Asp Lys Asp Val Ala Ala
    130                 135                 140

Leu Phe Ala Asp Glu Val Tyr Arg Val Leu Gln Glu Gly Thr Ala Leu
145                 150                 155                 160

Ala Ile Glu Gly Gly Thr Leu Thr Leu Asp Pro Asn Ser Lys Val Asp
                165                 170                 175

Pro Ser Lys Gly Val Tyr Ala Gly Leu Thr Asn Gly Thr Asn Tyr
        180                 185                 190

Gly Leu Thr Pro Asp Tyr Ser Gly Ala Ile Trp Asn Pro Ala Ser Thr
    195                 200                 205

Ser Asn Tyr Ala Val Ala Ser Arg Pro Thr Ser Asn Pro Ile Asn Ser
210                 215                 220

Val Ile Ile His Asp Thr Glu Gly Ser Tyr Ser Gly Ser Ile Asn Trp
225                 230                 235                 240

Phe Lys Asp Pro Ala Ala Gln Val Ser Ala His Tyr Ile Val Arg Ser
                245                 250                 255

Ser Asp Gly Gln Ile Thr Gln Leu Val Gln Asp Lys Asp Ile Ala Trp
            260                 265                 270

His Ala Arg Ser Phe Asn Thr Asn Gly Ile Gly Ile Glu His Glu Gly
        275                 280                 285

Tyr Ala Ala Gln Thr Gly Trp Tyr Thr Asp Ala Met Tyr Thr Ala Ser
    290                 295                 300

Ala Ala Leu Thr Arg Ala Val Cys Leu Lys Tyr Asn Ile Pro Met Asp
305                 310                 315                 320

Arg Asp His Ile Leu Ala His Ser Glu Leu Trp Gly Asn Asp His Thr
                325                 330                 335

```
Asp Pro Gly Val Asn Trp Asp Trp Asn Lys Tyr Met Ser Lys Val Thr
            340                 345                 350
Gly Val Thr Lys Asn Tyr Ala Ala Val Leu Val Asp Asn Thr Asp Ala
                355                 360                 365
Ser Ser Gly Phe Thr Leu Gly Gly Pro Ser Gln Tyr Trp His Pro Thr
    370                 375                 380
Ala Gly Tyr Gly Ile His Asn Gln Met Thr Tyr Thr Met Gly Asn Gly
385                 390                 395                 400
Thr Asn Pro Ile Ser Asn Tyr Ala Thr Trp Lys Pro Thr Ile Pro Thr
                405                 410                 415
Ala Gly Asn Tyr Gln Val Lys Val Phe Ile Pro Ser Asn Phe Ala Ala
                420                 425                 430
Thr Thr Asn Ala Lys Tyr Glu Ile His Tyr Asn Gly Gly Val Ile Thr
                435                 440                 445
Lys Thr Ile Ser Gln Ala Ala Tyr Ser Asn Gln Trp Val Ser Leu Gly
                450                 455                 460
Thr Tyr Ser Phe Ala Ala Gly Thr Ala Gly Tyr Val Lys Leu Gly Asp
465                 470                 475                 480
Asn Thr Gly Asp Thr Ala Tyr Val Gly Ile Asp Gly Met Arg Phe Leu
                485                 490                 495
Ala Gln

<210> SEQ ID NO 43
<211> LENGTH: 1506
<212> TYPE: DNA
<213> ORGANISM: Nonomuraea dietziae
<220> FEATURE:
<221> NAME/KEY: CDS
<222> LOCATION: (1)..(1503)
<220> FEATURE:
<221> NAME/KEY: sig_peptide
<222> LOCATION: (1)..(75)
<220> FEATURE:
<221> NAME/KEY: mat_peptide
<222> LOCATION: (76)..(1503)

<400> SEQUENCE: 43 atg act cga tta gcc gct ctt gtc gcc tca gcc ctc tcc gcc ctc ctc       48
Met Thr Arg Leu Ala Ala Leu Val Ala Ser Ala Leu Ser Ala Leu Leu
-25                 -20                 -15                 -10 atc ctc gcc ggt cag ccc gcc gcc gcc gac cgg gcg acc ccg ctc ggc       96
Ile Leu Ala Gly Gln Pro Ala Ala Ala Asp Arg Ala Thr Pro Leu Gly
            -5                  -1   1               5 gcc gcc ttc gac aag gcc gcc gcc gcc cag gac gtc ccc cgt gac ctg      144
Ala Ala Phe Asp Lys Ala Ala Ala Ala Gln Asp Val Pro Arg Asp Leu
            10                  15                  20 ctc gcc gcg atc gcc tac gcc gag acc cac ctc gac ggt cac aac ggc      192
Leu Ala Ala Ile Ala Tyr Ala Glu Thr His Leu Asp Gly His Asn Gly
            25                  30                  35 gag ccg agc gcc agc ggc ggc tac ggt gtg atg cac ctg gtc agc aac      240
Glu Pro Ser Ala Ser Gly Gly Tyr Gly Val Met His Leu Val Ser Asn
40                  45                  50                  55 ccc acc acg cac acc ctg gag aag gcc gcc gag ctc acg ggc ctg ccc      288
Pro Thr Thr His Thr Leu Glu Lys Ala Ala Glu Leu Thr Gly Leu Pro
                60                  65                  70 gcg gag aag ctg cgc gcc gac acc gag gcc aac atc ctc ggc ggc gcg      336
Ala Glu Lys Leu Arg Ala Asp Thr Glu Ala Asn Ile Leu Gly Gly Ala
            75                  80                  85
```

| | |
|---|---|
| gcc gtc ctg cgc tcc atc gcc gac ggg ctc ggc ctc gac gag gcc gcc<br>Ala Val Leu Arg Ser Ile Ala Asp Gly Leu Gly Leu Asp Glu Ala Ala<br>     90                      95                   100 | 384 |
| agg aag gag gag ggc cgc tgg tac gag gcc gtc gcc acg tac ggc aac<br>Arg Lys Glu Glu Gly Arg Trp Tyr Glu Ala Val Ala Thr Tyr Gly Asn<br>105                      110                   115 | 432 |
| gcc tcc tcg ccg gag ctg gcc cgc ctc tac gcc gac gcc gtc tac gag<br>Ala Ser Ser Pro Glu Leu Ala Arg Leu Tyr Ala Asp Ala Val Tyr Glu<br>120                      125                   130                   135 | 480 |
| ctg ctt ggc ctc ggc ttc aag gcc aag ggc ctg cgt gtg gcc ccc cgc<br>Leu Leu Gly Leu Gly Phe Lys Ala Lys Gly Leu Arg Val Ala Pro Arg<br>                   140                   145                   150 | 528 |
| gag gtc acc gcc gac agg gga gtg tac gca ggg gcc agg gac ctg aac<br>Glu Val Thr Ala Asp Arg Gly Val Tyr Ala Gly Ala Arg Asp Leu Asn<br>              155                     160                     165 | 576 |
| gcc aag gac tcc aac gcc ctg gcc gcc gcc ggc cct gac tac ccg aac<br>Ala Lys Asp Ser Asn Ala Leu Ala Ala Ala Gly Pro Asp Tyr Pro Asn<br>          170                     175                   180 | 624 |
| gcc agc tgg gtg ccc gcc agt tcg agc aac tac acc gtg tcg agc cgt<br>Ala Ser Trp Val Pro Ala Ser Ser Ser Asn Tyr Thr Val Ser Ser Arg<br>185                      190                   195 | 672 |
| cct tcg agc tac gcc atc gac cgg gtg gtc atc cac gtg acc cag ggc<br>Pro Ser Ser Tyr Ala Ile Asp Arg Val Val Ile His Val Thr Gln Gly<br>200                      205                   210                   215 | 720 |
| tcc tac gcc ggg tcc atc tcc tgg ttc cag aac ccg agc gcc cag gtc<br>Ser Tyr Ala Gly Ser Ile Ser Trp Phe Gln Asn Pro Ser Ala Gln Val<br>                   220                   225                   230 | 768 |
| tcc gcg cac tac gtg atc cgt tcc tcg gac ggc gcc atc acc cag atg<br>Ser Ala His Tyr Val Ile Arg Ser Ser Asp Gly Ala Ile Thr Gln Met<br>              235                     240                     245 | 816 |
| gtc cgt gag aag gac gtc gca tgg cac gcg ggc aac tgg agc tac aac<br>Val Arg Glu Lys Asp Val Ala Trp His Ala Gly Asn Trp Ser Tyr Asn<br>          250                     255                   260 | 864 |
| acc cgc tcc gtc ggc atc gag cac gag ggc ttc gtc aac gac gcc tcc<br>Thr Arg Ser Val Gly Ile Glu His Glu Gly Phe Val Asn Asp Ala Ser<br>265                      270                   275 | 912 |
| tgg ttc acc gac gcg atg tac cgc gcg tcc gcc gcc ctg acc cgc aac<br>Trp Phe Thr Asp Ala Met Tyr Arg Ala Ser Ala Ala Leu Thr Arg Asn<br>280                      285                   290                   295 | 960 |
| atc tgc gac aag tac ggc atc ccg aag gac cgc agc cac atc atc ggc<br>Ile Cys Asp Lys Tyr Gly Ile Pro Lys Asp Arg Ser His Ile Ile Gly<br>                   300                   305                   310 | 1008 |
| cac gtg gag gtc ccc ggc tcc acg cac acc gac ccc ggc ccg cac tgg<br>His Val Glu Val Pro Gly Ser Thr His Thr Asp Pro Gly Pro His Trp<br>              315                     320                     325 | 1056 |
| aac tgg aac acc tac atg tcg tac gtg acc ggt ggc ggc ggc tcg<br>Asn Trp Asn Thr Tyr Met Ser Tyr Val Thr Gly Gly Gly Gly Ser<br>          330                     335                   340 | 1104 |
| tgg tcc acc acg gtc gac aac acc ggc gcg ttc acc gcg agc ggc aac<br>Trp Ser Thr Thr Val Asp Asn Thr Gly Ala Phe Thr Ala Ser Gly Asn<br>345                      350                   355 | 1152 |
| tgg ggc act tcc agc tac tcc gcc cag cgc tac ggc gcc gac tac cgc<br>Trp Gly Thr Ser Ser Tyr Ser Ala Gln Arg Tyr Gly Ala Asp Tyr Arg<br>360                      365                   370                   375 | 1200 |
| ttc gcc aac ccg gtg gcc gcc agc gac ccc gcc tgg tac cgg gcg aac<br>Phe Ala Asn Pro Val Ala Ala Ser Asp Pro Ala Trp Tyr Arg Ala Asn<br>                   380                   385                   390 | 1248 |

```
ctg ccc agc acg ggc agc tac cgg gtc gag gtc tgg tac ccc tcc gac    1296
Leu Pro Ser Thr Gly Ser Tyr Arg Val Glu Val Trp Tyr Pro Ser Asp
        395                 400                 405 ccc ggc tac aac agc tcg gcc ccc tac atc gtc gcc gcc tcg ggc ggc    1344
Pro Gly Tyr Asn Ser Ser Ala Pro Tyr Ile Val Ala Ala Ser Gly Gly
        410                 415                 420 aac cag acg gtg tac gtc gac cag cga tcc ggc ggt ggc tgg cgc        1392
Asn Gln Thr Val Tyr Val Asp Gln Arg Ser Gly Gly Gly Trp Arg
    425                 430                 435 acc atc ggc acc ttc acc ctc aac gcc ggt gac cga gac gtc gtg ggt    1440
Thr Ile Gly Thr Phe Thr Leu Asn Ala Gly Asp Arg Asp Val Val Gly
440                 445                 450                 455 gtc agc cgc tgg acc tcg ggc acc ggc tac gtc gtc gcc gac gcc gtc    1488
Val Ser Arg Trp Thr Ser Gly Thr Gly Tyr Val Val Ala Asp Ala Val
                460                 465                 470 cgc atc acc cgc ctg taa                                            1506
Arg Ile Thr Arg Leu
                475

<210> SEQ ID NO 44
<211> LENGTH: 501
<212> TYPE: PRT
<213> ORGANISM: Nonomuraea dietziae

<400> SEQUENCE: 44

Met Thr Arg Leu Ala Ala Leu Val Ala Ser Ala Leu Ser Ala Leu Leu
-25                 -20                 -15                 -10

Ile Leu Ala Gly Gln Pro Ala Ala Ala Asp Arg Ala Thr Pro Leu Gly
                -5                  -1  1               5

Ala Ala Phe Asp Lys Ala Ala Ala Gln Asp Val Pro Arg Asp Leu
            10                  15                  20

Leu Ala Ala Ile Ala Tyr Ala Glu Thr His Leu Asp Gly His Asn Gly
        25                  30                  35

Glu Pro Ser Ala Ser Gly Gly Tyr Gly Val Met His Leu Val Ser Asn
40                  45                  50                  55

Pro Thr Thr His Thr Leu Glu Lys Ala Ala Glu Leu Thr Gly Leu Pro
                60                  65                  70

Ala Glu Lys Leu Arg Ala Asp Thr Glu Ala Asn Ile Leu Gly Gly Ala
            75                  80                  85

Ala Val Leu Arg Ser Ile Ala Asp Gly Leu Gly Leu Asp Glu Ala Ala
        90                  95                  100

Arg Lys Glu Glu Gly Arg Trp Tyr Glu Ala Val Ala Thr Tyr Gly Asn
    105                 110                 115

Ala Ser Ser Pro Glu Leu Ala Arg Leu Tyr Ala Asp Ala Val Tyr Glu
120                 125                 130                 135

Leu Leu Gly Leu Gly Phe Lys Ala Lys Gly Leu Arg Val Ala Pro Arg
                140                 145                 150

Glu Val Thr Ala Asp Arg Gly Val Tyr Ala Gly Ala Arg Asp Leu Asn
            155                 160                 165

Ala Lys Asp Ser Asn Ala Leu Ala Ala Gly Pro Asp Tyr Pro Asn
        170                 175                 180

Ala Ser Trp Val Pro Ala Ser Ser Asn Tyr Thr Val Ser Ser Arg
    185                 190                 195

Pro Ser Ser Tyr Ala Ile Asp Arg Val Val Ile His Val Thr Gln Gly
200                 205                 210                 215
```

Ser Tyr Ala Gly Ser Ile Ser Trp Phe Gln Asn Pro Ser Ala Gln Val
            220                 225                 230

Ser Ala His Tyr Val Ile Arg Ser Ser Asp Gly Ala Ile Thr Gln Met
            235                 240                 245

Val Arg Glu Lys Asp Val Ala Trp His Ala Gly Asn Trp Ser Tyr Asn
            250                 255                 260

Thr Arg Ser Val Gly Ile Glu His Glu Gly Phe Val Asn Asp Ala Ser
            265                 270                 275

Trp Phe Thr Asp Ala Met Tyr Arg Ala Ser Ala Leu Thr Arg Asn
280             285                 290                 295

Ile Cys Asp Lys Tyr Gly Ile Pro Lys Asp Arg Ser His Ile Ile Gly
            300                 305                 310

His Val Glu Val Pro Gly Ser Thr His Thr Asp Pro Gly Pro His Trp
            315                 320                 325

Asn Trp Asn Thr Tyr Met Ser Tyr Val Thr Gly Gly Gly Gly Ser
            330                 335                 340

Trp Ser Thr Thr Val Asp Asn Thr Gly Ala Phe Thr Ala Ser Gly Asn
            345                 350                 355

Trp Gly Thr Ser Ser Tyr Ser Ala Gln Arg Tyr Gly Ala Asp Tyr Arg
360             365                 370                 375

Phe Ala Asn Pro Val Ala Ala Ser Asp Pro Ala Trp Tyr Arg Ala Asn
            380                 385                 390

Leu Pro Ser Thr Gly Ser Tyr Arg Val Glu Val Trp Tyr Pro Ser Asp
            395                 400                 405

Pro Gly Tyr Asn Ser Ser Ala Pro Tyr Ile Val Ala Ala Ser Gly Gly
            410                 415                 420

Asn Gln Thr Val Tyr Val Asp Gln Arg Ser Gly Gly Gly Trp Arg
            425                 430                 435

Thr Ile Gly Thr Phe Thr Leu Asn Ala Gly Asp Arg Asp Val Val Gly
440             445                 450                 455

Val Ser Arg Trp Thr Ser Gly Thr Gly Tyr Val Val Ala Asp Ala Val
            460                 465                 470

Arg Ile Thr Arg Leu
            475

<210> SEQ ID NO 45
<211> LENGTH: 476
<212> TYPE: PRT
<213> ORGANISM: Nonomuraea dietziae

<400> SEQUENCE: 45

Asp Arg Ala Thr Pro Leu Gly Ala Ala Phe Asp Lys Ala Ala Ala Ala
1               5                   10                  15

Gln Asp Val Pro Arg Asp Leu Leu Ala Ala Ile Ala Tyr Ala Glu Thr
            20                  25                  30

His Leu Asp Gly His Asn Gly Glu Pro Ser Ala Ser Gly Gly Tyr Gly
        35                  40                  45

Val Met His Leu Val Ser Asn Pro Thr Thr His Thr Leu Glu Lys Ala
    50                  55                  60

Ala Glu Leu Thr Gly Leu Pro Ala Glu Lys Leu Arg Ala Asp Thr Glu
65                  70                  75                  80

Ala Asn Ile Leu Gly Gly Ala Ala Val Leu Arg Ser Ile Ala Asp Gly
                85                  90                  95

Leu Gly Leu Asp Glu Ala Ala Arg Lys Glu Gly Arg Trp Tyr Glu
            100                 105                 110

Ala Val Ala Thr Tyr Gly Asn Ala Ser Ser Pro Glu Leu Ala Arg Leu
        115                 120                 125

Tyr Ala Asp Ala Val Tyr Glu Leu Leu Gly Leu Gly Phe Lys Ala Lys
    130                 135                 140

Gly Leu Arg Val Ala Pro Arg Glu Val Thr Ala Asp Arg Gly Val Tyr
145                 150                 155                 160

Ala Gly Ala Arg Asp Leu Asn Ala Lys Asp Ser Asn Ala Leu Ala Ala
                165                 170                 175

Ala Gly Pro Asp Tyr Pro Asn Ala Ser Trp Val Pro Ala Ser Ser Ser
            180                 185                 190

Asn Tyr Thr Val Ser Ser Arg Pro Ser Tyr Ala Ile Asp Arg Val
        195                 200                 205

Val Ile His Val Thr Gln Gly Ser Tyr Ala Gly Ser Ile Ser Trp Phe
    210                 215                 220

Gln Asn Pro Ser Ala Gln Val Ser Ala His Tyr Val Ile Arg Ser Ser
225                 230                 235                 240

Asp Gly Ala Ile Thr Gln Met Val Arg Glu Lys Asp Val Ala Trp His
                245                 250                 255

Ala Gly Asn Trp Ser Tyr Asn Thr Arg Ser Val Gly Ile Glu His Glu
            260                 265                 270

Gly Phe Val Asn Asp Ala Ser Trp Phe Thr Asp Ala Met Tyr Arg Ala
        275                 280                 285

Ser Ala Ala Leu Thr Arg Asn Ile Cys Asp Lys Tyr Gly Ile Pro Lys
    290                 295                 300

Asp Arg Ser His Ile Ile Gly His Val Glu Val Pro Gly Ser Thr His
305                 310                 315                 320

Thr Asp Pro Gly Pro His Trp Asn Trp Asn Thr Tyr Met Ser Tyr Val
                325                 330                 335

Thr Gly Gly Gly Gly Ser Trp Ser Thr Thr Val Asp Asn Thr Gly
            340                 345                 350

Ala Phe Thr Ala Ser Gly Asn Trp Gly Thr Ser Ser Tyr Ser Ala Gln
        355                 360                 365

Arg Tyr Gly Ala Asp Tyr Arg Phe Ala Asn Pro Val Ala Ala Ser Asp
370                 375                 380

Pro Ala Trp Tyr Arg Ala Asn Leu Pro Ser Thr Gly Ser Tyr Arg Val
385                 390                 395                 400

Glu Val Trp Tyr Pro Ser Asp Pro Gly Tyr Asn Ser Ser Ala Pro Tyr
                405                 410                 415

Ile Val Ala Ala Ser Gly Gly Asn Gln Thr Val Tyr Val Asp Gln Arg
            420                 425                 430

Ser Gly Gly Gly Gly Trp Arg Thr Ile Gly Thr Phe Thr Leu Asn Ala
        435                 440                 445

Gly Asp Arg Asp Val Val Gly Val Ser Arg Trp Thr Ser Gly Thr Gly
450                 455                 460

Tyr Val Val Ala Asp Ala Val Arg Ile Thr Arg Leu
465                 470                 475

<210> SEQ ID NO 46
<211> LENGTH: 1509
<212> TYPE: DNA
<213> ORGANISM: Laceyella sacchari
<220> FEATURE:

```
<221> NAME/KEY: CDS
<222> LOCATION: (1)..(1506)
<220> FEATURE:
<221> NAME/KEY: sig_peptide
<222> LOCATION: (1)..(84)
<220> FEATURE:
<221> NAME/KEY: mat_peptide
<222> LOCATION: (85)..(1506)

<400> SEQUENCE: 46
```

| | | | | | | | | | | | | | | | | |
|---|---|---|---|---|---|---|---|---|---|---|---|---|---|---|---|---|
| ttg | aga | aag | cgt | ttg | ctc | tct | tgg | tta | gct | att | tgc | tgt | ctg | ctc | act | 48 |
| Leu | Arg | Lys | Arg | Leu | Leu | Ser | Trp | Leu | Ala | Ile | Cys | Cys | Leu | Leu | Thr | |
| | | | -25 | | | | -20 | | | | | -15 | | | | |
| ctg | cct | ttc | ctt | tca | gct | cca | ccg | ccc | gtt | gca | gcc | gag | gaa | cag | ccg | 96 |
| Leu | Pro | Phe | Leu | Ser | Ala | Pro | Pro | Pro | Val | Ala | Ala | Glu | Glu | Gln | Pro | |
| | -10 | | | | | -5 | | | | -1 | 1 | | | | | |
| tct | ttg | tcc | cat | gtc | ttc | gag | atg | gcc | gcc | gca | gag | ttt | gag | gtg | ccc | 144 |
| Ser | Leu | Ser | His | Val | Phe | Glu | Met | Ala | Ala | Ala | Glu | Phe | Glu | Val | Pro | |
| 5 | | | | 10 | | | | 15 | | | | | 20 | | | |
| gtt | gaa | gtg | ttg | ttg | gct | att | ggc | tat | gcc | gag | acg | agg | tgg | atg | gac | 192 |
| Val | Glu | Val | Leu | Leu | Ala | Ile | Gly | Tyr | Ala | Glu | Thr | Arg | Trp | Met | Asp | |
| | | | | 25 | | | | | 30 | | | | | 35 | | |
| cat | cag | ggc | caa | ccc | agc | cag | ctc | aac | gga | tac | ggc | att | atg | cat | ttg | 240 |
| His | Gln | Gly | Gln | Pro | Ser | Gln | Leu | Asn | Gly | Tyr | Gly | Ile | Met | His | Leu | |
| | | | 40 | | | | | 45 | | | | | 50 | | | |
| gcc | gaa | aac | ccc | acc | aat | gac | tca | ttg | gta | caa | gcc | agc | cga | ttg | ctg | 288 |
| Ala | Glu | Asn | Pro | Thr | Asn | Asp | Ser | Leu | Val | Gln | Ala | Ser | Arg | Leu | Leu | |
| | | 55 | | | | | 60 | | | | | 65 | | | | |
| ggc | ata | gat | aaa | caa | gtg | ctg | acc | cgg | gac | atc | cag | gct | aac | atc | cgt | 336 |
| Gly | Ile | Asp | Lys | Gln | Val | Leu | Thr | Arg | Asp | Ile | Gln | Ala | Asn | Ile | Arg | |
| 70 | | | | | 75 | | | | | 80 | | | | | | |
| ggc | gcg | gca | gcc | gtg | ttg | cag | caa | atc | tcc | aaa | gaa | caa | aac | cag | ggg | 384 |
| Gly | Ala | Ala | Ala | Val | Leu | Gln | Gln | Ile | Ser | Lys | Glu | Gln | Asn | Gln | Gly | |
| 85 | | | | | 90 | | | | | 95 | | | | | 100 | |
| cag | gtg | ccg | aaa | aag | ctg | gcc | gat | tgg | tac | act | gtt | gta | gcg | gaa | tac | 432 |
| Gln | Val | Pro | Lys | Lys | Leu | Ala | Asp | Trp | Tyr | Thr | Val | Val | Ala | Glu | Tyr | |
| | | | | 105 | | | | | 110 | | | | | 115 | | |
| agc | gga | cta | tcc | agc | caa | caa | acc | aaa | gca | tgg | tat | gcc | gat | gat | gta | 480 |
| Ser | Gly | Leu | Ser | Ser | Gln | Gln | Thr | Lys | Ala | Trp | Tyr | Ala | Asp | Asp | Val | |
| | | | 120 | | | | | 125 | | | | | 130 | | | |
| tat | gct | ctg | atc | aac | cgc | ggc | gtc | tct | cgt | gtt | atc | aac | ggc | caa | gag | 528 |
| Tyr | Ala | Leu | Ile | Asn | Arg | Gly | Val | Ser | Arg | Val | Ile | Asn | Gly | Gln | Glu | |
| | | | 135 | | | | | 140 | | | | | 145 | | | |
| gtg | cga | tta | gaa | ccc | aca | ccg | gtc | aca | ccc | aac | cgc | ggg | gaa | tac | ggt | 576 |
| Val | Arg | Leu | Glu | Pro | Thr | Pro | Val | Thr | Pro | Asn | Arg | Gly | Glu | Tyr | Gly | |
| | 150 | | | | | 155 | | | | | 160 | | | | | |
| gaa | cct | cgc | gat | ccg | tcc | ggc | caa | gcc | aca | ccc | gat | tat | ccc | gaa | gcg | 624 |
| Glu | Pro | Arg | Asp | Pro | Ser | Gly | Gln | Ala | Thr | Pro | Asp | Tyr | Pro | Glu | Ala | |
| 165 | | | | | 170 | | | | | 175 | | | | | 180 | |
| cgc | tgg | gtg | gcg | gca | tcc | agt | gcc | aac | tat | act | gcc | gcc | aac | agg | gaa | 672 |
| Arg | Trp | Val | Ala | Ala | Ser | Ser | Ala | Asn | Tyr | Thr | Ala | Ala | Asn | Arg | Glu | |
| | | | | 185 | | | | | 190 | | | | | 195 | | |
| tcc | gac | ggc | aat | gcc | atc | aac | tac | gtg | atc | atc | cac | acc | acg | caa | ggc | 720 |
| Ser | Asp | Gly | Asn | Ala | Ile | Asn | Tyr | Val | Ile | Ile | His | Thr | Thr | Gln | Gly | |
| | | | 200 | | | | | 205 | | | | | 210 | | | |
| tct | tat | aat | ggg | acg | atc | agt | tgg | ttt | caa | aat | ccc | tct | gcc | caa | gtg | 768 |
| Ser | Tyr | Asn | Gly | Thr | Ile | Ser | Trp | Phe | Gln | Asn | Pro | Ser | Ala | Gln | Val | |
| | | | 215 | | | | | 220 | | | | | 225 | | | |
| agc | gca | cat | tat | gtc | att | cgc | tcc | agt | gat | ggg | caa | gtg | acc | caa | atg | 816 |
| Ser | Ala | His | Tyr | Val | Ile | Arg | Ser | Ser | Asp | Gly | Gln | Val | Thr | Gln | Met | |
| | | 230 | | | | | 235 | | | | | 240 | | | | |

```
gtg cag aac aaa gac atc gct tgg cat gcg ggc aac tgg gat tac aat    864
Val Gln Asn Lys Asp Ile Ala Trp His Ala Gly Asn Trp Asp Tyr Asn
245                 250                 255                 260 gtc cac tcc gtg ggg atc gag cat gaa ggg tat gtc aat gat cca gcc    912
Val His Ser Val Gly Ile Glu His Glu Gly Tyr Val Asn Asp Pro Ala
                265                 270                 275 tgg tac act gat gcc atg tac cgc gcc tct gcc aag ctg acc cgc tgg    960
Trp Tyr Thr Asp Ala Met Tyr Arg Ala Ser Ala Lys Leu Thr Arg Trp
            280                 285                 290 ttg tgc aac agg tac ggg att ccc aaa gac cgc agt cac att atc ggc    1008
Leu Cys Asn Arg Tyr Gly Ile Pro Lys Asp Arg Ser His Ile Ile Gly
        295                 300                 305 cat aac caa gtt cca ggc gcc acc cac acc gac ccc ggc ccc aat tgg    1056
His Asn Gln Val Pro Gly Ala Thr His Thr Asp Pro Gly Pro Asn Trp
    310                 315                 320 gat tgg aac tat tac atg agc ttg gtc aat cag tcg ggc ggc ggt gcc    1104
Asp Trp Asn Tyr Tyr Met Ser Leu Val Asn Gln Ser Gly Gly Gly Ala
325                 330                 335                 340 gat ttg gtc act gat aac gcc act tcg aac cgc ttc act gcc agc gcc    1152
Asp Leu Val Thr Asp Asn Ala Thr Ser Asn Arg Phe Thr Ala Ser Ala
                345                 350                 355 aat tgg gcg ata ggc acg acc aat gcc caa aaa tac gga gcg gat tac    1200
Asn Trp Ala Ile Gly Thr Thr Asn Ala Gln Lys Tyr Gly Ala Asp Tyr
            360                 365                 370 cgc tat gcc aag cct gaa acg atc agt gac gca gct tgg tac aaa gta    1248
Arg Tyr Ala Lys Pro Glu Thr Ile Ser Asp Ala Ala Trp Tyr Lys Val
        375                 380                 385 aac ctc ccc acc tct gga agt tat gat gta tat gct tgg tgg ccg tca    1296
Asn Leu Pro Thr Ser Gly Ser Tyr Asp Val Tyr Ala Trp Trp Pro Ser
    390                 395                 400 ggc tcc atc tac aat gat cgg aca cct tat gtg atc aac acc acc agc    1344
Gly Ser Ile Tyr Asn Asp Arg Thr Pro Tyr Val Ile Asn Thr Thr Ser
405                 410                 415                 420 ggt agc cag acc gtc cac gtt tcc caa caa tcc agc gga ggt gtc tgg    1392
Gly Ser Gln Thr Val His Val Ser Gln Gln Ser Ser Gly Gly Val Trp
                425                 430                 435 aac cat ctg gga acc ttt aac ttt gcg gcg ggc gat gcc aac cgg att    1440
Asn His Leu Gly Thr Phe Asn Phe Ala Ala Gly Asp Ala Asn Arg Ile
            440                 445                 450 gcc gtg tcg cga tgg acg aca ggc acc ggt tat gtc atc gct gat gct    1488
Ala Val Ser Arg Trp Thr Thr Gly Thr Gly Tyr Val Ile Ala Asp Ala
        455                 460                 465 gtc aaa ttc gtg aaa aga tga                                        1509
Val Lys Phe Val Lys Arg
    470

<210> SEQ ID NO 47
<211> LENGTH: 502
<212> TYPE: PRT
<213> ORGANISM: Laceyella sacchari

<400> SEQUENCE: 47

Leu Arg Lys Arg Leu Leu Ser Trp Leu Ala Ile Cys Cys Leu Leu Thr
            -25                 -20                 -15

Leu Pro Phe Leu Ser Ala Pro Pro Val Ala Ala Glu Glu Gln Pro
        -10                 -5              -1  1

Ser Leu Ser His Val Phe Glu Met Ala Ala Glu Phe Glu Val Pro
5                   10                  15                  20

Val Glu Val Leu Leu Ala Ile Gly Tyr Ala Glu Thr Arg Trp Met Asp
            25                  30                  35
```

-continued

His Gln Gly Gln Pro Ser Gln Leu Asn Gly Tyr Gly Ile Met His Leu
            40                  45                  50

Ala Glu Asn Pro Thr Asn Asp Ser Leu Val Gln Ala Ser Arg Leu Leu
        55                  60                  65

Gly Ile Asp Lys Gln Val Leu Thr Arg Asp Ile Gln Ala Asn Ile Arg
    70                  75                  80

Gly Ala Ala Ala Val Leu Gln Gln Ile Ser Lys Glu Gln Asn Gln Gly
85                  90                  95                  100

Gln Val Pro Lys Lys Leu Ala Asp Trp Tyr Thr Val Val Ala Glu Tyr
                105                 110                 115

Ser Gly Leu Ser Ser Gln Gln Thr Lys Ala Trp Tyr Ala Asp Asp Val
            120                 125                 130

Tyr Ala Leu Ile Asn Arg Gly Val Ser Arg Val Ile Asn Gly Gln Glu
        135                 140                 145

Val Arg Leu Glu Pro Thr Pro Val Thr Pro Asn Arg Gly Glu Tyr Gly
    150                 155                 160

Glu Pro Arg Asp Pro Ser Gly Gln Ala Thr Pro Asp Tyr Pro Glu Ala
165                 170                 175                 180

Arg Trp Val Ala Ala Ser Ser Ala Asn Tyr Thr Ala Ala Asn Arg Glu
                185                 190                 195

Ser Asp Gly Asn Ala Ile Asn Tyr Val Ile His Thr Thr Gln Gly
            200                 205                 210

Ser Tyr Asn Gly Thr Ile Ser Trp Phe Gln Asn Pro Ser Ala Gln Val
        215                 220                 225

Ser Ala His Tyr Val Ile Arg Ser Ser Asp Gly Gln Val Thr Gln Met
    230                 235                 240

Val Gln Asn Lys Asp Ile Ala Trp His Ala Gly Asn Trp Asp Tyr Asn
245                 250                 255                 260

Val His Ser Val Gly Ile Glu His Glu Gly Tyr Val Asn Asp Pro Ala
                265                 270                 275

Trp Tyr Thr Asp Ala Met Tyr Arg Ala Ser Ala Lys Leu Thr Arg Trp
            280                 285                 290

Leu Cys Asn Arg Tyr Gly Ile Pro Lys Asp Arg Ser His Ile Ile Gly
        295                 300                 305

His Asn Gln Val Pro Gly Ala Thr His Thr Asp Pro Gly Pro Asn Trp
    310                 315                 320

Asp Trp Asn Tyr Tyr Met Ser Leu Val Asn Gln Ser Gly Gly Gly Ala
325                 330                 335                 340

Asp Leu Val Thr Asp Asn Ala Thr Ser Asn Arg Phe Thr Ala Ser Ala
                345                 350                 355

Asn Trp Ala Ile Gly Thr Thr Asn Ala Gln Lys Tyr Gly Ala Asp Tyr
            360                 365                 370

Arg Tyr Ala Lys Pro Glu Thr Ile Ser Asp Ala Ala Trp Tyr Lys Val
        375                 380                 385

Asn Leu Pro Thr Ser Gly Ser Tyr Asp Val Tyr Ala Trp Trp Pro Ser
    390                 395                 400

Gly Ser Ile Tyr Asn Asp Arg Thr Pro Tyr Val Ile Asn Thr Thr Ser
405                 410                 415                 420

Gly Ser Gln Thr Val His Val Ser Gln Gln Ser Ser Gly Val Trp
                425                 430                 435

Asn His Leu Gly Thr Phe Asn Phe Ala Ala Gly Asp Ala Asn Arg Ile
            440                 445                 450

```
Ala Val Ser Arg Trp Thr Thr Gly Thr Gly Tyr Val Ile Asp Ala
            455                 460                 465
Val Lys Phe Val Lys Arg
        470
```

<210> SEQ ID NO 48
<211> LENGTH: 474
<212> TYPE: PRT
<213> ORGANISM: Laceyella sacchari

<400> SEQUENCE: 48

```
Glu Glu Gln Pro Ser Leu Ser His Val Phe Glu Met Ala Ala Glu
1               5                   10                  15

Phe Glu Val Pro Val Glu Val Leu Leu Ala Ile Gly Tyr Ala Glu Thr
                20                  25                  30

Arg Trp Met Asp His Gln Gly Gln Pro Ser Gln Leu Asn Gly Tyr Gly
            35                  40                  45

Ile Met His Leu Ala Glu Asn Pro Thr Asn Asp Ser Leu Val Gln Ala
    50                  55                  60

Ser Arg Leu Leu Gly Ile Asp Lys Gln Val Leu Thr Arg Asp Ile Gln
65                  70                  75                  80

Ala Asn Ile Arg Gly Ala Ala Val Leu Gln Gln Ile Ser Lys Glu
                85                  90                  95

Gln Asn Gln Gly Gln Val Pro Lys Lys Leu Ala Asp Trp Tyr Thr Val
            100                 105                 110

Val Ala Glu Tyr Ser Gly Leu Ser Ser Gln Gln Thr Lys Ala Trp Tyr
            115                 120                 125

Ala Asp Asp Val Tyr Ala Leu Ile Asn Arg Gly Val Ser Arg Val Ile
130                 135                 140

Asn Gly Gln Glu Val Arg Leu Glu Pro Thr Pro Val Thr Pro Asn Arg
145                 150                 155                 160

Gly Glu Tyr Gly Glu Pro Arg Asp Pro Ser Gly Gln Ala Thr Pro Asp
                165                 170                 175

Tyr Pro Glu Ala Arg Trp Val Ala Ala Ser Ala Asn Tyr Thr Ala
            180                 185                 190

Ala Asn Arg Glu Ser Asp Gly Asn Ala Ile Asn Tyr Val Ile Ile His
            195                 200                 205

Thr Thr Gln Gly Ser Tyr Asn Gly Thr Ile Ser Trp Phe Gln Asn Pro
210                 215                 220

Ser Ala Gln Val Ser Ala His Tyr Val Ile Arg Ser Ser Asp Gly Gln
225                 230                 235                 240

Val Thr Gln Met Val Gln Asn Lys Asp Ile Ala Trp His Ala Gly Asn
                245                 250                 255

Trp Asp Tyr Asn Val His Ser Val Gly Ile Glu His Glu Gly Tyr Val
            260                 265                 270

Asn Asp Pro Ala Trp Tyr Thr Asp Ala Met Tyr Arg Ala Ser Ala Lys
            275                 280                 285

Leu Thr Arg Trp Leu Cys Asn Arg Tyr Gly Ile Pro Lys Asp Arg Ser
    290                 295                 300

His Ile Ile Gly His Asn Gln Val Pro Gly Ala Thr His Thr Asp Pro
305                 310                 315                 320

Gly Pro Asn Trp Asp Trp Asn Tyr Tyr Met Ser Leu Val Asn Gln Ser
                325                 330                 335

Gly Gly Gly Ala Asp Leu Val Thr Asp Asn Ala Thr Ser Asn Arg Phe
            340                 345                 350
```

-continued

```
    Thr Ala Ser Ala Asn Trp Ala Ile Gly Thr Thr Asn Ala Gln Lys Tyr
            355                 360                 365

Gly Ala Asp Tyr Arg Tyr Ala Lys Pro Glu Thr Ile Ser Asp Ala Ala
        370                 375                 380

Trp Tyr Lys Val Asn Leu Pro Thr Ser Gly Ser Tyr Asp Val Tyr Ala
    385                 390                 395                 400

Trp Trp Pro Ser Gly Ser Ile Tyr Asn Asp Arg Thr Pro Tyr Val Ile
                    405                 410                 415

Asn Thr Thr Ser Gly Ser Gln Thr Val His Val Ser Gln Gln Ser Ser
                420                 425                 430

Gly Gly Val Trp Asn His Leu Gly Thr Phe Asn Phe Ala Ala Gly Asp
            435                 440                 445

Ala Asn Arg Ile Ala Val Ser Arg Trp Thr Thr Gly Thr Gly Tyr Val
        450                 455                 460

Ile Ala Asp Ala Val Lys Phe Val Lys Arg
    465                 470

<210> SEQ ID NO 49
<211> LENGTH: 1506
<212> TYPE: DNA
<213> ORGANISM: Thermostaphylospora chromogena
<220> FEATURE:
<221> NAME/KEY: CDS
<222> LOCATION: (1)..(1506)
<220> FEATURE:
<221> NAME/KEY: sig_peptide
<222> LOCATION: (1)..(87)
<220> FEATURE:
<221> NAME/KEY: mat_peptide
<222> LOCATION: (88)..(1506)

<400> SEQUENCE: 49 atg cgc tct cgc tta atg gcg gta ttg gcg tgc gct ttc aca gtt ttg        48
Met Arg Ser Arg Leu Met Ala Val Leu Ala Cys Ala Phe Thr Val Leu
                -25                 -20                 -15 ttt ctt act gct gcg cca caa gca ggc cac gca cgt gct aat cct ctt        96
Phe Leu Thr Ala Ala Pro Gln Ala Gly His Ala Arg Ala Asn Pro Leu
            -10                 -5                  -1  1 gct gac gca ttt gca gaa gcg gct gca gcg cat gac gtt cca cgc gac       144
Ala Asp Ala Phe Ala Glu Ala Ala Ala Ala His Asp Val Pro Arg Asp
    5                   10                  15 ctt tta gta gcg ctt gct tac gct gaa act cgt tta gat gat cac gat       192
Leu Leu Val Ala Leu Ala Tyr Ala Glu Thr Arg Leu Asp Asp His Asp
20                  25                  30                  35 ggt gaa cct agc gct agc gga gga tat ggt gtt atg cat tta gtt tct       240
Gly Glu Pro Ser Ala Ser Gly Gly Tyr Gly Val Met His Leu Val Ser
                40                  45                  50 aac cct aca aat cac tct tta gaa cgt gca gca gag ctt act ggc ttg       288
Asn Pro Thr Asn His Ser Leu Glu Arg Ala Ala Glu Leu Thr Gly Leu
            55                  60                  65 cct gtt gaa aaa ctt cgt ggc gat aca gca gct aac atc atg ggt ggt       336
Pro Val Glu Lys Leu Arg Gly Asp Thr Ala Ala Asn Ile Met Gly Gly
        70                  75                  80 gct gct gtt tta cgt gcg cat gct gat gaa tta ggt ctt gat gag gct       384
Ala Ala Val Leu Arg Ala His Ala Asp Glu Leu Gly Leu Asp Glu Ala
    85                  90                  95 gca cgt aaa gac cca ggt cgt tgg tac act gct gtt gcg cgt tat ggt       432
Ala Arg Lys Asp Pro Gly Arg Trp Tyr Thr Ala Val Ala Arg Tyr Gly
100                 105                 110                 115
```

| | | | | | | | | | | | | | | | | |
|---|---|---|---|---|---|---|---|---|---|---|---|---|---|---|---|---|
| ggc | gct | tca | gat | cct | cgt | gta | gct | cgc | ctt | tac | gcg | gat | gcc | gta | ttc | 480 |
| Gly | Ala | Ser | Asp | Pro | Arg | Val | Ala | Arg | Leu | Tyr | Ala | Asp | Ala | Val | Phe | |
| | | | 120 | | | | 125 | | | | | 130 | | | | |
| gaa | ttg | ctt | gga | ttg | ggc | att | gac | gca | gca | ggc | gta | act | gta | gca | cca | 528 |
| Glu | Leu | Leu | Gly | Leu | Gly | Ile | Asp | Ala | Ala | Gly | Val | Thr | Val | Ala | Pro | |
| | | | | 135 | | | | | 140 | | | | | 145 | | |
| caa | gaa | gta | acg | gtt | gac | cgt | ggt | gaa | tac | gct | gat | gtt | gaa | gac | tta | 576 |
| Gln | Glu | Val | Thr | Val | Asp | Arg | Gly | Glu | Tyr | Ala | Asp | Val | Glu | Asp | Leu | |
| | | 150 | | | | | 155 | | | | | 160 | | | | |
| aac | gct | cca | aaa | gct | cgc | gtt | ttg | tct | gca | gat | tat | ccg | cct | gct | gca | 624 |
| Asn | Ala | Pro | Lys | Ala | Arg | Val | Leu | Ser | Ala | Asp | Tyr | Pro | Pro | Ala | Ala | |
| | 165 | | | | | 170 | | | | | 175 | | | | | |
| tgg | gta | gct | gca | cac | agc | agc | aat | tac | acg | gct | agc | tct | cgt | cct | tct | 672 |
| Trp | Val | Ala | Ala | His | Ser | Ser | Asn | Tyr | Thr | Ala | Ser | Ser | Arg | Pro | Ser | |
| 180 | | | | | 185 | | | | | 190 | | | | | 195 | |
| tct | tat | gct | atc | gac | cgt | gtt | atc | att | cac | gtt | act | caa | ggt | tct | tac | 720 |
| Ser | Tyr | Ala | Ile | Asp | Arg | Val | Ile | Ile | His | Val | Thr | Gln | Gly | Ser | Tyr | |
| | | | | 200 | | | | | 205 | | | | | 210 | | |
| gct | ggt | act | atc | tct | tgg | ttc | caa | aac | cct | tca | gcg | aac | gta | tct | gct | 768 |
| Ala | Gly | Thr | Ile | Ser | Trp | Phe | Gln | Asn | Pro | Ser | Ala | Asn | Val | Ser | Ala | |
| | | | 215 | | | | | 220 | | | | | 225 | | | |
| cac | tat | gtt | att | cgt | tct | tct | gac | gga | gca | gta | act | caa | atg | gta | cgt | 816 |
| His | Tyr | Val | Ile | Arg | Ser | Ser | Asp | Gly | Ala | Val | Thr | Gln | Met | Val | Arg | |
| | | 230 | | | | | 235 | | | | | 240 | | | | |
| gaa | aaa | gat | gtt | gct | tgg | cat | gct | gga | aat | tgg | aat | tac | aac | aca | cgc | 864 |
| Glu | Lys | Asp | Val | Ala | Trp | His | Ala | Gly | Asn | Trp | Asn | Tyr | Asn | Thr | Arg | |
| | 245 | | | | | 250 | | | | | 255 | | | | | |
| tct | atc | ggt | att | gag | cat | gaa | ggt | tgg | gtt | gat | aac | cca | tct | tgg | ttc | 912 |
| Ser | Ile | Gly | Ile | Glu | His | Glu | Gly | Trp | Val | Asp | Asn | Pro | Ser | Trp | Phe | |
| 260 | | | | | 265 | | | | | 270 | | | | | 275 | |
| act | gac | gct | atg | tac | cgt | gcg | tct | gca | gcg | ctt | aca | cgt | cac | att | tgc | 960 |
| Thr | Asp | Ala | Met | Tyr | Arg | Ala | Ser | Ala | Ala | Leu | Thr | Arg | His | Ile | Cys | |
| | | | | 280 | | | | | 285 | | | | | 290 | | |
| gac | aag | tac | ggt | atc | cca | aaa | gac | cgt | act | cat | atc | att | ggt | cat | aac | 1008 |
| Asp | Lys | Tyr | Gly | Ile | Pro | Lys | Asp | Arg | Thr | His | Ile | Ile | Gly | His | Asn | |
| | | | 295 | | | | | 300 | | | | | 305 | | | |
| caa | gtt | cca | ggt | gcg | act | cac | act | gat | ccg | gga | cct | aat | tgg | gat | tgg | 1056 |
| Gln | Val | Pro | Gly | Ala | Thr | His | Thr | Asp | Pro | Gly | Pro | Asn | Trp | Asp | Trp | |
| | | 310 | | | | | 315 | | | | | 320 | | | | |
| aac | cgc | ttc | atg | gaa | tac | gta | act | ggt | aat | ggc | gga | act | ccg | act | tgg | 1104 |
| Asn | Arg | Phe | Met | Glu | Tyr | Val | Thr | Gly | Asn | Gly | Gly | Thr | Pro | Thr | Trp | |
| | 325 | | | | | 330 | | | | | 335 | | | | | |
| cag | gtt | act | gta | gat | aac | gct | aca | gct | ggc | aag | ttt | aca | gct | tct | gaa | 1152 |
| Gln | Val | Thr | Val | Asp | Asn | Ala | Thr | Ala | Gly | Lys | Phe | Thr | Ala | Ser | Glu | |
| 340 | | | | | 345 | | | | | 350 | | | | | 355 | |
| aac | tgg | ggc | act | tct | aca | tgg | tct | tct | caa | cgt | tac | gga | gct | gat | tac | 1200 |
| Asn | Trp | Gly | Thr | Ser | Thr | Trp | Ser | Ser | Gln | Arg | Tyr | Gly | Ala | Asp | Tyr | |
| | | | 360 | | | | | 365 | | | | | 370 | | | |
| cgt | ttt | gcg | acg | cca | gta | ctt | gca | tca | gat | cct | gca | tgg | ttc | cgt | gca | 1248 |
| Arg | Phe | Ala | Thr | Pro | Val | Leu | Ala | Ser | Asp | Pro | Ala | Trp | Phe | Arg | Ala | |
| | | | | 375 | | | | | 380 | | | | | 385 | | |
| aca | atc | cct | tct | gcg | ggt | gaa | tac | cgt | atc | gaa | gtt | tac | tac | cct | tca | 1296 |
| Thr | Ile | Pro | Ser | Ala | Gly | Glu | Tyr | Arg | Ile | Glu | Val | Tyr | Tyr | Pro | Ser | |
| | | | 390 | | | | | 395 | | | | | 400 | | | |
| gat | cct | ggc | tac | aat | tca | tct | act | ccg | tat | atc | atc | gcg | acg | tct | tca | 1344 |
| Asp | Pro | Gly | Tyr | Asn | Ser | Ser | Thr | Pro | Tyr | Ile | Ile | Ala | Thr | Ser | Ser | |
| | | 405 | | | | | 410 | | | | | 415 | | | | |

-continued

```
ggt aac cgc act gta tat gtt gac cag cgt tct ggt ggt ggc acg tgg      1392
Gly Asn Arg Thr Val Tyr Val Asp Gln Arg Ser Gly Gly Gly Thr Trp
420             425                 430                 435 cgc agc ctt ggt act ttt agc ctt aat gca ggc gat cag aat gtt gtt      1440
Arg Ser Leu Gly Thr Phe Ser Leu Asn Ala Gly Asp Gln Asn Val Val
            440                 445                 450 gct gta tca cgt tgg aca tct gga aca ggc tac gtt atc gcg gac gct      1488
Ala Val Ser Arg Trp Thr Ser Gly Thr Gly Tyr Val Ile Ala Asp Ala
        455                 460                 465 gtt cgc atc aca cgt tac                                              1506
Val Arg Ile Thr Arg Tyr
        470

<210> SEQ ID NO 50
<211> LENGTH: 502
<212> TYPE: PRT
<213> ORGANISM: Thermostaphylospora chromogena

<400> SEQUENCE: 50

Met Arg Ser Arg Leu Met Ala Val Leu Ala Cys Ala Phe Thr Val Leu
                -25                 -20                 -15

Phe Leu Thr Ala Ala Pro Gln Ala Gly His Ala Arg Ala Asn Pro Leu
            -10                  -5                 -1   1

Ala Asp Ala Phe Ala Glu Ala Ala Ala His Asp Val Pro Arg Asp
  5                  10                  15

Leu Leu Val Ala Leu Ala Tyr Ala Glu Thr Arg Leu Asp Asp His Asp
 20                  25                  30                  35

Gly Glu Pro Ser Ala Ser Gly Tyr Gly Val Met His Leu Val Ser
                 40                  45                  50

Asn Pro Thr Asn His Ser Leu Glu Arg Ala Ala Glu Leu Thr Gly Leu
             55                  60                  65

Pro Val Glu Lys Leu Arg Gly Asp Thr Ala Ala Asn Ile Met Gly Gly
         70                  75                  80

Ala Ala Val Leu Arg Ala His Ala Asp Glu Leu Gly Leu Asp Glu Ala
 85                  90                  95

Ala Arg Lys Asp Pro Gly Arg Trp Tyr Thr Ala Val Ala Arg Tyr Gly
100                 105                 110                 115

Gly Ala Ser Asp Pro Arg Val Ala Arg Leu Tyr Ala Asp Ala Val Phe
                120                 125                 130

Glu Leu Leu Gly Leu Gly Ile Asp Ala Ala Gly Val Thr Val Ala Pro
            135                 140                 145

Gln Glu Val Thr Val Asp Arg Gly Glu Tyr Ala Asp Val Glu Asp Leu
        150                 155                 160

Asn Ala Pro Lys Ala Arg Val Leu Ser Ala Asp Tyr Pro Pro Ala Ala
165                 170                 175

Trp Val Ala Ala His Ser Ser Asn Tyr Thr Ala Ser Ser Arg Pro Ser
180                 185                 190                 195

Ser Tyr Ala Ile Asp Arg Val Ile His Val Thr Gln Gly Ser Tyr
                200                 205                 210

Ala Gly Thr Ile Ser Trp Phe Gln Asn Pro Ser Ala Asn Val Ser Ala
            215                 220                 225

His Tyr Val Ile Arg Ser Ser Asp Gly Ala Val Thr Gln Met Val Arg
        230                 235                 240

Glu Lys Asp Val Ala Trp His Ala Gly Asn Trp Asn Tyr Asn Thr Arg
245                 250                 255
```

```
Ser Ile Gly Ile Glu His Glu Gly Trp Val Asp Asn Pro Ser Trp Phe
260                 265                 270                 275

Thr Asp Ala Met Tyr Arg Ala Ser Ala Ala Leu Thr Arg His Ile Cys
            280                 285                 290

Asp Lys Tyr Gly Ile Pro Lys Asp Arg Thr His Ile Ile Gly His Asn
                295                 300                 305

Gln Val Pro Gly Ala Thr His Thr Asp Pro Gly Pro Asn Trp Asp Trp
            310                 315                 320

Asn Arg Phe Met Glu Tyr Val Thr Gly Asn Gly Thr Pro Thr Trp
    325                 330                 335

Gln Val Thr Val Asp Asn Ala Thr Ala Gly Lys Phe Thr Ala Ser Glu
340                 345                 350                 355

Asn Trp Gly Thr Ser Thr Trp Ser Ser Gln Arg Tyr Gly Ala Asp Tyr
                360                 365                 370

Arg Phe Ala Thr Pro Val Leu Ala Ser Asp Pro Ala Trp Phe Arg Ala
            375                 380                 385

Thr Ile Pro Ser Ala Gly Glu Tyr Arg Ile Glu Val Tyr Tyr Pro Ser
            390                 395                 400

Asp Pro Gly Tyr Asn Ser Ser Thr Pro Tyr Ile Ile Ala Thr Ser Ser
            405                 410                 415

Gly Asn Arg Thr Val Tyr Val Asp Gln Arg Ser Gly Gly Thr Trp
420                 425                 430                 435

Arg Ser Leu Gly Thr Phe Ser Leu Asn Ala Gly Asp Gln Asn Val Val
                440                 445                 450

Ala Val Ser Arg Trp Thr Ser Gly Thr Gly Tyr Val Ile Ala Asp Ala
            455                 460                 465

Val Arg Ile Thr Arg Tyr
            470

<210> SEQ ID NO 51
<211> LENGTH: 473
<212> TYPE: PRT
<213> ORGANISM: Thermostaphylospora chromogena

<400> SEQUENCE: 51

Asn Pro Leu Ala Asp Ala Phe Ala Glu Ala Ala Ala His Asp Val
1               5                   10                  15

Pro Arg Asp Leu Leu Val Ala Leu Ala Tyr Ala Glu Thr Arg Leu Asp
            20                  25                  30

Asp His Asp Gly Glu Pro Ser Ala Ser Gly Gly Tyr Gly Val Met His
        35                  40                  45

Leu Val Ser Asn Pro Thr Asn His Ser Leu Glu Arg Ala Ala Glu Leu
50                  55                  60

Thr Gly Leu Pro Val Glu Lys Leu Arg Gly Asp Thr Ala Ala Asn Ile
65                  70                  75                  80

Met Gly Gly Ala Ala Val Leu Arg Ala His Ala Asp Glu Leu Gly Leu
                85                  90                  95

Asp Glu Ala Ala Arg Lys Asp Pro Gly Arg Trp Tyr Thr Ala Val Ala
            100                 105                 110

Arg Tyr Gly Gly Ala Ser Asp Pro Arg Val Ala Arg Leu Tyr Ala Asp
        115                 120                 125

Ala Val Phe Glu Leu Leu Gly Leu Gly Ile Asp Ala Ala Gly Val Thr
    130                 135                 140

Val Ala Pro Gln Glu Val Thr Val Asp Arg Gly Glu Tyr Ala Asp Val
145                 150                 155                 160
```

```
Glu Asp Leu Asn Ala Pro Lys Ala Arg Val Leu Ser Ala Asp Tyr Pro
                165                 170                 175

Pro Ala Ala Trp Val Ala Ala His Ser Ser Asn Tyr Thr Ala Ser Ser
            180                 185                 190

Arg Pro Ser Ser Tyr Ala Ile Asp Arg Val Ile Ile His Val Thr Gln
        195                 200                 205

Gly Ser Tyr Ala Gly Thr Ile Ser Trp Phe Gln Asn Pro Ser Ala Asn
    210                 215                 220

Val Ser Ala His Tyr Val Ile Arg Ser Asp Gly Ala Val Thr Gln
225                 230                 235                 240

Met Val Arg Glu Lys Asp Val Ala Trp His Ala Gly Asn Trp Asn Tyr
                245                 250                 255

Asn Thr Arg Ser Ile Gly Ile Glu His Glu Gly Trp Val Asp Asn Pro
            260                 265                 270

Ser Trp Phe Thr Asp Ala Met Tyr Arg Ala Ser Ala Ala Leu Thr Arg
        275                 280                 285

His Ile Cys Asp Lys Tyr Gly Ile Pro Lys Asp Arg Thr His Ile Ile
    290                 295                 300

Gly His Asn Gln Val Pro Gly Ala Thr His Thr Asp Pro Gly Pro Asn
305                 310                 315                 320

Trp Asp Trp Asn Arg Phe Met Glu Tyr Val Thr Gly Asn Gly Gly Thr
                325                 330                 335

Pro Thr Trp Gln Val Thr Val Asp Asn Ala Thr Ala Gly Lys Phe Thr
            340                 345                 350

Ala Ser Glu Asn Trp Gly Thr Ser Thr Trp Ser Ser Gln Arg Tyr Gly
        355                 360                 365

Ala Asp Tyr Arg Phe Ala Thr Pro Val Leu Ala Ser Asp Pro Ala Trp
    370                 375                 380

Phe Arg Ala Thr Ile Pro Ser Ala Gly Glu Tyr Arg Ile Glu Val Tyr
385                 390                 395                 400

Tyr Pro Ser Asp Pro Gly Tyr Asn Ser Ser Thr Pro Tyr Ile Ile Ala
                405                 410                 415

Thr Ser Ser Gly Asn Arg Thr Val Tyr Val Asp Gln Arg Ser Gly Gly
            420                 425                 430

Gly Thr Trp Arg Ser Leu Gly Thr Phe Ser Leu Asn Ala Gly Asp Gln
        435                 440                 445

Asn Val Val Ala Val Ser Arg Trp Thr Ser Gly Thr Gly Tyr Val Ile
450                 455                 460

Ala Asp Ala Val Arg Ile Thr Arg Tyr
465                 470

<210> SEQ ID NO 52
<211> LENGTH: 1320
<212> TYPE: DNA
<213> ORGANISM: Kribbella aluminosa
<220> FEATURE:
<221> NAME/KEY: CDS
<222> LOCATION: (1)..(1317)
<220> FEATURE:
<221> NAME/KEY: sig_peptide
<222> LOCATION: (1)..(75)
<220> FEATURE:
<221> NAME/KEY: mat_peptide
<222> LOCATION: (76)..(1317)
```

<400> SEQUENCE: 52

```
atg tcc cga tta gca aag ctg tgc gca gcc ctg gcc gtc ggc gcg ctc        48
Met Ser Arg Leu Ala Lys Leu Cys Ala Ala Leu Ala Val Gly Ala Leu
-25                 -20                 -15                 -10 gcg ctg acc gcc ctc ccg agc aac gcg gca tcg cca ccc gcc ggc tct        96
Ala Leu Thr Ala Leu Pro Ser Asn Ala Ala Ser Pro Pro Ala Gly Ser
            -5                  -1  1                   5 cac ctc gcc gag gcc ttc acg acc gcc gcg aag tac gac gta ccg           144
His Leu Ala Glu Ala Phe Thr Thr Ala Ala Ala Lys Tyr Asp Val Pro
        10                  15                  20 cgg gaa gtg ctg gtc ggt gtc ggc ttc gcc gaa acc cat ctc gac ggt       192
Arg Glu Val Leu Val Gly Val Gly Phe Ala Glu Thr His Leu Asp Gly
    25                  30                  35 cac gac ggc acg ccg agc cag gcc aac ggg tac ggc gtg atg cac ctg       240
His Asp Gly Thr Pro Ser Gln Ala Asn Gly Tyr Gly Val Met His Leu
40                  45                  50                  55 gcg agc aac aac gtg aac aag acg atg tcc gag gca agc aaa ctg acc       288
Ala Ser Asn Asn Val Asn Lys Thr Met Ser Glu Ala Ser Lys Leu Thr
                60                  65                  70 ggc gtg ccg gtc gcg aag ctg tcc aag gac gac gcg tcg aac gtc ctc       336
Gly Val Pro Val Ala Lys Leu Ser Lys Asp Asp Ala Ser Asn Val Leu
            75                  80                  85 ggc gcc gcc gcg gtc ctc gac tcc tac gcg gag cag gcc aag ctc aaa       384
Gly Ala Ala Ala Val Leu Asp Ser Tyr Ala Glu Gln Ala Lys Leu Lys
        90                  95                  100 gac cgg gca gac ctc ggc aag tgg tac ggc gtg atc gcg aag tac tcg       432
Asp Arg Ala Asp Leu Gly Lys Trp Tyr Gly Val Ile Ala Lys Tyr Ser
    105                 110                 115 cac tcc gcc gac gcg tcg acc gca cgg ctc tac acc gac gag gtc tac       480
His Ser Ala Asp Ala Ser Thr Ala Arg Leu Tyr Thr Asp Glu Val Tyr
120                 125                 130                 135 cga atc att gcc cgg ggt gtc cgc gcc gcc ggc gtc tcg acc gac ccg       528
Arg Ile Ile Ala Arg Gly Val Arg Ala Ala Gly Val Ser Thr Asp Pro
                140                 145                 150 aag ccg gtc agc ccg gac cgc ggc gcg tac gcg aag gcc gct ccg ctc       576
Lys Pro Val Ser Pro Asp Arg Gly Ala Tyr Ala Lys Ala Ala Pro Leu
            155                 160                 165 ggg acc gcc gcc gtc gac tac ccg agc gcg atc tgg aac ccg gcg agc       624
Gly Thr Ala Ala Val Asp Tyr Pro Ser Ala Ile Trp Asn Pro Ala Ser
        170                 175                 180 acc agc aac tac cgc gtc ggc cgg acc gcg gcg atc acc acg atc gtc       672
Thr Ser Asn Tyr Arg Val Gly Arg Thr Ala Ala Ile Thr Thr Ile Val
    185                 190                 195 atc cac gtc acc cag ggc tcg tac gcc ggc acc atc agc tgg ttc aag       720
Ile His Val Thr Gln Gly Ser Tyr Ala Gly Thr Ile Ser Trp Phe Lys
200                 205                 210                 215 aac ccg tcc gcg cag gtc agc gcg cac tac gtg gtc cgc tcg agc gac       768
Asn Pro Ser Ala Gln Val Ser Ala His Tyr Val Val Arg Ser Ser Asp
                220                 225                 230 ggc gag gtc acc cag atg gtg gcc gag aag gac acc gcg tgg cac gtc       816
Gly Glu Val Thr Gln Met Val Ala Glu Lys Asp Thr Ala Trp His Val
            235                 240                 245 cgg acc gag aac ccg tac acg atc ggc atc gag cac gaa ggg tac gtc       864
Arg Thr Glu Asn Pro Tyr Thr Ile Gly Ile Glu His Glu Gly Tyr Val
        250                 255                 260 gac cag ccg tcg tgg ttc acc gat gcg atg tac cgg tcg tcg gcc gcg       912
Asp Gln Pro Ser Trp Phe Thr Asp Ala Met Tyr Arg Ser Ser Ala Ala
    265                 270                 275
```

```
ctg acc cgc aac atc gcc gac cgg cgg ggc atc ccg aag gac cgg gcc    960
Leu Thr Arg Asn Ile Ala Asp Arg Arg Gly Ile Pro Lys Asp Arg Ala
280             285                 290                 295 cac atc aag ggc cac aac gag atg ccg aac aac gac cac acc gac ccg    1008
His Ile Lys Gly His Asn Glu Met Pro Asn Asn Asp His Thr Asp Pro
                300                 305                 310 gga ccg aac tgg aac tgg gac tac tac acg cag ctg gtg aac ggc ggc    1056
Gly Pro Asn Trp Asn Trp Asp Tyr Tyr Thr Gln Leu Val Asn Gly Gly
            315                 320                 325 gac ccg aac ccg ccg gag tac aac ttc acc acc tgg ggt gag ggc gtg    1104
Asp Pro Asn Pro Pro Glu Tyr Asn Phe Thr Thr Trp Gly Glu Gly Val
        330                 335                 340 aac gtc cgc tcg gcg ccg aag ctg tcc gcg tcg gtc gtc acc acg ctt    1152
Asn Val Arg Ser Ala Pro Lys Leu Ser Ala Ser Val Val Thr Thr Leu
    345                 350                 355 ccc ggc ccg acc cgc gta ttc gtc gag tgc cag gtg cag ggc gac acc    1200
Pro Gly Pro Thr Arg Val Phe Val Glu Cys Gln Val Gln Gly Asp Thr
360                 365                 370                 375 gtg acg gcg ggc ggc tac acc aac aac tgg tgg gcc aag ctg cgc gac    1248
Val Thr Ala Gly Gly Tyr Thr Asn Asn Trp Trp Ala Lys Leu Arg Asp
                380                 385                 390 cag cac ggg tac atg acc aac atc tac atc gac gac ccg aac cag aag    1296
Gln His Gly Tyr Met Thr Asn Ile Tyr Ile Asp Asp Pro Asn Gln Lys
            395                 400                 405 ctg cca ggc gta ccg gac tgc tag                                    1320
Leu Pro Gly Val Pro Asp Cys
        410

<210> SEQ ID NO 53
<211> LENGTH: 439
<212> TYPE: PRT
<213> ORGANISM: Kribbella aluminosa

<400> SEQUENCE: 53

Met Ser Arg Leu Ala Lys Leu Cys Ala Ala Leu Ala Val Gly Ala Leu
-25                 -20                 -15                 -10

Ala Leu Thr Ala Leu Pro Ser Asn Ala Ala Ser Pro Pro Ala Gly Ser
                -5                  -1  1               5

His Leu Ala Glu Ala Phe Thr Thr Ala Ala Lys Tyr Asp Val Pro
        10                  15                  20

Arg Glu Val Leu Val Gly Val Gly Phe Ala Glu Thr His Leu Asp Gly
    25                  30                  35

His Asp Gly Thr Pro Ser Gln Ala Asn Gly Tyr Gly Val Met His Leu
40                  45                  50                  55

Ala Ser Asn Asn Val Asn Lys Thr Met Ser Glu Ala Ser Lys Leu Thr
                60                  65                  70

Gly Val Pro Val Ala Lys Leu Ser Lys Asp Asp Ala Ser Asn Val Leu
            75                  80                  85

Gly Ala Ala Ala Val Leu Asp Ser Tyr Ala Glu Gln Ala Lys Leu Lys
        90                  95                  100

Asp Arg Ala Asp Leu Gly Lys Trp Tyr Gly Val Ile Ala Lys Tyr Ser
    105                 110                 115

His Ser Ala Asp Ala Ser Thr Ala Arg Leu Tyr Thr Asp Glu Val Tyr
120                 125                 130                 135

Arg Ile Ile Ala Arg Gly Val Arg Ala Ala Gly Val Ser Thr Asp Pro
                140                 145                 150

Lys Pro Val Ser Pro Asp Arg Gly Ala Tyr Ala Lys Ala Pro Leu
            155                 160                 165
```

Gly Thr Ala Ala Val Asp Tyr Pro Ser Ala Ile Trp Asn Pro Ala Ser
        170                 175                 180

Thr Ser Asn Tyr Arg Val Gly Arg Thr Ala Ala Ile Thr Thr Ile Val
    185                 190                 195

Ile His Val Thr Gln Gly Ser Tyr Ala Gly Thr Ile Ser Trp Phe Lys
200                 205                 210                 215

Asn Pro Ser Ala Gln Val Ser Ala His Tyr Val Val Arg Ser Ser Asp
                220                 225                 230

Gly Glu Val Thr Gln Met Val Ala Glu Lys Asp Thr Ala Trp His Val
                235                 240                 245

Arg Thr Glu Asn Pro Tyr Thr Ile Gly Ile Glu His Glu Gly Tyr Val
                250                 255                 260

Asp Gln Pro Ser Trp Phe Thr Asp Ala Met Tyr Arg Ser Ser Ala Ala
            265                 270                 275

Leu Thr Arg Asn Ile Ala Asp Arg Arg Gly Ile Pro Lys Asp Arg Ala
280                 285                 290                 295

His Ile Lys Gly His Asn Glu Met Pro Asn Asn Asp His Thr Asp Pro
                300                 305                 310

Gly Pro Asn Trp Asn Trp Asp Tyr Tyr Thr Gln Leu Val Asn Gly Gly
            315                 320                 325

Asp Pro Asn Pro Pro Glu Tyr Asn Phe Thr Thr Trp Gly Glu Gly Val
            330                 335                 340

Asn Val Arg Ser Ala Pro Lys Leu Ser Ala Ser Val Val Thr Thr Leu
        345                 350                 355

Pro Gly Pro Thr Arg Val Phe Val Glu Cys Gln Val Gln Gly Asp Thr
360                 365                 370                 375

Val Thr Ala Gly Gly Tyr Thr Asn Asn Trp Trp Ala Lys Leu Arg Asp
                380                 385                 390

Gln His Gly Tyr Met Thr Asn Ile Tyr Ile Asp Asp Pro Asn Gln Lys
            395                 400                 405

Leu Pro Gly Val Pro Asp Cys
        410

<210> SEQ ID NO 54
<211> LENGTH: 414
<212> TYPE: PRT
<213> ORGANISM: Kribbella aluminosa

<400> SEQUENCE: 54

Ala Ser Pro Pro Ala Gly Ser His Leu Ala Glu Ala Phe Thr Thr Ala
1               5                   10                  15

Ala Ala Lys Tyr Asp Val Pro Arg Glu Val Leu Val Gly Val Gly Phe
                20                  25                  30

Ala Glu Thr His Leu Asp Gly His Asp Gly Thr Pro Ser Gln Ala Asn
            35                  40                  45

Gly Tyr Gly Val Met His Leu Ala Ser Asn Asn Val Asn Lys Thr Met
        50                  55                  60

Ser Glu Ala Ser Lys Leu Thr Gly Val Pro Val Ala Lys Leu Ser Lys
65                  70                  75                  80

Asp Asp Ala Ser Asn Val Leu Gly Ala Ala Val Leu Asp Ser Tyr
                85                  90                  95

Ala Glu Gln Ala Lys Leu Lys Asp Arg Ala Asp Leu Gly Lys Trp Tyr
                100                 105                 110

-continued

```
Gly Val Ile Ala Lys Tyr Ser His Ser Ala Asp Ala Ser Thr Ala Arg
            115                 120                 125

Leu Tyr Thr Asp Glu Val Tyr Arg Ile Ile Ala Arg Gly Val Arg Ala
        130                 135                 140

Ala Gly Val Ser Thr Asp Pro Lys Pro Val Ser Pro Asp Arg Gly Ala
145                 150                 155                 160

Tyr Ala Lys Ala Ala Pro Leu Gly Thr Ala Val Asp Tyr Pro Ser
                165                 170                 175

Ala Ile Trp Asn Pro Ala Ser Thr Ser Asn Tyr Arg Val Gly Arg Thr
            180                 185                 190

Ala Ala Ile Thr Thr Ile Val Ile His Val Thr Gln Gly Ser Tyr Ala
            195                 200                 205

Gly Thr Ile Ser Trp Phe Lys Asn Pro Ser Ala Gln Val Ser Ala His
        210                 215                 220

Tyr Val Val Arg Ser Ser Asp Gly Glu Val Thr Gln Met Val Ala Glu
225                 230                 235                 240

Lys Asp Thr Ala Trp His Val Arg Thr Glu Asn Pro Tyr Thr Ile Gly
                245                 250                 255

Ile Glu His Glu Gly Tyr Val Asp Gln Pro Ser Trp Phe Thr Asp Ala
            260                 265                 270

Met Tyr Arg Ser Ser Ala Ala Leu Thr Arg Asn Ile Ala Asp Arg Arg
        275                 280                 285

Gly Ile Pro Lys Asp Arg Ala His Ile Lys Gly His Asn Glu Met Pro
        290                 295                 300

Asn Asn Asp His Thr Asp Pro Gly Pro Asn Trp Asn Trp Asp Tyr Tyr
305                 310                 315                 320

Thr Gln Leu Val Asn Gly Gly Asp Pro Asn Pro Glu Tyr Asn Phe
                325                 330                 335

Thr Thr Trp Gly Glu Gly Val Asn Val Arg Ser Ala Pro Lys Leu Ser
            340                 345                 350

Ala Ser Val Val Thr Thr Leu Pro Gly Pro Thr Arg Val Phe Val Glu
        355                 360                 365

Cys Gln Val Gln Gly Asp Thr Val Thr Ala Gly Gly Tyr Thr Asn Asn
    370                 375                 380

Trp Trp Ala Lys Leu Arg Asp Gln His Gly Tyr Met Thr Asn Ile Tyr
385                 390                 395                 400

Ile Asp Asp Pro Asn Gln Lys Leu Pro Gly Val Pro Asp Cys
                405                 410
```

<210> SEQ ID NO 55
<211> LENGTH: 1332
<212> TYPE: DNA
<213> ORGANISM: Streptomyces griseus
<220> FEATURE:
<221> NAME/KEY: CDS
<222> LOCATION: (1)..(1329)
<220> FEATURE:
<221> NAME/KEY: sig_peptide
<222> LOCATION: (1)..(93)
<220> FEATURE:
<221> NAME/KEY: mat_peptide
<222> LOCATION: (94)..(1329)

<400> SEQUENCE: 55

```
atg acg tcg aag cag agg atg aga ctc gcg ctc gca ctg acc gcg gcc    48
Met Thr Ser Lys Gln Arg Met Arg Leu Ala Leu Ala Leu Thr Ala Ala
    -30                 -25                 -20
```

-continued

| | | |
|---|---|---|
| ggg gcg ctg agc gtg gcg ctc ctc tcc ccg gcc gca gcc ggc gcg gac<br>Gly Ala Leu Ser Val Ala Leu Leu Ser Pro Ala Ala Ala Gly Ala Asp<br>-15                     -10                   -5                     -1 1 | | 96 |
| acc gta cga ccg gaa tgc ccg cgg tcc ctg gcc tgc gac tgg gtc ccc<br>Thr Val Arg Pro Glu Cys Pro Arg Ser Leu Ala Cys Asp Trp Val Pro<br>             5                     10                    15 | | 144 |
| gcg gcc tac cag cag acc gga gat ccg gag gac aag gac acc tac ggc<br>Ala Ala Tyr Gln Gln Thr Gly Asp Pro Glu Asp Lys Asp Thr Tyr Gly<br>            20                    25                  30 | | 192 |
| aac tac gac acg gcg aac cgc ccc gac agc aac gcc gtc aag ttc atc<br>Asn Tyr Asp Thr Ala Asn Arg Pro Asp Ser Asn Ala Val Lys Phe Ile<br>35                     40                    45 | | 240 |
| gtc ctg cac gac acc gag gtc gac tac gac acc acc ctg aag atc ttc<br>Val Leu His Asp Thr Glu Val Asp Tyr Asp Thr Thr Leu Lys Ile Phe<br>50                     55                    60                  65 | | 288 |
| cag aac ccg gcc aac cag acg tcc gcc cac tac gtg gtg cgc tcg gcg<br>Gln Asn Pro Ala Asn Gln Thr Ser Ala His Tyr Val Val Arg Ser Ala<br>            70                    75                  80 | | 336 |
| gac ggc cac gtc aca cag atg gtg aag aac aag gac gtc gcc tgg cag<br>Asp Gly His Val Thr Gln Met Val Lys Asn Lys Asp Val Ala Trp Gln<br>              85                    90                  95 | | 384 |
| gcg ggc aac tgg tac ctc aac acc cac tcc atc ggc atc gag cag gag<br>Ala Gly Asn Trp Tyr Leu Asn Thr His Ser Ile Gly Ile Glu Gln Glu<br>              100                 105               110 | | 432 |
| ggc gtc gca gcg gag ggt gcc acg tgg tac acc tcc gag atg tac cgg<br>Gly Val Ala Ala Glu Gly Ala Thr Trp Tyr Thr Ser Glu Met Tyr Arg<br>115                     120                 125 | | 480 |
| tcg acc gcg cgc ctg gtg cgg tac ctg gcc gcg aag tac gac atc ccg<br>Ser Thr Ala Arg Leu Val Arg Tyr Leu Ala Ala Lys Tyr Asp Ile Pro<br>130                     135                 140               145 | | 528 |
| ctc gac cgg caa cac atc ctc ggg cac gac ggt gtg ccg ccc acc agc<br>Leu Asp Arg Gln His Ile Leu Gly His Asp Gly Val Pro Pro Thr Ser<br>                 150                 155               160 | | 576 |
| gcc gcc gga acg aag aac atg cac tgg gac ccg gga ccc tac tgg gac<br>Ala Ala Gly Thr Lys Asn Met His Trp Asp Pro Gly Pro Tyr Trp Asp<br>            165                 170               175 | | 624 |
| tgg aac cgc ttc atg gcg cta ctc ggc gcg ccc acc gcg ccc agc gcc<br>Trp Asn Arg Phe Met Ala Leu Leu Gly Ala Pro Thr Ala Pro Ser Ala<br>180                     185                 190 | | 672 |
| ccg aag cgc agc gaa ctg gtc acc gtc agc gcg gac ttc gcg agg aac<br>Pro Lys Arg Ser Glu Leu Val Thr Val Ser Ala Asp Phe Ala Arg Asn<br>            195                 200               205 | | 720 |
| cag cag gag ttc cgc gac tgc gag aag aac gtc gac ctt ccc cgg cag<br>Gln Gln Glu Phe Arg Asp Cys Glu Lys Asn Val Asp Leu Pro Arg Gln<br>210                     215                 220               225 | | 768 |
| ggg agc agc gcg gtc cct ctg cac acg gag ccg tcg gcg gac gcg cct<br>Gly Ser Ser Ala Val Pro Leu His Thr Glu Pro Ser Ala Asp Ala Pro<br>               230                 235               240 | | 816 |
| ctc ttc tcc gac ccg ggg ctg cat ccg gac ggc tcg ccg ggg acg aac<br>Leu Phe Ser Asp Pro Gly Leu His Pro Asp Gly Ser Pro Gly Thr Asn<br>            245                 250               255 | | 864 |
| tgc gcc gct gac tgg ggc agc aag atc agt gcg acc cag cag gcc gtc<br>Cys Ala Ala Asp Trp Gly Ser Lys Ile Ser Ala Thr Gln Gln Ala Val<br>260                     265                 270 | | 912 |
| gtc gcc gac cgg gta ccc ggc tgg acg gcg atc tgg tgg tac ggg gag<br>Val Ala Asp Arg Val Pro Gly Trp Thr Ala Ile Trp Trp Tyr Gly Glu<br>            275                 280               285 | | 960 |
| aag gct tgg ttc agc act ccg ccc ggt acc agg gtc acc acc ccg acc<br>Lys Ala Trp Phe Ser Thr Pro Pro Gly Thr Arg Val Thr Thr Pro Thr<br>290                     295                 300               305 | | 1008 |

```
cgc ggc agt gtg gtg cgg ccg aag ccg ggc acg tcc gaa gtg ctg gtg      1056
Arg Gly Ser Val Val Arg Pro Lys Pro Gly Thr Ser Glu Val Leu Val
            310                 315                 320 tac ggc gtc gcc tac ccc gag aag gcc gag tac ccc acg gac ttc gtc      1104
Tyr Gly Val Ala Tyr Pro Glu Lys Ala Glu Tyr Pro Thr Asp Phe Val
            325                 330                 335 aag ccg acc gtg ggc acg ccg ctc gtc tac acc atc aag gcg ggt cag      1152
Lys Pro Thr Val Gly Thr Pro Leu Val Tyr Thr Ile Lys Ala Gly Gln
            340                 345                 350 gcc ttc ccc ggc ggc ggc gag gcg ccc acc ggc tac tac tac gca ccg      1200
Ala Phe Pro Gly Gly Gly Glu Ala Pro Thr Gly Tyr Tyr Tyr Ala Pro
            355                 360                 365 acg atc gac acc tcg aag ccg tac gac cac acg tac ttc ggt ggt gcg      1248
Thr Ile Asp Thr Ser Lys Pro Tyr Asp His Thr Tyr Phe Gly Gly Ala
370                 375                 380                 385 cag aag tac gtg acg gtc cag atc ggc cac cgc atc ggc ttc gtc aag      1296
Gln Lys Tyr Val Thr Val Gln Ile Gly His Arg Ile Gly Phe Val Lys
            390                 395                 400 gcg tcc gac gtg gac gtg gtc cga gcc ggc tca tga                      1332
Ala Ser Asp Val Asp Val Val Arg Ala Gly Ser
            405                 410

<210> SEQ ID NO 56
<211> LENGTH: 443
<212> TYPE: PRT
<213> ORGANISM: Streptomyces griseus

<400> SEQUENCE: 56

Met Thr Ser Lys Gln Arg Met Arg Leu Ala Leu Ala Leu Thr Ala Ala
-30                 -25                 -20

Gly Ala Leu Ser Val Ala Leu Leu Ser Pro Ala Ala Gly Ala Asp
-15                 -10                 -5                  -1  1

Thr Val Arg Pro Glu Cys Pro Arg Ser Leu Ala Cys Asp Trp Val Pro
                5                   10                  15

Ala Ala Tyr Gln Gln Thr Gly Asp Pro Glu Asp Lys Asp Thr Tyr Gly
            20                  25                  30

Asn Tyr Asp Thr Ala Asn Arg Pro Asp Ser Asn Ala Val Lys Phe Ile
    35                  40                  45

Val Leu His Asp Thr Glu Val Asp Tyr Asp Thr Thr Leu Lys Ile Phe
50                  55                  60                  65

Gln Asn Pro Ala Asn Gln Thr Ser Ala His Tyr Val Arg Ser Ala
                70                  75                  80

Asp Gly His Val Thr Gln Met Val Lys Asn Lys Asp Val Ala Trp Gln
            85                  90                  95

Ala Gly Asn Trp Tyr Leu Asn Thr His Ser Ile Gly Ile Glu Gln Glu
            100                 105                 110

Gly Val Ala Ala Glu Gly Ala Thr Trp Tyr Thr Ser Glu Met Tyr Arg
            115                 120                 125

Ser Thr Ala Arg Leu Val Arg Tyr Leu Ala Ala Lys Tyr Asp Ile Pro
130                 135                 140                 145

Leu Asp Arg Gln His Ile Leu Gly His Asp Gly Val Pro Pro Thr Ser
                150                 155                 160

Ala Ala Gly Thr Lys Asn Met His Trp Asp Pro Gly Pro Tyr Trp Asp
            165                 170                 175

Trp Asn Arg Phe Met Ala Leu Leu Gly Ala Pro Thr Ala Pro Ser Ala
            180                 185                 190
```

```
Pro Lys Arg Ser Glu Leu Val Thr Val Ser Ala Asp Phe Ala Arg Asn
    195                 200                 205

Gln Gln Glu Phe Arg Asp Cys Glu Lys Asn Val Asp Leu Pro Arg Gln
210                 215                 220                 225

Gly Ser Ser Ala Val Pro Leu His Thr Glu Pro Ser Ala Asp Ala Pro
                230                 235                 240

Leu Phe Ser Asp Pro Gly Leu His Pro Asp Gly Ser Pro Gly Thr Asn
                245                 250                 255

Cys Ala Ala Asp Trp Gly Ser Lys Ile Ser Ala Thr Gln Gln Ala Val
                260                 265                 270

Val Ala Asp Arg Val Pro Gly Trp Thr Ala Ile Trp Trp Tyr Gly Glu
275                 280                 285

Lys Ala Trp Phe Ser Thr Pro Pro Gly Thr Arg Val Thr Thr Pro Thr
290                 295                 300                 305

Arg Gly Ser Val Val Arg Pro Lys Pro Gly Thr Ser Glu Val Leu Val
                310                 315                 320

Tyr Gly Val Ala Tyr Pro Glu Lys Ala Glu Tyr Pro Thr Asp Phe Val
                325                 330                 335

Lys Pro Thr Val Gly Thr Pro Leu Val Tyr Thr Ile Lys Ala Gly Gln
                340                 345                 350

Ala Phe Pro Gly Gly Gly Glu Ala Pro Thr Gly Tyr Tyr Tyr Ala Pro
                355                 360                 365

Thr Ile Asp Thr Ser Lys Pro Tyr Asp His Thr Tyr Phe Gly Gly Ala
370                 375                 380                 385

Gln Lys Tyr Val Thr Val Gln Ile Gly His Arg Ile Gly Phe Val Lys
                390                 395                 400

Ala Ser Asp Val Asp Val Val Arg Ala Gly Ser
                405                 410

<210> SEQ ID NO 57
<211> LENGTH: 412
<212> TYPE: PRT
<213> ORGANISM: Streptomyces griseus

<400> SEQUENCE: 57

Asp Thr Val Arg Pro Glu Cys Pro Arg Ser Leu Ala Cys Asp Trp Val
1               5                   10                  15

Pro Ala Ala Tyr Gln Gln Thr Gly Asp Pro Glu Asp Lys Asp Thr Tyr
                20                  25                  30

Gly Asn Tyr Asp Thr Ala Asn Arg Pro Asp Ser Asn Ala Val Lys Phe
                35                  40                  45

Ile Val Leu His Asp Thr Glu Val Asp Tyr Asp Thr Thr Leu Lys Ile
            50                  55                  60

Phe Gln Asn Pro Ala Asn Gln Thr Ser Ala His Tyr Val Val Arg Ser
65                  70                  75                  80

Ala Asp Gly His Val Thr Gln Met Val Lys Asn Lys Asp Val Ala Trp
                85                  90                  95

Gln Ala Gly Asn Trp Tyr Leu Asn Thr His Ser Ile Gly Ile Glu Gln
                100                 105                 110

Glu Gly Val Ala Ala Glu Gly Ala Thr Trp Tyr Thr Ser Glu Met Tyr
            115                 120                 125

Arg Ser Thr Ala Arg Leu Val Arg Tyr Leu Ala Ala Lys Tyr Asp Ile
    130                 135                 140

Pro Leu Asp Arg Gln His Ile Leu Gly His Asp Gly Val Pro Pro Thr
145                 150                 155                 160
```

```
Ser Ala Ala Gly Thr Lys Asn Met His Trp Asp Pro Gly Pro Tyr Trp
                165                 170                 175

Asp Trp Asn Arg Phe Met Ala Leu Leu Gly Ala Pro Thr Ala Pro Ser
            180                 185                 190

Ala Pro Lys Arg Ser Glu Leu Val Thr Val Ser Ala Asp Phe Ala Arg
        195                 200                 205

Asn Gln Gln Glu Phe Arg Asp Cys Glu Lys Asn Val Asp Leu Pro Arg
    210                 215                 220

Gln Gly Ser Ser Ala Val Pro Leu His Thr Glu Pro Ser Ala Asp Ala
225                 230                 235                 240

Pro Leu Phe Ser Asp Pro Gly Leu His Pro Asp Gly Ser Pro Gly Thr
                245                 250                 255

Asn Cys Ala Ala Asp Trp Gly Ser Lys Ile Ser Ala Thr Gln Gln Ala
            260                 265                 270

Val Val Ala Asp Arg Val Pro Gly Trp Thr Ala Ile Trp Trp Tyr Gly
        275                 280                 285

Glu Lys Ala Trp Phe Ser Thr Pro Pro Gly Thr Arg Val Thr Thr Pro
    290                 295                 300

Thr Arg Gly Ser Val Val Arg Pro Lys Pro Gly Thr Ser Glu Val Leu
305                 310                 315                 320

Val Tyr Gly Val Ala Tyr Pro Glu Lys Ala Glu Tyr Pro Thr Asp Phe
                325                 330                 335

Val Lys Pro Thr Val Gly Thr Pro Leu Val Tyr Thr Ile Lys Ala Gly
            340                 345                 350

Gln Ala Phe Pro Gly Gly Glu Ala Pro Thr Gly Tyr Tyr Ala
        355                 360                 365

Pro Thr Ile Asp Thr Ser Lys Pro Tyr Asp His Thr Tyr Phe Gly Gly
    370                 375                 380

Ala Gln Lys Tyr Val Thr Val Gln Ile Gly His Arg Ile Gly Phe Val
385                 390                 395                 400

Lys Ala Ser Asp Val Asp Val Val Arg Ala Gly Ser
                405                 410

<210> SEQ ID NO 58
<211> LENGTH: 2019
<212> TYPE: DNA
<213> ORGANISM: Micromonospora peucetia
<220> FEATURE:
<221> NAME/KEY: CDS
<222> LOCATION: (1)..(2016)
<220> FEATURE:
<221> NAME/KEY: sig_peptide
<222> LOCATION: (1)..(105)
<220> FEATURE:
<221> NAME/KEY: mat_peptide
<222> LOCATION: (106)..(2016)

<400> SEQUENCE: 58 atg cac ctg tca gcg aca acg agg agc aga cgc gtc ctg ctg gcc acc      48
Met His Leu Ser Ala Thr Thr Arg Ser Arg Arg Val Leu Leu Ala Thr
-35                 -30                 -25                 -20 gcc gtg gcc gcc gtc atg gtg gcg acg ccg ctc acc gcc gcc gga tcc      96
Ala Val Ala Ala Val Met Val Ala Thr Pro Leu Thr Ala Ala Gly Ser
            -15                 -10                 -5 gcc gcc gcc gca ccg gcg acc gac cgg cag cag cag tac gcc gcc gcg     144
Ala Ala Ala Ala Pro Ala Thr Asp Arg Gln Gln Gln Tyr Ala Ala Ala
        -1  1               5                   10
```

```
gca gcc gag tac ggc gtg ccg gag agc gtc ctg ctc ggc gtc tcc tat    192
Ala Ala Glu Tyr Gly Val Pro Glu Ser Val Leu Leu Gly Val Ser Tyr
    15                  20                  25 cta cag tcc cgc tgg gac acc aac gcc ggc acg ccg agc acc agc gcc    240
Leu Gln Ser Arg Trp Asp Thr Asn Ala Gly Thr Pro Ser Thr Ser Ala
 30                  35                  40                  45 ggc tac gga ccg atg cac ctc acc gac gcc gag cac gtc gcc gcc ctg    288
Gly Tyr Gly Pro Met His Leu Thr Asp Ala Glu His Val Ala Ala Leu
                 50                  55                  60 ccc ggg ggc acc cac cac gac gag ggc acc gag gac ccg cgc ggc gac    336
Pro Gly Gly Thr His His Asp Glu Gly Thr Glu Asp Pro Arg Gly Asp
             65                  70                  75 gac tcc cgc ccg tcc ctg gcg gag gcg cgc gag ccg gcc gag ccg gct    384
Asp Ser Arg Pro Ser Leu Ala Glu Ala Arg Glu Pro Ala Glu Pro Ala
         80                  85                  90 ccc gcc gag gcg gcg ctc cgg acg ctc gac gcc gcc gcc gga ctc acc    432
Pro Ala Glu Ala Ala Leu Arg Thr Leu Asp Ala Ala Ala Gly Leu Thr
     95                 100                 105 ggc gcc agc gag gag gcg ctg cgg acg gac gtc acg gcg aac atc cgg    480
Gly Ala Ser Glu Glu Ala Leu Arg Thr Asp Val Thr Ala Asn Ile Arg
110                 115                 120                 125 ggc ggc gcg gcg ctg ctg gcc gcg tac cag aag gag atc ggt gcc ccg    528
Gly Gly Ala Ala Leu Leu Ala Ala Tyr Gln Lys Glu Ile Gly Ala Pro
                130                 135                 140 gtc ggt gcc gag acc gac ccg gcg gcc tgg tac ggc gcg gtg gcc cgc    576
Val Gly Ala Glu Thr Asp Pro Ala Ala Trp Tyr Gly Ala Val Ala Arg
            145                 150                 155 tac tcc ggc gcc gac acc acc gac gcc gcg gcg gcc ttc gcc aac gag    624
Tyr Ser Gly Ala Asp Thr Thr Asp Ala Ala Ala Ala Phe Ala Asn Glu
        160                 165                 170 gtg tac gcc acc atc gcc acg ggc gac acc cga ctg acc gac gac ggg    672
Val Tyr Ala Thr Ile Ala Thr Gly Asp Thr Arg Leu Thr Asp Asp Gly
    175                 180                 185 cag cgg gtc acc ctc gcc gcc cgc gag gtc cag ccg gag cgt tcc tgg    720
Gln Arg Val Thr Leu Ala Ala Arg Glu Val Gln Pro Glu Arg Ser Trp
190                 195                 200                 205 ctg gac cgg ctg ggc ctg cgc aag ctc gcc cgg ccc gac ggg ctg gag    768
Leu Asp Arg Leu Gly Leu Arg Lys Leu Ala Arg Pro Asp Gly Leu Glu
                210                 215                 220 tgc ccg agc gac atc tcg tgc gag tgg atc ccg gcg ccc tac cag aac    816
Cys Pro Ser Asp Ile Ser Cys Glu Trp Ile Pro Ala Pro Tyr Gln Asn
            225                 230                 235 tac ggc acc acc ctc ggc gcg tac ggc aac cac gac ctg gct gac cgg    864
Tyr Gly Thr Thr Leu Gly Ala Tyr Gly Asn His Asp Leu Ala Asp Arg
        240                 245                 250 ccc gca cag cag aag atc gag tac atc gtc atc cac gac acc gag ggc    912
Pro Ala Gln Gln Lys Ile Glu Tyr Ile Val Ile His Asp Thr Glu Gly
    255                 260                 265 tac ttc ggg ccc agc gtg aac ctg gtc aag gac ccg aag cgg gtg ggt    960
Tyr Phe Gly Pro Ser Val Asn Leu Val Lys Asp Pro Lys Arg Val Gly
270                 275                 280                 285 tgg cac tac acc ctg cgc tcg gtg gac ggc cac atc gcc cag cac atc    1008
Trp His Tyr Thr Leu Arg Ser Val Asp Gly His Ile Ala Gln His Ile
                290                 295                 300 aag acc aag aac gtc ggc tgg cac gcc ggc aac tgg tac gtg aac tcc    1056
Lys Thr Lys Asn Val Gly Trp His Ala Gly Asn Trp Tyr Val Asn Ser
            305                 310                 315
```

```
aag tcc atc ggc ctt gag cac gag ggc ttc gcg gga cac ggc acc tgg    1104
Lys Ser Ile Gly Leu Glu His Glu Gly Phe Ala Gly His Gly Thr Trp
        320                 325                 330 tac acc gag gcg atg tac cgc acc tcc gcc aag ctg gtc cgc cac ctg    1152
Tyr Thr Glu Ala Met Tyr Arg Thr Ser Ala Lys Leu Val Arg His Leu
    335                 340                 345 gcg cgg cag tac aac atc ccg ctg gac cgc aac cac atc atc ggg cac    1200
Ala Arg Gln Tyr Asn Ile Pro Leu Asp Arg Asn His Ile Ile Gly His
350                 355                 360                 365 gac aac gtc ccc ggc acg gtc gcg aac gtg cgt ggc atg cac tgg        1248
Asp Asn Val Pro Gly Thr Val Ala Asn Val Arg Gly Met His Trp
                370                 375                 380 gac gcg ggc ccg tac tgg gac tgg tcg cac tac ttc gac ctg ctg aag    1296
Asp Ala Gly Pro Tyr Trp Asp Trp Ser His Tyr Phe Asp Leu Leu Lys
            385                 390                 395 gcg ccg ttc tgg tcg acc ggc acg cac cgg acc gga ctg gtc acc atc    1344
Ala Pro Phe Trp Ser Thr Gly Thr His Arg Thr Gly Leu Val Thr Ile
        400                 405                 410 gac ccg gac ttc gcc acc aac cag ccg cag ttc acc ggc tgc aac cgg    1392
Asp Pro Asp Phe Ala Thr Asn Gln Pro Gln Phe Thr Gly Cys Asn Arg
    415                 420                 425 cag ccg ccg ggc gtg ccg aac ccg ccc ccg acg gct ccc tgc ccg        1440
Gln Pro Pro Gly Val Pro Asn Pro Pro Pro Thr Ala Pro Cys Pro
430                 435                 440                 445 ctg cgc ggc tcg tcg gcg ctg ccc ctg cac aac gcg ccg agc cag gac    1488
Leu Arg Gly Ser Ser Ala Leu Pro Leu His Asn Ala Pro Ser Gln Asp
                450                 455                 460 gcg ccg ctg gtc aac gac atc gcg ctg cgg ccc gac ggc acc ccg aac    1536
Ala Pro Leu Val Asn Asp Ile Ala Leu Arg Pro Asp Gly Thr Pro Asn
            465                 470                 475 acc atg tac gtc tcc gac cac ggc gcc cgg gtc tcg gca gga cag acg    1584
Thr Met Tyr Val Ser Asp His Gly Ala Arg Val Ser Ala Gly Gln Thr
        480                 485                 490 tac gcc ctg gcc gag gtg cgg ggt gac tgg acg gcg atc tgg tac ctc    1632
Tyr Ala Leu Ala Glu Val Arg Gly Asp Trp Thr Ala Ile Trp Tyr Leu
    495                 500                 505 ggc cag aag gcg tgg ttc cac aac ccg gcc tcg gcg cgg acc gcc aag    1680
Gly Gln Lys Ala Trp Phe His Asn Pro Ala Ser Ala Arg Thr Ala Lys
510                 515                 520                 525 tgg tcc gtc ggc ctg gtc gcc acc ccg aag gca ggc aag acc acc atc    1728
Trp Ser Val Gly Leu Val Ala Thr Pro Lys Ala Gly Lys Thr Thr Ile
                530                 535                 540 ccg gtg tac ggc cgg gcg tac ccg gag gag gcg gcc tac ccg gcc ggc    1776
Pro Val Tyr Gly Arg Ala Tyr Pro Glu Glu Ala Ala Tyr Pro Ala Gly
            545                 550                 555 gtg ccg tac cag acg atc tcg ccg ctc cag tac acg ctc tcg gcc ggt    1824
Val Pro Tyr Gln Thr Ile Ser Pro Leu Gln Tyr Thr Leu Ser Ala Gly
        560                 565                 570 gag cgg tac gcc gtc ggc aac ctg ctc ccc ggc gag tac tac cgg gcc    1872
Glu Arg Tyr Ala Val Gly Asn Leu Leu Pro Gly Glu Tyr Tyr Arg Ala
    575                 580                 585 acc acg ttc gac ggc tcc gcc ccg ggt gac cgg acc gtc atc cgc ggc    1920
Thr Thr Phe Asp Gly Ser Ala Pro Gly Asp Arg Thr Val Ile Arg Gly
590                 595                 600                 605 gag aac aag tac gtg cag atc cag ttc ggc cac cgc atc atg tac gtc    1968
Glu Asn Lys Tyr Val Gln Ile Gln Phe Gly His Arg Ile Met Tyr Val
                610                 615                 620
```

```
aac ctg gcc gac gtg aac ctg ctg ccc tcg ccg ctg ggc gcg ccc cgc    2016
Asn Leu Ala Asp Val Asn Leu Leu Pro Ser Pro Leu Gly Ala Pro Arg
            625                 630                 635 tga                                                                 2019
```

<210> SEQ ID NO 59
<211> LENGTH: 672
<212> TYPE: PRT
<213> ORGANISM: Micromonospora peucetia

<400> SEQUENCE: 59

```
Met His Leu Ser Ala Thr Thr Arg Ser Arg Val Leu Leu Ala Thr
-35             -30             -25             -20

Ala Val Ala Ala Val Met Val Ala Thr Pro Leu Thr Ala Ala Gly Ser
        -15             -10              -5

Ala Ala Ala Ala Pro Ala Thr Asp Arg Gln Gln Tyr Ala Ala Ala
        -1  1           5               10

Ala Ala Glu Tyr Gly Val Pro Glu Ser Val Leu Leu Gly Val Ser Tyr
        15              20              25

Leu Gln Ser Arg Trp Asp Thr Asn Ala Gly Thr Pro Ser Thr Ser Ala
30              35              40              45

Gly Tyr Gly Pro Met His Leu Thr Asp Ala Glu His Val Ala Ala Leu
                50              55              60

Pro Gly Gly Thr His His Asp Glu Gly Thr Glu Asp Pro Arg Gly Asp
                65              70              75

Asp Ser Arg Pro Ser Leu Ala Glu Ala Arg Glu Pro Ala Glu Pro Ala
        80              85              90

Pro Ala Glu Ala Ala Leu Arg Thr Leu Asp Ala Ala Ala Gly Leu Thr
        95              100             105

Gly Ala Ser Glu Glu Ala Leu Arg Thr Asp Val Thr Ala Asn Ile Arg
110             115             120             125

Gly Gly Ala Ala Leu Leu Ala Ala Tyr Gln Lys Glu Ile Gly Ala Pro
                130             135             140

Val Gly Ala Glu Thr Asp Pro Ala Ala Trp Tyr Gly Ala Val Ala Arg
                145             150             155

Tyr Ser Gly Ala Asp Thr Thr Asp Ala Ala Ala Phe Ala Asn Glu
                160             165             170

Val Tyr Ala Thr Ile Ala Thr Gly Asp Thr Arg Leu Thr Asp Asp Gly
        175             180             185

Gln Arg Val Thr Leu Ala Ala Arg Glu Val Gln Pro Glu Arg Ser Trp
190             195             200             205

Leu Asp Arg Leu Gly Leu Arg Lys Leu Ala Arg Pro Asp Gly Leu Glu
                210             215             220

Cys Pro Ser Asp Ile Ser Cys Glu Trp Ile Pro Ala Pro Tyr Gln Asn
                225             230             235

Tyr Gly Thr Thr Leu Gly Ala Tyr Gly Asn His Asp Leu Ala Asp Arg
                240             245             250

Pro Ala Gln Gln Lys Ile Glu Tyr Ile Val Ile His Asp Thr Glu Gly
        255             260             265

Tyr Phe Gly Pro Ser Val Asn Leu Val Lys Asp Pro Lys Arg Val Gly
270             275             280             285

Trp His Tyr Thr Leu Arg Ser Val Asp Gly His Ile Ala Gln His Ile
                290             295             300
```

```
Lys Thr Lys Asn Val Gly Trp His Ala Gly Asn Trp Tyr Val Asn Ser
            305                 310                 315

Lys Ser Ile Gly Leu Glu His Glu Gly Phe Ala Gly His Gly Thr Trp
        320                 325                 330

Tyr Thr Glu Ala Met Tyr Arg Thr Ser Ala Lys Leu Val Arg His Leu
    335                 340                 345

Ala Arg Gln Tyr Asn Ile Pro Leu Asp Arg Asn His Ile Ile Gly His
350                 355                 360                 365

Asp Asn Val Pro Gly Thr Val Ala Ala Asn Val Arg Gly Met His Trp
                370                 375                 380

Asp Ala Gly Pro Tyr Trp Asp Trp Ser His Tyr Phe Asp Leu Leu Lys
            385                 390                 395

Ala Pro Phe Trp Ser Thr Gly Thr His Arg Thr Gly Leu Val Thr Ile
        400                 405                 410

Asp Pro Asp Phe Ala Thr Asn Gln Pro Gln Phe Thr Gly Cys Asn Arg
    415                 420                 425

Gln Pro Pro Gly Val Pro Asn Pro Pro Pro Thr Ala Pro Cys Pro
430                 435                 440                 445

Leu Arg Gly Ser Ser Ala Leu Pro Leu His Asn Ala Pro Ser Gln Asp
                450                 455                 460

Ala Pro Leu Val Asn Asp Ile Ala Leu Arg Pro Asp Gly Thr Pro Asn
            465                 470                 475

Thr Met Tyr Val Ser Asp His Gly Ala Arg Val Ser Ala Gly Gln Thr
        480                 485                 490

Tyr Ala Leu Ala Glu Val Arg Gly Asp Trp Thr Ala Ile Trp Tyr Leu
    495                 500                 505

Gly Gln Lys Ala Trp Phe His Asn Pro Ala Ser Ala Arg Thr Ala Lys
510                 515                 520                 525

Trp Ser Val Gly Leu Val Ala Thr Pro Lys Ala Gly Lys Thr Thr Ile
                530                 535                 540

Pro Val Tyr Gly Arg Ala Tyr Pro Glu Glu Ala Ala Tyr Pro Ala Gly
            545                 550                 555

Val Pro Tyr Gln Thr Ile Ser Pro Leu Gln Tyr Thr Leu Ser Ala Gly
        560                 565                 570

Glu Arg Tyr Ala Val Gly Asn Leu Leu Pro Gly Glu Tyr Tyr Arg Ala
    575                 580                 585

Thr Thr Phe Asp Gly Ser Ala Pro Gly Asp Arg Thr Val Ile Arg Gly
590                 595                 600                 605

Glu Asn Lys Tyr Val Gln Ile Gln Phe Gly His Arg Ile Met Tyr Val
                610                 615                 620

Asn Leu Ala Asp Val Asn Leu Leu Pro Ser Pro Leu Gly Ala Pro Arg
            625                 630                 635

<210> SEQ ID NO 60
<211> LENGTH: 637
<212> TYPE: PRT
<213> ORGANISM: Micromonospora peucetia

<400> SEQUENCE: 60

Ala Pro Ala Thr Asp Arg Gln Gln Gln Tyr Ala Ala Ala Ala Glu
1               5                   10                  15

Tyr Gly Val Pro Glu Ser Val Leu Leu Gly Val Ser Tyr Leu Gln Ser
            20                  25                  30
```

```
Arg Trp Asp Thr Asn Ala Gly Thr Pro Ser Thr Ser Ala Gly Tyr Gly
        35                  40                  45

Pro Met His Leu Thr Asp Ala Glu His Val Ala Ala Leu Pro Gly Gly
        50                  55                  60

Thr His His Asp Glu Gly Thr Glu Asp Pro Arg Gly Asp Asp Ser Arg
65                  70                  75                  80

Pro Ser Leu Ala Glu Ala Arg Glu Pro Ala Glu Pro Ala Pro Ala Glu
                85                  90                  95

Ala Ala Leu Arg Thr Leu Asp Ala Ala Ala Gly Leu Thr Gly Ala Ser
                100                 105                 110

Glu Glu Ala Leu Arg Thr Asp Val Thr Ala Asn Ile Arg Gly Gly Ala
                115                 120                 125

Ala Leu Leu Ala Ala Tyr Gln Lys Glu Ile Gly Ala Pro Val Gly Ala
                130                 135                 140

Glu Thr Asp Pro Ala Ala Trp Tyr Gly Ala Val Ala Arg Tyr Ser Gly
145                 150                 155                 160

Ala Asp Thr Thr Asp Ala Ala Ala Phe Ala Asn Glu Val Tyr Ala
                165                 170                 175

Thr Ile Ala Thr Gly Asp Thr Arg Leu Thr Asp Gly Gln Arg Val
                180                 185                 190

Thr Leu Ala Ala Arg Glu Val Gln Pro Glu Arg Ser Trp Leu Asp Arg
                195                 200                 205

Leu Gly Leu Arg Lys Leu Ala Arg Pro Asp Gly Leu Glu Cys Pro Ser
                210                 215                 220

Asp Ile Ser Cys Glu Trp Ile Pro Ala Pro Tyr Gln Asn Tyr Gly Thr
225                 230                 235                 240

Thr Leu Gly Ala Tyr Gly Asn His Asp Leu Ala Asp Arg Pro Ala Gln
                245                 250                 255

Gln Lys Ile Glu Tyr Ile Val Ile His Asp Thr Glu Gly Tyr Phe Gly
                260                 265                 270

Pro Ser Val Asn Leu Val Lys Asp Pro Lys Arg Val Gly Trp His Tyr
                275                 280                 285

Thr Leu Arg Ser Val Asp Gly His Ile Ala Gln His Ile Lys Thr Lys
                290                 295                 300

Asn Val Gly Trp His Ala Gly Asn Trp Tyr Val Asn Ser Lys Ser Ile
305                 310                 315                 320

Gly Leu Glu His Glu Gly Phe Ala Gly His Gly Thr Trp Tyr Thr Glu
                325                 330                 335

Ala Met Tyr Arg Thr Ser Ala Lys Leu Val Arg His Leu Ala Arg Gln
                340                 345                 350

Tyr Asn Ile Pro Leu Asp Arg Asn His Ile Ile Gly His Asp Asn Val
                355                 360                 365

Pro Gly Thr Val Ala Ala Asn Val Arg Gly Met His Trp Asp Ala Gly
                370                 375                 380

Pro Tyr Trp Asp Trp Ser His Tyr Phe Asp Leu Leu Lys Ala Pro Phe
385                 390                 395                 400

Trp Ser Thr Gly Thr His Arg Thr Gly Leu Val Thr Ile Asp Pro Asp
                405                 410                 415

Phe Ala Thr Asn Gln Pro Gln Phe Thr Gly Cys Asn Arg Gln Pro Pro
                420                 425                 430

Gly Val Pro Asn Pro Pro Thr Ala Pro Cys Pro Leu Arg Gly
                435                 440                 445
```

```
Ser Ser Ala Leu Pro Leu His Asn Ala Pro Ser Gln Asp Ala Pro Leu
    450                 455                 460

Val Asn Asp Ile Ala Leu Arg Pro Asp Gly Thr Pro Asn Thr Met Tyr
465                 470                 475                 480

Val Ser Asp His Gly Ala Arg Val Ser Ala Gly Gln Thr Tyr Ala Leu
                485                 490                 495

Ala Glu Val Arg Gly Asp Trp Thr Ala Ile Trp Tyr Leu Gly Gln Lys
            500                 505                 510

Ala Trp Phe His Asn Pro Ala Ser Ala Arg Thr Ala Lys Trp Ser Val
        515                 520                 525

Gly Leu Val Ala Thr Pro Lys Ala Gly Lys Thr Thr Ile Pro Val Tyr
    530                 535                 540

Gly Arg Ala Tyr Pro Glu Glu Ala Ala Tyr Pro Ala Gly Val Pro Tyr
545                 550                 555                 560

Gln Thr Ile Ser Pro Leu Gln Tyr Thr Leu Ser Ala Gly Glu Arg Tyr
                565                 570                 575

Ala Val Gly Asn Leu Leu Pro Gly Glu Tyr Tyr Arg Ala Thr Thr Phe
            580                 585                 590

Asp Gly Ser Ala Pro Gly Asp Arg Thr Val Ile Arg Gly Glu Asn Lys
        595                 600                 605

Tyr Val Gln Ile Gln Phe Gly His Arg Ile Met Tyr Val Asn Leu Ala
    610                 615                 620

Asp Val Asn Leu Leu Pro Ser Pro Leu Gly Ala Pro Arg
625                 630                 635

<210> SEQ ID NO 61
<211> LENGTH: 1899
<212> TYPE: DNA
<213> ORGANISM: Bacillus sp
<220> FEATURE:
<221> NAME/KEY: CDS
<222> LOCATION: (1)..(1896)
<220> FEATURE:
<221> NAME/KEY: sig_peptide
<222> LOCATION: (1)..(99)
<220> FEATURE:
<221> NAME/KEY: mat_peptide
<222> LOCATION: (100)..(1896)

<400> SEQUENCE: 61 ttg gga ttt aaa aag cta tca tca gcc att tta acg ttc tcc tta acc      48
Leu Gly Phe Lys Lys Leu Ser Ser Ala Ile Leu Thr Phe Ser Leu Thr
        -30                 -25                 -20 gca agc ctc ttg gct atc ccc gct gac ttt aca cca agc gca act tct      96
Ala Ser Leu Leu Ala Ile Pro Ala Asp Phe Thr Pro Ser Ala Thr Ser
    -15                 -10                  -5 gca gcc tca aca gaa aac agc aat gaa gcg cac cac ctg caa aag gct     144
Ala Ala Ser Thr Glu Asn Ser Asn Glu Ala His His Leu Gln Lys Ala
-1   1                   5                  10                  15 ttt gaa aca gcg gcg aag gaa ttt gga gta cct gaa tct gtc ctt ctc     192
Phe Glu Thr Ala Ala Lys Glu Phe Gly Val Pro Glu Ser Val Leu Leu
                20                  25                  30 gcc gtc gct tat aac cag tca cgc tgg gag cac cat gaa ggc cat agt     240
Ala Val Ala Tyr Asn Gln Ser Arg Trp Glu His His Glu Gly His Ser
            35                  40                  45 gag gtc gga ggc tat ggc att atg aat ctt gca gac ttg cca gcc gac     288
Glu Val Gly Gly Tyr Gly Ile Met Asn Leu Ala Asp Leu Pro Ala Asp
        50                  55                  60
```

```
atg agc gcc agg ggc aag cat gac gac gga atc att gcg gct ttg gat      336
Met Ser Ala Arg Gly Lys His Asp Asp Gly Ile Ile Ala Ala Leu Asp
 65                  70                  75 aat gaa aat agc atg ctt aaa aca gcc gca aat ctt cta aat gaa gat      384
Asn Glu Asn Ser Met Leu Lys Thr Ala Ala Asn Leu Leu Asn Glu Asp
 80                  85                  90                  95 ccg gaa gcc tta aaa aaa gac cct gaa caa aat atc cgg ggc ggg gca      432
Pro Glu Ala Leu Lys Lys Asp Pro Glu Gln Asn Ile Arg Gly Gly Ala
                100                 105                 110 gct ctt tta gca gag ttt gca cgc caa acg aca ggg gaa ctt cct tcc      480
Ala Leu Leu Ala Glu Phe Ala Arg Gln Thr Thr Gly Glu Leu Pro Ser
            115                 120                 125 gat gaa gca gac tgg tac ggt gcc gtc gtt aaa tac agc gga aca gat      528
Asp Glu Ala Asp Trp Tyr Gly Ala Val Val Lys Tyr Ser Gly Thr Asp
        130                 135                 140 cag gaa gtc atc gct aag gac ttt gca gat caa gtc ttt gag acc att      576
Gln Glu Val Ile Ala Lys Asp Phe Ala Asp Gln Val Phe Glu Thr Ile
    145                 150                 155 cag caa ggt gct gcc aga aaa aac ctt gat gga caa aga gtc gta tta      624
Gln Gln Gly Ala Ala Arg Lys Asn Leu Asp Gly Gln Arg Val Val Leu
160                 165                 170                 175 aac gcc aag gaa att aca cca aat aag act aca gct ggc act atc cct      672
Asn Ala Lys Glu Ile Thr Pro Asn Lys Thr Thr Ala Gly Thr Ile Pro
                180                 185                 190 ctt cgc aac acc aaa tac aca aat acc gac tgt cca aat ggc ctt gat      720
Leu Arg Asn Thr Lys Tyr Thr Asn Thr Asp Cys Pro Asn Gly Leu Asp
            195                 200                 205 tgc act ttc att cct gct gct tat aag caa ttt tcg agc agc aca agt      768
Cys Thr Phe Ile Pro Ala Ala Tyr Lys Gln Phe Ser Ser Ser Thr Ser
        210                 215                 220 aat tac ggc aac tac gat atc gcc aat cgg cca aag gac gat tta gat      816
Asn Tyr Gly Asn Tyr Asp Ile Ala Asn Arg Pro Lys Asp Asp Leu Asp
    225                 230                 235 att cgc tat att att att cat gat att gag ggc acg gct gaa tcc gcc      864
Ile Arg Tyr Ile Ile Ile His Asp Ile Glu Gly Thr Ala Glu Ser Ala
240                 245                 250                 255 atc agc cac ttc cag aat ccg tcc tac gtt agt gca cac tat gtc ata      912
Ile Ser His Phe Gln Asn Pro Ser Tyr Val Ser Ala His Tyr Val Ile
                260                 265                 270 gat tca gag acc gga aaa atc acc cag atg gta cgt cct gaa gat gtg      960
Asp Ser Glu Thr Gly Lys Ile Thr Gln Met Val Arg Pro Glu Asp Val
            275                 280                 285 cca tgg cat gca gga aac tgg tat ttt aat atg cat tcg atc gga ttg     1008
Pro Trp His Ala Gly Asn Trp Tyr Phe Asn Met His Ser Ile Gly Leu
        290                 295                 300 gag cat gaa gga tat gct gca gaa ggc gct gac tgg tac agt gag caa     1056
Glu His Glu Gly Tyr Ala Ala Glu Gly Ala Asp Trp Tyr Ser Glu Gln
    305                 310                 315 atg tat cgc tct acc gca aaa ctt gta aga tac ctt tca gac cga ttt     1104
Met Tyr Arg Ser Thr Ala Lys Leu Val Arg Tyr Leu Ser Asp Arg Phe
320                 325                 330                 335 aac att cct ttg gac aga cag cac att atc ggc cat gat gag ata cct     1152
Asn Ile Pro Leu Asp Arg Gln His Ile Ile Gly His Asp Glu Ile Pro
                340                 345                 350 ggc tta aca aca gca aaa cat agg agc atg cac tgg gat ccg ggc gct     1200
Gly Leu Thr Thr Ala Lys His Arg Ser Met His Trp Asp Pro Gly Ala
            355                 360                 365
```

```
tat tgg gat tgg gga cac ttt ttc gac ctt ctt gga gct tcc att aat    1248
Tyr Trp Asp Trp Gly His Phe Phe Asp Leu Leu Gly Ala Ser Ile Asn
            370                 375                 380 cca agc agc gga gac aaa gac agt aat atc gtc aca atc cgc cca aat    1296
Pro Ser Ser Gly Asp Lys Asp Ser Asn Ile Val Thr Ile Arg Pro Asn
385                 390                 395 ttc aat aca aat cag cca gac ttt acg tat aga gga att aaa cag gaa    1344
Phe Asn Thr Asn Gln Pro Asp Phe Thr Tyr Arg Gly Ile Lys Gln Glu
400                 405                 410                 415 cct gag tct tca agc ctg att cat tta tac agc gaa ccc agc ttt gag    1392
Pro Glu Ser Ser Ser Leu Ile His Leu Tyr Ser Glu Pro Ser Phe Glu
            420                 425                 430 gca cca ttg gtc agt gat ccc ctg ctt cat cct ggc ggc acc agc aca    1440
Ala Pro Leu Val Ser Asp Pro Leu Leu His Pro Gly Gly Thr Ser Thr
                435                 440                 445 aga att aat gac tgg ggc aat aaa gct gcg atg gga cag agt ttc       1488
Arg Asn Ile Asn Asp Trp Gly Asn Lys Ala Ala Met Gly Gln Ser Phe
            450                 455                 460 tat aaa gcc ggg cag gaa ggc gat tgg aca gct att tac tac gcc ggc    1536
Tyr Lys Ala Gly Gln Glu Gly Asp Trp Thr Ala Ile Tyr Tyr Ala Gly
465                 470                 475 caa aaa gcc tgg ttc tat aat ccg aac aat aaa aat agc gtc cca ggc    1584
Gln Lys Ala Trp Phe Tyr Asn Pro Asn Asn Lys Asn Ser Val Pro Gly
480                 485                 490                 495 agc ggg acc ctc atc acg cca aaa gaa ggg ctt gat tcc ata cct gta    1632
Ser Gly Thr Leu Ile Thr Pro Lys Glu Gly Leu Asp Ser Ile Pro Val
            500                 505                 510 tat ggt gcc gcc tat cct gac gac gca gct tac gaa gag gcc gga att    1680
Tyr Gly Ala Ala Tyr Pro Asp Asp Ala Ala Tyr Glu Glu Ala Gly Ile
            515                 520                 525 gcg gaa tgg gca aga gga aaa gca cag gtt cta tac cag atg ccg gct    1728
Ala Glu Trp Ala Arg Gly Lys Ala Gln Val Leu Tyr Gln Met Pro Ala
            530                 535                 540 ggc caa atc tat aca gca aca gca cca att cag tcc gat tac tat cat    1776
Gly Gln Ile Tyr Thr Ala Thr Ala Pro Ile Gln Ser Asp Tyr Tyr His
545                 550                 555 gcg aag tat tat aat gac ccg gct aca aat aag gtt gta aag ggg aat    1824
Ala Lys Tyr Tyr Asn Asp Pro Ala Thr Asn Lys Val Val Lys Gly Asn
560                 565                 570                 575 gat gaa tac tat cag att ttt tac aat cat cgt ctg gga ttc gtg aag    1872
Asp Glu Tyr Tyr Gln Ile Phe Tyr Asn His Arg Leu Gly Phe Val Lys
            580                 585                 590 aaa agc gat gta gaa gtt gta aat taa                                1899
Lys Ser Asp Val Glu Val Val Asn
            595

<210> SEQ ID NO 62
<211> LENGTH: 632
<212> TYPE: PRT
<213> ORGANISM: Bacillus sp

<400> SEQUENCE: 62

Leu Gly Phe Lys Lys Leu Ser Ser Ala Ile Leu Thr Phe Ser Leu Thr
            -30                 -25                 -20

Ala Ser Leu Leu Ala Ile Pro Ala Asp Phe Thr Pro Ser Ala Thr Ser
        -15                 -10                  -5

Ala Ala Ser Thr Glu Asn Ser Asn Glu Ala His His Leu Gln Lys Ala
 -1  1               5                  10                  15
```

```
Phe Glu Thr Ala Ala Lys Glu Phe Gly Val Pro Ser Val Leu Leu
                20              25              30

Ala Val Ala Tyr Asn Gln Ser Arg Trp Glu His His Glu Gly His Ser
            35              40              45

Glu Val Gly Gly Tyr Gly Ile Met Asn Leu Ala Asp Leu Pro Ala Asp
        50              55              60

Met Ser Ala Arg Gly Lys His Asp Asp Gly Ile Ile Ala Ala Leu Asp
65              70              75

Asn Glu Asn Ser Met Leu Lys Thr Ala Ala Asn Leu Leu Asn Glu Asp
80              85              90              95

Pro Glu Ala Leu Lys Lys Asp Pro Glu Gln Asn Ile Arg Gly Gly Ala
            100             105             110

Ala Leu Leu Ala Glu Phe Ala Arg Gln Thr Thr Gly Glu Leu Pro Ser
        115             120             125

Asp Glu Ala Asp Trp Tyr Gly Ala Val Val Lys Tyr Ser Gly Thr Asp
    130             135             140

Gln Glu Val Ile Ala Lys Asp Phe Ala Asp Gln Val Phe Glu Thr Ile
    145             150             155

Gln Gln Gly Ala Ala Arg Lys Asn Leu Asp Gly Gln Arg Val Val Leu
160             165             170             175

Asn Ala Lys Glu Ile Thr Pro Asn Lys Thr Thr Ala Gly Thr Ile Pro
            180             185             190

Leu Arg Asn Thr Lys Tyr Thr Asn Thr Asp Cys Pro Asn Gly Leu Asp
            195             200             205

Cys Thr Phe Ile Pro Ala Ala Tyr Lys Gln Phe Ser Ser Thr Ser
        210             215             220

Asn Tyr Gly Asn Tyr Asp Ile Ala Asn Arg Pro Lys Asp Asp Leu Asp
225             230             235

Ile Arg Tyr Ile Ile Ile His Asp Ile Glu Gly Thr Ala Glu Ser Ala
240             245             250             255

Ile Ser His Phe Gln Asn Pro Ser Tyr Val Ser Ala His Tyr Val Ile
            260             265             270

Asp Ser Glu Thr Gly Lys Ile Thr Gln Met Val Arg Pro Glu Asp Val
        275             280             285

Pro Trp His Ala Gly Asn Trp Tyr Phe Asn Met His Ser Ile Gly Leu
    290             295             300

Glu His Glu Gly Tyr Ala Ala Glu Gly Ala Asp Trp Tyr Ser Glu Gln
    305             310             315

Met Tyr Arg Ser Thr Ala Lys Leu Val Arg Tyr Leu Ser Asp Arg Phe
320             325             330             335

Asn Ile Pro Leu Asp Arg Gln His Ile Ile Gly His Asp Glu Ile Pro
            340             345             350

Gly Leu Thr Thr Ala Lys His Arg Ser Met His Trp Asp Pro Gly Ala
        355             360             365

Tyr Trp Asp Trp Gly His Phe Phe Asp Leu Leu Gly Ala Ser Ile Asn
    370             375             380

Pro Ser Ser Gly Asp Lys Asp Ser Asn Ile Val Thr Ile Arg Pro Asn
385             390             395

Phe Asn Thr Asn Gln Pro Asp Phe Thr Tyr Arg Gly Ile Lys Gln Glu
400             405             410             415

Pro Glu Ser Ser Ser Leu Ile His Leu Tyr Ser Glu Pro Ser Phe Glu
            420             425             430
```

```
Ala Pro Leu Val Ser Asp Pro Leu Leu His Pro Gly Gly Thr Ser Thr
                435                 440                 445

Arg Asn Ile Asn Asp Trp Gly Asn Lys Ala Ala Met Gly Gln Ser Phe
        450                 455                 460

Tyr Lys Ala Gly Gln Glu Gly Asp Trp Thr Ala Ile Tyr Tyr Ala Gly
    465                 470                 475

Gln Lys Ala Trp Phe Tyr Asn Pro Asn Asn Lys Asn Ser Val Pro Gly
480                 485                 490                 495

Ser Gly Thr Leu Ile Thr Pro Lys Glu Gly Leu Asp Ser Ile Pro Val
                500                 505                 510

Tyr Gly Ala Ala Tyr Pro Asp Asp Ala Ala Tyr Glu Glu Ala Gly Ile
            515                 520                 525

Ala Glu Trp Ala Arg Gly Lys Ala Gln Val Leu Tyr Gln Met Pro Ala
        530                 535                 540

Gly Gln Ile Tyr Thr Ala Thr Ala Pro Ile Gln Ser Asp Tyr Tyr His
    545                 550                 555

Ala Lys Tyr Tyr Asn Asp Pro Ala Thr Asn Lys Val Val Lys Gly Asn
560                 565                 570                 575

Asp Glu Tyr Tyr Gln Ile Phe Tyr Asn His Arg Leu Gly Phe Val Lys
                580                 585                 590

Lys Ser Asp Val Glu Val Val Asn
                595

<210> SEQ ID NO 63
<211> LENGTH: 599
<212> TYPE: PRT
<213> ORGANISM: Bacillus sp

<400> SEQUENCE: 63

Ala Ser Thr Glu Asn Ser Asn Glu Ala His His Leu Gln Lys Ala Phe
1               5                   10                  15

Glu Thr Ala Ala Lys Glu Phe Gly Val Pro Glu Ser Val Leu Leu Ala
                20                  25                  30

Val Ala Tyr Asn Gln Ser Arg Trp Glu His His Glu Gly His Ser Glu
            35                  40                  45

Val Gly Gly Tyr Gly Ile Met Asn Leu Ala Asp Leu Pro Ala Asp Met
    50                  55                  60

Ser Ala Arg Gly Lys His Asp Asp Gly Ile Ile Ala Ala Leu Asp Asn
65                  70                  75                  80

Glu Asn Ser Met Leu Lys Thr Ala Ala Asn Leu Leu Asn Glu Asp Pro
                85                  90                  95

Glu Ala Leu Lys Lys Asp Pro Glu Gln Asn Ile Arg Gly Gly Ala Ala
                100                 105                 110

Leu Leu Ala Glu Phe Ala Arg Gln Thr Thr Gly Glu Leu Pro Ser Asp
            115                 120                 125

Glu Ala Asp Trp Tyr Gly Ala Val Val Lys Tyr Ser Gly Thr Asp Gln
    130                 135                 140

Glu Val Ile Ala Lys Asp Phe Ala Asp Gln Val Phe Glu Thr Ile Gln
145                 150                 155                 160

Gln Gly Ala Ala Arg Lys Asn Leu Asp Gly Gln Arg Val Val Leu Asn
                165                 170                 175

Ala Lys Glu Ile Thr Pro Asn Lys Thr Thr Ala Gly Thr Ile Pro Leu
            180                 185                 190

Arg Asn Thr Lys Tyr Thr Asn Thr Asp Cys Pro Asn Gly Leu Asp Cys
    195                 200                 205
```

Thr Phe Ile Pro Ala Ala Tyr Lys Gln Phe Ser Ser Thr Ser Asn
        210                 215                 220

Tyr Gly Asn Tyr Asp Ile Ala Asn Arg Pro Lys Asp Asp Leu Asp Ile
225                 230                 235                 240

Arg Tyr Ile Ile Ile His Asp Ile Glu Gly Thr Ala Glu Ser Ala Ile
                245                 250                 255

Ser His Phe Gln Asn Pro Ser Tyr Val Ser Ala His Tyr Val Ile Asp
            260                 265                 270

Ser Glu Thr Gly Lys Ile Thr Gln Met Val Arg Pro Glu Asp Val Pro
        275                 280                 285

Trp His Ala Gly Asn Trp Tyr Phe Asn Met His Ser Ile Gly Leu Glu
        290                 295                 300

His Glu Gly Tyr Ala Ala Glu Gly Ala Asp Trp Tyr Ser Glu Gln Met
305                 310                 315                 320

Tyr Arg Ser Thr Ala Lys Leu Val Arg Tyr Leu Ser Asp Arg Phe Asn
                325                 330                 335

Ile Pro Leu Asp Arg Gln His Ile Ile Gly His Asp Glu Ile Pro Gly
            340                 345                 350

Leu Thr Thr Ala Lys His Arg Ser Met His Trp Asp Pro Gly Ala Tyr
        355                 360                 365

Trp Asp Trp Gly His Phe Phe Asp Leu Leu Gly Ala Ser Ile Asn Pro
370                 375                 380

Ser Ser Gly Asp Lys Asp Ser Asn Ile Val Thr Ile Arg Pro Asn Phe
385                 390                 395                 400

Asn Thr Asn Gln Pro Asp Phe Thr Tyr Arg Gly Ile Lys Gln Glu Pro
                405                 410                 415

Glu Ser Ser Ser Leu Ile His Leu Tyr Ser Glu Pro Ser Phe Glu Ala
            420                 425                 430

Pro Leu Val Ser Asp Pro Leu Leu His Pro Gly Gly Thr Ser Thr Arg
        435                 440                 445

Asn Ile Asn Asp Trp Gly Asn Lys Ala Ala Met Gly Gln Ser Phe Tyr
450                 455                 460

Lys Ala Gly Gln Glu Gly Asp Trp Thr Ala Ile Tyr Tyr Ala Gly Gln
465                 470                 475                 480

Lys Ala Trp Phe Tyr Asn Pro Asn Asn Lys Asn Ser Val Pro Gly Ser
                485                 490                 495

Gly Thr Leu Ile Thr Pro Lys Glu Gly Leu Asp Ser Ile Pro Val Tyr
            500                 505                 510

Gly Ala Ala Tyr Pro Asp Asp Ala Ala Tyr Glu Glu Ala Gly Ile Ala
        515                 520                 525

Glu Trp Ala Arg Gly Lys Ala Gln Val Leu Tyr Gln Met Pro Ala Gly
530                 535                 540

Gln Ile Tyr Thr Ala Thr Ala Pro Ile Gln Ser Asp Tyr Tyr His Ala
545                 550                 555                 560

Lys Tyr Tyr Asn Asp Pro Ala Thr Asn Lys Val Val Lys Gly Asn Asp
                565                 570                 575

Glu Tyr Tyr Gln Ile Phe Tyr Asn His Arg Leu Gly Phe Val Lys Lys
            580                 585                 590

Ser Asp Val Glu Val Val Asn
        595

<210> SEQ ID NO 64
<211> LENGTH: 1911

<212> TYPE: DNA
<213> ORGANISM: Bacillus sporothermodurans
<220> FEATURE:
<221> NAME/KEY: CDS
<222> LOCATION: (1)..(1908)
<220> FEATURE:
<221> NAME/KEY: sig_peptide
<222> LOCATION: (1)..(93)
<220> FEATURE:
<221> NAME/KEY: mat_peptide
<222> LOCATION: (94)..(1908)

<400> SEQUENCE: 64

```
atg tta tta cga cgt ctt aaa aat cgt aca tta ttg ttc aca ttc atc        48
Met Leu Leu Arg Arg Leu Lys Asn Arg Thr Leu Leu Phe Thr Phe Ile
    -30             -25                 -20 ctt att ttt agc tta ctt gtt atg cca ttc gga gta tca gaa gca agt        96
Leu Ile Phe Ser Leu Leu Val Met Pro Phe Gly Val Ser Glu Ala Ser
-15                 -10                  -5              -1  1 aaa cat tat acg att gat aca aat cat cat tct cct ttg cag caa gca       144
Lys His Tyr Thr Ile Asp Thr Asn His His Ser Pro Leu Gln Gln Ala
              5                  10                  15 ttt act aag gct gca aaa gag ttt cat gtc cca gaa agc tta tta atg       192
Phe Thr Lys Ala Ala Lys Glu Phe His Val Pro Glu Ser Leu Leu Met
         20                  25                  30 tcc gtt gcc tac aat gag tca cgt tgg cta gat cat cat ggt cag cca       240
Ser Val Ala Tyr Asn Glu Ser Arg Trp Leu Asp His His Gly Gln Pro
 35                  40                  45 agc aca tca ggt ggc tat gga atc atg cat tta act gaa gcc aag cct       288
Ser Thr Ser Gly Gly Tyr Gly Ile Met His Leu Thr Glu Ala Lys Pro
 50                  55                  60                  65 tca caa agt ttg agt gct aaa gga aac gga ata gca cat tca tct gct       336
Ser Gln Ser Leu Ser Ala Lys Gly Asn Gly Ile Ala His Ser Ser Ala
                 70                  75                  80 att aat gtg caa caa atg tat acg ttg aaa acg gca gct aaa ctt cta       384
Ile Asn Val Gln Gln Met Tyr Thr Leu Lys Thr Ala Ala Lys Leu Leu
             85                  90                  95 gga gta aag gac aat gtg ata aaa gtt aac ccc gaa cag aac att cgc       432
Gly Val Lys Asp Asn Val Ile Lys Val Asn Pro Glu Gln Asn Ile Arg
        100                 105                 110 ggt ggt gct gca tta ctt ttg gaa tat gct cgt gat acg gtt ggc cat       480
Gly Gly Ala Ala Leu Leu Leu Glu Tyr Ala Arg Asp Thr Val Gly His
115                 120                 125 ata ccg aga agt ctc gct gat tgg tat ggg gca gtt gct aag tat agc       528
Ile Pro Arg Ser Leu Ala Asp Trp Tyr Gly Ala Val Ala Lys Tyr Ser
130                 135                 140                 145 ggc tca aac aat caa gtt gtc gct aat gat ttt gca gac caa gtg tat       576
Gly Ser Asn Asn Gln Val Val Ala Asn Asp Phe Ala Asp Gln Val Tyr
                150                 155                 160 gct acg att caa gaa ggt gca gaa gag gtg ttg gcc gat ggg caa cat       624
Ala Thr Ile Gln Glu Gly Ala Glu Glu Val Leu Ala Asp Gly Gln His
            165                 170                 175 ctt gtg ctc aaa cca aat aag gtg att cca aat aaa aag aca agt gac       672
Leu Val Leu Lys Pro Asn Lys Val Ile Pro Asn Lys Lys Thr Ser Asp
        180                 185                 190 aaa ctg aag ttt caa aaa acg aaa gaa atg gat gta gat tgt cct aaa       720
Lys Leu Lys Phe Gln Lys Thr Lys Glu Met Asp Val Asp Cys Pro Lys
195                 200                 205 gga gta gat tgc aga tat att cca gca gca tat aaa caa ttt tct agt       768
Gly Val Asp Cys Arg Tyr Ile Pro Ala Ala Tyr Lys Gln Phe Ser Ser
210                 215                 220                 225
```

```
ctt aca gat tac gga aat tat gat ctt gct acc agg cca aag gat gga        816
Leu Thr Asp Tyr Gly Asn Tyr Asp Leu Ala Thr Arg Pro Lys Asp Gly
            230                 235                 240 aat gat att cgt tat att att atc cac gat act gaa ggc agc tat gat        864
Asn Asp Ile Arg Tyr Ile Ile Ile His Asp Thr Glu Gly Ser Tyr Asp
        245                 250                 255 tcg gcc atc aac tgg ttt caa gat cag tca tat gct agt gct cac tat        912
Ser Ala Ile Asn Trp Phe Gln Asp Gln Ser Tyr Ala Ser Ala His Tyr
    260                 265                 270 gtt att cgt tct tcc gat ggt caa att aca gaa atg gta aaa ccg gag        960
Val Ile Arg Ser Ser Asp Gly Gln Ile Thr Glu Met Val Lys Pro Glu
275                 280                 285 gat gtt gct tgg caa gca ggc aac tgg tac ttt aat gca cat tcc atc       1008
Asp Val Ala Trp Gln Ala Gly Asn Trp Tyr Phe Asn Ala His Ser Ile
290                 295                 300                 305 gga att gag cat gag ggt tat gca gtc caa ggg gct act tgg tat agt       1056
Gly Ile Glu His Glu Gly Tyr Ala Val Gln Gly Ala Thr Trp Tyr Ser
            310                 315                 320 gaa caa atg tat cat gca tct gca aaa cta gta aaa tat tta gct gaa       1104
Glu Gln Met Tyr His Ala Ser Ala Lys Leu Val Lys Tyr Leu Ala Glu
        325                 330                 335 aaa tat cat gtt ccg tta gat cga gca cat att ctc ggc cac gac aac       1152
Lys Tyr His Val Pro Leu Asp Arg Ala His Ile Leu Gly His Asp Asn
    340                 345                 350 gtc cct ggt tta acg cca gcc gcc caa acc cgt atg cat tgg gat cct       1200
Val Pro Gly Leu Thr Pro Ala Ala Gln Thr Arg Met His Trp Asp Pro
355                 360                 365 gca gct tat tgg aac tgg gag cat ttt ttc aaa aaa ctg gga gta ccg       1248
Ala Ala Tyr Trp Asn Trp Glu His Phe Phe Lys Lys Leu Gly Val Pro
370                 375                 380                 385 att cat cca acg aaa gga aag aaa aac agt cgg atc gtt acg att gcc       1296
Ile His Pro Thr Lys Gly Lys Lys Asn Ser Arg Ile Val Thr Ile Ala
            390                 395                 400 cct aaa tat tta aag aac atg ccg cca tta act tat caa aat gaa caa       1344
Pro Lys Tyr Leu Lys Asn Met Pro Pro Leu Thr Tyr Gln Asn Glu Gln
        405                 410                 415 tta gag aag caa ccg gca aat ttc gtc tat ttg cac acg gaa cca agt       1392
Leu Glu Lys Gln Pro Ala Asn Phe Val Tyr Leu His Thr Glu Pro Ser
    420                 425                 430 ttc tct gcc ccg tac att ggt gat ccg gca ctt cat gcg gat gga tca       1440
Phe Ser Ala Pro Tyr Ile Gly Asp Pro Ala Leu His Ala Asp Gly Ser
435                 440                 445 cct ggt acg aca gca atc aat gac tgg gga gat aaa gca tcg act gga       1488
Pro Gly Thr Thr Ala Ile Asn Asp Trp Gly Asp Lys Ala Ser Thr Gly
450                 455                 460                 465 caa agt ttc tat gta gct gat cat aag ggt gac tgg atg gca atc tat       1536
Gln Ser Phe Tyr Val Ala Asp His Lys Gly Asp Trp Met Ala Ile Tyr
            470                 475                 480 tat gga ggg aaa aaa gct tgg ttt ttc aac ccg aaa agg aaa aat acg       1584
Tyr Gly Gly Lys Lys Ala Trp Phe Phe Asn Pro Lys Arg Lys Asn Thr
        485                 490                 495 gta tct gga aaa gga att ctt gta aca cca aag aaa ggt ctc gat gcc       1632
Val Ser Gly Lys Gly Ile Leu Val Thr Pro Lys Lys Gly Leu Asp Ala
    500                 505                 510 atc cct gta tat ggt acc gcc tca cca gaa aac agc gct tat gaa gga       1680
Ile Pro Val Tyr Gly Thr Ala Ser Pro Glu Asn Ser Ala Tyr Glu Gly
515                 520                 525
```

-continued

```
aca ggc att cct act ggg tca gaa ggg aaa att aca ccg cta caa tat    1728
Thr Gly Ile Pro Thr Gly Ser Glu Gly Lys Ile Thr Pro Leu Gln Tyr
530             535                 540                 545 acc att gca gcc ggc caa gta tat gtc gca aca aat cct gta aaa gct    1776
Thr Ile Ala Ala Gly Gln Val Tyr Val Ala Thr Asn Pro Val Lys Ala
                550                 555                 560 gac tat tac tat gcc aag tta ttt aat cgg ctt tca gaa aat aaa gtc    1824
Asp Tyr Tyr Tyr Ala Lys Leu Phe Asn Arg Leu Ser Glu Asn Lys Val
            565                 570                 575 gta aaa ggc aat gac gaa tac tat caa att ttc ttt aac cac cgt gtc    1872
Val Lys Gly Asn Asp Glu Tyr Tyr Gln Ile Phe Phe Asn His Arg Val
        580                 585                 590 gca ttt gta aag aag agt gat gta gag gtg aaa aag taa                1911
Ala Phe Val Lys Lys Ser Asp Val Glu Val Lys Lys
    595                 600                 605

<210> SEQ ID NO 65
<211> LENGTH: 636
<212> TYPE: PRT
<213> ORGANISM: Bacillus sporothermodurans

<400> SEQUENCE: 65

Met Leu Leu Arg Arg Leu Lys Asn Arg Thr Leu Leu Phe Thr Phe Ile
    -30                 -25                 -20

Leu Ile Phe Ser Leu Leu Val Met Pro Phe Gly Val Ser Glu Ala Ser
-15                 -10                  -5                  -1   1

Lys His Tyr Thr Ile Asp Thr Asn His His Ser Pro Leu Gln Gln Ala
                5                  10                  15

Phe Thr Lys Ala Ala Lys Glu Phe His Val Pro Glu Ser Leu Leu Met
            20                  25                  30

Ser Val Ala Tyr Asn Glu Ser Arg Trp Leu Asp His His Gly Gln Pro
        35                  40                  45

Ser Thr Ser Gly Gly Tyr Gly Ile Met His Leu Thr Glu Ala Lys Pro
50                  55                  60                  65

Ser Gln Ser Leu Ser Ala Lys Gly Asn Gly Ile Ala His Ser Ser Ala
                70                  75                  80

Ile Asn Val Gln Gln Met Tyr Thr Leu Lys Thr Ala Ala Lys Leu Leu
            85                  90                  95

Gly Val Lys Asp Asn Val Ile Lys Val Asn Pro Glu Gln Asn Ile Arg
        100                 105                 110

Gly Gly Ala Ala Leu Leu Leu Glu Tyr Ala Arg Asp Thr Val Gly His
115                 120                 125

Ile Pro Arg Ser Leu Ala Asp Trp Tyr Gly Ala Val Ala Lys Tyr Ser
130                 135                 140                 145

Gly Ser Asn Asn Gln Val Val Ala Asn Asp Phe Ala Asp Gln Val Tyr
                150                 155                 160

Ala Thr Ile Gln Glu Gly Ala Glu Val Leu Ala Asp Gly Gln His
            165                 170                 175

Leu Val Leu Lys Pro Asn Lys Val Ile Pro Asn Lys Lys Thr Ser Asp
        180                 185                 190

Lys Leu Lys Phe Gln Lys Thr Lys Glu Met Asp Val Asp Cys Pro Lys
    195                 200                 205

Gly Val Asp Cys Arg Tyr Ile Pro Ala Ala Tyr Lys Gln Phe Ser Ser
210                 215                 220                 225

Leu Thr Asp Tyr Gly Asn Tyr Asp Leu Ala Thr Arg Pro Lys Asp Gly
                230                 235                 240
```

```
Asn Asp Ile Arg Tyr Ile Ile Ile His Asp Thr Glu Gly Ser Tyr Asp
                245                 250                 255

Ser Ala Ile Asn Trp Phe Gln Asp Gln Ser Tyr Ala Ser Ala His Tyr
            260                 265                 270

Val Ile Arg Ser Ser Asp Gly Gln Ile Thr Glu Met Val Lys Pro Glu
275                 280                 285

Asp Val Ala Trp Gln Ala Gly Asn Trp Tyr Phe Asn Ala His Ser Ile
290                 295                 300                 305

Gly Ile Glu His Glu Gly Tyr Ala Val Gln Gly Ala Thr Trp Tyr Ser
                310                 315                 320

Glu Gln Met Tyr His Ala Ser Ala Lys Leu Val Lys Tyr Leu Ala Glu
                325                 330                 335

Lys Tyr His Val Pro Leu Asp Arg Ala His Ile Leu Gly His Asp Asn
                340                 345                 350

Val Pro Gly Leu Thr Pro Ala Ala Gln Thr Arg Met His Trp Asp Pro
355                 360                 365

Ala Ala Tyr Trp Asn Trp Glu His Phe Phe Lys Lys Leu Gly Val Pro
370                 375                 380                 385

Ile His Pro Thr Lys Gly Lys Lys Asn Ser Arg Ile Val Thr Ile Ala
                390                 395                 400

Pro Lys Tyr Leu Lys Asn Met Pro Pro Leu Thr Tyr Gln Asn Glu Gln
                405                 410                 415

Leu Glu Lys Gln Pro Ala Asn Phe Val Tyr Leu His Thr Glu Pro Ser
                420                 425                 430

Phe Ser Ala Pro Tyr Ile Gly Asp Pro Ala Leu His Ala Asp Gly Ser
435                 440                 445

Pro Gly Thr Thr Ala Ile Asn Asp Trp Gly Asp Lys Ala Ser Thr Gly
450                 455                 460                 465

Gln Ser Phe Tyr Val Ala Asp His Lys Gly Asp Trp Met Ala Ile Tyr
                470                 475                 480

Tyr Gly Gly Lys Lys Ala Trp Phe Phe Asn Pro Lys Arg Lys Asn Thr
                485                 490                 495

Val Ser Gly Lys Gly Ile Leu Val Thr Pro Lys Lys Gly Leu Asp Ala
                500                 505                 510

Ile Pro Val Tyr Gly Thr Ala Tyr Pro Glu Asn Ser Ala Tyr Glu Gly
                515                 520                 525

Thr Gly Ile Pro Thr Gly Ser Glu Gly Lys Ile Thr Pro Leu Gln Tyr
530                 535                 540                 545

Thr Ile Ala Ala Gly Gln Val Tyr Val Ala Thr Asn Pro Val Lys Ala
                550                 555                 560

Asp Tyr Tyr Tyr Ala Lys Leu Phe Asn Arg Leu Ser Glu Asn Lys Val
                565                 570                 575

Val Lys Gly Asn Asp Glu Tyr Tyr Gln Ile Phe Phe Asn His Arg Val
                580                 585                 590

Ala Phe Val Lys Lys Ser Asp Val Glu Val Lys Lys
                595                 600                 605

<210> SEQ ID NO 66
<211> LENGTH: 605
<212> TYPE: PRT
<213> ORGANISM: Bacillus sporothermodurans
```

<400> SEQUENCE: 66

Ser Lys His Tyr Thr Ile Asp Thr Asn His His Ser Pro Leu Gln Gln
1               5                   10                  15

Ala Phe Thr Lys Ala Ala Lys Glu Phe His Val Pro Glu Ser Leu Leu
            20                  25                  30

Met Ser Val Ala Tyr Asn Glu Ser Arg Trp Leu Asp His His Gly Gln
        35                  40                  45

Pro Ser Thr Ser Gly Gly Tyr Gly Ile Met His Leu Thr Glu Ala Lys
    50                  55                  60

Pro Ser Gln Ser Leu Ser Ala Lys Gly Asn Gly Ile Ala His Ser Ser
65                  70                  75                  80

Ala Ile Asn Val Gln Gln Met Tyr Thr Leu Lys Thr Ala Ala Lys Leu
                85                  90                  95

Leu Gly Val Lys Asp Asn Val Ile Lys Val Asn Pro Glu Gln Asn Ile
            100                 105                 110

Arg Gly Gly Ala Ala Leu Leu Leu Glu Tyr Ala Arg Asp Thr Val Gly
        115                 120                 125

His Ile Pro Arg Ser Leu Ala Asp Trp Tyr Gly Ala Val Ala Lys Tyr
    130                 135                 140

Ser Gly Ser Asn Asn Gln Val Val Ala Asn Asp Phe Ala Asp Gln Val
145                 150                 155                 160

Tyr Ala Thr Ile Gln Glu Gly Ala Glu Val Leu Ala Asp Gly Gln
                165                 170                 175

His Leu Val Leu Lys Pro Asn Lys Val Ile Pro Asn Lys Lys Thr Ser
            180                 185                 190

Asp Lys Leu Lys Phe Gln Lys Thr Lys Glu Met Asp Val Asp Cys Pro
        195                 200                 205

Lys Gly Val Asp Cys Arg Tyr Ile Pro Ala Ala Tyr Lys Gln Phe Ser
    210                 215                 220

Ser Leu Thr Asp Tyr Gly Asn Tyr Asp Leu Ala Thr Arg Pro Lys Asp
225                 230                 235                 240

Gly Asn Asp Ile Arg Tyr Ile Ile His Asp Thr Glu Gly Ser Tyr
                245                 250                 255

Asp Ser Ala Ile Asn Trp Phe Gln Asp Gln Ser Tyr Ala Ser Ala His
            260                 265                 270

Tyr Val Ile Arg Ser Ser Asp Gly Gln Ile Thr Glu Met Val Lys Pro
        275                 280                 285

Glu Asp Val Ala Trp Gln Ala Gly Asn Trp Tyr Phe Asn Ala His Ser
    290                 295                 300

Ile Gly Ile Glu His Glu Gly Tyr Ala Val Gln Gly Ala Thr Trp Tyr
305                 310                 315                 320

Ser Glu Gln Met Tyr His Ala Ser Ala Lys Leu Val Lys Tyr Leu Ala
                325                 330                 335

Glu Lys Tyr His Val Pro Leu Asp Arg Ala His Ile Leu Gly His Asp
            340                 345                 350

Asn Val Pro Gly Leu Thr Pro Ala Ala Gln Thr Arg Met His Trp Asp
        355                 360                 365

Pro Ala Ala Tyr Trp Asn Trp Glu His Phe Phe Lys Lys Leu Gly Val
    370                 375                 380

Pro Ile His Pro Thr Lys Gly Lys Lys Asn Ser Arg Ile Val Thr Ile
385                 390                 395                 400

```
Ala Pro Lys Tyr Leu Lys Asn Met Pro Pro Leu Thr Tyr Gln Asn Glu
        405                 410                 415

Gln Leu Glu Lys Gln Pro Ala Asn Phe Val Tyr Leu His Thr Glu Pro
            420                 425                 430

Ser Phe Ser Ala Pro Tyr Ile Gly Asp Pro Ala Leu His Ala Asp Gly
        435                 440                 445

Ser Pro Gly Thr Thr Ala Ile Asn Asp Trp Gly Asp Lys Ala Ser Thr
    450                 455                 460

Gly Gln Ser Phe Tyr Val Ala Asp His Lys Gly Asp Trp Met Ala Ile
465                 470                 475                 480

Tyr Tyr Gly Gly Lys Lys Ala Trp Phe Phe Asn Pro Lys Arg Lys Asn
            485                 490                 495

Thr Val Ser Gly Lys Gly Ile Leu Val Thr Pro Lys Lys Gly Leu Asp
            500                 505                 510

Ala Ile Pro Val Tyr Gly Thr Ala Tyr Pro Glu Asn Ser Ala Tyr Glu
            515                 520                 525

Gly Thr Gly Ile Pro Thr Gly Ser Glu Gly Lys Ile Thr Pro Leu Gln
    530                 535                 540

Tyr Thr Ile Ala Ala Gly Gln Val Tyr Val Ala Thr Asn Pro Val Lys
545                 550                 555                 560

Ala Asp Tyr Tyr Tyr Ala Lys Leu Phe Asn Arg Leu Ser Glu Asn Lys
            565                 570                 575

Val Val Lys Gly Asn Asp Glu Tyr Tyr Gln Ile Phe Asn His Arg
            580                 585                 590

Val Ala Phe Val Lys Lys Ser Asp Val Glu Val Lys Lys
        595                 600                 605

<210> SEQ ID NO 67
<211> LENGTH: 1941
<212> TYPE: DNA
<213> ORGANISM: Paenibacillus pini
<220> FEATURE:
<221> NAME/KEY: CDS
<222> LOCATION: (1)..(1938)
<220> FEATURE:
<221> NAME/KEY: sig_peptide
<222> LOCATION: (1)..(108)
<220> FEATURE:
<221> NAME/KEY: mat_peptide
<222> LOCATION: (109)..(1938)

<400> SEQUENCE: 67 ttg aaa cta ctg cga aca atc caa tgg aaa aag ctg tcg ctc gca ctc      48
Leu Lys Leu Leu Arg Thr Ile Gln Trp Lys Lys Leu Ser Leu Ala Leu
    -35                 -30                 -25 aca gtc gcc tca ctg gcg gtt tcc gga ttc aca ccc gga ctt cct gat      96
Thr Val Ala Ser Leu Ala Val Ser Gly Phe Thr Pro Gly Leu Pro Asp
        -20                 -15                 -10              -5 cca ttc aag gcc gta cct tct gta tat gcg gag caa gac aag acg aat     144
Pro Phe Lys Ala Val Pro Ser Val Tyr Ala Glu Gln Asp Lys Thr Asn
            -1  1               5                   10 tcg ttg caa caa gcc ttc gaa tca gcg gct aag gag ttc gga gtg cct     192
Ser Leu Gln Gln Ala Phe Glu Ser Ala Ala Lys Glu Phe Gly Val Pro
        15                  20                  25 gtg agc att ttg atg tcc gtt tcc tac aac ctt aca agg tgg gag cat     240
Val Ser Ile Leu Met Ser Val Ser Tyr Asn Leu Thr Arg Trp Glu His
    30                  35                  40
```

-continued

| | | |
|---|---|---|
| cat cat ggc caa ccc agt act tct ggt gga tac ggt atc atg cat ttg<br>His His Gly Gln Pro Ser Thr Ser Gly Gly Tyr Gly Ile Met His Leu<br>45                         50                      55                      60 | 288 |
| acc gac ttg ccg gta cag gat aaa gaa gac cat aac gga acc gac gac<br>Thr Asp Leu Pro Val Gln Asp Lys Glu Asp His Asn Gly Thr Asp Asp<br>                      65                      70                      75 | 336 |
| gaa gag aac cca tcg act tcg gac gat ccg agc gtt cat acc cta tct<br>Glu Glu Asn Pro Ser Thr Ser Asp Asp Pro Ser Val His Thr Leu Ser<br>            80                      85                      90 | 384 |
| gcg gcg gca caa cta ttg aat ctt gat ccg gac tta ctg aag cag gat<br>Ala Ala Ala Gln Leu Leu Asn Leu Asp Pro Asp Leu Leu Lys Gln Asp<br>        95                      100                     105 | 432 |
| cct gtg tgc aac att cga ggc gga gcc gca ttg ctg gcg aag tac gct<br>Pro Val Cys Asn Ile Arg Gly Gly Ala Ala Leu Leu Ala Lys Tyr Ala<br>110                        115                     120 | 480 |
| cag gaa acc ctc ggt aaa ctg acg gca tcg gaa tcc gat tgg tat ggt<br>Gln Glu Thr Leu Gly Lys Leu Thr Ala Ser Glu Ser Asp Trp Tyr Gly<br>125                        130                     135                   140 | 528 |
| ggc gtt gcc aaa tac agc ggt tct caa gat tcg ggg gcc tct ctg gag<br>Gly Val Ala Lys Tyr Ser Gly Ser Gln Asp Ser Gly Ala Ser Leu Glu<br>                      145                     150                     155 | 576 |
| ttt gcc aat aat gta ttt gat acg att cag cag gga ata tcg cgg caa<br>Phe Ala Asn Asn Val Phe Asp Thr Ile Gln Gln Gly Ile Ser Arg Gln<br>                160                     165                     170 | 624 |
| act tcg gaa gga cag atg cta cgt ctt cca tcc aag gag gtg aag cct<br>Thr Ser Glu Gly Gln Met Leu Arg Leu Pro Ser Lys Glu Val Lys Pro<br>175                        180                     185 | 672 |
| aac ctg gat acc gtt caa acg ctt cat ctg cgt cca tcg aaa ccc gat<br>Asn Leu Asp Thr Val Gln Thr Leu His Leu Arg Pro Ser Lys Pro Asp<br>            190                     195                     200 | 720 |
| aac gtc gag tgc cct cgc aat ctc cac tgc aga tct gtt cct gca gcc<br>Asn Val Glu Cys Pro Arg Asn Leu His Cys Arg Ser Val Pro Ala Ala<br>205                        210                     215                   220 | 768 |
| tat cag cag aac ggg gat gac ccg tcg gat tat tcc aat tat gat ctt<br>Tyr Gln Gln Asn Gly Asp Asp Pro Ser Asp Tyr Ser Asn Tyr Asp Leu<br>                      225                     230                     235 | 816 |
| gcc gac cgt ccc aaa ttt ggt cct gat att cgc tat att gtc att cat<br>Ala Asp Arg Pro Lys Phe Gly Pro Asp Ile Arg Tyr Ile Val Ile His<br>240                        245                     250 | 864 |
| gat acc gaa gaa acc tat cag gat acg ctc aat ata ttt acc aat ccg<br>Asp Thr Glu Glu Thr Tyr Gln Asp Thr Leu Asn Ile Phe Thr Asn Pro<br>                255                     260                     265 | 912 |
| aat tcg aat gtc agc gcc cac tat gtt ctc cgt tcg tcc gac ggg cag<br>Asn Ser Asn Val Ser Ala His Tyr Val Leu Arg Ser Ser Asp Gly Gln<br>270                        275                     280 | 960 |
| atc acg caa atg gtc aag aca aag gat gta ccg tgg cat gca ggc aac<br>Ile Thr Gln Met Val Lys Thr Lys Asp Val Pro Trp His Ala Gly Asn<br>285                        290                     295                   300 | 1008 |
| tgg tat ttc aat atg cac tcg att ggc gta gag cat gag ggc ttt gct<br>Trp Tyr Phe Asn Met His Ser Ile Gly Val Glu His Glu Gly Phe Ala<br>                      305                     310                     315 | 1056 |
| atg gaa gga gca acc tgg ttc acc gag agg ctt tac cgt tca tct gca<br>Met Glu Gly Ala Thr Trp Phe Thr Glu Arg Leu Tyr Arg Ser Ser Ala<br>                      320                     325                     330 | 1104 |
| gca ttg gta cat tat ctg gcg gag aaa tat gat att ccg ctc gat cgg<br>Ala Leu Val His Tyr Leu Ala Glu Lys Tyr Asp Ile Pro Leu Asp Arg<br>335                        340                     345 | 1152 |

| | | | | | | | | | | | | | | |
|---|---|---|---|---|---|---|---|---|---|---|---|---|---|---|
| gcc | cat | att | atc | ggc | cat | gat | gaa | ata | ccg | ggt | ctc | act | cca | gcc cgt | 1200 |
| Ala | His | Ile | Ile | Gly | His | Asp | Glu | Ile | Pro | Gly | Leu | Thr | Pro | Ala Arg | |
| | 350 | | | | 355 | | | | 360 | | | | | | |

```
gcc cat att atc ggc cat gat gaa ata ccg ggt ctc act cca gcc cgt       1200
Ala His Ile Ile Gly His Asp Glu Ile Pro Gly Leu Thr Pro Ala Arg
    350             355             360 caa ggt gtt atg cat cag gat ccc ggc cct ttt tgg gat tgg gag cac       1248
Gln Gly Val Met His Gln Asp Pro Gly Pro Phe Trp Asp Trp Glu His
365             370             375             380 tac atg gag cta gtt gga gca ccg atc cac tcc aaa cat ggt act aaa       1296
Tyr Met Glu Leu Val Gly Ala Pro Ile His Ser Lys His Gly Thr Lys
                385             390             395 gac att gtg aca atc aag cct ggc ttt aaa acc aat caa cca gat atc       1344
Asp Ile Val Thr Ile Lys Pro Gly Phe Lys Thr Asn Gln Pro Asp Ile
        400             405             410 aat gat gcg cct gct cag cca tct aac ttc ctt tac tta tat aaa gag       1392
Asn Asp Ala Pro Ala Gln Pro Ser Asn Phe Leu Tyr Leu Tyr Lys Glu
            415             420             425 ccc gac ttt aac gct gag ctg att gat gat ccc gcc ctt gtc tct caa       1440
Pro Asp Phe Asn Ala Glu Leu Ile Asp Asp Pro Ala Leu Val Ser Gln
430             435             440 aac aag aaa gac ggg ttc agc ata gga gcc aag gct acc ata ggg caa       1488
Asn Lys Lys Asp Gly Phe Ser Ile Gly Ala Lys Ala Thr Ile Gly Gln
445             450             455             460 acc ttc tca ctt gcc ggc aag cag ggg gat tgg acc gca atc tgg ttc       1536
Thr Phe Ser Leu Ala Gly Lys Gln Gly Asp Trp Thr Ala Ile Trp Phe
                465             470             475 gga gga cag aaa gcc tgg ttc tat aat ccg aaa gga aaa aat acg gtt       1584
Gly Gly Gln Lys Ala Trp Phe Tyr Asn Pro Lys Gly Lys Asn Thr Val
        480             485             490 tca ggt aag ggg atg cta gtc act ccg aaa gcc ggc gca gct tcc att       1632
Ser Gly Lys Gly Met Leu Val Thr Pro Lys Ala Gly Ala Ala Ser Ile
            495             500             505 ccg gtc tat ggt gca gct tat ccg gaa gcc gca tat cca gcc gat           1680
Pro Val Tyr Gly Ala Ala Tyr Pro Glu Ala Ala Tyr Pro Ala Asp
510             515             520 atc acg cct aat gtg ctg gtt ccg ctg cag tac act att tcg cat gga       1728
Ile Thr Pro Asn Val Leu Val Pro Leu Gln Tyr Thr Ile Ser His Gly
525             530             535             540 cag tcg tat gtt gcc gta gaa aaa aac aaa agc gat gat tac tat gct       1776
Gln Ser Tyr Val Ala Val Glu Lys Asn Lys Ser Asp Asp Tyr Tyr Ala
                545             550             555 ccg gta tac acg aat gac cct tat gcg acg aat aag ctg atc aag agc       1824
Pro Val Tyr Thr Asn Asp Pro Tyr Ala Thr Asn Lys Leu Ile Lys Ser
        560             565             570 aaa gaa gag ttc tac cga ata tac ttc aat cac cgt ttc gcc ttt gtg       1872
Lys Glu Glu Phe Tyr Arg Ile Tyr Phe Asn His Arg Phe Ala Phe Val
            575             580             585 aaa gcc tct gat gtc gag aag gta cgg aag cag tcg gtg aat gaa aca       1920
Lys Ala Ser Asp Val Glu Lys Val Arg Lys Gln Ser Val Asn Glu Thr
590             595             600 aca cgt cag gat atc cca taa                                           1941
Thr Arg Gln Asp Ile Pro
605             610
```

<210> SEQ ID NO 68
<211> LENGTH: 646
<212> TYPE: PRT
<213> ORGANISM: Paenibacillus pini

<400> SEQUENCE: 68

```
Leu Lys Leu Leu Arg Thr Ile Gln Trp Lys Lys Leu Ser Leu Ala Leu
    -35             -30             -25
```

```
Thr Val Ala Ser Leu Ala Val Ser Gly Phe Thr Pro Gly Leu Pro Asp
-20             -15                 -10                 -5

Pro Phe Lys Ala Val Pro Ser Val Tyr Ala Glu Gln Asp Lys Thr Asn
        -1  1               5                   10

Ser Leu Gln Gln Ala Phe Glu Ser Ala Ala Lys Glu Phe Gly Val Pro
        15              20                  25

Val Ser Ile Leu Met Ser Val Ser Tyr Asn Leu Thr Arg Trp Glu His
    30              35                  40

His His Gly Gln Pro Ser Thr Ser Gly Gly Tyr Gly Ile Met His Leu
45              50                  55                      60

Thr Asp Leu Pro Val Gln Asp Lys Glu Asp His Asn Gly Thr Asp Asp
            65                  70                  75

Glu Glu Asn Pro Ser Thr Ser Asp Asp Pro Ser Val His Thr Leu Ser
            80                  85                  90

Ala Ala Ala Gln Leu Leu Asn Leu Asp Pro Asp Leu Leu Lys Gln Asp
            95                  100                 105

Pro Val Cys Asn Ile Arg Gly Gly Ala Ala Leu Leu Ala Lys Tyr Ala
            110                 115                 120

Gln Glu Thr Leu Gly Lys Leu Thr Ala Ser Glu Ser Asp Trp Tyr Gly
125                 130                 135                 140

Gly Val Ala Lys Tyr Ser Gly Ser Gln Asp Ser Gly Ala Ser Leu Glu
                145                 150                 155

Phe Ala Asn Asn Val Phe Asp Thr Ile Gln Gln Gly Ile Ser Arg Gln
                160                 165                 170

Thr Ser Glu Gly Gln Met Leu Arg Leu Pro Ser Lys Glu Val Lys Pro
            175                 180                 185

Asn Leu Asp Thr Val Gln Thr Leu His Leu Arg Pro Ser Lys Pro Asp
            190                 195                 200

Asn Val Glu Cys Pro Arg Asn Leu His Cys Arg Ser Val Pro Ala Ala
205                 210                 215                 220

Tyr Gln Gln Asn Gly Asp Asp Pro Ser Asp Tyr Ser Asn Tyr Asp Leu
                225                 230                 235

Ala Asp Arg Pro Lys Phe Gly Pro Asp Ile Arg Tyr Ile Val Ile His
            240                 245                 250

Asp Thr Glu Glu Thr Tyr Gln Asp Thr Leu Asn Ile Phe Thr Asn Pro
            255                 260                 265

Asn Ser Asn Val Ser Ala His Tyr Val Leu Arg Ser Ser Asp Gly Gln
            270                 275                 280

Ile Thr Gln Met Val Lys Thr Lys Asp Val Pro Trp His Ala Gly Asn
285                 290                 295                 300

Trp Tyr Phe Asn Met His Ser Ile Gly Val Glu His Glu Gly Phe Ala
                305                 310                 315

Met Glu Gly Ala Thr Trp Phe Thr Glu Arg Leu Tyr Arg Ser Ser Ala
            320                 325                 330

Ala Leu Val His Tyr Leu Ala Glu Lys Tyr Asp Ile Pro Leu Asp Arg
            335                 340                 345

Ala His Ile Ile Gly His Asp Glu Ile Pro Gly Leu Thr Pro Ala Arg
            350                 355                 360

Gln Gly Val Met His Gln Asp Pro Gly Pro Phe Trp Asp Trp Glu His
365                 370                 375                 380

Tyr Met Glu Leu Val Gly Ala Pro Ile His Ser Lys Gly Thr Lys
                385                 390                 395
```

Asp Ile Val Thr Ile Lys Pro Gly Phe Lys Thr Asn Gln Pro Asp Ile
            400                 405                 410

Asn Asp Ala Pro Ala Gln Pro Ser Asn Phe Leu Tyr Leu Tyr Lys Glu
            415                 420                 425

Pro Asp Phe Asn Ala Glu Leu Ile Asp Asp Pro Ala Leu Val Ser Gln
            430                 435                 440

Asn Lys Lys Asp Gly Phe Ser Ile Gly Ala Lys Ala Thr Ile Gly Gln
445                 450                 455                 460

Thr Phe Ser Leu Ala Gly Lys Gln Gly Asp Trp Thr Ala Ile Trp Phe
                465                 470                 475

Gly Gly Gln Lys Ala Trp Phe Tyr Asn Pro Lys Gly Lys Asn Thr Val
            480                 485                 490

Ser Gly Lys Gly Met Leu Val Thr Pro Lys Ala Gly Ala Ala Ser Ile
            495                 500                 505

Pro Val Tyr Gly Ala Ala Tyr Pro Glu Ala Ala Ala Tyr Pro Ala Asp
            510                 515                 520

Ile Thr Pro Asn Val Leu Val Pro Leu Gln Tyr Thr Ile Ser His Gly
525                 530                 535                 540

Gln Ser Tyr Val Ala Val Glu Lys Asn Lys Ser Asp Asp Tyr Tyr Ala
                545                 550                 555

Pro Val Tyr Thr Asn Asp Pro Tyr Ala Thr Asn Lys Leu Ile Lys Ser
            560                 565                 570

Lys Glu Glu Phe Tyr Arg Ile Tyr Phe Asn His Arg Phe Ala Phe Val
            575                 580                 585

Lys Ala Ser Asp Val Glu Lys Val Arg Lys Ser Val Asn Glu Thr
            590                 595                 600

Thr Arg Gln Asp Ile Pro
605                 610

<210> SEQ ID NO 69
<211> LENGTH: 610
<212> TYPE: PRT
<213> ORGANISM: Paenibacillus pini

<400> SEQUENCE: 69

Val Pro Ser Val Tyr Ala Glu Gln Asp Lys Thr Asn Ser Leu Gln Gln
1               5                   10                  15

Ala Phe Glu Ser Ala Ala Lys Glu Phe Gly Val Pro Val Ser Ile Leu
            20                  25                  30

Met Ser Val Ser Tyr Asn Leu Thr Arg Trp Glu His His Gly Gln
            35                  40                  45

Pro Ser Thr Ser Gly Gly Tyr Gly Ile Met His Leu Thr Asp Leu Pro
50                  55                  60

Val Gln Asp Lys Glu Asp His Asn Gly Thr Asp Glu Glu Asn Pro
65                  70                  75                  80

Ser Thr Ser Asp Asp Pro Ser Val His Thr Leu Ser Ala Ala Ala Gln
            85                  90                  95

Leu Leu Asn Leu Asp Pro Asp Leu Leu Lys Gln Asp Pro Val Cys Asn
            100                 105                 110

Ile Arg Gly Gly Ala Ala Leu Leu Ala Lys Tyr Ala Gln Glu Thr Leu
            115                 120                 125

Gly Lys Leu Thr Ala Ser Glu Ser Asp Trp Tyr Gly Gly Val Ala Lys
            130                 135                 140

Tyr Ser Gly Ser Gln Asp Ser Gly Ala Ser Leu Glu Phe Ala Asn Asn
145                 150                 155                 160

```
Val Phe Asp Thr Ile Gln Gln Gly Ile Ser Arg Gln Thr Ser Glu Gly
                165                 170                 175

Gln Met Leu Arg Leu Pro Ser Lys Glu Val Lys Pro Asn Leu Asp Thr
            180                 185                 190

Val Gln Thr Leu His Leu Arg Pro Ser Lys Pro Asp Asn Val Glu Cys
        195                 200                 205

Pro Arg Asn Leu His Cys Arg Ser Val Pro Ala Ala Tyr Gln Gln Asn
    210                 215                 220

Gly Asp Asp Pro Ser Asp Tyr Ser Asn Tyr Asp Leu Ala Asp Arg Pro
225                 230                 235                 240

Lys Phe Gly Pro Asp Ile Arg Tyr Ile Val Ile His Asp Thr Glu Glu
                245                 250                 255

Thr Tyr Gln Asp Thr Leu Asn Ile Phe Thr Asn Pro Asn Ser Asn Val
            260                 265                 270

Ser Ala His Tyr Val Leu Arg Ser Ser Asp Gly Gln Ile Thr Gln Met
        275                 280                 285

Val Lys Thr Lys Asp Val Pro Trp His Ala Gly Asn Trp Tyr Phe Asn
    290                 295                 300

Met His Ser Ile Gly Val Glu His Glu Gly Phe Ala Met Glu Gly Ala
305                 310                 315                 320

Thr Trp Phe Thr Glu Arg Leu Tyr Arg Ser Ser Ala Ala Leu Val His
                325                 330                 335

Tyr Leu Ala Glu Lys Tyr Asp Ile Pro Leu Asp Arg Ala His Ile Ile
            340                 345                 350

Gly His Asp Glu Ile Pro Gly Leu Thr Pro Ala Arg Gln Gly Val Met
        355                 360                 365

His Gln Asp Pro Gly Pro Phe Trp Asp Trp Glu His Tyr Met Glu Leu
    370                 375                 380

Val Gly Ala Pro Ile His Ser Lys His Gly Thr Lys Asp Ile Val Thr
385                 390                 395                 400

Ile Lys Pro Gly Phe Lys Thr Asn Gln Pro Asp Ile Asn Asp Ala Pro
                405                 410                 415

Ala Gln Pro Ser Asn Phe Leu Tyr Leu Tyr Lys Glu Pro Asp Phe Asn
            420                 425                 430

Ala Glu Leu Ile Asp Asp Pro Ala Leu Val Ser Gln Asn Lys Lys Asp
        435                 440                 445

Gly Phe Ser Ile Gly Ala Lys Ala Thr Ile Gly Gln Thr Phe Ser Leu
    450                 455                 460

Ala Gly Lys Gln Gly Asp Trp Thr Ala Ile Trp Phe Gly Gly Gln Lys
465                 470                 475                 480

Ala Trp Phe Tyr Asn Pro Lys Gly Lys Asn Thr Val Ser Gly Lys Gly
                485                 490                 495

Met Leu Val Thr Pro Lys Ala Gly Ala Ala Ser Ile Pro Val Tyr Gly
            500                 505                 510

Ala Ala Tyr Pro Glu Ala Ala Ala Tyr Pro Ala Asp Ile Thr Pro Asn
        515                 520                 525

Val Leu Val Pro Leu Gln Tyr Thr Ile Ser His Gly Gln Ser Tyr Val
    530                 535                 540

Ala Val Glu Lys Asn Lys Ser Asp Asp Tyr Tyr Ala Pro Val Tyr Thr
545                 550                 555                 560

Asn Asp Pro Tyr Ala Thr Asn Lys Leu Ile Lys Ser Lys Glu Glu Phe
                565                 570                 575
```

```
Tyr Arg Ile Tyr Phe Asn His Arg Phe Ala Phe Val Lys Ala Ser Asp
            580                 585                 590

Val Glu Lys Val Arg Lys Gln Ser Val Asn Glu Thr Thr Arg Gln Asp
        595                 600                 605

Ile Pro
    610

<210> SEQ ID NO 70
<211> LENGTH: 711
<212> TYPE: DNA
<213> ORGANISM: Bacillus cohnii
<220> FEATURE:
<221> NAME/KEY: CDS
<222> LOCATION: (1)..(708)
<220> FEATURE:
<221> NAME/KEY: sig_peptide
<222> LOCATION: (1)..(60)
<220> FEATURE:
<221> NAME/KEY: mat_peptide
<222> LOCATION: (61)..(708)

<400> SEQUENCE: 70 atg aaa ata gta gca act ttt tta tgt gta ttt att ttt gtc tgt ggt        48
Met Lys Ile Val Ala Thr Phe Leu Cys Val Phe Ile Phe Val Cys Gly
-20             -15                 -10                 -5 tgt tca aag gct gaa gtc aca aat gtc gag agt gat gag aca ata tca       96
Cys Ser Lys Ala Glu Val Thr Asn Val Glu Ser Asp Glu Thr Ile Ser
        -1  1               5                   10 tta gtt aaa aaa gaa gat gaa tta act tat aaa aag cca gat aca aat      144
Leu Val Lys Lys Glu Asp Glu Leu Thr Tyr Lys Lys Pro Asp Thr Asn
            15                  20                  25 ccg agt gaa tct tta tat gta act tcg tac tat tta cct aac gat aat      192
Pro Ser Glu Ser Leu Tyr Val Thr Ser Tyr Tyr Leu Pro Asn Asp Asn
        30                  35                  40 tcg cga cgg aga aca gca gaa gtt aca cat ata atg att cat tac acc      240
Ser Arg Arg Arg Thr Ala Glu Val Thr His Ile Met Ile His Tyr Thr
45                  50                  55                  60 agt aac gca gca agg aat cca cag aac ccg tat gta ata gaa gat att      288
Ser Asn Ala Ala Arg Asn Pro Gln Asn Pro Tyr Val Ile Glu Asp Ile
                65                  70                  75 tac gca ctg ttt gaa gaa tat ggc gtt tca gca cat tat att att gat      336
Tyr Ala Leu Phe Glu Glu Tyr Gly Val Ser Ala His Tyr Ile Ile Asp
            80                  85                  90 cgc gaa ggt aat att ttt caa tta gtg gat gag agt aga gtg gcg ttt      384
Arg Glu Gly Asn Ile Phe Gln Leu Val Asp Glu Ser Arg Val Ala Phe
        95                  100                 105 cat gca gga aaa gga aac gat tta aac ttt ttg gac tac cga aat aac      432
His Ala Gly Lys Gly Asn Asp Leu Asn Phe Leu Asp Tyr Arg Asn Asn
    110                 115                 120 atg aat gaa tat tca att ggt atc gaa ctt atg gca att gga acg aaa      480
Met Asn Glu Tyr Ser Ile Gly Ile Glu Leu Met Ala Ile Gly Thr Lys
125                 130                 135                 140 gaa gaa atg agc cta aat tta cag gaa ggt caa tac gaa cta ata cca      528
Glu Glu Met Ser Leu Asn Leu Gln Glu Gly Gln Tyr Glu Leu Ile Pro
                145                 150                 155 cca tca cat ata ggt tat aca gat gag caa tat cac tca tta gca aaa      576
Pro Ser His Ile Gly Tyr Thr Asp Glu Gln Tyr His Ser Leu Ala Lys
            160                 165                 170 ctg tta gaa gac ttg tat gag cgt tat cca aag gta tta aaa aac aga      624
Leu Leu Glu Asp Leu Tyr Glu Arg Tyr Pro Lys Val Leu Lys Asn Arg
        175                 180                 185
```

```
gag aac gta gta ggg cat gat gaa tac gca cct gtt cga aaa tca gat        672
Glu Asn Val Val Gly His Asp Glu Tyr Ala Pro Val Arg Lys Ser Asp
    190                 195                 200 cct gga agt tta ttc gat tgg aat aaa att ggt ttc tga                    711
Pro Gly Ser Leu Phe Asp Trp Asn Lys Ile Gly Phe
205                 210                 215
```

<210> SEQ ID NO 71
<211> LENGTH: 236
<212> TYPE: PRT
<213> ORGANISM: Bacillus cohnii

<400> SEQUENCE: 71

```
Met Lys Ile Val Ala Thr Phe Leu Cys Val Phe Ile Phe Val Cys Gly
-20             -15                 -10                 -5

Cys Ser Lys Ala Glu Val Thr Asn Val Glu Ser Asp Glu Thr Ile Ser
            -1  1               5                   10

Leu Val Lys Lys Glu Asp Glu Leu Thr Tyr Lys Lys Pro Asp Thr Asn
        15                  20                  25

Pro Ser Glu Ser Leu Tyr Val Thr Ser Tyr Tyr Leu Pro Asn Asp Asn
30                  35                  40

Ser Arg Arg Arg Thr Ala Glu Val Thr His Ile Met Ile His Tyr Thr
45                  50                  55                  60

Ser Asn Ala Ala Arg Asn Pro Gln Asn Pro Tyr Val Ile Glu Asp Ile
                65                  70                  75

Tyr Ala Leu Phe Glu Glu Tyr Gly Val Ser Ala His Tyr Ile Ile Asp
                80                  85                  90

Arg Glu Gly Asn Ile Phe Gln Leu Val Asp Glu Ser Arg Val Ala Phe
            95                  100                 105

His Ala Gly Lys Gly Asn Asp Leu Asn Phe Leu Asp Tyr Arg Asn Asn
        110                 115                 120

Met Asn Glu Tyr Ser Ile Gly Ile Glu Leu Met Ala Ile Gly Thr Lys
125                 130                 135                 140

Glu Glu Met Ser Leu Asn Leu Gln Glu Gly Gln Tyr Glu Leu Ile Pro
                145                 150                 155

Pro Ser His Ile Gly Tyr Thr Asp Glu Gln Tyr His Ser Leu Ala Lys
                160                 165                 170

Leu Leu Glu Asp Leu Tyr Glu Arg Tyr Pro Lys Val Leu Lys Asn Arg
            175                 180                 185

Glu Asn Val Val Gly His Asp Glu Tyr Ala Pro Val Arg Lys Ser Asp
        190                 195                 200

Pro Gly Ser Leu Phe Asp Trp Asn Lys Ile Gly Phe
205                 210                 215
```

<210> SEQ ID NO 72
<211> LENGTH: 216
<212> TYPE: PRT
<213> ORGANISM: Bacillus cohnii

<400> SEQUENCE: 72

```
Glu Val Thr Asn Val Glu Ser Asp Glu Thr Ile Ser Leu Val Lys Lys
1               5                   10                  15

Glu Asp Glu Leu Thr Tyr Lys Lys Pro Asp Thr Asn Pro Ser Glu Ser
            20                  25                  30

Leu Tyr Val Thr Ser Tyr Tyr Leu Pro Asn Asp Asn Ser Arg Arg Arg
        35                  40                  45
```

```
Thr Ala Glu Val Thr His Ile Met Ile His Tyr Thr Ser Asn Ala Ala
    50                  55                  60

Arg Asn Pro Gln Asn Pro Tyr Val Ile Glu Asp Ile Tyr Ala Leu Phe
65                  70                  75                  80

Glu Glu Tyr Gly Val Ser Ala His Tyr Ile Ile Asp Arg Glu Gly Asn
                85                  90                  95

Ile Phe Gln Leu Val Asp Glu Ser Arg Val Ala Phe His Ala Gly Lys
                100                 105                 110

Gly Asn Asp Leu Asn Phe Leu Asp Tyr Arg Asn Asn Met Asn Glu Tyr
                115                 120                 125

Ser Ile Gly Ile Glu Leu Met Ala Ile Gly Thr Lys Glu Glu Met Ser
130                 135                 140

Leu Asn Leu Gln Glu Gly Gln Tyr Glu Leu Ile Pro Pro Ser His Ile
145                 150                 155                 160

Gly Tyr Thr Asp Glu Gln Tyr His Ser Leu Ala Lys Leu Leu Glu Asp
                165                 170                 175

Leu Tyr Glu Arg Tyr Pro Lys Val Leu Lys Asn Arg Glu Asn Val Val
                180                 185                 190

Gly His Asp Glu Tyr Ala Pro Val Arg Lys Ser Asp Pro Gly Ser Leu
                195                 200                 205

Phe Asp Trp Asn Lys Ile Gly Phe
        210                 215

<210> SEQ ID NO 73
<211> LENGTH: 1356
<212> TYPE: DNA
<213> ORGANISM: Kribbella sp
<220> FEATURE:
<221> NAME/KEY: CDS
<222> LOCATION: (1)..(1353)
<220> FEATURE:
<221> NAME/KEY: sig_peptide
<222> LOCATION: (1)..(78)
<220> FEATURE:
<221> NAME/KEY: mat_peptide
<222> LOCATION: (79)..(1353)

<400> SEQUENCE: 73 atg agt cac aaa gtt ccc aga ctg gtc gcg gtg ctc gcc gcc ggc gca     48
Met Ser His Lys Val Pro Arg Leu Val Ala Val Leu Ala Ala Gly Ala
    -25                 -20                 -15 ctg gcc ttc agc gcg ctc ccc agc aac gca tcc acg ccg gtc gag acc     96
Leu Ala Phe Ser Ala Leu Pro Ser Asn Ala Ser Thr Pro Val Glu Thr
-10                  -5                  -1 1               5 ggc agc acc tcg acg ctg tcc gag gcc ttc aag acc gcc gcg acc cag    144
Gly Ser Thr Ser Thr Leu Ser Glu Ala Phe Lys Thr Ala Ala Thr Gln
                10                  15                  20 tac gac gta ccg cgt gag ctc ctg gtc ggc atc ggg tac gcc gag tcg    192
Tyr Asp Val Pro Arg Glu Leu Leu Val Gly Ile Gly Tyr Ala Glu Ser
            25                  30                  35 cac ctc gac ggc cac gac ggt cag ccc agc cag gcc aac ggg tac ggc    240
His Leu Asp Gly His Asp Gly Gln Pro Ser Gln Ala Asn Gly Tyr Gly
        40                  45                  50 gtc atg cac ctg gcc agc aac ccg agc aac ccg acc atg tcc gag gcg    288
Val Met His Leu Ala Ser Asn Pro Ser Asn Pro Thr Met Ser Glu Ala
55                  60                  65                  70 gcg aag ctc acc ggc ctc ccg gtc gag aag ctg gcc aag gac gag agc    336
Ala Lys Leu Thr Gly Leu Pro Val Glu Lys Leu Ala Lys Asp Glu Ser
                75                  80                  85
```

```
gcg aac gtg ctc ggc gcg gcc gcc gta ctc gac gcg tac gcc gac aag     384
Ala Asn Val Leu Gly Ala Ala Ala Val Leu Asp Ala Tyr Ala Asp Lys
         90                  95                 100 gcc ggc ctg caa ggg caa acg cgt gac gac atc ggc aag tgg tac gag     432
Ala Gly Leu Gln Gly Gln Thr Arg Asp Asp Ile Gly Lys Trp Tyr Glu
        105                 110                 115 gtc gtc gcc cag tac tcg cac tcc gcc gac ggc ccg acc gcg cgc ctc     480
Val Val Ala Gln Tyr Ser His Ser Ala Asp Gly Pro Thr Ala Arg Leu
    120                 125                 130 tac acc gac gag gtc tac cgg atc gtc ggc ctc gga gtc ggc gcc gaa     528
Tyr Thr Asp Glu Val Tyr Arg Ile Val Gly Leu Gly Val Gly Ala Glu
135                 140                 145                 150 ggc gtc tcc acc cag ccg gtc aag gtg acg ccg gac cgc ggc aag tac     576
Gly Val Ser Thr Gln Pro Val Lys Val Thr Pro Asp Arg Gly Lys Tyr
                155                 160                 165 gcg aac gtc gcc ccg ctc ggc acc cgg acg ccg gcc tcg atc cag gcc     624
Ala Asn Val Ala Pro Leu Gly Thr Arg Thr Pro Ala Ser Ile Gln Ala
            170                 175                 180 gtc gac tac ccg ggc gcg atc tgg aac gcg gcc agc acc agc aac tac     672
Val Asp Tyr Pro Gly Ala Ile Trp Asn Ala Ala Ser Thr Ser Asn Tyr
        185                 190                 195 cgc gtc gga cgc acc tcc gcg atc agc acg atc gtc atc cac gtg acc     720
Arg Val Gly Arg Thr Ser Ala Ile Ser Thr Ile Val Ile His Val Thr
    200                 205                 210 caa ggc tcg tac gcc ggc acg atc agc tgg ttc aag aac gcg tcg gcg     768
Gln Gly Ser Tyr Ala Gly Thr Ile Ser Trp Phe Lys Asn Ala Ser Ala
215                 220                 225                 230 cag gtc agc gcg cac tac gtg gtg cgt tcc agc gac ggg cag atc acc     816
Gln Val Ser Ala His Tyr Val Val Arg Ser Ser Asp Gly Gln Ile Thr
                235                 240                 245 cag atg gtg gcc gag aag gac acc gcc tgg cac gcc cgc agc gcg aac     864
Gln Met Val Ala Glu Lys Asp Thr Ala Trp His Ala Arg Ser Ala Asn
            250                 255                 260 ccg tac tcg gtc ggc atc gag cac gag ggc tgg gtc gac cag ccg tcg     912
Pro Tyr Ser Val Gly Ile Glu His Glu Gly Trp Val Asp Gln Pro Ser
        265                 270                 275 tgg ttc acc gac gcg atg tac cgc gcg tcc gcg gcg ctg acc cgc aac     960
Trp Phe Thr Asp Ala Met Tyr Arg Ala Ser Ala Ala Leu Thr Arg Asn
    280                 285                 290 atc gcc gac cgg cgc ggc atc ccg aag acc cgg acg tac atc aag ggc    1008
Ile Ala Asp Arg Arg Gly Ile Pro Lys Thr Arg Thr Tyr Ile Lys Gly
295                 300                 305                 310 cac agc gag atg ccc gac aac gac cac acc gac ccg ggt ccg aac tgg    1056
His Ser Glu Met Pro Asp Asn Asp His Thr Asp Pro Gly Pro Asn Trp
                315                 320                 325 aac tgg acc tac tac atg cag ctg gtg aac ggc agc aac ccg aac ccg    1104
Asn Trp Thr Tyr Tyr Met Gln Leu Val Asn Gly Ser Asn Pro Asn Pro
            330                 335                 340 ccg acg tac aac ttc acc acg tac ggc agt ggc gtc cgg gtc cgc tcg    1152
Pro Thr Tyr Asn Phe Thr Thr Tyr Gly Ser Gly Val Arg Val Arg Ser
        345                 350                 355 gac gcg aag ctg acc gcg tcc atc gtc acc acc ctg ccc ggc ccg acg    1200
Asp Ala Lys Leu Thr Ala Ser Ile Val Thr Thr Leu Pro Gly Pro Thr
    360                 365                 370 cag gtc ttc gtc acc tgc cag aag cag ggc gac ctg gtc acc gcc gag    1248
Gln Val Phe Val Thr Cys Gln Lys Gln Gly Asp Leu Val Thr Ala Glu
375                 380                 385                 390
```

```
ggc acc agc aac aac tgg tgg tcc aag ctg cgc gac cag ggc ggc tac      1296
Gly Thr Ser Asn Asn Trp Trp Ser Lys Leu Arg Asp Gln Gly Gly Tyr
            395                 400                 405 atg acc aac atc tac atc gac cac ccc gac gcc aag ctc ccg ggc gtc      1344
Met Thr Asn Ile Tyr Ile Asp His Pro Asp Ala Lys Leu Pro Gly Val
        410                 415                 420 ccc gtc tgc tga                                                      1356
Pro Val Cys
    425
```

<210> SEQ ID NO 74
<211> LENGTH: 451
<212> TYPE: PRT
<213> ORGANISM: Kribbella sp

<400> SEQUENCE: 74

```
Met Ser His Lys Val Pro Arg Leu Val Ala Val Leu Ala Gly Ala
    -25                 -20                 -15

Leu Ala Phe Ser Ala Leu Pro Ser Asn Ala Ser Thr Pro Val Glu Thr
-10                  -5                 -1  1                  5

Gly Ser Thr Ser Thr Leu Ser Glu Ala Phe Lys Thr Ala Ala Thr Gln
                10                  15                  20

Tyr Asp Val Pro Arg Glu Leu Leu Val Gly Ile Gly Tyr Ala Glu Ser
            25                  30                  35

His Leu Asp Gly His Asp Gly Gln Pro Ser Gln Ala Asn Gly Tyr Gly
        40                  45                  50

Val Met His Leu Ala Ser Asn Pro Ser Asn Pro Thr Met Ser Glu Ala
55                  60                  65                  70

Ala Lys Leu Thr Gly Leu Pro Val Glu Lys Leu Ala Lys Asp Glu Ser
                75                  80                  85

Ala Asn Val Leu Gly Ala Ala Val Leu Asp Ala Tyr Ala Asp Lys
            90                  95                  100

Ala Gly Leu Gln Gly Gln Thr Arg Asp Asp Ile Gly Lys Trp Tyr Glu
        105                 110                 115

Val Val Ala Gln Tyr Ser His Ser Ala Asp Gly Pro Thr Ala Arg Leu
    120                 125                 130

Tyr Thr Asp Glu Val Tyr Arg Ile Val Gly Leu Gly Val Gly Ala Glu
135                 140                 145                 150

Gly Val Ser Thr Gln Pro Val Lys Val Thr Pro Asp Arg Gly Lys Tyr
                155                 160                 165

Ala Asn Val Ala Pro Leu Gly Thr Arg Thr Pro Ala Ser Ile Gln Ala
            170                 175                 180

Val Asp Tyr Pro Gly Ala Ile Trp Asn Ala Ala Ser Thr Ser Asn Tyr
        185                 190                 195

Arg Val Gly Arg Thr Ser Ala Ile Ser Thr Ile Val His Val Thr
    200                 205                 210

Gln Gly Ser Tyr Ala Gly Thr Ile Ser Trp Phe Lys Asn Ala Ser Ala
215                 220                 225                 230

Gln Val Ser Ala His Tyr Val Arg Ser Ser Asp Gly Gln Ile Thr
                235                 240                 245

Gln Met Val Ala Glu Lys Asp Thr Ala Trp His Ala Arg Ser Ala Asn
            250                 255                 260

Pro Tyr Ser Val Gly Ile Glu His Glu Gly Trp Val Asp Gln Pro Ser
        265                 270                 275
```

```
Trp Phe Thr Asp Ala Met Tyr Arg Ala Ser Ala Ala Leu Thr Arg Asn
        280                 285                 290

Ile Ala Asp Arg Arg Gly Ile Pro Lys Thr Arg Thr Tyr Ile Lys Gly
295                 300                 305                 310

His Ser Glu Met Pro Asp Asn Asp His Thr Asp Pro Gly Pro Asn Trp
                315                 320                 325

Asn Trp Thr Tyr Tyr Met Gln Leu Val Asn Gly Ser Asn Pro Asn Pro
            330                 335                 340

Pro Thr Tyr Asn Phe Thr Thr Tyr Gly Ser Gly Val Arg Val Arg Ser
        345                 350                 355

Asp Ala Lys Leu Thr Ala Ser Ile Val Thr Thr Leu Pro Gly Pro Thr
    360                 365                 370

Gln Val Phe Val Thr Cys Gln Lys Gln Gly Asp Leu Val Thr Ala Glu
375                 380                 385                 390

Gly Thr Ser Asn Asn Trp Trp Ser Lys Leu Arg Asp Gln Gly Gly Tyr
                395                 400                 405

Met Thr Asn Ile Tyr Ile Asp His Pro Asp Ala Lys Leu Pro Gly Val
            410                 415                 420

Pro Val Cys
        425

<210> SEQ ID NO 75
<211> LENGTH: 425
<212> TYPE: PRT
<213> ORGANISM: Kribbella sp

<400> SEQUENCE: 75

Ser Thr Pro Val Glu Thr Gly Ser Thr Ser Thr Leu Ser Glu Ala Phe
1               5                   10                  15

Lys Thr Ala Ala Thr Gln Tyr Asp Val Pro Arg Glu Leu Leu Val Gly
            20                  25                  30

Ile Gly Tyr Ala Glu Ser His Leu Asp Gly His Asp Gly Gln Pro Ser
        35                  40                  45

Gln Ala Asn Gly Tyr Gly Val Met His Leu Ala Ser Asn Pro Ser Asn
    50                  55                  60

Pro Thr Met Ser Glu Ala Ala Lys Leu Thr Gly Leu Pro Val Glu Lys
65                  70                  75                  80

Leu Ala Lys Asp Glu Ser Ala Asn Val Leu Gly Ala Ala Val Leu
                85                  90                  95

Asp Ala Tyr Ala Asp Lys Ala Gly Leu Gln Gly Gln Thr Arg Asp Asp
                100                 105                 110

Ile Gly Lys Trp Tyr Glu Val Ala Gln Tyr Ser His Ser Ala Asp
            115                 120                 125

Gly Pro Thr Ala Arg Leu Tyr Thr Asp Glu Val Tyr Arg Ile Val Gly
        130                 135                 140

Leu Gly Val Gly Ala Glu Gly Val Ser Thr Gln Pro Val Lys Val Thr
145                 150                 155                 160

Pro Asp Arg Gly Lys Tyr Ala Asn Val Ala Pro Leu Gly Thr Arg Thr
                165                 170                 175

Pro Ala Ser Ile Gln Ala Val Asp Tyr Pro Gly Ala Ile Trp Asn Ala
            180                 185                 190

Ala Ser Thr Ser Asn Tyr Arg Val Gly Arg Thr Ser Ala Ile Ser Thr
        195                 200                 205
```

```
Ile Val Ile His Val Thr Gln Gly Ser Tyr Ala Gly Thr Ile Ser Trp
    210                 215                 220
Phe Lys Asn Ala Ser Ala Gln Val Ser Ala His Tyr Val Val Arg Ser
225                 230                 235                 240
Ser Asp Gly Gln Ile Thr Gln Met Val Ala Glu Lys Asp Thr Ala Trp
                245                 250                 255
His Ala Arg Ser Ala Asn Pro Tyr Ser Val Gly Ile Glu His Glu Gly
            260                 265                 270
Trp Val Asp Gln Pro Ser Trp Phe Thr Asp Ala Met Tyr Arg Ala Ser
        275                 280                 285
Ala Ala Leu Thr Arg Asn Ile Ala Asp Arg Arg Gly Ile Pro Lys Thr
    290                 295                 300
Arg Thr Tyr Ile Lys Gly His Ser Glu Met Pro Asp Asn Asp His Thr
305                 310                 315                 320
Asp Pro Gly Pro Asn Trp Asn Trp Thr Tyr Tyr Met Gln Leu Val Asn
                325                 330                 335
Gly Ser Asn Pro Asn Pro Pro Thr Tyr Asn Phe Thr Thr Tyr Gly Ser
            340                 345                 350
Gly Val Arg Val Arg Ser Asp Ala Lys Leu Thr Ala Ser Ile Val Thr
        355                 360                 365
Thr Leu Pro Gly Pro Thr Gln Val Phe Val Thr Cys Gln Lys Gln Gly
    370                 375                 380
Asp Leu Val Thr Ala Glu Gly Thr Ser Asn Asn Trp Trp Ser Lys Leu
385                 390                 395                 400
Arg Asp Gln Gly Gly Tyr Met Thr Asn Ile Tyr Ile Asp His Pro Asp
                405                 410                 415
Ala Lys Leu Pro Gly Val Pro Val Cys
            420                 425

<210> SEQ ID NO 76
<211> LENGTH: 990
<212> TYPE: DNA
<213> ORGANISM: Bacillus sp
<220> FEATURE:
<221> NAME/KEY: CDS
<222> LOCATION: (1)..(987)
<220> FEATURE:
<221> NAME/KEY: sig_peptide
<222> LOCATION: (1)..(75)
<220> FEATURE:
<221> NAME/KEY: mat_peptide
<222> LOCATION: (76)..(987)

<400> SEQUENCE: 76 atg aaa agg ctc gtt ctt gta ttt agt atc att gcc gta ctt ttt atg    48
Met Lys Arg Leu Val Leu Val Phe Ser Ile Ile Ala Val Leu Phe Met
-25                 -20                 -15                 -10 agc att tct cct gtt cat aca gtt gca gaa aac cat agc aat ctg tat    96
Ser Ile Ser Pro Val His Thr Val Ala Glu Asn His Ser Asn Leu Tyr
            -5                  -1  1               5 gat gtg aga tcc gga gat aca tta tgg aag atc gcc aat aaa tac ggt   144
Asp Val Arg Ser Gly Asp Thr Leu Trp Lys Ile Ala Asn Lys Tyr Gly
        10                  15                  20 aca tct gtc caa aat cta aaa gaa aca aat gga ttg caa tct gat tta   192
Thr Ser Val Gln Asn Leu Lys Glu Thr Asn Gly Leu Gln Ser Asp Leu
    25                  30                  35 ttg tta gtt ggt cag aga ttg ttt gtt cca atg agg tat gaa gtc gtt   240
Leu Leu Val Gly Gln Arg Leu Phe Val Pro Met Arg Tyr Glu Val Val
40                  45                  50                  55
```

```
gct gga gat aca ctt tgg aag ctt tca aga gca tat aac tct tcc gtt    288
Ala Gly Asp Thr Leu Trp Lys Leu Ser Arg Ala Tyr Asn Ser Ser Val
             60                  65                  70 caa gcg ata aaa gca aca aat gga ctt aca tcg gat gta ttg tac ata    336
Gln Ala Ile Lys Ala Thr Asn Gly Leu Thr Ser Asp Val Leu Tyr Ile
         75                  80                  85 ggg caa aag ttg aaa att cct cct aag aaa tta cct atg gat ggt cag    384
Gly Gln Lys Leu Lys Ile Pro Pro Lys Lys Leu Pro Met Asp Gly Gln
     90                  95                 100 tat gtt ctc atg acg aga gag gaa ttt aaa gac tgg tta ttt aac cat    432
Tyr Val Leu Met Thr Arg Glu Glu Phe Lys Asp Trp Leu Phe Asn His
    105                 110                 115 gaa ttc acg agg aac ata agc ctc att caa cag cac cac acg tgg tca    480
Glu Phe Thr Arg Asn Ile Ser Leu Ile Gln Gln His His Thr Trp Ser
120                 125                 130                 135 ccg gct tat gga cat ttt aat ggc aaa aat cac ttt tcg ttg ctt aag    528
Pro Ala Tyr Gly His Phe Asn Gly Lys Asn His Phe Ser Leu Leu Lys
                140                 145                 150 ggg atg gag tat tat cat acg aaa gaa gtg ggc tgg gaa aac att gcc    576
Gly Met Glu Tyr Tyr His Thr Lys Glu Val Gly Trp Glu Asn Ile Ala
            155                 160                 165 cag aac att aca aca ttc cca gac gga aaa ata gcc gta tct aga cca    624
Gln Asn Ile Thr Thr Phe Pro Asp Gly Lys Ile Ala Val Ser Arg Pro
        170                 175                 180 ttt aac agt gct cct gac ggc tcg att ggt cca aag gca aat tct gtt    672
Phe Asn Ser Ala Pro Asp Gly Ser Ile Gly Pro Lys Ala Asn Ser Val
    185                 190                 195 ggg tta aac atc gaa cat gtt ggg aat ttt gac tta ggc aat gat caa    720
Gly Leu Asn Ile Glu His Val Gly Asn Phe Asp Leu Gly Asn Asp Gln
200                 205                 210                 215 atg act gcc gaa cat agg gaa acg att atc tat ctt acg gca ttg ctt    768
Met Thr Ala Glu His Arg Glu Thr Ile Ile Tyr Leu Thr Ala Leu Leu
                220                 225                 230 tgt atg aag ttt ggg tta act cct tct gtt gac agc atc aca tat cat    816
Cys Met Lys Phe Gly Leu Thr Pro Ser Val Asp Ser Ile Thr Tyr His
            235                 240                 245 cgt tgg tgg gat atg aac aca aag gag aga gtg ttg gat cga agt gaa    864
Arg Trp Trp Asp Met Asn Thr Lys Glu Arg Val Leu Asp Arg Ser Glu
        250                 255                 260 gga gtt tct gta aaa aca tgc cca gga acg gga ttt ttc gga ggg aat    912
Gly Val Ser Val Lys Thr Cys Pro Gly Thr Gly Phe Phe Gly Gly Asn
    265                 270                 275 aca aca gaa agt gca aag aat aat ttt tat cct tta gtg tca cgt aaa    960
Thr Thr Glu Ser Ala Lys Asn Asn Phe Tyr Pro Leu Val Ser Arg Lys
280                 285                 290                 295 atg caa gag att agg gca tcc atg aat taa                            990
Met Gln Glu Ile Arg Ala Ser Met Asn
                300

<210> SEQ ID NO 77
<211> LENGTH: 329
<212> TYPE: PRT
<213> ORGANISM: Bacillus sp

<400> SEQUENCE: 77

Met Lys Arg Leu Val Leu Val Phe Ser Ile Ile Ala Val Leu Phe Met
-25                 -20                 -15                 -10

Ser Ile Ser Pro Val His Thr Val Ala Glu Asn His Ser Asn Leu Tyr
            -5                  -1  1                   5
```

Asp Val Arg Ser Gly Asp Thr Leu Trp Lys Ile Ala Asn Lys Tyr Gly
            10                  15                  20

Thr Ser Val Gln Asn Leu Lys Glu Thr Asn Gly Leu Gln Ser Asp Leu
 25                  30                  35

Leu Leu Val Gly Gln Arg Leu Phe Val Pro Met Arg Tyr Glu Val Val
40                  45                  50                  55

Ala Gly Asp Thr Leu Trp Lys Leu Ser Arg Ala Tyr Asn Ser Ser Val
                 60                  65                  70

Gln Ala Ile Lys Ala Thr Asn Gly Leu Thr Ser Asp Val Leu Tyr Ile
             75                  80                  85

Gly Gln Lys Leu Lys Ile Pro Pro Lys Lys Leu Pro Met Asp Gly Gln
         90                  95                 100

Tyr Val Leu Met Thr Arg Glu Glu Phe Lys Asp Trp Leu Phe Asn His
105                 110                 115

Glu Phe Thr Arg Asn Ile Ser Leu Ile Gln Gln His His Thr Trp Ser
120                 125                 130                 135

Pro Ala Tyr Gly His Phe Asn Gly Lys Asn His Phe Ser Leu Leu Lys
                140                 145                 150

Gly Met Glu Tyr Tyr His Thr Lys Glu Val Gly Trp Glu Asn Ile Ala
             155                 160                 165

Gln Asn Ile Thr Thr Phe Pro Asp Gly Lys Ile Ala Val Ser Arg Pro
         170                 175                 180

Phe Asn Ser Ala Pro Asp Gly Ser Ile Gly Pro Lys Ala Asn Ser Val
     185                 190                 195

Gly Leu Asn Ile Glu His Val Gly Asn Phe Asp Leu Gly Asn Asp Gln
200                 205                 210                 215

Met Thr Ala Glu His Arg Glu Thr Ile Ile Tyr Leu Thr Ala Leu Leu
                220                 225                 230

Cys Met Lys Phe Gly Leu Thr Pro Ser Val Asp Ser Ile Thr Tyr His
             235                 240                 245

Arg Trp Trp Asp Met Asn Thr Lys Glu Arg Val Leu Asp Arg Ser Glu
         250                 255                 260

Gly Val Ser Val Lys Thr Cys Pro Gly Thr Gly Phe Phe Gly Gly Asn
     265                 270                 275

Thr Thr Glu Ser Ala Lys Asn Asn Phe Tyr Pro Leu Val Ser Arg Lys
280                 285                 290                 295

Met Gln Glu Ile Arg Ala Ser Met Asn
                300

<210> SEQ ID NO 78
<211> LENGTH: 304
<212> TYPE: PRT
<213> ORGANISM: Bacillus sp

<400> SEQUENCE: 78

Glu Asn His Ser Asn Leu Tyr Asp Val Arg Ser Gly Asp Thr Leu Trp
1               5                  10                  15

Lys Ile Ala Asn Lys Tyr Gly Thr Ser Val Gln Asn Leu Lys Glu Thr
             20                  25                  30

Asn Gly Leu Gln Ser Asp Leu Leu Leu Val Gly Gln Arg Leu Phe Val
         35                  40                  45

Pro Met Arg Tyr Glu Val Val Ala Gly Asp Thr Leu Trp Lys Leu Ser
     50                  55                  60

Arg Ala Tyr Asn Ser Ser Val Gln Ala Ile Lys Ala Thr Asn Gly Leu
65                  70                  75                  80

```
Thr Ser Asp Val Leu Tyr Ile Gly Gln Lys Leu Lys Ile Pro Pro Lys
                85                  90                  95

Lys Leu Pro Met Asp Gly Gln Tyr Val Leu Met Thr Arg Glu Glu Phe
               100                 105                 110

Lys Asp Trp Leu Phe Asn His Glu Phe Thr Arg Asn Ile Ser Leu Ile
           115                 120                 125

Gln Gln His His Thr Trp Ser Pro Ala Tyr Gly His Phe Asn Gly Lys
       130                 135                 140

Asn His Phe Ser Leu Leu Lys Gly Met Glu Tyr Tyr His Thr Lys Glu
145                 150                 155                 160

Val Gly Trp Glu Asn Ile Ala Gln Asn Ile Thr Thr Phe Pro Asp Gly
               165                 170                 175

Lys Ile Ala Val Ser Arg Pro Phe Asn Ser Ala Pro Asp Gly Ser Ile
               180                 185                 190

Gly Pro Lys Ala Asn Ser Val Gly Leu Asn Ile Glu His Val Gly Asn
               195                 200                 205

Phe Asp Leu Gly Asn Asp Gln Met Thr Ala Glu His Arg Glu Thr Ile
       210                 215                 220

Ile Tyr Leu Thr Ala Leu Leu Cys Met Lys Phe Gly Leu Thr Pro Ser
225                 230                 235                 240

Val Asp Ser Ile Thr Tyr His Arg Trp Trp Asp Met Asn Thr Lys Glu
               245                 250                 255

Arg Val Leu Asp Arg Ser Glu Gly Val Ser Val Lys Thr Cys Pro Gly
               260                 265                 270

Thr Gly Phe Phe Gly Gly Asn Thr Thr Glu Ser Ala Lys Asn Asn Phe
               275                 280                 285

Tyr Pro Leu Val Ser Arg Lys Met Gln Glu Ile Arg Ala Ser Met Asn
               290                 295                 300

<210> SEQ ID NO 79
<211> LENGTH: 993
<212> TYPE: DNA
<213> ORGANISM: Bacillus sp
<220> FEATURE:
<221> NAME/KEY: CDS
<222> LOCATION: (1)..(990)
<220> FEATURE:
<221> NAME/KEY: sig_peptide
<222> LOCATION: (1)..(72)
<220> FEATURE:
<221> NAME/KEY: mat_peptide
<222> LOCATION: (73)..(990)

<400> SEQUENCE: 79 atg aag aaa aac ctt gtc ctc att tgt agt tta atc cta atc ata ttc      48
Met Lys Lys Asn Leu Val Leu Ile Cys Ser Leu Ile Leu Ile Ile Phe
                -20                 -15                 -10 atg aat atc ctt cct gtt cac gcg att tca aat aac cat agc aac ctt      96
Met Asn Ile Leu Pro Val His Ala Ile Ser Asn Asn His Ser Asn Leu
         -5             -1   1               5 tat gta gta aaa gct gga gat aca tta cct gaa att gca gat aaa ttc     144
Tyr Val Val Lys Ala Gly Asp Thr Leu Pro Glu Ile Ala Asp Lys Phe
             10                  15                  20 gat act acc ata gag gag ttg aag cta aca aat ggt ttg caa tcc gat     192
Asp Thr Thr Ile Glu Glu Leu Lys Leu Thr Asn Gly Leu Gln Ser Asp
 25                  30                  35                  40 tct cta ttt gtt gaa caa aaa tta tgg gtt cct att atg cat gaa gtt     240
Ser Leu Phe Val Glu Gln Lys Leu Trp Val Pro Ile Met His Glu Val
                 45                  50                  55
```

| | | | | | | | | | | | | | | | |
|---|---|---|---|---|---|---|---|---|---|---|---|---|---|---|---|
| gtt | aca | gga | gaa | aca | ctg | cag | gac | att | gca | tca | act | tac | cat | tct | tca | 288 |
| Val | Thr | Gly | Glu | Thr | Leu | Gln | Asp | Ile | Ala | Ser | Thr | Tyr | His | Ser | Ser | |
| | | | 60 | | | | | 65 | | | | | 70 | | | |
| ata | gaa | acc | ata | aaa | aaa | gca | aat | gga | ctc | gtt | tct | gat | gag | cta | tat | 336 |
| Ile | Glu | Thr | Ile | Lys | Lys | Ala | Asn | Gly | Leu | Val | Ser | Asp | Glu | Leu | Tyr | |
| | | 75 | | | | | 80 | | | | | 85 | | | | |
| gca | ggg | caa | ata | tta | aaa | gtt | act | cct | aaa | aaa | atg | atc | atg | caa | ggt | 384 |
| Ala | Gly | Gln | Ile | Leu | Lys | Val | Thr | Pro | Lys | Lys | Met | Ile | Met | Gln | Gly | |
| | 90 | | | | | 95 | | | | | 100 | | | | | |
| caa | cat | atc | ctt | atg | aca | aag | gaa | gaa | ttt | aaa | gat | tgg | ttg | ttt | aac | 432 |
| Gln | His | Ile | Leu | Met | Thr | Lys | Glu | Glu | Phe | Lys | Asp | Trp | Leu | Phe | Asn | |
| 105 | | | | | 110 | | | | | 115 | | | | | 120 | |
| aac | caa | ttt | aat | cgt | gat | att | cgt | atc | atc | caa | caa | cat | cac | aca | tgg | 480 |
| Asn | Gln | Phe | Asn | Arg | Asp | Ile | Arg | Ile | Ile | Gln | Gln | His | His | Thr | Trp | |
| | | | | 125 | | | | | 130 | | | | | 135 | | |
| tta | cct | tct | tat | aag | caa | ttt | aaa | ggt | aca | aac | cat | ttt | caa | atg | tta | 528 |
| Leu | Pro | Ser | Tyr | Lys | Gln | Phe | Lys | Gly | Thr | Asn | His | Phe | Gln | Met | Leu | |
| | | | 140 | | | | | 145 | | | | | 150 | | | |
| caa | agt | atg | gag | aat | ttt | cat | aag | aag | gaa | atg | ggc | tgg | cat | aat | att | 576 |
| Gln | Ser | Met | Glu | Asn | Phe | His | Lys | Lys | Glu | Met | Gly | Trp | His | Asn | Ile | |
| | | 155 | | | | | 160 | | | | | 165 | | | | |
| gcg | caa | aac | ata | acg | acc | ttc | cct | gat | gga | aaa | gta | gca | gta | tct | aga | 624 |
| Ala | Gln | Asn | Ile | Thr | Thr | Phe | Pro | Asp | Gly | Lys | Val | Ala | Val | Ser | Arg | |
| | 170 | | | | | 175 | | | | | 180 | | | | | |
| cca | ttt | aac | att | gcc | cca | gaa | ggt | tca | att | gga | tca | aag | gcg | aat | tca | 672 |
| Pro | Phe | Asn | Ile | Ala | Pro | Glu | Gly | Ser | Ile | Gly | Ser | Lys | Ala | Asn | Ser | |
| 185 | | | | | 190 | | | | | 195 | | | | | 200 | |
| gta | ggg | cta | acc | atc | gaa | aat | att | ggt | aac | ttt | gat | cta | ggt | cac | gat | 720 |
| Val | Gly | Leu | Thr | Ile | Glu | Asn | Ile | Gly | Asn | Phe | Asp | Leu | Gly | His | Asp | |
| | | | | 205 | | | | | 210 | | | | | 215 | | |
| gta | atg | acc | aag | gaa | cag | cag | gat | aca | att | gtt | tac | ata | act | gcc | ttg | 768 |
| Val | Met | Thr | Lys | Glu | Gln | Gln | Asp | Thr | Ile | Val | Tyr | Ile | Thr | Ala | Leu | |
| | | | 220 | | | | | 225 | | | | | 230 | | | |
| ctt | tgt | atc | aag | ttc | ggc | tta | acc | cct | tca | att | gac | agt | att | act | tat | 816 |
| Leu | Cys | Ile | Lys | Phe | Gly | Leu | Thr | Pro | Ser | Ile | Asp | Ser | Ile | Thr | Tyr | |
| | | 235 | | | | | 240 | | | | | 245 | | | | |
| cat | cat | tgg | tgg | aat | tta | caa | aca | aag | gaa | aga | gta | tta | gat | aac | gga | 864 |
| His | His | Trp | Trp | Asn | Leu | Gln | Thr | Lys | Glu | Arg | Val | Leu | Asp | Asn | Gly | |
| | 250 | | | | | 255 | | | | | 260 | | | | | |
| ccg | gat | tat | aat | gtg | aag | act | tgt | ccc | ggt | act | aat | ttt | ttc | gga | ggc | 912 |
| Pro | Asp | Tyr | Asn | Val | Lys | Thr | Cys | Pro | Gly | Thr | Asn | Phe | Phe | Gly | Gly | |
| 265 | | | | | 270 | | | | | 275 | | | | | 280 | |
| aat | gcc | act | aac | gat | gca | aag | aaa | cac | ttt | tac | cct | ctt | gta | tcc | gca | 960 |
| Asn | Ala | Thr | Asn | Asp | Ala | Lys | Lys | His | Phe | Tyr | Pro | Leu | Val | Ser | Ala | |
| | | | | 285 | | | | | 290 | | | | | 295 | | |
| aag | ata | gaa | gaa | att | gta | gca | aca | atg | gat | tga | | | | | | 993 |
| Lys | Ile | Glu | Glu | Ile | Val | Ala | Thr | Met | Asp | | | | | | | |
| | | | 300 | | | | | 305 | | | | | | | | |

<210> SEQ ID NO 80
<211> LENGTH: 330
<212> TYPE: PRT
<213> ORGANISM: Bacillus sp

<400> SEQUENCE: 80

Met Lys Lys Asn Leu Val Leu Ile Cys Ser Leu Ile Leu Ile Ile Phe
                -20                 -15                 -10

Met Asn Ile Leu Pro Val His Ala Ile Ser Asn Asn His Ser Asn Leu
         -5                  -1   1                   5

Tyr Val Val Lys Ala Gly Asp Thr Leu Pro Glu Ile Ala Asp Lys Phe
            10                  15                  20

Asp Thr Thr Ile Glu Glu Leu Lys Leu Thr Asn Gly Leu Gln Ser Asp
 25                  30                  35                  40

Ser Leu Phe Val Glu Gln Lys Leu Trp Val Pro Ile Met His Glu Val
                 45                  50                  55

Val Thr Gly Glu Thr Leu Gln Asp Ile Ala Ser Thr Tyr His Ser Ser
             60                  65                  70

Ile Glu Thr Ile Lys Lys Ala Asn Gly Leu Val Ser Asp Glu Leu Tyr
         75                  80                  85

Ala Gly Gln Ile Leu Lys Val Thr Pro Lys Lys Met Ile Met Gln Gly
 90                  95                 100

Gln His Ile Leu Met Thr Lys Glu Glu Phe Lys Asp Trp Leu Phe Asn
105                 110                 115                 120

Asn Gln Phe Asn Arg Asp Ile Arg Ile Ile Gln Gln His His Thr Trp
                125                 130                 135

Leu Pro Ser Tyr Lys Gln Phe Lys Gly Thr Asn His Phe Gln Met Leu
            140                 145                 150

Gln Ser Met Glu Asn Phe His Lys Lys Glu Met Gly Trp His Asn Ile
        155                 160                 165

Ala Gln Asn Ile Thr Thr Phe Pro Asp Gly Lys Val Ala Val Ser Arg
170                 175                 180

Pro Phe Asn Ile Ala Pro Glu Gly Ser Ile Gly Ser Lys Ala Asn Ser
185                 190                 195                 200

Val Gly Leu Thr Ile Glu Asn Ile Gly Asn Phe Asp Leu Gly His Asp
                205                 210                 215

Val Met Thr Lys Glu Gln Gln Asp Thr Ile Val Tyr Ile Thr Ala Leu
            220                 225                 230

Leu Cys Ile Lys Phe Gly Leu Thr Pro Ser Ile Asp Ser Ile Thr Tyr
        235                 240                 245

His His Trp Trp Asn Leu Gln Thr Lys Glu Arg Val Leu Asp Asn Gly
250                 255                 260

Pro Asp Tyr Asn Val Lys Thr Cys Pro Gly Thr Asn Phe Phe Gly Gly
265                 270                 275                 280

Asn Ala Thr Asn Asp Ala Lys Lys His Phe Tyr Pro Leu Val Ser Ala
                285                 290                 295

Lys Ile Glu Glu Ile Val Ala Thr Met Asp
            300                 305

<210> SEQ ID NO 81
<211> LENGTH: 306
<212> TYPE: PRT
<213> ORGANISM: Bacillus sp

<400> SEQUENCE: 81

Ile Ser Asn Asn His Ser Asn Leu Tyr Val Val Lys Ala Gly Asp Thr
 1               5                  10                  15

Leu Pro Glu Ile Ala Asp Lys Phe Asp Thr Thr Ile Glu Glu Leu Lys
            20                  25                  30

Leu Thr Asn Gly Leu Gln Ser Asp Ser Leu Phe Val Glu Gln Lys Leu
        35                  40                  45

Trp Val Pro Ile Met His Glu Val Val Thr Gly Glu Thr Leu Gln Asp
 50                  55                  60

Ile Ala Ser Thr Tyr His Ser Ser Ile Glu Thr Ile Lys Lys Ala Asn
 65                  70                  75                  80

```
Gly Leu Val Ser Asp Glu Leu Tyr Ala Gly Gln Ile Leu Lys Val Thr
                85                  90                  95

Pro Lys Lys Met Ile Met Gln Gly Gln His Ile Leu Met Thr Lys Glu
            100                 105                 110

Glu Phe Lys Asp Trp Leu Phe Asn Asn Gln Phe Asn Arg Asp Ile Arg
        115                 120                 125

Ile Ile Gln Gln His His Thr Trp Leu Pro Ser Tyr Lys Gln Phe Lys
130                 135                 140

Gly Thr Asn His Phe Gln Met Leu Gln Ser Met Glu Asn Phe His Lys
145                 150                 155                 160

Lys Glu Met Gly Trp His Asn Ile Ala Gln Asn Ile Thr Thr Phe Pro
                165                 170                 175

Asp Gly Lys Val Ala Val Ser Arg Pro Phe Asn Ile Ala Pro Glu Gly
            180                 185                 190

Ser Ile Gly Ser Lys Ala Asn Ser Val Gly Leu Thr Ile Glu Asn Ile
        195                 200                 205

Gly Asn Phe Asp Leu Gly His Asp Val Met Thr Lys Glu Gln Gln Asp
210                 215                 220

Thr Ile Val Tyr Ile Thr Ala Leu Leu Cys Ile Lys Phe Gly Leu Thr
225                 230                 235                 240

Pro Ser Ile Asp Ser Ile Thr Tyr His His Trp Trp Asn Leu Gln Thr
                245                 250                 255

Lys Glu Arg Val Leu Asp Asn Gly Pro Asp Tyr Asn Val Lys Thr Cys
            260                 265                 270

Pro Gly Thr Asn Phe Phe Gly Gly Asn Ala Thr Asn Asp Ala Lys Lys
        275                 280                 285

His Phe Tyr Pro Leu Val Ser Ala Lys Ile Glu Glu Ile Val Ala Thr
290                 295                 300

Met Asp
305

<210> SEQ ID NO 82
<211> LENGTH: 990
<212> TYPE: DNA
<213> ORGANISM: Bacillus sp
<220> FEATURE:
<221> NAME/KEY: CDS
<222> LOCATION: (1)..(987)
<220> FEATURE:
<221> NAME/KEY: sig_peptide
<222> LOCATION: (1)..(69)
<220> FEATURE:
<221> NAME/KEY: mat_peptide
<222> LOCATION: (70)..(987)

<400> SEQUENCE: 82 atg aaa agg ctc gtt ctt gta gtt agt tta att gcc ata ctt ttt gtg      48
Met Lys Arg Leu Val Leu Val Val Ser Leu Ile Ala Ile Leu Phe Val
            -20                 -15                 -10 agc att tct cct gtt tct gca gct gcc gaa aac cat agc aat ctg tat      96
Ser Ile Ser Pro Val Ser Ala Ala Ala Glu Asn His Ser Asn Leu Tyr
        -5                  -1  1                   5 gat gtg aga tct gga gat aca tta tgg aag atc gcc aat aaa tat ggt     144
Asp Val Arg Ser Gly Asp Thr Leu Trp Lys Ile Ala Asn Lys Tyr Gly
10                  15                  20                  25 aca tct gtc caa aat tta aaa gaa aca aat gga ctg caa tct gat ttg     192
Thr Ser Val Gln Asn Leu Lys Glu Thr Asn Gly Leu Gln Ser Asp Leu
                30                  35                  40
```

| | | | | | | | | | | | | | | | |
|---|---|---|---|---|---|---|---|---|---|---|---|---|---|---|---|
| ctg | tta | gtt | ggt | caa | aga | ttg | ttt | gtt | cca | atg | agc | tac | gaa | gtc | gtt |
| Leu | Leu | Val | Gly | Gln | Arg | Leu | Phe | Val | Pro | Met | Ser | Tyr | Glu | Val | Val |
| | | | 45 | | | | | 50 | | | | | 55 | | |

240

| tct | gga | gat | aca | ctt | tgg | aag | ctt | tca | aga | gca | tat | aat | tct | tca | gtc |
|---|---|---|---|---|---|---|---|---|---|---|---|---|---|---|---|
| Ser | Gly | Asp | Thr | Leu | Trp | Lys | Leu | Ser | Arg | Ala | Tyr | Asn | Ser | Ser | Val |
| | | | 60 | | | | | 65 | | | | | 70 | | |

288

| caa | gca | ata | aaa | gaa | aca | aat | gga | ctt | aca | tcg | gat | gta | ttg | tac | ata |
|---|---|---|---|---|---|---|---|---|---|---|---|---|---|---|---|
| Gln | Ala | Ile | Lys | Glu | Thr | Asn | Gly | Leu | Thr | Ser | Asp | Val | Leu | Tyr | Ile |
| | 75 | | | | | 80 | | | | | 85 | | | | |

336

| ggg | caa | aag | tta | aaa | atc | cct | cct | aag | aaa | tta | cct | atg | gat | ggt | cag |
|---|---|---|---|---|---|---|---|---|---|---|---|---|---|---|---|
| Gly | Gln | Lys | Leu | Lys | Ile | Pro | Pro | Lys | Lys | Leu | Pro | Met | Asp | Gly | Gln |
| 90 | | | | | 95 | | | | | 100 | | | | | 105 |

384

| tat | gtt | ctc | atg | acg | cga | gag | gaa | ttt | aaa | gat | tgg | tta | ttt | aac | cat |
|---|---|---|---|---|---|---|---|---|---|---|---|---|---|---|---|
| Tyr | Val | Leu | Met | Thr | Arg | Glu | Glu | Phe | Lys | Asp | Trp | Leu | Phe | Asn | His |
| | | | | 110 | | | | | 115 | | | | | 120 | |

432

| gaa | ttt | acg | aga | aac | ata | agc | ctt | att | caa | cag | cac | cac | acg | tgg | tcg |
|---|---|---|---|---|---|---|---|---|---|---|---|---|---|---|---|
| Glu | Phe | Thr | Arg | Asn | Ile | Ser | Leu | Ile | Gln | Gln | His | His | Thr | Trp | Ser |
| | | | 125 | | | | | 130 | | | | | 135 | | |

480

| ccg | gcc | tat | ggc | cat | ttt | aat | gga | aac | aat | cac | ttt | tcg | tta | ctt | aag |
|---|---|---|---|---|---|---|---|---|---|---|---|---|---|---|---|
| Pro | Ala | Tyr | Gly | His | Phe | Asn | Gly | Asn | Asn | His | Phe | Ser | Leu | Leu | Lys |
| | | 140 | | | | | 145 | | | | | 150 | | | |

528

| gga | atg | gag | tat | tat | cat | acg | aaa | gaa | gtg | ggt | tgg | gaa | aat | ata | gct |
|---|---|---|---|---|---|---|---|---|---|---|---|---|---|---|---|
| Gly | Met | Glu | Tyr | Tyr | His | Thr | Lys | Glu | Val | Gly | Trp | Glu | Asn | Ile | Ala |
| 155 | | | | | 160 | | | | | 165 | | | | | |

576

| cag | aac | ctt | aca | aca | ttc | ccc | gat | ggg | aga | ata | gca | gtc | tct | agg | cca |
|---|---|---|---|---|---|---|---|---|---|---|---|---|---|---|---|
| Gln | Asn | Leu | Thr | Thr | Phe | Pro | Asp | Gly | Arg | Ile | Ala | Val | Ser | Arg | Pro |
| 170 | | | | | 175 | | | | | 180 | | | | | 185 |

624

| ttt | aac | agt | gct | ccg | gat | ggt | agt | att | gga | cca | aaa | gct | aac | tcg | ata |
|---|---|---|---|---|---|---|---|---|---|---|---|---|---|---|---|
| Phe | Asn | Ser | Ala | Pro | Asp | Gly | Ser | Ile | Gly | Pro | Lys | Ala | Asn | Ser | Ile |
| | | | | 190 | | | | | 195 | | | | | 200 | |

672

| gga | tta | aac | atc | gaa | cat | atc | ggg | aat | ttt | gat | tta | ggt | aat | gat | caa |
|---|---|---|---|---|---|---|---|---|---|---|---|---|---|---|---|
| Gly | Leu | Asn | Ile | Glu | His | Ile | Gly | Asn | Phe | Asp | Leu | Gly | Asn | Asp | Gln |
| | | | 205 | | | | | 210 | | | | | 215 | | |

720

| atg | aca | gct | gaa | cat | aga | gaa | acg | att | atc | tat | ctt | acg | gcg | ttg | cta |
|---|---|---|---|---|---|---|---|---|---|---|---|---|---|---|---|
| Met | Thr | Ala | Glu | His | Arg | Glu | Thr | Ile | Ile | Tyr | Leu | Thr | Ala | Leu | Leu |
| | 220 | | | | | 225 | | | | | 230 | | | | |

768

| tgt | atg | aag | ttc | gga | tta | act | cct | tct | att | gac | agc | atc | aca | tat | cat |
|---|---|---|---|---|---|---|---|---|---|---|---|---|---|---|---|
| Cys | Met | Lys | Phe | Gly | Leu | Thr | Pro | Ser | Ile | Asp | Ser | Ile | Thr | Tyr | His |
| 235 | | | | | 240 | | | | | 245 | | | | | |

816

| cgt | tgg | tgg | gat | atg | aac | aca | aag | gag | cgt | gtg | ttg | gat | cga | agt | gaa |
|---|---|---|---|---|---|---|---|---|---|---|---|---|---|---|---|
| Arg | Trp | Trp | Asp | Met | Asn | Thr | Lys | Glu | Arg | Val | Leu | Asp | Arg | Ser | Glu |
| 250 | | | | | 255 | | | | | 260 | | | | | 265 |

864

| gga | gtt | tct | gtg | aaa | act | tgt | cca | ggt | act | gga | ttt | ttc | ggc | ggg | aat |
|---|---|---|---|---|---|---|---|---|---|---|---|---|---|---|---|
| Gly | Val | Ser | Val | Lys | Thr | Cys | Pro | Gly | Thr | Gly | Phe | Phe | Gly | Gly | Asn |
| | | | | 270 | | | | | 275 | | | | | 280 | |

912

| acg | aca | gaa | agt | gct | aag | agt | aat | ttt | tat | cct | tta | gtg | tca | cgt | aaa |
|---|---|---|---|---|---|---|---|---|---|---|---|---|---|---|---|
| Thr | Thr | Glu | Ser | Ala | Lys | Ser | Asn | Phe | Tyr | Pro | Leu | Val | Ser | Arg | Lys |
| | | | | 285 | | | | | 290 | | | | | 295 | |

960

| ata | gaa | gag | att | aga | gca | act | ttg | aat | taa | | | | | | |
|---|---|---|---|---|---|---|---|---|---|---|---|---|---|---|---|
| Ile | Glu | Glu | Ile | Arg | Ala | Thr | Leu | Asn | | | | | | | |
| | 300 | | | | | 305 | | | | | | | | | |

990

<210> SEQ ID NO 83
<211> LENGTH: 329
<212> TYPE: PRT
<213> ORGANISM: Bacillus sp

<400> SEQUENCE: 83

Met Lys Arg Leu Val Leu Val Val Ser Leu Ile Ala Ile Leu Phe Val
            -20                 -15                 -10

Ser Ile Ser Pro Val Ser Ala Ala Glu Asn His Ser Asn Leu Tyr
    -5              -1  1                   5

Asp Val Arg Ser Gly Asp Thr Leu Trp Lys Ile Ala Asn Lys Tyr Gly
10              15                  20                  25

Thr Ser Val Gln Asn Leu Lys Glu Thr Asn Gly Leu Gln Ser Asp Leu
                30                  35                  40

Leu Leu Val Gly Gln Arg Leu Phe Val Pro Met Ser Tyr Glu Val Val
            45                  50                  55

Ser Gly Asp Thr Leu Trp Lys Leu Ser Arg Ala Tyr Asn Ser Ser Val
        60                  65                  70

Gln Ala Ile Lys Glu Thr Asn Gly Leu Thr Ser Asp Val Leu Tyr Ile
    75                  80                  85

Gly Gln Lys Leu Lys Ile Pro Pro Lys Lys Leu Pro Met Asp Gly Gln
90              95                  100                 105

Tyr Val Leu Met Thr Arg Glu Glu Phe Lys Asp Trp Leu Phe Asn His
                110                 115                 120

Glu Phe Thr Arg Asn Ile Ser Leu Ile Gln Gln His His Thr Trp Ser
                125                 130                 135

Pro Ala Tyr Gly His Phe Asn Gly Asn Asn His Phe Ser Leu Leu Lys
            140                 145                 150

Gly Met Glu Tyr Tyr His Thr Lys Glu Val Gly Trp Glu Asn Ile Ala
    155                 160                 165

Gln Asn Leu Thr Thr Phe Pro Asp Gly Arg Ile Ala Val Ser Arg Pro
170                 175                 180                 185

Phe Asn Ser Ala Pro Asp Gly Ser Ile Gly Pro Lys Ala Asn Ser Ile
                190                 195                 200

Gly Leu Asn Ile Glu His Ile Gly Asn Phe Asp Leu Gly Asn Asp Gln
            205                 210                 215

Met Thr Ala Glu His Arg Glu Thr Ile Ile Tyr Leu Thr Ala Leu Leu
    220                 225                 230

Cys Met Lys Phe Gly Leu Thr Pro Ser Ile Asp Ser Ile Thr Tyr His
    235                 240                 245

Arg Trp Trp Asp Met Asn Thr Lys Glu Arg Val Leu Asp Arg Ser Glu
250                 255                 260                 265

Gly Val Ser Val Lys Thr Cys Pro Gly Thr Gly Phe Phe Gly Gly Asn
                270                 275                 280

Thr Thr Glu Ser Ala Lys Ser Asn Phe Tyr Pro Leu Val Ser Arg Lys
            285                 290                 295

Ile Glu Glu Ile Arg Ala Thr Leu Asn
            300                 305

<210> SEQ ID NO 84
<211> LENGTH: 306
<212> TYPE: PRT
<213> ORGANISM: Bacillus sp

<400> SEQUENCE: 84

Ala Ala Glu Asn His Ser Asn Leu Tyr Asp Val Arg Ser Gly Asp Thr
1               5                   10                  15

Leu Trp Lys Ile Ala Asn Lys Tyr Gly Thr Ser Val Gln Asn Leu Lys
            20                  25                  30

Glu Thr Asn Gly Leu Gln Ser Asp Leu Leu Val Gly Gln Arg Leu
        35                  40                  45

Phe Val Pro Met Ser Tyr Glu Val Val Ser Gly Asp Thr Leu Trp Lys
    50                  55                  60

```
Leu Ser Arg Ala Tyr Asn Ser Ser Val Gln Ala Ile Lys Glu Thr Asn
 65                  70                  75                  80

Gly Leu Thr Ser Asp Val Leu Tyr Ile Gly Gln Lys Leu Lys Ile Pro
                 85                  90                  95

Pro Lys Lys Leu Pro Met Asp Gly Gln Tyr Val Leu Met Thr Arg Glu
            100                 105                 110

Glu Phe Lys Asp Trp Leu Phe Asn His Glu Phe Thr Arg Asn Ile Ser
        115                 120                 125

Leu Ile Gln Gln His His Thr Trp Ser Pro Ala Tyr Gly His Phe Asn
130                 135                 140

Gly Asn Asn His Phe Ser Leu Leu Lys Gly Met Glu Tyr Tyr His Thr
145                 150                 155                 160

Lys Glu Val Gly Trp Glu Asn Ile Ala Gln Asn Leu Thr Thr Phe Pro
                165                 170                 175

Asp Gly Arg Ile Ala Val Ser Arg Pro Phe Asn Ser Ala Pro Asp Gly
            180                 185                 190

Ser Ile Gly Pro Lys Ala Asn Ser Ile Gly Leu Asn Ile Glu His Ile
        195                 200                 205

Gly Asn Phe Asp Leu Gly Asn Asp Gln Met Thr Ala Glu His Arg Glu
210                 215                 220

Thr Ile Ile Tyr Leu Thr Ala Leu Leu Cys Met Lys Phe Gly Leu Thr
225                 230                 235                 240

Pro Ser Ile Asp Ser Ile Thr Tyr His Arg Trp Trp Asp Met Asn Thr
                245                 250                 255

Lys Glu Arg Val Leu Asp Arg Ser Glu Gly Val Ser Val Lys Thr Cys
            260                 265                 270

Pro Gly Thr Gly Phe Phe Gly Gly Asn Thr Thr Glu Ser Ala Lys Ser
        275                 280                 285

Asn Phe Tyr Pro Leu Val Ser Arg Lys Ile Glu Glu Ile Arg Ala Thr
290                 295                 300

Leu Asn
305

<210> SEQ ID NO 85
<211> LENGTH: 2004
<212> TYPE: DNA
<213> ORGANISM: Streptomyces sp
<220> FEATURE:
<221> NAME/KEY: CDS
<222> LOCATION: (1)..(2001)
<220> FEATURE:
<221> NAME/KEY: sig_peptide
<222> LOCATION: (1)..(105)
<220> FEATURE:
<221> NAME/KEY: mat_peptide
<222> LOCATION: (106)..(2001)

<400> SEQUENCE: 85 atg aag aaa ccg ttg ggg aaa att gtc gca agc acc gca cta ctc att      48
Met Lys Lys Pro Leu Gly Lys Ile Val Ala Ser Thr Ala Leu Leu Ile
-35                 -30                 -25                 -20 tct gtt gct ttt agt tca tcg ata gca tca gca cat cat cat cac cat      96
Ser Val Ala Phe Ser Ser Ser Ile Ala Ser Ala His His His His His
            -15                 -10                  -5 cat cct agg gac gac gac acc ggc gtg ctc cag gcg gcg ttc gcc gac     144
His Pro Arg Asp Asp Asp Thr Gly Val Leu Gln Ala Ala Phe Ala Asp
     -1   1                   5                  10
```

```
gcg gcc gag cgc tac cag gtg ccg gag gaa gtg ctg ctc ggc gtc tcc    192
Ala Ala Glu Arg Tyr Gln Val Pro Glu Glu Val Leu Leu Gly Val Ser
            15                  20                  25 tat ctc cag tcc cgc tgg gac ggc cac cgt ggc gcg gcg agc gtg acc    240
Tyr Leu Gln Ser Arg Trp Asp Gly His Arg Gly Ala Ala Ser Val Thr
 30              35                  40                  45 ggc ggc tac ggc ccg atg cat ctg acg gac gcg cac acc gcg ctc agc    288
Gly Gly Tyr Gly Pro Met His Leu Thr Asp Ala His Thr Ala Leu Ser
                     50                  55                  60 cgg gag gcg ggc gcg gtg gac aac cac cat ctg cac ggg gag gag gac    336
Arg Glu Ala Gly Ala Val Asp Asn His His Leu His Gly Glu Glu Asp
             65                  70                  75 ccg cgc ggc gac gac gga cgg gtc ctt gag atg ccg gag gag gag atc    384
Pro Arg Gly Asp Asp Gly Arg Val Leu Glu Met Pro Glu Glu Glu Ile
         80                  85                  90 ccg ccg gtt ccg gag cgc tcc gag gtg ccc gaa cgg ctc cag acg gtg    432
Pro Pro Val Pro Glu Arg Ser Glu Val Pro Glu Arg Leu Gln Thr Val
 95                 100                 105 gac cgg gcg gcg gag ctg acc ggg ctc gac ccg gag gac ctg cgg tcc    480
Asp Arg Ala Ala Glu Leu Thr Gly Leu Asp Pro Glu Asp Leu Arg Ser
110                 115                 120                 125 agc aac gcg gcg aac gta cag ggc ggc gcc gcg ctg ctg gcc gcg gcg    528
Ser Asn Ala Ala Asn Val Gln Gly Gly Ala Ala Leu Leu Ala Ala Ala
                130                 135                 140 cag cgc gac ctc ggc ctg gag ccg agc gac gac ccg gcg gac tgg tac    576
Gln Arg Asp Leu Gly Leu Glu Pro Ser Asp Asp Pro Ala Asp Trp Tyr
            145                 150                 155 gcc gcc gtc gcc tcc tac gcg ggc tcc gcc tcg cgg gag gcg gcg cgg    624
Ala Ala Val Ala Ser Tyr Ala Gly Ser Ala Ser Arg Glu Ala Ala Arg
        160                 165                 170 ttc ttc gcc gac gag gtg tac tcg gtg atc aac gag ggc gcc cgg cac    672
Phe Phe Ala Asp Glu Val Tyr Ser Val Ile Asn Glu Gly Ala Arg His
    175                 180                 185 acc acc ggc gag ggc cag gtg gtg gag ctg ccc gcc acc gag gtg acc    720
Thr Thr Gly Glu Gly Gln Val Val Glu Leu Pro Ala Thr Glu Val Thr
190                 195                 200                 205 ccg cgc acc ggg cag gcg tcc gcg ctg gcc ctg ccg gag cag cgg cgc    768
Pro Arg Thr Gly Gln Ala Ser Ala Leu Ala Leu Pro Glu Gln Arg Arg
                210                 215                 220 gat ccc cgg gtg gag tgc ccg ccc acg gtc tcc tgc gag tgg atc ccg    816
Asp Pro Arg Val Glu Cys Pro Pro Thr Val Ser Cys Glu Trp Ile Pro
            225                 230                 235 gcg gcc tac gag gag tac gag cgc gcc gac ggc tcg gtg acg tac ggc    864
Ala Ala Tyr Glu Glu Tyr Glu Arg Ala Asp Gly Ser Val Thr Tyr Gly
        240                 245                 250 aac cac gac aag ggc gac cgg ccg gac ggg cag cgg gtg cgc tac atc    912
Asn His Asp Lys Gly Asp Arg Pro Asp Gly Gln Arg Val Arg Tyr Ile
    255                 260                 265 gtc atc cac gac atg gag ggc tac ttc tgg ccg tcc atc gga ctg gtg    960
Val Ile His Asp Met Glu Gly Tyr Phe Trp Pro Ser Ile Gly Leu Val
270                 275                 280                 285 cag aac ccg acc tgg gcg tcc tgg cag tac agc ctc cag gcg tcg gac   1008
Gln Asn Pro Thr Trp Ala Ser Trp Gln Tyr Ser Leu Gln Ala Ser Asp
                290                 295                 300 ggg cac atc gcg cag cac atc ctg gcc aag gac gtc ggc tgg cag gcc   1056
Gly His Ile Ala Gln His Ile Leu Ala Lys Asp Val Gly Trp Gln Ala
            305                 310                 315
```

-continued

| | |
|---|---|
| ggc aac tgg tac gtc aac gcc acg tcc atc ggc ctg gag cac gag ggt<br>Gly Asn Trp Tyr Val Asn Ala Thr Ser Ile Gly Leu Glu His Glu Gly<br>       320                       325                      330 | 1104 |
| ttc ctg cgg gcc ccg gac gcc tgg tac acc gag gtg atg tac cgc tcc<br>Phe Leu Arg Ala Pro Asp Ala Trp Tyr Thr Glu Val Met Tyr Arg Ser<br>335                     340                     345 | 1152 |
| tcg gcg cgg ctg gtg cgc tac ctg gcc cgg cag cac gac atc ccg ctg<br>Ser Ala Arg Leu Val Arg Tyr Leu Ala Arg Gln His Asp Ile Pro Leu<br>350                     355                     360                  365 | 1200 |
| gac cgg cac cac atc atc ggc cac tac aac gtg ccg ggc atc ggc acc<br>Asp Arg His His Ile Ile Gly His Tyr Asn Val Pro Gly Ile Gly Thr<br>                     370                     375                      380 | 1248 |
| gcc aac atc ccc ggg atg cac acc gac ccc ggt ccg tac tgg gac tgg<br>Ala Asn Ile Pro Gly Met His Thr Asp Pro Gly Pro Tyr Trp Asp Trp<br>                385                     390                     395 | 1296 |
| gcg cac tac ttc cgg ctg atg ggc gcg ccg atc acg ccc agc gcc cgg<br>Ala His Tyr Phe Arg Leu Met Gly Ala Pro Ile Thr Pro Ser Ala Arg<br>          400                     405                     410 | 1344 |
| ccg cac agc gcg ctg gtg acg atc cgt ccc gac tac gac aac cac cgc<br>Pro His Ser Ala Leu Val Thr Ile Arg Pro Asp Tyr Asp Asn His Arg<br>415                     420                     425 | 1392 |
| ccg gtg ttc acc ggc tgc gac ccg gcg gac gcc gcg ccg tgc gcg<br>Pro Val Phe Thr Gly Cys Asp Pro Ala Asp Ala Ala Pro Cys Ala<br>430                     435                     440                  445 | 1440 |
| ccg cac ggc tcc agc gcg gtg cgg ctg cac gtg gcg ccg agt cat gac<br>Pro His Gly Ser Ser Ala Val Arg Leu His Val Ala Pro Ser His Asp<br>                     450                     455                     460 | 1488 |
| gcg gcg ctg gtg ccg gac atc ggc acc cat ccg ggc agc ggc ggc cgg<br>Ala Ala Leu Val Pro Asp Ile Gly Thr His Pro Gly Ser Gly Gly Arg<br>               465                     470                     475 | 1536 |
| tcc ggc atc tcg atc tac gac atc ggc gcc cgc gcc tcg acc ggc cag<br>Ser Gly Ile Ser Ile Tyr Asp Ile Gly Ala Arg Ala Ser Thr Gly Gln<br>         480                     485                     490 | 1584 |
| cag tac gcg gtg gcg gag cgc gcc ggc gag tgg acg gcg atc tgg ttc<br>Gln Tyr Ala Val Ala Glu Arg Ala Gly Glu Trp Thr Ala Ile Trp Phe<br>495                     500                     505 | 1632 |
| aac ggc gag aag gcg tgg ttc cac gac ccg gcc cgg cag cgg acc tcg<br>Asn Gly Glu Lys Ala Trp Phe His Asp Pro Ala Arg Gln Arg Thr Ser<br>510                     515                     520                  525 | 1680 |
| gtc ccg agc cgg ggc tgg atc gcc acc ccg aag gag ggc gtg gac cgg<br>Val Pro Ser Arg Gly Trp Ile Ala Thr Pro Lys Glu Gly Val Asp Arg<br>                     530                     535                     540 | 1728 |
| gtg ccg gtc tac ggc gtg gcg tac ccg gag ccg gag gac tac ccg ccg<br>Val Pro Val Tyr Gly Val Ala Tyr Pro Glu Pro Glu Asp Tyr Pro Pro<br>         545                     550                     555 | 1776 |
| ggc gtg ccg gtg cgc gcg ttc gcg ccg ctg ccg tac cag ttc acg gcc<br>Gly Val Pro Val Arg Ala Phe Ala Pro Leu Pro Tyr Gln Phe Thr Ala<br>                 560                     565                     570 | 1824 |
| ggt cag tcg tac gcg gtg ggg cgc ggc ggc gag gcg ttc gac ggg gag<br>Gly Gln Ser Tyr Ala Val Gly Arg Gly Gly Glu Ala Phe Asp Gly Glu<br>575                     580                     585 | 1872 |
| ttc tac tcg gcg acc cgc ttc gac acg gtg ggc agc cag gtg atc cgg<br>Phe Tyr Ser Ala Thr Arg Phe Asp Thr Val Gly Ser Gln Val Ile Arg<br>590                     595                     600                  605 | 1920 |
| ggg cag cgg tac tac cag atc cag ctc ggc cac cgg cac gcg tat gtg<br>Gly Gln Arg Tyr Tyr Gln Ile Gln Leu Gly His Arg His Ala Tyr Val<br>                     610                     615                  620 | 1968 |

```
aag gcg gag gac gtg gac gtg gtg ccc gtg cgc tga                    2004
Lys Ala Glu Asp Val Asp Val Val Pro Val Arg
            625                 630
```

<210> SEQ ID NO 86
<211> LENGTH: 667
<212> TYPE: PRT
<213> ORGANISM: Streptomyces sp

<400> SEQUENCE: 86

```
Met Lys Lys Pro Leu Gly Lys Ile Val Ala Ser Thr Ala Leu Leu Ile
-35             -30             -25             -20

Ser Val Ala Phe Ser Ser Ile Ala Ser Ala His His His His
            -15             -10             -5

His Pro Arg Asp Asp Asp Thr Gly Val Leu Gln Ala Ala Phe Ala Asp
        -1  1               5                   10

Ala Ala Glu Arg Tyr Gln Val Pro Glu Val Leu Leu Gly Val Ser
            15              20              25

Tyr Leu Gln Ser Arg Trp Asp Gly His Arg Gly Ala Ala Ser Val Thr
30              35              40                      45

Gly Gly Tyr Gly Pro Met His Leu Thr Asp Ala His Thr Ala Leu Ser
                50              55                      60

Arg Glu Ala Gly Ala Val Asp Asn His His Leu His Gly Glu Glu Asp
            65              70              75

Pro Arg Gly Asp Asp Gly Arg Val Leu Glu Met Pro Glu Glu Glu Ile
        80              85              90

Pro Pro Val Pro Glu Arg Ser Glu Val Pro Glu Arg Leu Gln Thr Val
    95              100             105

Asp Arg Ala Ala Glu Leu Thr Gly Leu Asp Pro Glu Asp Leu Arg Ser
110             115             120             125

Ser Asn Ala Ala Asn Val Gln Gly Gly Ala Ala Leu Leu Ala Ala Ala
            130             135             140

Gln Arg Asp Leu Gly Leu Glu Pro Ser Asp Pro Ala Asp Trp Tyr
        145             150             155

Ala Ala Val Ala Ser Tyr Ala Gly Ser Ala Ser Arg Glu Ala Ala Arg
        160             165             170

Phe Phe Ala Asp Glu Val Tyr Ser Val Ile Asn Glu Gly Ala Arg His
    175             180             185

Thr Thr Gly Glu Gly Gln Val Val Glu Leu Pro Ala Thr Glu Val Thr
190             195             200             205

Pro Arg Thr Gly Gln Ala Ser Ala Leu Ala Leu Pro Glu Gln Arg Arg
            210             215             220

Asp Pro Arg Val Glu Cys Pro Pro Thr Val Ser Cys Gly Trp Ile Pro
        225             230             235

Ala Ala Tyr Glu Glu Tyr Glu Arg Ala Asp Gly Ser Val Thr Tyr Gly
        240             245             250

Asn His Asp Lys Gly Asp Arg Pro Asp Gly Gln Arg Val Arg Tyr Ile
        255             260             265

Val Ile His Asp Met Glu Gly Tyr Phe Trp Pro Ser Ile Gly Leu Val
270             275             280             285

Gln Asn Pro Thr Trp Ala Ser Trp Gln Tyr Ser Leu Gln Ala Ser Asp
            290             295             300

Gly His Ile Ala Gln His Ile Leu Ala Lys Asp Val Gly Trp Gln Ala
            305             310             315
```

Gly Asn Trp Tyr Val Asn Ala Thr Ser Ile Gly Leu Glu His Glu Gly
            320                 325                 330

Phe Leu Arg Ala Pro Asp Ala Trp Tyr Thr Glu Val Met Tyr Arg Ser
        335                 340                 345

Ser Ala Arg Leu Val Arg Tyr Leu Ala Arg Gln His Asp Ile Pro Leu
350                 355                 360                 365

Asp Arg His His Ile Ile Gly His Tyr Asn Val Pro Gly Ile Gly Thr
                370                 375                 380

Ala Asn Ile Pro Gly Met His Thr Asp Pro Gly Pro Tyr Trp Asp Trp
            385                 390                 395

Ala His Tyr Phe Arg Leu Met Gly Ala Pro Ile Thr Pro Ser Ala Arg
        400                 405                 410

Pro His Ser Ala Leu Val Thr Ile Arg Pro Asp Tyr Asp Asn His Arg
415                 420                 425

Pro Val Phe Thr Gly Cys Asp Pro Ala Asp Ala Ala Pro Cys Ala
430                 435                 440                 445

Pro His Gly Ser Ser Ala Val Arg Leu His Val Ala Pro Ser His Asp
                450                 455                 460

Ala Ala Leu Val Pro Asp Ile Gly Thr His Pro Gly Ser Gly Gly Arg
            465                 470                 475

Ser Gly Ile Ser Ile Tyr Asp Ile Gly Ala Arg Ala Ser Thr Gly Gln
        480                 485                 490

Gln Tyr Ala Val Ala Glu Arg Ala Gly Glu Trp Thr Ala Ile Trp Phe
    495                 500                 505

Asn Gly Glu Lys Ala Trp Phe His Asp Pro Ala Arg Gln Arg Thr Ser
510                 515                 520                 525

Val Pro Ser Arg Gly Trp Ile Ala Thr Pro Lys Glu Gly Val Asp Arg
                530                 535                 540

Val Pro Val Tyr Gly Val Ala Tyr Pro Glu Pro Glu Asp Tyr Pro Pro
            545                 550                 555

Gly Val Pro Val Arg Ala Phe Ala Pro Leu Pro Tyr Gln Phe Thr Ala
        560                 565                 570

Gly Gln Ser Tyr Ala Val Gly Arg Gly Gly Glu Ala Phe Asp Gly Glu
    575                 580                 585

Phe Tyr Ser Ala Thr Arg Phe Asp Thr Val Gly Ser Gln Val Ile Arg
590                 595                 600                 605

Gly Gln Arg Tyr Tyr Gln Ile Gln Leu Gly His Arg His Ala Tyr Val
                610                 615                 620

Lys Ala Glu Asp Val Asp Val Val Pro Val Arg
            625                 630

<210> SEQ ID NO 87
<211> LENGTH: 632
<212> TYPE: PRT
<213> ORGANISM: Streptomyces sp

<400> SEQUENCE: 87

Asp Asp Asp Thr Gly Val Leu Gln Ala Ala Phe Ala Asp Ala Ala Glu
1               5                   10                  15

Arg Tyr Gln Val Pro Glu Glu Val Leu Leu Gly Val Ser Tyr Leu Gln
                20                  25                  30

Ser Arg Trp Asp Gly His Arg Gly Ala Ala Ser Val Thr Gly Gly Tyr
        35                  40                  45

Gly Pro Met His Leu Thr Asp Ala His Thr Ala Leu Ser Arg Glu Ala
    50                  55                  60

-continued

```
Gly Ala Val Asp Asn His His Leu His Gly Glu Glu Asp Pro Arg Gly
 65                  70                  75                  80

Asp Asp Gly Arg Val Leu Glu Met Pro Glu Glu Ile Pro Pro Val
                 85                  90                  95

Pro Glu Arg Ser Glu Val Pro Glu Arg Leu Gln Thr Val Asp Arg Ala
                100                 105                 110

Ala Glu Leu Thr Gly Leu Asp Pro Glu Asp Leu Arg Ser Ser Asn Ala
                115                 120                 125

Ala Asn Val Gln Gly Gly Ala Ala Leu Leu Ala Ala Ala Gln Arg Asp
130                 135                 140

Leu Gly Leu Glu Pro Ser Asp Asp Pro Ala Asp Trp Tyr Ala Ala Val
145                 150                 155                 160

Ala Ser Tyr Ala Gly Ser Ala Ser Arg Glu Ala Ala Arg Phe Phe Ala
                165                 170                 175

Asp Glu Val Tyr Ser Val Ile Asn Glu Gly Ala Arg His Thr Thr Gly
                180                 185                 190

Glu Gly Gln Val Val Glu Leu Pro Ala Thr Glu Val Thr Pro Arg Thr
                195                 200                 205

Gly Gln Ala Ser Ala Leu Ala Leu Pro Glu Gln Arg Arg Asp Pro Arg
210                 215                 220

Val Glu Cys Pro Pro Thr Val Ser Cys Glu Trp Ile Pro Ala Ala Tyr
225                 230                 235                 240

Glu Glu Tyr Glu Arg Ala Asp Gly Ser Val Thr Tyr Gly Asn His Asp
                245                 250                 255

Lys Gly Asp Arg Pro Asp Gly Gln Arg Val Arg Tyr Ile Val Ile His
                260                 265                 270

Asp Met Glu Gly Tyr Phe Trp Pro Ser Ile Gly Leu Val Gln Asn Pro
                275                 280                 285

Thr Trp Ala Ser Trp Gln Tyr Ser Leu Gln Ala Ser Asp Gly His Ile
                290                 295                 300

Ala Gln His Ile Leu Ala Lys Asp Val Gly Trp Gln Ala Gly Asn Trp
305                 310                 315                 320

Tyr Val Asn Ala Thr Ser Ile Gly Leu Glu His Glu Gly Phe Leu Arg
                325                 330                 335

Ala Pro Asp Ala Trp Tyr Thr Glu Val Met Tyr Arg Ser Ser Ala Arg
                340                 345                 350

Leu Val Arg Tyr Leu Ala Arg Gln His Asp Ile Pro Leu Asp Arg His
                355                 360                 365

His Ile Ile Gly His Tyr Asn Val Pro Gly Ile Gly Thr Ala Asn Ile
                370                 375                 380

Pro Gly Met His Thr Asp Pro Gly Pro Tyr Trp Asp Trp Ala His Tyr
385                 390                 395                 400

Phe Arg Leu Met Gly Ala Pro Ile Thr Pro Ser Ala Arg Pro His Ser
                405                 410                 415

Ala Leu Val Thr Ile Arg Pro Asp Tyr Asp Asn His Arg Pro Val Phe
                420                 425                 430

Thr Gly Cys Asp Pro Ala Asp Ala Ala Pro Cys Ala Pro His Gly
                435                 440                 445

Ser Ser Ala Val Arg Leu His Val Ala Pro Ser His Asp Ala Ala Leu
                450                 455                 460

Val Pro Asp Ile Gly Thr His Pro Gly Ser Gly Gly Arg Ser Gly Ile
465                 470                 475                 480
```

```
Ser Ile Tyr Asp Ile Gly Ala Arg Ala Ser Thr Gly Gln Gln Tyr Ala
            485                 490                 495
Val Ala Glu Arg Ala Gly Glu Trp Thr Ala Ile Trp Phe Asn Gly Glu
        500                 505                 510
Lys Ala Trp Phe His Asp Pro Ala Arg Gln Arg Thr Ser Val Pro Ser
        515                 520                 525
Arg Gly Trp Ile Ala Thr Pro Lys Glu Gly Val Asp Arg Val Pro Val
        530                 535                 540
Tyr Gly Val Ala Tyr Pro Glu Pro Glu Asp Tyr Pro Pro Gly Val Pro
545                 550                 555                 560
Val Arg Ala Phe Ala Pro Leu Pro Tyr Gln Phe Thr Ala Gly Gln Ser
                565                 570                 575
Tyr Ala Val Gly Arg Gly Gly Glu Ala Phe Asp Gly Glu Phe Tyr Ser
                580                 585                 590
Ala Thr Arg Phe Asp Thr Val Gly Ser Gln Val Ile Arg Gly Gln Arg
                595                 600                 605
Tyr Tyr Gln Ile Gln Leu Gly His Arg His Ala Tyr Val Lys Ala Glu
            610                 615                 620
Asp Val Asp Val Val Pro Val Arg
625                 630

<210> SEQ ID NO 88
<211> LENGTH: 723
<212> TYPE: DNA
<213> ORGANISM: Bacillus sp
<220> FEATURE:
<221> NAME/KEY: CDS
<222> LOCATION: (1)..(720)
<220> FEATURE:
<221> NAME/KEY: sig_peptide
<222> LOCATION: (1)..(72)
<220> FEATURE:
<221> NAME/KEY: mat_peptide
<222> LOCATION: (73)..(720)

<400> SEQUENCE: 88 atg gta aga aac tta gga ata aat ata ctc att gta acc tta ttt tta     48
Met Val Arg Asn Leu Gly Ile Asn Ile Leu Ile Val Thr Leu Phe Leu
            -20                 -15                 -10 ata gga tgc aca aca gct gaa aat tcc caa acg atc gga aaa gac aca     96
Ile Gly Cys Thr Thr Ala Glu Asn Ser Gln Thr Ile Gly Lys Asp Thr
        -5                  -1   1               5 tta caa gca atg gaa gat tcg aag ata gag aag aag gac ttg atg ctt    144
Leu Gln Ala Met Glu Asp Ser Lys Ile Glu Lys Lys Asp Leu Met Leu
     10                  15                  20 cag tcg gcg gag aca aga aac gat aat aat ccc gta gat tat ctt cta    192
Gln Ser Ala Glu Thr Arg Asn Asp Asn Asn Pro Val Asp Tyr Leu Leu
 25                  30                  35                  40 cca ctg gaa aac tca aaa ccg cgg acg gag gca atc acc cat gtc atg    240
Pro Leu Glu Asn Ser Lys Pro Arg Thr Glu Ala Ile Thr His Val Met
                 45                  50                  55 gtt cat ttt ata agc aat gct gcg aga aat cca gaa gat cct tat aat    288
Val His Phe Ile Ser Asn Ala Ala Arg Asn Pro Glu Asp Pro Tyr Asn
                 60                  65                  70 act att gat atc tat tcc att ttt gtg gaa tat ggt gtg tca gca cat    336
Thr Ile Asp Ile Tyr Ser Ile Phe Val Glu Tyr Gly Val Ser Ala His
             75                  80                  85 tat atg att gga aga gat ggg aca gtg ttt cgg ctt gta tca gaa gat    384
Tyr Met Ile Gly Arg Asp Gly Thr Val Phe Arg Leu Val Ser Glu Asp
         90                  95                 100
```

| | | | | | | | | | | | | | | | | |
|---|---|---|---|---|---|---|---|---|---|---|---|---|---|---|---|---|
| cgt | gtc | gct | tat | cat | gct | ggg | gca | gga | gag | ctt | gaa | gat | tat | cct | gac | 432 |
| Arg | Val | Ala | Tyr | His | Ala | Gly | Ala | Gly | Glu | Leu | Glu | Asp | Tyr | Pro | Asp | |
| 105 | | | | 110 | | | | 115 | | | | 120 | | | | |
| tat | acg | gac | agc | tta | aat | gaa | ttt | tcg | ata | ggt | att | gaa | ctc | ctt | gct | 480 |
| Tyr | Thr | Asp | Ser | Leu | Asn | Glu | Phe | Ser | Ile | Gly | Ile | Glu | Leu | Leu | Ala | |
| | | | | 125 | | | | | 130 | | | | | 135 | | |
| atc | ggc | act | agg | gaa | gag | atg | ttt | cct | gct | ata | cca | gta | cgt | gtc | tac | 528 |
| Ile | Gly | Thr | Arg | Glu | Glu | Met | Phe | Pro | Ala | Ile | Pro | Val | Arg | Val | Tyr | |
| | | | 140 | | | | | 145 | | | | | 150 | | | |
| aat | gta | ata | gat | cca | aga | tta | gta | ggc | tat | aca | gat | gaa | caa | tac | gaa | 576 |
| Asn | Val | Ile | Asp | Pro | Arg | Leu | Val | Gly | Tyr | Thr | Asp | Glu | Gln | Tyr | Glu | |
| | | 155 | | | | | 160 | | | | | 165 | | | | |
| tcg | ctt | aac | gtt | tta | ttg | gat | gat | att | ttc | cag | aga | aac | cca | tca | ata | 624 |
| Ser | Leu | Asn | Val | Leu | Leu | Asp | Asp | Ile | Phe | Gln | Arg | Asn | Pro | Ser | Ile | |
| | 170 | | | | | 175 | | | | | 180 | | | | | |
| aat | aga | gat | aga | aat | cat | gtg | att | ggg | cat | gat | gaa | tac | gca | cct | gga | 672 |
| Asn | Arg | Asp | Arg | Asn | His | Val | Ile | Gly | His | Asp | Glu | Tyr | Ala | Pro | Gly | |
| 185 | | | | 190 | | | | | 195 | | | | | 200 | | |
| aga | aaa | gct | gat | cca | ggc | tca | tta | ttt | gat | tgg | tct | aaa | ctc | ggg | tta | 720 |
| Arg | Lys | Ala | Asp | Pro | Gly | Ser | Leu | Phe | Asp | Trp | Ser | Lys | Leu | Gly | Leu | |
| | | | 205 | | | | | 210 | | | | | 215 | | | |
| tag | | | | | | | | | | | | | | | | 723 |

<210> SEQ ID NO 89
<211> LENGTH: 240
<212> TYPE: PRT
<213> ORGANISM: Bacillus sp

<400> SEQUENCE: 89

Met Val Arg Asn Leu Gly Ile Asn Ile Leu Ile Val Thr Leu Phe Leu
            -20              -15               -10

Ile Gly Cys Thr Thr Ala Glu Asn Ser Gln Thr Ile Gly Lys Asp Thr
         -5               -1  1                5

Leu Gln Ala Met Glu Asp Ser Lys Ile Glu Lys Lys Asp Leu Met Leu
         10              15              20

Gln Ser Ala Glu Thr Arg Asn Asp Asn Asn Pro Val Asp Tyr Leu Leu
25              30              35                      40

Pro Leu Glu Asn Ser Lys Pro Arg Thr Glu Ala Ile Thr His Val Met
                45              50              55

Val His Phe Ile Ser Asn Ala Ala Arg Asn Pro Glu Asp Pro Tyr Asn
             60              65              70

Thr Ile Asp Ile Tyr Ser Ile Phe Val Glu Tyr Gly Val Ser Ala His
         75              80              85

Tyr Met Ile Gly Arg Asp Gly Thr Val Phe Arg Leu Val Ser Glu Asp
90              95                      100

Arg Val Ala Tyr His Ala Gly Ala Gly Glu Leu Glu Asp Tyr Pro Asp
105                      110             115             120

Tyr Thr Asp Ser Leu Asn Glu Phe Ser Ile Gly Ile Glu Leu Leu Ala
                125             130             135

Ile Gly Thr Arg Glu Glu Met Phe Pro Ala Ile Pro Val Arg Val Tyr
             140             145             150

Asn Val Ile Asp Pro Arg Leu Val Gly Tyr Thr Asp Glu Gln Tyr Glu
        155             160             165

Ser Leu Asn Val Leu Leu Asp Asp Ile Phe Gln Arg Asn Pro Ser Ile
    170             175             180

Asn Arg Asp Arg Asn His Val Ile Gly His Asp Glu Tyr Ala Pro Gly
185             190             195             200

```
Arg Lys Ala Asp Pro Gly Ser Leu Phe Asp Trp Ser Lys Leu Gly Leu
            205                 210                 215

<210> SEQ ID NO 90
<211> LENGTH: 216
<212> TYPE: PRT
<213> ORGANISM: Bacillus sp

<400> SEQUENCE: 90

Ser Gln Thr Ile Gly Lys Asp Thr Leu Gln Ala Met Glu Asp Ser Lys
1               5                   10                  15

Ile Glu Lys Lys Asp Leu Met Leu Gln Ser Ala Glu Thr Arg Asn Asp
            20                  25                  30

Asn Asn Pro Val Asp Tyr Leu Leu Pro Leu Glu Asn Ser Lys Pro Arg
        35                  40                  45

Thr Glu Ala Ile Thr His Val Met Val His Phe Ile Ser Asn Ala Ala
    50                  55                  60

Arg Asn Pro Glu Asp Pro Tyr Asn Thr Ile Asp Ile Tyr Ser Ile Phe
65                  70                  75                  80

Val Glu Tyr Gly Val Ser Ala His Tyr Met Ile Gly Arg Asp Gly Thr
                85                  90                  95

Val Phe Arg Leu Val Ser Glu Asp Arg Val Ala Tyr His Ala Gly Ala
            100                 105                 110

Gly Glu Leu Glu Asp Tyr Pro Asp Tyr Thr Asp Ser Leu Asn Glu Phe
        115                 120                 125

Ser Ile Gly Ile Glu Leu Leu Ala Ile Gly Thr Arg Glu Glu Met Phe
    130                 135                 140

Pro Ala Ile Pro Val Arg Val Tyr Asn Val Ile Asp Pro Arg Leu Val
145                 150                 155                 160

Gly Tyr Thr Asp Glu Gln Tyr Glu Ser Leu Asn Val Leu Leu Asp Asp
                165                 170                 175

Ile Phe Gln Arg Asn Pro Ser Ile Asn Arg Asp Arg Asn His Val Ile
            180                 185                 190

Gly His Asp Glu Tyr Ala Pro Gly Arg Lys Ala Asp Pro Gly Ser Leu
        195                 200                 205

Phe Asp Trp Ser Lys Leu Gly Leu
    210                 215

<210> SEQ ID NO 91
<211> LENGTH: 1002
<212> TYPE: DNA
<213> ORGANISM: Bacillus sp
<220> FEATURE:
<221> NAME/KEY: CDS
<222> LOCATION: (1)..(999)
<220> FEATURE:
<221> NAME/KEY: sig_peptide
<222> LOCATION: (1)..(81)
<220> FEATURE:
<221> NAME/KEY: mat_peptide
<222> LOCATION: (82)..(999)

<400> SEQUENCE: 91 atg gtt aga ggg ata tgt ata gcg gtt ttt att tgt ttt ctt agt atg    48
Met Val Arg Gly Ile Cys Ile Ala Val Phe Ile Cys Phe Leu Ser Met
        -25                 -20                 -15 aca ggt ttt ttg aat tta cca caa gcc caa gca ata gcg cac aat cat    96
Thr Gly Phe Leu Asn Leu Pro Gln Ala Gln Ala Ile Ala His Asn His
    -10                 -5              -1  1               5
```

| | | |
|---|---|---|
| agc aac att tat gac atc aaa tca ggt gat aca ttg tgg aaa ata gct<br>Ser Asn Ile Tyr Asp Ile Lys Ser Gly Asp Thr Leu Trp Lys Ile Ala<br>           10                    15                 20 | | 144 |
| caa agc tat ggg aca act gtg aaa gat tta aag caa acg aac gga tta<br>Gln Ser Tyr Gly Thr Thr Val Lys Asp Leu Lys Gln Thr Asn Gly Leu<br>          25                    30                 35 | | 192 |
| acc tcc gat tta ctt tta ata ggt caa agg ttg ttc gta cct atg aga<br>Thr Ser Asp Leu Leu Leu Ile Gly Gln Arg Leu Phe Val Pro Met Arg<br>        40                    45                50 | | 240 |
| tat gaa gtc gtc tct gga gat acg cta tgg aaa ttg tca cag caa tac<br>Tyr Glu Val Val Ser Gly Asp Thr Leu Trp Lys Leu Ser Gln Gln Tyr<br>55                    60                65 | | 288 |
| aac tcc aca gta ccg tca atc aaa ttg gca aac ggt tta cca tca gac<br>Asn Ser Thr Val Pro Ser Ile Lys Leu Ala Asn Gly Leu Pro Ser Asp<br>70                    75                80                    85 | | 336 |
| atg att tac ata gga caa aag ttg aaa atc cca caa cga aag tta cga<br>Met Ile Tyr Ile Gly Gln Lys Leu Lys Ile Pro Gln Arg Lys Leu Arg<br>                90                    95               100 | | 384 |
| atg gat ggc caa cat gtt tta atg aca aaa gag gag ttt agg ggc tgg<br>Met Asp Gly Gln His Val Leu Met Thr Lys Glu Glu Phe Arg Gly Trp<br>          105                   110                115 | | 432 |
| cta ttt aat caa aaa atc aac cgt aat att tct atc atc caa gaa cac<br>Leu Phe Asn Gln Lys Ile Asn Arg Asn Ile Ser Ile Ile Gln Glu His<br>            120                  125               130 | | 480 |
| cac act tgg tta cca gat tat agt cgc ttt aat gaa aca aac cat ttc<br>His Thr Trp Leu Pro Asp Tyr Ser Arg Phe Asn Glu Thr Asn His Phe<br>135                     140                145 | | 528 |
| caa cta ctt aaa gga atg gaa tac ttt cat gtg cat gaa atg gga tgg<br>Gln Leu Leu Lys Gly Met Glu Tyr Phe His Val His Glu Met Gly Trp<br>150                    155                160               165 | | 576 |
| agt aac att gcc cag aat atc acg acc ttc cca gat gga aca gtg gcg<br>Ser Asn Ile Ala Gln Asn Ile Thr Thr Phe Pro Asp Gly Thr Val Ala<br>            170                  175               180 | | 624 |
| gtt tct cgt cca cta aac gtg cct cca gac ggt tct att ggg aat tac<br>Val Ser Arg Pro Leu Asn Val Pro Pro Asp Gly Ser Ile Gly Asn Tyr<br>               185                 190                195 | | 672 |
| gcg aac tct atc gga atc aac att gaa agc gta gga aat ttc gac ata<br>Ala Asn Ser Ile Gly Ile Asn Ile Glu Ser Val Gly Asn Phe Asp Ile<br>          200                   205                210 | | 720 |
| gga aac gat caa atg tca cag gcg caa aaa gaa aca att ctc tat gtt<br>Gly Asn Asp Gln Met Ser Gln Ala Gln Lys Glu Thr Ile Leu Tyr Val<br>            215                  220               225 | | 768 |
| act gct ctt cta tca att aaa cta ggc ctt acg cca tct att gac acc<br>Thr Ala Leu Leu Ser Ile Lys Leu Gly Leu Thr Pro Ser Ile Asp Thr<br>230                     235                240               245 | | 816 |
| atc aca tat cac cac tgg tgg gat atg cgt aca ggt aaa aga gtg tta<br>Ile Thr Tyr His His Trp Trp Asp Met Arg Thr Gly Lys Arg Val Leu<br>               250                 255                260 | | 864 |
| gac aat aac gaa gga tat tcc gtc aaa aca tgc cca ggg aca gca ttc<br>Asp Asn Asn Glu Gly Tyr Ser Val Lys Thr Cys Pro Gly Thr Ala Phe<br>          265                   270                275 | | 912 |
| ttt ggc ggc aat agc aca aaa agt gcc aaa aca aac ttt tat cca ctt<br>Phe Gly Gly Asn Ser Thr Lys Ser Ala Lys Thr Asn Phe Tyr Pro Leu<br>          280                   285                290 | | 960 |
| gta tct aag aaa ata gag gaa atc aag aaa aca atg gat tag<br>Val Ser Lys Lys Ile Glu Glu Ile Lys Lys Thr Met Asp<br>295                     300                305 | | 1002 |

<210> SEQ ID NO 92
<211> LENGTH: 333

```
<212> TYPE: PRT
<213> ORGANISM: Bacillus sp

<400> SEQUENCE: 92

Met Val Arg Gly Ile Cys Ile Ala Val Phe Ile Cys Phe Leu Ser Met
        -25                 -20                 -15
Thr Gly Phe Leu Asn Leu Pro Gln Ala Gln Ala Ile Ala His Asn His
        -10                  -5             -1   1                   5
Ser Asn Ile Tyr Asp Ile Lys Ser Gly Asp Thr Leu Trp Lys Ile Ala
                     10                  15                  20
Gln Ser Tyr Gly Thr Thr Val Lys Asp Leu Lys Gln Thr Asn Gly Leu
                 25                  30                  35
Thr Ser Asp Leu Leu Leu Ile Gly Gln Arg Leu Phe Val Pro Met Arg
                 40                  45                  50
Tyr Glu Val Val Ser Gly Asp Thr Leu Trp Lys Leu Ser Gln Gln Tyr
             55                  60                  65
Asn Ser Thr Val Pro Ser Ile Lys Leu Ala Asn Gly Leu Pro Ser Asp
70                   75                  80                  85
Met Ile Tyr Ile Gly Gln Lys Leu Lys Ile Pro Gln Arg Lys Leu Arg
                 90                  95                 100
Met Asp Gly Gln His Val Leu Met Thr Lys Glu Phe Arg Gly Trp
                105                 110                 115
Leu Phe Asn Gln Lys Ile Asn Arg Asn Ile Ser Ile Ile Gln Glu His
                120                 125                 130
His Thr Trp Leu Pro Asp Tyr Ser Arg Phe Asn Glu Thr Asn His Phe
    135                 140                 145
Gln Leu Leu Lys Gly Met Glu Tyr Phe His Val His Glu Met Gly Trp
150                 155                 160                 165
Ser Asn Ile Ala Gln Asn Ile Thr Thr Phe Pro Asp Gly Thr Val Ala
                170                 175                 180
Val Ser Arg Pro Leu Asn Val Pro Pro Asp Gly Ser Ile Gly Asn Tyr
                185                 190                 195
Ala Asn Ser Ile Gly Ile Asn Ile Glu Ser Val Gly Asn Phe Asp Ile
                200                 205                 210
Gly Asn Asp Gln Met Ser Gln Ala Gln Lys Glu Thr Ile Leu Tyr Val
                215                 220                 225
Thr Ala Leu Leu Ser Ile Lys Leu Gly Leu Thr Pro Ser Ile Asp Thr
230                 235                 240                 245
Ile Thr Tyr His His Trp Trp Asp Met Arg Thr Gly Lys Arg Val Leu
                250                 255                 260
Asp Asn Asn Glu Gly Tyr Ser Val Lys Thr Cys Pro Gly Thr Ala Phe
                265                 270                 275
Phe Gly Gly Asn Ser Thr Lys Ser Ala Lys Thr Asn Phe Tyr Pro Leu
                280                 285                 290
Val Ser Lys Lys Ile Glu Glu Ile Lys Lys Thr Met Asp
295                 300                 305

<210> SEQ ID NO 93
<211> LENGTH: 306
<212> TYPE: PRT
<213> ORGANISM: Bacillus sp

<400> SEQUENCE: 93

Ile Ala His Asn His Ser Asn Ile Tyr Asp Ile Lys Ser Gly Asp Thr
1               5                  10                  15
```

```
        Leu Trp Lys Ile Ala Gln Ser Tyr Gly Thr Thr Val Lys Asp Leu Lys
                     20                  25                  30

Gln Thr Asn Gly Leu Thr Ser Asp Leu Leu Ile Gly Gln Arg Leu
                 35                  40                  45

Phe Val Pro Met Arg Tyr Glu Val Val Ser Gly Asp Thr Leu Trp Lys
         50                  55                  60

Leu Ser Gln Gln Tyr Asn Ser Thr Val Pro Ser Ile Lys Leu Ala Asn
         65                  70                  75                  80

Gly Leu Pro Ser Asp Met Ile Tyr Ile Gly Gln Lys Leu Lys Ile Pro
                         85                  90                  95

Gln Arg Lys Leu Arg Met Asp Gly Gln His Val Leu Met Thr Lys Glu
                    100                 105                 110

Glu Phe Arg Gly Trp Leu Phe Asn Gln Lys Ile Asn Arg Asn Ile Ser
                115                 120                 125

Ile Ile Gln Glu His His Thr Trp Leu Pro Asp Tyr Ser Arg Phe Asn
        130                 135                 140

Glu Thr Asn His Phe Gln Leu Leu Lys Gly Met Glu Tyr Phe His Val
        145                 150                 155                 160

His Glu Met Gly Trp Ser Asn Ile Ala Gln Asn Ile Thr Thr Phe Pro
                        165                 170                 175

Asp Gly Thr Val Ala Val Ser Arg Pro Leu Asn Val Pro Pro Asp Gly
                    180                 185                 190

Ser Ile Gly Asn Tyr Ala Asn Ser Ile Gly Ile Asn Ile Glu Ser Val
                195                 200                 205

Gly Asn Phe Asp Ile Gly Asn Asp Gln Met Ser Gln Ala Gln Lys Glu
        210                 215                 220

Thr Ile Leu Tyr Val Thr Ala Leu Leu Ser Ile Lys Leu Gly Leu Thr
        225                 230                 235                 240

Pro Ser Ile Asp Thr Ile Thr Tyr His His Trp Trp Asp Met Arg Thr
                        245                 250                 255

Gly Lys Arg Val Leu Asp Asn Asn Glu Gly Tyr Ser Val Lys Thr Cys
                    260                 265                 270

Pro Gly Thr Ala Phe Phe Gly Gly Asn Ser Thr Lys Ser Ala Lys Thr
                275                 280                 285

Asn Phe Tyr Pro Leu Val Ser Lys Lys Ile Glu Glu Ile Lys Lys Thr
        290                 295                 300

Met Asp
        305

<210> SEQ ID NO 94
<211> LENGTH: 1449
<212> TYPE: DNA
<213> ORGANISM: Nonomuraea guangzhouensis
<220> FEATURE:
<221> NAME/KEY: CDS
<222> LOCATION: (1)..(1446)
<220> FEATURE:
<221> NAME/KEY: sig_peptide
<222> LOCATION: (1)..(87)
<220> FEATURE:
<221> NAME/KEY: mat_peptide
<222> LOCATION: (88)..(1446)

<400> SEQUENCE: 94 ttg aag gcc cga ctc cgc cat tcg gcc gcg ctg ctg gcc ggc gcg ctc         48
Leu Lys Ala Arg Leu Arg His Ser Ala Ala Leu Leu Ala Gly Ala Leu
            -25                 -20                 -15
```

```
atc ccc ctc tcg ctg ctc gca ggg cag ccg gcc gga gcc gca tcc gct      96
Ile Pro Leu Ser Leu Leu Ala Gly Gln Pro Ala Gly Ala Ala Ser Ala
        -10             -5              -1  1 gat ccc atg agc gac gcg ttc gcc cgt gcg gcc acc acg tac gag gtg     144
Asp Pro Met Ser Asp Ala Phe Ala Arg Ala Ala Thr Thr Tyr Glu Val
     5              10                 15 ccc cgc gac ctg ctg gtc tcg ctc gcc tac gcc gaa acc cac ctg gac     192
Pro Arg Asp Leu Leu Val Ser Leu Ala Tyr Ala Glu Thr His Leu Asp
 20              25                 30                  35 gga cac cgc ggc gaa ccc agc gcg agc ggc ggc tac ggg gtg atg cac     240
Gly His Arg Gly Glu Pro Ser Ala Ser Gly Gly Tyr Gly Val Met His
             40                  45                  50 ctg gtc agc aac ccc gtc agg cac acg ctc gag cgc gcg gcc acg ctg     288
Leu Val Ser Asn Pro Val Arg His Thr Leu Glu Arg Ala Ala Thr Leu
             55                  60                  65 acg aag cag ccc gtc tcg gcc ttg aag gcg gac gac gcg gcc aac atc     336
Thr Lys Gln Pro Val Ser Ala Leu Lys Ala Asp Asp Ala Ala Asn Ile
             70                  75                  80 acg ggc ggc gcc gcc gtg ctg cgc gcc tac gcc gac gag ctc gga ctg     384
Thr Gly Gly Ala Ala Val Leu Arg Ala Tyr Ala Asp Glu Leu Gly Leu
 85                  90                  95 gac gcc gcg gcc cgc aag gac gcg ggc aag tgg tat cag gcg gtg gcc     432
Asp Ala Ala Ala Arg Lys Asp Ala Gly Lys Trp Tyr Gln Ala Val Ala
100             105                 110                 115 aag tac ggc ggc gcc tcg tcg gcg gac gtc gcc cgg ttg tac gcc gac     480
Lys Tyr Gly Gly Ala Ser Ser Ala Asp Val Ala Arg Leu Tyr Ala Asp
                120                 125                 130 acc gtc tac gac cag ctg tcc caa ggg atc aag gtc acc acg ccg gcc     528
Thr Val Tyr Asp Gln Leu Ser Gln Gly Ile Lys Val Thr Thr Pro Ala
            135                 140                 145 ggt gag acc ctc acg gcg acg ccg cgg acc gtc cag ccc gac cgc ggc     576
Gly Glu Thr Leu Thr Ala Thr Pro Arg Thr Val Gln Pro Asp Arg Gly
                150                 155                 160 tcc tac gcc aag gca cag gag ctg ggc aag acc aat acg ctc gcg gcg     624
Ser Tyr Ala Lys Ala Gln Glu Leu Gly Lys Thr Asn Thr Leu Ala Ala
165                 170                 175 gca gtg gac tac ccg tcg gcg gcg tgg gcg gcg gcg cac agc acc aac     672
Ala Val Asp Tyr Pro Ser Ala Ala Trp Ala Ala Ala His Ser Thr Asn
180                 185                 190                 195 tac gcc gtc tcc aac cgc ccg acc agt gac gcg atc gac cgc atc atc     720
Tyr Ala Val Ser Asn Arg Pro Thr Ser Asp Ala Ile Asp Arg Ile Ile
                200                 205                 210 atc cac gtg gcc cag ggc acg tac gcc ggg acg atc gac tgg ttc cag     768
Ile His Val Ala Gln Gly Thr Tyr Ala Gly Thr Ile Asp Trp Phe Gln
                215                 220                 225 acc ggg ccc agg ccg aac ccc acc tcg tcg cac tac gtc gtc cgt tcg     816
Thr Gly Pro Arg Pro Asn Pro Thr Ser Ser His Tyr Val Val Arg Ser
            230                 235                 240 tcg gac ggc gcc gtc acc cag atg gtc agg gag aag gac cgg gcc ttc     864
Ser Asp Gly Ala Val Thr Gln Met Val Arg Glu Lys Asp Arg Ala Phe
245                 250                 255 cac gcg ggc gac tcc aac agg cgc tcg gtc ggc atc gag cac gag ggc     912
His Ala Gly Asp Ser Asn Arg Arg Ser Val Gly Ile Glu His Glu Gly
260                 265                 270                 275 tgg gtc gag cag gcc tcc tgg ttc acc gac acg atg tac cgt tcc tcg     960
Trp Val Glu Gln Ala Ser Trp Phe Thr Asp Thr Met Tyr Arg Ser Ser
                280                 285                 290
```

```
gcc gcg ctg acc cgc aac atc gcc gac agg tac ggc atc ccc aag gac      1008
Ala Ala Leu Thr Arg Asn Ile Ala Asp Arg Tyr Gly Ile Pro Lys Asp
            295                 300                 305 cgc acc cac atc atc ggc cac agc gag gct ccc ggc gcc agc cac acc      1056
Arg Thr His Ile Ile Gly His Ser Glu Ala Pro Gly Ala Ser His Thr
    310                 315                 320 gac ccc ggt ccg aac tgg aac tgg acc aag tac atg cag tac gtc acc      1104
Asp Pro Gly Pro Asn Trp Asn Trp Thr Lys Tyr Met Gln Tyr Val Thr
325                 330                 335 aac ggc agc ggt ggc ggc acc aac ccg cac acc gcc gag tcg gtg tgc      1152
Asn Gly Ser Gly Gly Gly Thr Asn Pro His Thr Ala Glu Ser Val Cys
340                 345                 350                 355 ggc acc ggc ttc acg gtg atc gac tcg gcg ccc ctg ggg acg gcg ggc      1200
Gly Thr Gly Phe Thr Val Ile Asp Ser Ala Pro Leu Gly Thr Ala Gly
                360                 365                 370 aac gtc tac ctg acg tac aac tcg ggc acc ggc gcc aac tgc gtg gcc      1248
Asn Val Tyr Leu Thr Tyr Asn Ser Gly Thr Gly Ala Asn Cys Val Ala
                375                 380                 385 acg atc aag ctg acc aac ctc ggc acg gcc acg gcc acc agc gcc tac      1296
Thr Ile Lys Leu Thr Asn Leu Gly Thr Ala Thr Ala Thr Ser Ala Tyr
            390                 395                 400 ctg gag gtg gag ggc cag aca cgc gtc acc gac agc ggt aac ttc ggc      1344
Leu Glu Val Glu Gly Gln Thr Arg Val Thr Asp Ser Gly Asn Phe Gly
405                 410                 415 tac tac gcg ggt ccg gtg cgg gcc agc gcg gcc gac aag tgc gtc tac      1392
Tyr Tyr Ala Gly Pro Val Arg Ala Ser Ala Ala Asp Lys Cys Val Tyr
420                 425                 430                 435 tgg ggc ggc aag gcc ggt acg gcc acc tac aac agc ccc ctc gaa cac      1440
Trp Gly Gly Lys Ala Gly Thr Ala Thr Tyr Asn Ser Pro Leu Glu His
                440                 445                 450 tgc ggg taa                                                          1449
Cys Gly <210> SEQ ID NO 95
<211> LENGTH: 482
<212> TYPE: PRT
<213> ORGANISM: Nonomuraea guangzhouensis

<400> SEQUENCE: 95

Leu Lys Ala Arg Leu Arg His Ser Ala Ala Leu Leu Ala Gly Ala Leu
                -25                 -20                 -15

Ile Pro Leu Ser Leu Leu Ala Gly Gln Pro Ala Gly Ala Ala Ser Ala
            -10                 -5                  -1  1

Asp Pro Met Ser Asp Ala Phe Ala Arg Ala Ala Thr Thr Tyr Glu Val
5                   10                  15

Pro Arg Asp Leu Leu Val Ser Leu Ala Tyr Ala Glu Thr His Leu Asp
20                  25                  30                  35

Gly His Arg Gly Glu Pro Ser Ala Ser Gly Gly Tyr Gly Val Met His
                40                  45                  50

Leu Val Ser Asn Pro Val Arg His Thr Leu Glu Arg Ala Ala Thr Leu
            55                  60                  65

Thr Lys Gln Pro Val Ser Ala Leu Lys Ala Asp Asp Ala Ala Asn Ile
        70                  75                  80

Thr Gly Gly Ala Ala Val Leu Arg Ala Tyr Ala Asp Glu Leu Gly Leu
    85                  90                  95

Asp Ala Ala Ala Arg Lys Asp Ala Gly Lys Trp Tyr Gln Ala Val Ala
100                 105                 110                 115
```

Lys Tyr Gly Gly Ala Ser Ser Ala Asp Val Ala Arg Leu Tyr Ala Asp
            120                 125                 130

Thr Val Tyr Asp Gln Leu Ser Gln Gly Ile Lys Val Thr Thr Pro Ala
        135                 140                 145

Gly Glu Thr Leu Thr Ala Thr Pro Arg Thr Val Gln Pro Asp Arg Gly
        150                 155                 160

Ser Tyr Ala Lys Ala Gln Glu Leu Gly Lys Thr Asn Thr Leu Ala Ala
165                 170                 175

Ala Val Asp Tyr Pro Ser Ala Ala Trp Ala Ala His Ser Thr Asn
180                 185                 190                 195

Tyr Ala Val Ser Asn Arg Pro Thr Ser Asp Ala Ile Asp Arg Ile Ile
                200                 205                 210

Ile His Val Ala Gln Gly Thr Tyr Ala Gly Thr Ile Asp Trp Phe Gln
            215                 220                 225

Thr Gly Pro Arg Pro Asn Pro Thr Ser Ser His Tyr Val Val Arg Ser
        230                 235                 240

Ser Asp Gly Ala Val Thr Gln Met Val Arg Glu Lys Asp Arg Ala Phe
245                 250                 255

His Ala Gly Asp Ser Asn Arg Arg Ser Val Gly Ile Glu His Glu Gly
260                 265                 270                 275

Trp Val Glu Gln Ala Ser Trp Phe Thr Asp Thr Met Tyr Arg Ser Ser
                280                 285                 290

Ala Ala Leu Thr Arg Asn Ile Ala Asp Arg Tyr Gly Ile Pro Lys Asp
            295                 300                 305

Arg Thr His Ile Ile Gly His Ser Glu Ala Pro Gly Ala Ser His Thr
        310                 315                 320

Asp Pro Gly Pro Asn Trp Asn Trp Thr Lys Tyr Met Gln Tyr Val Thr
        325                 330                 335

Asn Gly Ser Gly Gly Gly Thr Asn Pro His Thr Ala Glu Ser Val Cys
340                 345                 350                 355

Gly Thr Gly Phe Thr Val Ile Asp Ser Ala Pro Leu Gly Thr Ala Gly
                360                 365                 370

Asn Val Tyr Leu Thr Tyr Asn Ser Gly Thr Gly Ala Asn Cys Val Ala
            375                 380                 385

Thr Ile Lys Leu Thr Asn Leu Gly Thr Ala Thr Ala Thr Ser Ala Tyr
        390                 395                 400

Leu Glu Val Glu Gly Gln Thr Arg Val Thr Asp Ser Gly Asn Phe Gly
        405                 410                 415

Tyr Tyr Ala Gly Pro Val Arg Ala Ser Ala Ala Asp Lys Cys Val Tyr
420                 425                 430                 435

Trp Gly Gly Lys Ala Gly Thr Ala Thr Tyr Asn Ser Pro Leu Glu His
                440                 445                 450

Cys Gly

<210> SEQ ID NO 96
<211> LENGTH: 453
<212> TYPE: PRT
<213> ORGANISM: Nonomuraea guangzhouensis

<400> SEQUENCE: 96

Ala Ser Ala Asp Pro Met Ser Asp Ala Phe Ala Arg Ala Ala Thr Thr
1               5                   10                  15

Tyr Glu Val Pro Arg Asp Leu Leu Val Ser Leu Ala Tyr Ala Glu Thr
            20                  25                  30

```
His Leu Asp Gly His Arg Gly Glu Pro Ser Ala Ser Gly Gly Tyr Gly
         35                  40                  45

Val Met His Leu Val Ser Asn Pro Val Arg His Thr Leu Glu Arg Ala
 50                  55                  60

Ala Thr Leu Thr Lys Gln Pro Val Ser Ala Leu Lys Ala Asp Asp Ala
 65                  70                  75                  80

Ala Asn Ile Thr Gly Gly Ala Ala Val Leu Arg Ala Tyr Ala Asp Glu
                 85                  90                  95

Leu Gly Leu Asp Ala Ala Arg Lys Asp Ala Gly Lys Trp Tyr Gln
                100                 105                 110

Ala Val Ala Lys Tyr Gly Gly Ala Ser Ser Ala Asp Val Ala Arg Leu
                115                 120                 125

Tyr Ala Asp Thr Val Tyr Asp Gln Leu Ser Gln Gly Ile Lys Val Thr
                130                 135                 140

Thr Pro Ala Gly Glu Thr Leu Thr Ala Thr Pro Arg Thr Val Gln Pro
145                 150                 155                 160

Asp Arg Gly Ser Tyr Ala Lys Ala Gln Glu Leu Gly Lys Thr Asn Thr
                165                 170                 175

Leu Ala Ala Ala Val Asp Tyr Pro Ser Ala Ala Trp Ala Ala Ala His
                180                 185                 190

Ser Thr Asn Tyr Ala Val Ser Asn Arg Pro Thr Ser Asp Ala Ile Asp
                195                 200                 205

Arg Ile Ile Ile His Val Ala Gln Gly Thr Tyr Ala Gly Thr Ile Asp
                210                 215                 220

Trp Phe Gln Thr Gly Pro Arg Pro Asn Pro Thr Ser His Tyr Val
225                 230                 235                 240

Val Arg Ser Ser Asp Gly Ala Val Thr Gln Met Val Arg Glu Lys Asp
                245                 250                 255

Arg Ala Phe His Ala Gly Asp Ser Asn Arg Arg Ser Val Gly Ile Glu
                260                 265                 270

His Glu Gly Trp Val Glu Gln Ala Ser Trp Phe Thr Asp Thr Met Tyr
                275                 280                 285

Arg Ser Ser Ala Ala Leu Thr Arg Asn Ile Ala Asp Arg Tyr Gly Ile
290                 295                 300

Pro Lys Asp Arg Thr His Ile Ile Gly His Ser Glu Ala Pro Gly Ala
305                 310                 315                 320

Ser His Thr Asp Pro Gly Pro Asn Trp Asn Trp Thr Lys Tyr Met Gln
                325                 330                 335

Tyr Val Thr Asn Gly Ser Gly Gly Thr Asn Pro His Thr Ala Glu
                340                 345                 350

Ser Val Cys Gly Thr Gly Phe Thr Val Ile Asp Ser Ala Pro Leu Gly
                355                 360                 365

Thr Ala Gly Asn Val Tyr Leu Thr Tyr Asn Ser Gly Thr Gly Ala Asn
                370                 375                 380

Cys Val Ala Thr Ile Lys Leu Thr Asn Leu Gly Thr Ala Thr Ala Thr
385                 390                 395                 400

Ser Ala Tyr Leu Glu Val Glu Gly Gln Thr Arg Val Thr Asp Ser Gly
                405                 410                 415

Asn Phe Gly Tyr Tyr Ala Gly Pro Val Arg Ala Ser Ala Ala Asp Lys
                420                 425                 430
```

-continued

```
                Cys Val Tyr Trp Gly Gly Lys Ala Gly Thr Ala Thr Tyr Asn Ser Pro
                        435                 440                 445

Leu Glu His Cys Gly
                    450

<210> SEQ ID NO 97
<211> LENGTH: 1509
<212> TYPE: DNA
<213> ORGANISM: Nonomuraea guangzhouensis
<220> FEATURE:
<221> NAME/KEY: CDS
<222> LOCATION: (1)..(1506)
<220> FEATURE:
<221> NAME/KEY: sig_peptide
<222> LOCATION: (1)..(87)
<220> FEATURE:
<221> NAME/KEY: mat_peptide
<222> LOCATION: (88)..(1506)

<400> SEQUENCE: 97 atg tca ctc tcc ccc aag cga tta aca gct ctc gtc tct tcc gtc ctc       48
Met Ser Leu Ser Pro Lys Arg Leu Thr Ala Leu Val Ser Ser Val Leu
                -25                 -20                 -15 gcc gcc ctc ctg gtc ttc gcc ggc cag ccc gcc atc gcg gcc aag gac       96
Ala Ala Leu Leu Val Phe Ala Gly Gln Pro Ala Ile Ala Ala Lys Asp
        -10                 -5                  -1  1 aca ccg cta tcc gac gcg ttc gcc cgc gcc gcg gcc cag gac atc          144
Thr Pro Leu Ser Asp Ala Phe Ala Arg Ala Ala Ala Gln Asp Ile
    5                   10                  15 ccc cgc gac ctg ctc gtc gcg ctc gcc tac gcc gag acc cac ctg gac      192
Pro Arg Asp Leu Leu Val Ala Leu Ala Tyr Ala Glu Thr His Leu Asp
20                  25                  30                  35 ggc cac aac ggc gag ccc agc gcc agc ggc ggc tac ggt gtg atg cac      240
Gly His Asn Gly Glu Pro Ser Ala Ser Gly Gly Tyr Gly Val Met His
                40                  45                  50 ctg gtc agc aac ccc acc acg aaa gcg ctg gag aag gcg tcg ggg ctc      288
Leu Val Ser Asn Pro Thr Thr Lys Ala Leu Glu Lys Ala Ser Gly Leu
            55                  60                  65 acc ggg ctg ccg gtc aag aag ttg cgc gcc gac acc gag gcc aac atc      336
Thr Gly Leu Pro Val Lys Lys Leu Arg Ala Asp Thr Glu Ala Asn Ile
        70                  75                  80 ctg ggc ggc gcc gca ctg ctg cgc gcc aac gcc gac gag ctc ggc ctg      384
Leu Gly Gly Ala Ala Leu Leu Arg Ala Asn Ala Asp Glu Leu Gly Leu
    85                  90                  95 gag gag gcc gcc agg aag gac ccc ggc cgc tgg tac gag tcc gtg gcc      432
Asp Glu Ala Ala Arg Lys Asp Pro Gly Arg Trp Tyr Glu Ser Val Ala
100                 105                 110                 115 aag tac ggc aac gcc gcc tcg ccc cag ctc gcc cgc gtc tac gcc gac      480
Lys Tyr Gly Asn Ala Ala Ser Pro Gln Leu Ala Arg Val Tyr Ala Asp
                120                 125                 130 gcc gtc tac gag ctg ctc ggc ctc ggc atc cag gcc aag gac gtg cgc      528
Ala Val Tyr Glu Leu Leu Gly Leu Gly Ile Gln Ala Lys Asp Val Arg
            135                 140                 145 gtg gca ccg caa gag gtg acc gcc gac cgc ggc aag tac gcc gac aca      576
Val Ala Pro Gln Glu Val Thr Ala Asp Arg Gly Lys Tyr Ala Asp Thr
        150                 155                 160 ccc tcg ctc aag gcc gag gtg gcc agc ccc gac tac ccg gac gcc gcc      624
Pro Ser Leu Lys Ala Glu Val Ala Ser Pro Asp Tyr Pro Asp Ala Ala
    165                 170                 175 tgg gtg ccc gcg aac tcc ggc aac tac acc gcc tcc agc cgc ccg tcg      672
Trp Val Pro Ala Asn Ser Gly Asn Tyr Thr Ala Ser Ser Arg Pro Ser
180                 185                 190                 195
```

```
agc tac gcc atc gac cgc gtg atc att cac gtg gcg cag ggc tcg tac      720
Ser Tyr Ala Ile Asp Arg Val Ile Ile His Val Ala Gln Gly Ser Tyr
            200                 205                 210 gcc ggg acc atc tcc tgg ttc cag aac ccg agc gcc aac gtc tcg gcc      768
Ala Gly Thr Ile Ser Trp Phe Gln Asn Pro Ser Ala Asn Val Ser Ala
        215                 220                 225 cac tac gtg gtc aag tcg tcg aac ggg gcc gtc acc cag acg gtc cgc      816
His Tyr Val Val Lys Ser Ser Asn Gly Ala Val Thr Gln Thr Val Arg
    230                 235                 240 gac aag gac gtc gcc tgg cac gcc ggc aac tgg tcc tac aac acc agg      864
Asp Lys Asp Val Ala Trp His Ala Gly Asn Trp Ser Tyr Asn Thr Arg
245                 250                 255 tcc atc ggc atc gag cac gag ggc ttc gtc aac gag gcc tcg tgg ttc      912
Ser Ile Gly Ile Glu His Glu Gly Phe Val Asn Glu Ala Ser Trp Phe
260                 265                 270                 275 acc gac gcg atg tac cgc tcc tcg gcc gcg ctg acc aag tac atc tgc      960
Thr Asp Ala Met Tyr Arg Ser Ser Ala Ala Leu Thr Lys Tyr Ile Cys
                280                 285                 290 gac aag tac ggc atc ccg aag gac cgc acg cac atc atc ggc cac aac     1008
Asp Lys Tyr Gly Ile Pro Lys Asp Arg Thr His Ile Ile Gly His Asn
            295                 300                 305 cag gtg ccg ggc gcc acc cac acc gac ccg ggt ccg aac tgg aac tgg     1056
Gln Val Pro Gly Ala Thr His Thr Asp Pro Gly Pro Asn Trp Asn Trp
        310                 315                 320 acc acg tac atg aac tac gtg acc ggt ggc ggc ggc acg ccg tcg tgg     1104
Thr Thr Tyr Met Asn Tyr Val Thr Gly Gly Gly Gly Thr Pro Ser Trp
    325                 330                 335 acc acc acg gtc gac aac gcc acc tcc gga cag ttc acc gcc agc gcg     1152
Thr Thr Thr Val Asp Asn Ala Thr Ser Gly Gln Phe Thr Ala Ser Ala
340                 345                 350                 355 aac tgg ggc acc tcc acc tac tcc acc cag cgc tac ggc gcg gac tac     1200
Asn Trp Gly Thr Ser Thr Tyr Ser Thr Gln Arg Tyr Gly Ala Asp Tyr
                360                 365                 370 cgg ttc gcc gac ccc gtg tcc gcc agt gac gcc gcc tgg tat cag gcg     1248
Arg Phe Ala Asp Pro Val Ser Ala Ser Asp Ala Ala Trp Tyr Gln Ala
            375                 380                 385 acc ctc ccc agc gcg ggc acc tac cgc gtg gag gtc tgg tat ccg gac     1296
Thr Leu Pro Ser Ala Gly Thr Tyr Arg Val Glu Val Trp Tyr Pro Asp
        390                 395                 400 gac gcc ggc tac aac agc tcc gcg ccc tac atc gtc gcc gcc tcc agc     1344
Asp Ala Gly Tyr Asn Ser Ser Ala Pro Tyr Ile Val Ala Ala Ser Ser
    405                 410                 415 ggc aac cag acg gtg tac gtg gac caa cgc tcc ggc ggc ggc agc tgg     1392
Gly Asn Gln Thr Val Tyr Val Asp Gln Arg Ser Gly Gly Gly Ser Trp
420                 425                 430                 435 cac agc ttg ggc aat ttc tcc ctc aac gcg ggc acc gcc aac gtc gtg     1440
His Ser Leu Gly Asn Phe Ser Leu Asn Ala Gly Thr Ala Asn Val Val
                440                 445                 450 gga gtc agc cgg tgg acc tcc ggc acc ggc ctc gtc atc gcg gac gcc     1488
Gly Val Ser Arg Trp Thr Ser Gly Thr Gly Leu Val Ile Ala Asp Ala
            455                 460                 465 gtc cgc atc agc aag gtc tga                                          1509
Val Arg Ile Ser Lys Val
        470

<210> SEQ ID NO 98
<211> LENGTH: 502
<212> TYPE: PRT
<213> ORGANISM: Nonomuraea guangzhouensis
```

<400> SEQUENCE: 98

```
Met Ser Leu Ser Pro Lys Arg Leu Thr Ala Leu Val Ser Ser Val Leu
                -25                 -20                 -15
Ala Ala Leu Leu Val Phe Ala Gly Gln Pro Ala Ile Ala Ala Lys Asp
            -10                  -5              -1   1
Thr Pro Leu Ser Asp Ala Phe Ala Arg Ala Ala Ala Gln Asp Ile
      5                  10                  15
Pro Arg Asp Leu Leu Val Ala Leu Ala Tyr Ala Glu Thr His Leu Asp
 20                  25                  30                  35
Gly His Asn Gly Glu Pro Ser Ala Ser Gly Gly Tyr Gly Val Met His
                 40                  45                  50
Leu Val Ser Asn Pro Thr Thr Lys Ala Leu Glu Lys Ala Ser Gly Leu
                 55                  60                  65
Thr Gly Leu Pro Val Lys Lys Leu Arg Ala Asp Thr Glu Ala Asn Ile
             70                  75                  80
Leu Gly Gly Ala Ala Leu Leu Arg Ala Asn Ala Asp Glu Leu Gly Leu
         85                  90                  95
Asp Glu Ala Ala Arg Lys Asp Pro Gly Arg Trp Tyr Glu Ser Val Ala
100                 105                 110                 115
Lys Tyr Gly Asn Ala Ala Ser Pro Gln Leu Ala Arg Val Tyr Ala Asp
                120                 125                 130
Ala Val Tyr Glu Leu Leu Gly Leu Gly Ile Gln Ala Lys Asp Val Arg
            135                 140                 145
Val Ala Pro Gln Glu Val Thr Ala Asp Arg Gly Lys Tyr Ala Asp Thr
            150                 155                 160
Pro Ser Leu Lys Ala Glu Val Ala Ser Pro Asp Tyr Pro Asp Ala Ala
        165                 170                 175
Trp Val Pro Ala Asn Ser Gly Asn Tyr Thr Ala Ser Ser Arg Pro Ser
180                 185                 190                 195
Ser Tyr Ala Ile Asp Arg Val Ile Ile His Val Ala Gln Gly Ser Tyr
                200                 205                 210
Ala Gly Thr Ile Ser Trp Phe Gln Asn Pro Ser Ala Asn Val Ser Ala
            215                 220                 225
His Tyr Val Val Lys Ser Ser Asn Gly Ala Val Thr Gln Thr Val Arg
        230                 235                 240
Asp Lys Asp Val Ala Trp His Ala Gly Asn Trp Ser Tyr Asn Thr Arg
245                 250                 255
Ser Ile Gly Ile Glu His Glu Gly Phe Val Asn Glu Ala Ser Trp Phe
260                 265                 270                 275
Thr Asp Ala Met Tyr Arg Ser Ser Ala Ala Leu Thr Lys Tyr Ile Cys
            280                 285                 290
Asp Lys Tyr Gly Ile Pro Lys Asp Arg Thr His Ile Ile Gly His Asn
        295                 300                 305
Gln Val Pro Gly Ala Thr His Thr Asp Pro Gly Pro Asn Trp Asn Trp
    310                 315                 320
Thr Thr Tyr Met Asn Tyr Val Thr Gly Gly Gly Thr Pro Ser Trp
325                 330                 335
Thr Thr Thr Val Asp Asn Ala Thr Ser Gly Gln Phe Thr Ala Ser Ala
340                 345                 350                 355
Asn Trp Gly Thr Ser Thr Tyr Ser Thr Gln Arg Tyr Gly Ala Asp Tyr
            360                 365                 370
Arg Phe Ala Asp Pro Val Ser Ala Ser Asp Ala Ala Trp Tyr Gln Ala
        375                 380                 385
```

```
Thr Leu Pro Ser Ala Gly Thr Tyr Arg Val Glu Val Trp Tyr Pro Asp
        390                 395                 400

Asp Ala Gly Tyr Asn Ser Ser Ala Pro Tyr Ile Val Ala Ala Ser Ser
    405                 410                 415

Gly Asn Gln Thr Val Tyr Val Asp Gln Arg Ser Gly Gly Ser Trp
420                 425                 430                 435

His Ser Leu Gly Asn Phe Ser Leu Asn Ala Gly Thr Ala Asn Val Val
                440                 445                 450

Gly Val Ser Arg Trp Thr Ser Gly Thr Gly Leu Val Ile Ala Asp Ala
            455                 460                 465

Val Arg Ile Ser Lys Val
            470

<210> SEQ ID NO 99
<211> LENGTH: 473
<212> TYPE: PRT
<213> ORGANISM: Nonomuraea guangzhouensis

<400> SEQUENCE: 99

Ala Lys Asp Thr Pro Leu Ser Asp Ala Phe Ala Arg Ala Ala Ala
1               5                   10                  15

Gln Asp Ile Pro Arg Asp Leu Leu Val Ala Leu Ala Tyr Ala Glu Thr
                20                  25                  30

His Leu Asp Gly His Asn Gly Glu Pro Ser Ala Ser Gly Gly Tyr Gly
            35                  40                  45

Val Met His Leu Val Ser Asn Pro Thr Thr Lys Ala Leu Glu Lys Ala
50                  55                  60

Ser Gly Leu Thr Gly Leu Pro Val Lys Lys Leu Arg Ala Asp Thr Glu
65                  70                  75                  80

Ala Asn Ile Leu Gly Gly Ala Ala Leu Leu Arg Ala Asn Ala Asp Glu
                85                  90                  95

Leu Gly Leu Asp Glu Ala Ala Arg Lys Asp Pro Gly Arg Trp Tyr Glu
            100                 105                 110

Ser Val Ala Lys Tyr Gly Asn Ala Ala Ser Pro Gln Leu Ala Arg Val
            115                 120                 125

Tyr Ala Asp Ala Val Tyr Glu Leu Leu Gly Leu Gly Ile Gln Ala Lys
130                 135                 140

Asp Val Arg Val Ala Pro Gln Glu Val Thr Ala Asp Arg Gly Lys Tyr
145                 150                 155                 160

Ala Asp Thr Pro Ser Leu Lys Ala Glu Val Ala Ser Pro Asp Tyr Pro
                165                 170                 175

Asp Ala Ala Trp Val Pro Ala Asn Ser Gly Asn Tyr Thr Ala Ser Ser
            180                 185                 190

Arg Pro Ser Ser Tyr Ala Ile Asp Arg Val Ile His Val Ala Gln
            195                 200                 205

Gly Ser Tyr Ala Gly Thr Ile Ser Trp Phe Gln Asn Pro Ser Ala Asn
    210                 215                 220

Val Ser Ala His Tyr Val Lys Ser Ser Asn Gly Ala Val Thr Gln
225                 230                 235                 240

Thr Val Arg Asp Lys Asp Val Ala Trp His Ala Gly Asn Trp Ser Tyr
                245                 250                 255

Asn Thr Arg Ser Ile Gly Ile Glu His Glu Gly Phe Val Asn Glu Ala
            260                 265                 270
```

-continued

```
Ser Trp Phe Thr Asp Ala Met Tyr Arg Ser Ser Ala Ala Leu Thr Lys
    275                 280                 285

Tyr Ile Cys Asp Lys Tyr Gly Ile Pro Lys Asp Arg Thr His Ile Ile
290                 295                 300

Gly His Asn Gln Val Pro Gly Ala Thr His Thr Asp Pro Gly Pro Asn
305                 310                 315                 320

Trp Asn Trp Thr Thr Tyr Met Asn Tyr Val Thr Gly Gly Gly Thr
                325                 330                 335

Pro Ser Trp Thr Thr Val Asp Asn Ala Thr Ser Gly Gln Phe Thr
                340                 345                 350

Ala Ser Ala Asn Trp Gly Thr Ser Thr Tyr Ser Thr Gln Arg Tyr Gly
    355                 360                 365

Ala Asp Tyr Arg Phe Ala Asp Pro Val Ser Ala Ser Asp Ala Ala Trp
370                 375                 380

Tyr Gln Ala Thr Leu Pro Ser Ala Gly Thr Tyr Arg Val Glu Val Trp
385                 390                 395                 400

Tyr Pro Asp Asp Ala Gly Tyr Asn Ser Ser Ala Pro Tyr Ile Val Ala
                405                 410                 415

Ala Ser Ser Gly Asn Gln Thr Val Tyr Val Asp Gln Arg Ser Gly Gly
            420                 425                 430

Gly Ser Trp His Ser Leu Gly Asn Phe Ser Leu Asn Ala Gly Thr Ala
        435                 440                 445

Asn Val Val Gly Val Ser Arg Trp Thr Ser Gly Thr Gly Leu Val Ile
    450                 455                 460

Ala Asp Ala Val Arg Ile Ser Lys Val
465                 470

<210> SEQ ID NO 100
<211> LENGTH: 711
<212> TYPE: DNA
<213> ORGANISM: Bacillus cohnii
<220> FEATURE:
<221> NAME/KEY: CDS
<222> LOCATION: (1)..(708)
<220> FEATURE:
<221> NAME/KEY: sig_peptide
<222> LOCATION: (1)..(81)
<220> FEATURE:
<221> NAME/KEY: mat_peptide
<222> LOCATION: (82)..(708)

<400> SEQUENCE: 100 atg aaa aaa ata gca act atc tta tgt gtc gtt atg tta gtc aac ggt      48
Met Lys Lys Ile Ala Thr Ile Leu Cys Val Val Met Leu Val Asn Gly
        -25                 -20                 -15 tgt tca aac gtt gga atc aca aat gtt gag aga aat gag aca gtt tca      96
Cys Ser Asn Val Gly Ile Thr Asn Val Glu Arg Asn Glu Thr Val Ser
    -10                  -5             -1  1                   5 tta gtt aaa aat aaa gat gaa tta act tat aaa aag cca aat aca aat     144
Leu Val Lys Asn Lys Asp Glu Leu Thr Tyr Lys Lys Pro Asn Thr Asn
                10                  15                  20 ccg agt gaa tct tta cat gta act ccc tac tat tta cct gac gaa aat     192
Pro Ser Glu Ser Leu His Val Thr Pro Tyr Tyr Leu Pro Asp Glu Asn
            25                  30                  35 tcg cga cga aga act gca gaa gtt aca cat gta atg att cat tac aca     240
Ser Arg Arg Arg Thr Ala Glu Val Thr His Val Met Ile His Tyr Thr
        40                  45                  50
```

| | | | | | | | | | | | | | | | |
|---|---|---|---|---|---|---|---|---|---|---|---|---|---|---|---|
| agt | aat | gca | gca | aga | aat | cca | gag | aat | ccg | tat | gta | tta | gaa | gac | att | 288 |
| Ser | Asn | Ala | Ala | Arg | Asn | Pro | Glu | Asn | Pro | Tyr | Val | Leu | Glu | Asp | Ile |
| 55 | | | | | 60 | | | | | 65 | | | | | |

```
agt aat gca gca aga aat cca gag aat ccg tat gta tta gaa gac att      288
Ser Asn Ala Ala Arg Asn Pro Glu Asn Pro Tyr Val Leu Glu Asp Ile
 55                  60                  65 tac tcg ctg ttt gaa gaa tat ggc gtt tct gca cat tat att att gat      336
Tyr Ser Leu Phe Glu Glu Tyr Gly Val Ser Ala His Tyr Ile Ile Asp
 70                  75                  80                  85 cgg gaa ggt act atc ttt caa tta gta gat gaa agt aga gta gcg ttt      384
Arg Glu Gly Thr Ile Phe Gln Leu Val Asp Glu Ser Arg Val Ala Phe
                 90                  95                 100 cat gca gga aaa gga atg gat tta aac tac cta caa tac cga aat agc      432
His Ala Gly Lys Gly Met Asp Leu Asn Tyr Leu Gln Tyr Arg Asn Ser
            105                 110                 115 atg aat gaa tat tca att ggt atc gaa ctt atg gca att gga aca aag      480
Met Asn Glu Tyr Ser Ile Gly Ile Glu Leu Met Ala Ile Gly Thr Lys
        120                 125                 130 gaa gaa atg aat tta aat ttg cag gaa ggt caa tac gaa cta ata ccg      528
Glu Glu Met Asn Leu Asn Leu Gln Glu Gly Gln Tyr Glu Leu Ile Pro
    135                 140                 145 cca tcc tat ata ggg tat aca gat gag caa tat cac tca tta gca aaa      576
Pro Ser Tyr Ile Gly Tyr Thr Asp Glu Gln Tyr His Ser Leu Ala Lys
150                 155                 160                 165 ctg tta gaa gac ttg tat gag cgt tat cca aaa gta ttg aga aac aga      624
Leu Leu Glu Asp Leu Tyr Glu Arg Tyr Pro Lys Val Leu Arg Asn Arg
                170                 175                 180 gag aac gta gta ggg cat gat gaa tac gca cct gtt cga aaa tca gac      672
Glu Asn Val Val Gly His Asp Glu Tyr Ala Pro Val Arg Lys Ser Asp
            185                 190                 195 cct gga agt tta ttt gac tgg gaa aaa att ggg ttc tga                  711
Pro Gly Ser Leu Phe Asp Trp Glu Lys Ile Gly Phe
        200                 205

<210> SEQ ID NO 101
<211> LENGTH: 236
<212> TYPE: PRT
<213> ORGANISM: Bacillus cohnii

<400> SEQUENCE: 101

Met Lys Lys Ile Ala Thr Ile Leu Cys Val Val Met Leu Val Asn Gly
        -25                 -20                 -15

Cys Ser Asn Val Gly Ile Thr Asn Val Glu Arg Asn Glu Thr Val Ser
    -10                  -5                  -1   1               5

Leu Val Lys Asn Lys Asp Glu Leu Thr Tyr Lys Lys Pro Asn Thr Asn
                 10                  15                  20

Pro Ser Glu Ser Leu His Val Thr Pro Tyr Tyr Leu Pro Asp Glu Asn
            25                  30                  35

Ser Arg Arg Arg Thr Ala Glu Val Thr His Val Met Ile His Tyr Thr
        40                  45                  50

Ser Asn Ala Ala Arg Asn Pro Glu Asn Pro Tyr Val Leu Glu Asp Ile
    55                  60                  65

Tyr Ser Leu Phe Glu Glu Tyr Gly Val Ser Ala His Tyr Ile Ile Asp
 70                  75                  80                  85

Arg Glu Gly Thr Ile Phe Gln Leu Val Asp Glu Ser Arg Val Ala Phe
                 90                  95                 100

His Ala Gly Lys Gly Met Asp Leu Asn Tyr Leu Gln Tyr Arg Asn Ser
            105                 110                 115

Met Asn Glu Tyr Ser Ile Gly Ile Glu Leu Met Ala Ile Gly Thr Lys
        120                 125                 130
```

```
Glu Glu Met Asn Leu Asn Leu Gln Glu Gly Gln Tyr Glu Leu Ile Pro
    135                 140                 145

Pro Ser Tyr Ile Gly Tyr Thr Asp Glu Gln Tyr His Ser Leu Ala Lys
150                 155                 160                 165

Leu Leu Glu Asp Leu Tyr Glu Arg Tyr Pro Lys Val Leu Arg Asn Arg
                170                 175                 180

Glu Asn Val Val Gly His Asp Glu Tyr Ala Pro Val Arg Lys Ser Asp
            185                 190                 195

Pro Gly Ser Leu Phe Asp Trp Glu Lys Ile Gly Phe
        200                 205

<210> SEQ ID NO 102
<211> LENGTH: 209
<212> TYPE: PRT
<213> ORGANISM: Bacillus cohnii

<400> SEQUENCE: 102

Asn Glu Thr Val Ser Leu Val Lys Asn Lys Asp Glu Leu Thr Tyr Lys
1               5                   10                  15

Lys Pro Asn Thr Asn Pro Ser Glu Ser Leu His Val Thr Pro Tyr Tyr
            20                  25                  30

Leu Pro Asp Glu Asn Ser Arg Arg Thr Ala Glu Val Thr His Val
        35                  40                  45

Met Ile His Tyr Thr Ser Asn Ala Ala Arg Asn Pro Glu Asn Pro Tyr
    50                  55                  60

Val Leu Glu Asp Ile Tyr Ser Leu Phe Glu Glu Tyr Gly Val Ser Ala
65                  70                  75                  80

His Tyr Ile Ile Asp Arg Glu Gly Thr Ile Phe Gln Leu Val Asp Glu
                85                  90                  95

Ser Arg Val Ala Phe His Ala Gly Lys Gly Met Asp Leu Asn Tyr Leu
            100                 105                 110

Gln Tyr Arg Asn Ser Met Asn Glu Tyr Ser Ile Gly Ile Glu Leu Met
        115                 120                 125

Ala Ile Gly Thr Lys Glu Glu Met Asn Leu Asn Leu Gln Glu Gly Gln
    130                 135                 140

Tyr Glu Leu Ile Pro Pro Ser Tyr Ile Gly Tyr Thr Asp Glu Gln Tyr
145                 150                 155                 160

His Ser Leu Ala Lys Leu Leu Glu Asp Leu Tyr Glu Arg Tyr Pro Lys
                165                 170                 175

Val Leu Arg Asn Arg Glu Asn Val Val Gly His Asp Glu Tyr Ala Pro
            180                 185                 190

Val Arg Lys Ser Asp Pro Gly Ser Leu Phe Asp Trp Glu Lys Ile Gly
        195                 200                 205

Phe

<210> SEQ ID NO 103
<211> LENGTH: 918
<212> TYPE: DNA
<213> ORGANISM: Halomonas sp
<220> FEATURE:
<221> NAME/KEY: CDS
<222> LOCATION: (1)..(915)
<220> FEATURE:
<221> NAME/KEY: sig_peptide
<222> LOCATION: (1)..(72)
<220> FEATURE:
<221> NAME/KEY: mat_peptide
<222> LOCATION: (73)..(915)
```

<400> SEQUENCE: 103

| | | |
|---|---|---|
| atg gcg cgc ttt ttc gtc gtc act ctc gcc atg ctg gtg ctg ctg gcc<br>Met Ala Arg Phe Phe Val Val Thr Leu Ala Met Leu Val Leu Leu Ala<br>                -20                        -15                        -10 | 48 |
| ggc tgc gcc acg ccg gag caa tac gag cgg cgt gac ggc tat gtg gtg<br>Gly Cys Ala Thr Pro Glu Gln Tyr Glu Arg Arg Asp Gly Tyr Val Val<br>            -5                      -1  1                        5 | 96 |
| gac cac acc cat gtg tcg ccc tcc cac aac agc cgg gta cgg cat ctg<br>Asp His Thr His Val Ser Pro Ser His Asn Ser Arg Val Arg His Leu<br>      10                    15                    20 | 144 |
| gtg atg cac tac acc gat gtg gac gag gcc gaa tcc ctg gcg acc ctg<br>Val Met His Tyr Thr Asp Val Asp Glu Ala Glu Ser Leu Ala Thr Leu<br>25                  30                    35                  40 | 192 |
| acc ggt ccc cat gtc agc agc cac tac gtg ctg ccg cta ccg gca cgg<br>Thr Gly Pro His Val Ser Ser His Tyr Val Leu Pro Leu Pro Ala Arg<br>                  45                    50                  55 | 240 |
| gca cat cgc ggc gag ccg ctg gtc tac cag ctc gtc gac gag gag cgc<br>Ala His Arg Gly Glu Pro Leu Val Tyr Gln Leu Val Asp Glu Glu Arg<br>            60                    65                  70 | 288 |
| cgc gcc tgg cac gcc ggg gcc agc gcc tgg aag cgc cgc acc aac atc<br>Arg Ala Trp His Ala Gly Ala Ser Ala Trp Lys Arg Arg Thr Asn Ile<br>        75                    80                  85 | 336 |
| aac gac acc tcc atc ggc atc gag atc gtc aat acc ggc ccc gac cgc<br>Asn Asp Thr Ser Ile Gly Ile Glu Ile Val Asn Thr Gly Pro Asp Arg<br>      90                    95                    100 | 384 |
| ccc tac gcc gag gtg gag cgg gcg ctg gag gag cac ccg gaa agc gat<br>Pro Tyr Ala Glu Val Glu Arg Ala Leu Glu Glu His Pro Glu Ser Asp<br>105                110                  115                120 | 432 |
| ccc gcc atc cac tgg gcg ccc tac ccc gag gca cag atc gag gcg ctg<br>Pro Ala Ile His Trp Ala Pro Tyr Pro Glu Ala Gln Ile Glu Ala Leu<br>                  125                  130                135 | 480 |
| atc gcc ctg tcg cgg gat atc atc acg cgc aac aat att cac cct acc<br>Ile Ala Leu Ser Arg Asp Ile Ile Thr Arg Asn Asn Ile His Pro Thr<br>140                145                  150 | 528 |
| gac gtg gtg gcc cac tcg gat atc tcg ccg acg cgc aag atc gac ccg<br>Asp Val Val Ala His Ser Asp Ile Ser Pro Thr Arg Lys Ile Asp Pro<br>            155                    160                165 | 576 |
| ggc ccg gcg ttt ccc tgg cat gcc ctg tac gaa gcg ggt atc ggc gta<br>Gly Pro Ala Phe Pro Trp His Ala Leu Tyr Glu Ala Gly Ile Gly Val<br>170                175                  180 | 624 |
| tgg ccc gaa gca gcc acc gtg gca cgc tat cgc acc cgc ttc gat cag<br>Trp Pro Glu Ala Ala Thr Val Ala Arg Tyr Arg Thr Arg Phe Asp Gln<br>185                190                  195                200 | 672 |
| gcg ctg ccc gaa ctc gcc acc ctg cag gcg gcg ctc cag gcc tgg ggc<br>Ala Leu Pro Glu Leu Ala Thr Leu Gln Ala Ala Leu Gln Ala Trp Gly<br>                  205                  210                215 | 720 |
| tat ccg ctg gcg gtc agc gac gaa ctg gat tca cag act cgc gcg gta<br>Tyr Pro Leu Ala Val Ser Asp Glu Leu Asp Ser Gln Thr Arg Ala Val<br>220                225                  230 | 768 |
| ctg cgc gcc ttc cag atg cgc ttt cgt ccc gcc gac tat cgt ggc cgg<br>Leu Arg Ala Phe Gln Met Arg Phe Arg Pro Ala Asp Tyr Arg Gly Arg<br>            235                    240                245 | 816 |
| ccc gac gcc gag act gcg gcg atc ctc tgg gca ctg ctg gaa aga tat<br>Pro Asp Ala Glu Thr Ala Ala Ile Leu Trp Ala Leu Leu Glu Arg Tyr<br>250                255                  260 | 864 |

```
cgc ccc ctc gac ctg gag cgg ttc gag ggg gcg atg gaa gag ccg gag     912
Arg Pro Leu Asp Leu Glu Arg Phe Glu Gly Ala Met Glu Glu Pro Glu
265                 270                 275                 280 gca tga                                                              918
Ala
```

<210> SEQ ID NO 104
<211> LENGTH: 305
<212> TYPE: PRT
<213> ORGANISM: Halomonas sp

<400> SEQUENCE: 104

```
Met Ala Arg Phe Phe Val Val Thr Leu Ala Met Leu Val Leu Leu Ala
                -20                 -15                 -10

Gly Cys Ala Thr Pro Glu Gln Tyr Glu Arg Arg Asp Gly Tyr Val Val
             -5                  -1   1               5

Asp His Thr His Val Ser Pro Ser His Asn Ser Arg Val Arg His Leu
             10                  15                  20

Val Met His Tyr Thr Asp Val Asp Glu Ala Glu Ser Leu Ala Thr Leu
 25                  30                  35                  40

Thr Gly Pro His Val Ser Ser His Tyr Val Leu Pro Leu Pro Ala Arg
                 45                  50                  55

Ala His Arg Gly Glu Pro Leu Val Tyr Gln Leu Val Asp Glu Glu Arg
                 60                  65                  70

Arg Ala Trp His Ala Gly Ala Ser Ala Trp Lys Arg Arg Thr Asn Ile
                 75                  80                  85

Asn Asp Thr Ser Ile Gly Ile Glu Ile Val Asn Thr Gly Pro Asp Arg
 90                  95                 100

Pro Tyr Ala Glu Val Glu Arg Ala Leu Glu Glu His Pro Glu Ser Asp
105                 110                 115                 120

Pro Ala Ile His Trp Ala Pro Tyr Pro Glu Ala Gln Ile Glu Ala Leu
                125                 130                 135

Ile Ala Leu Ser Arg Asp Ile Ile Thr Arg Asn Asn Ile His Pro Thr
                140                 145                 150

Asp Val Val Ala His Ser Asp Ile Ser Pro Thr Arg Lys Ile Asp Pro
                155                 160                 165

Gly Pro Ala Phe Pro Trp His Ala Leu Tyr Glu Ala Gly Ile Gly Val
170                 175                 180

Trp Pro Glu Ala Ala Thr Val Ala Arg Tyr Arg Thr Arg Phe Asp Gln
185                 190                 195                 200

Ala Leu Pro Glu Leu Ala Thr Leu Gln Ala Leu Gln Ala Trp Gly
                205                 210                 215

Tyr Pro Leu Ala Val Ser Asp Glu Leu Asp Ser Gln Thr Arg Ala Val
                220                 225                 230

Leu Arg Ala Phe Gln Met Arg Phe Arg Pro Ala Asp Tyr Arg Gly Arg
                235                 240                 245

Pro Asp Ala Glu Thr Ala Ala Ile Leu Trp Ala Leu Leu Glu Arg Tyr
250                 255                 260

Arg Pro Leu Asp Leu Glu Arg Phe Glu Gly Ala Met Glu Glu Pro Glu
265                 270                 275                 280

Ala
```

<210> SEQ ID NO 105
<211> LENGTH: 281
<212> TYPE: PRT

<213> ORGANISM: Halomonas sp

<400> SEQUENCE: 105

```
Glu Arg Arg Asp Gly Tyr Val Val Asp His Thr His Val Ser Pro Ser
1               5                   10                  15
His Asn Ser Arg Val Arg His Leu Val Met His Tyr Thr Asp Val Asp
            20                  25                  30
Glu Ala Glu Ser Leu Ala Thr Leu Thr Gly Pro His Val Ser Ser His
        35                  40                  45
Tyr Val Leu Pro Leu Pro Ala Arg Ala His Arg Gly Glu Pro Leu Val
    50                  55                  60
Tyr Gln Leu Val Asp Glu Glu Arg Ala Trp His Ala Gly Ala Ser
65                  70                  75                  80
Ala Trp Lys Arg Arg Thr Asn Ile Asn Asp Thr Ser Ile Gly Ile Glu
                85                  90                  95
Ile Val Asn Thr Gly Pro Asp Arg Pro Tyr Ala Glu Val Glu Arg Ala
            100                 105                 110
Leu Glu Glu His Pro Glu Ser Asp Pro Ala Ile His Trp Ala Pro Tyr
        115                 120                 125
Pro Glu Ala Gln Ile Glu Ala Leu Ile Ala Leu Ser Arg Asp Ile Ile
    130                 135                 140
Thr Arg Asn Asn Ile His Pro Thr Asp Val Val Ala His Ser Asp Ile
145                 150                 155                 160
Ser Pro Thr Arg Lys Ile Asp Pro Gly Pro Ala Phe Pro Trp His Ala
                165                 170                 175
Leu Tyr Glu Ala Gly Ile Gly Val Trp Pro Gly Ala Ala Thr Val Ala
            180                 185                 190
Arg Tyr Arg Thr Arg Phe Asp Gln Ala Leu Pro Glu Leu Ala Thr Leu
        195                 200                 205
Gln Ala Ala Leu Gln Ala Trp Gly Tyr Pro Leu Ala Val Ser Asp Glu
    210                 215                 220
Leu Asp Ser Gln Thr Arg Ala Val Leu Arg Ala Phe Gln Met Arg Phe
225                 230                 235                 240
Arg Pro Ala Asp Tyr Arg Gly Arg Pro Asp Ala Glu Thr Ala Ala Ile
                245                 250                 255
Leu Trp Ala Leu Leu Glu Arg Tyr Arg Pro Leu Asp Leu Glu Arg Phe
            260                 265                 270
Glu Gly Ala Met Glu Glu Pro Glu Ala
        275                 280
```

<210> SEQ ID NO 106
<211> LENGTH: 1920
<212> TYPE: DNA
<213> ORGANISM: Lysobacter capsici
<220> FEATURE:
<221> NAME/KEY: CDS
<222> LOCATION: (1)..(1917)
<220> FEATURE:
<221> NAME/KEY: sig_peptide
<222> LOCATION: (1)..(171)
<220> FEATURE:
<221> NAME/KEY: mat_peptide
<222> LOCATION: (172)..(1917)

<400> SEQUENCE: 106

```
atg aac gaa tat tcc act gca cgc cgt ggg gtg gtg acc ggc gtg cgt     48
Met Asn Glu Tyr Ser Thr Ala Arg Arg Gly Val Val Thr Gly Val Arg
    -55                 -50                 -45
```

| | | |
|---|---|---|
| tcg ttg tcg ggg tcg ttg acc gtc gct gtg ctg gcg ctc gcc gcg cca<br>Ser Leu Ser Gly Ser Leu Thr Val Ala Val Leu Ala Leu Ala Ala Pro<br>-40                  -35                      -30 | 96 |
| ttg gcc gcg cag gcg cag gcc gcg ccc gaa gac cgc gcc ctg gca cag<br>Leu Ala Ala Gln Ala Gln Ala Ala Pro Glu Asp Arg Ala Leu Ala Gln<br>-25                  -20                      -15                      -10 | 144 |
| cac ctg cag atc gag gaa tcg ctg caa cgc gtc gac cgc gcg ctg tac<br>His Leu Gln Ile Glu Glu Ser Leu Gln Arg Val Asp Arg Ala Leu Tyr<br>                      -5                           -1  1                    5 | 192 |
| gcg gac tac ttc cgc cag gcc tat gcg cgt tac ccg tcg att ccg gcc<br>Ala Asp Tyr Phe Arg Gln Ala Tyr Ala Arg Tyr Pro Ser Ile Pro Ala<br>          10                      15                      20 | 240 |
| ggc acg ctg gaa tcc atc gcc tac gtg atg agc cgc tgg cag caa ctg<br>Gly Thr Leu Glu Ser Ile Ala Tyr Val Met Ser Arg Trp Gln Gln Leu<br>    25                      30                      35 | 288 |
| cag ccc ggc tcg gtc gcg gcc tac ggc gaa cag cac cag cac atg ccg<br>Gln Pro Gly Ser Val Ala Ala Tyr Gly Glu Gln His Gln His Met Pro<br>40                      45                      50                      55 | 336 |
| cgc tcg tac ggg gtc atg ggc ttg tac cac ggc gaa ggc ttc gcc gat<br>Arg Ser Tyr Gly Val Met Gly Leu Tyr His Gly Glu Gly Phe Ala Asp<br>                60                      65                      70 | 384 |
| caa gtc ggc gaa ggc gcg cgc ctg atc ggc gtg ccg gcc gcg cgc gtg<br>Gln Val Gly Glu Gly Ala Arg Leu Ile Gly Val Pro Ala Ala Arg Val<br>          75                      80                      85 | 432 |
| cag cgc gat ccg ctc agc aac atc ctc gcc tcg gcg gcc ttg ctc gat<br>Gln Arg Asp Pro Leu Ser Asn Ile Leu Ala Ser Ala Ala Leu Leu Asp<br>        90                      95                      100 | 480 |
| cgc gag ttg cgc gcc gac ggg atc ggc gcc aag tcg gcg gtc gaa gcc<br>Arg Glu Leu Arg Ala Asp Gly Ile Gly Ala Lys Ser Ala Val Glu Ala<br>105                      110                      115 | 528 |
| acg cgc ccg gcg ctg gag cgt tac gcc ggt ttc gcc ggc aat gcg ggc<br>Thr Arg Pro Ala Leu Glu Arg Tyr Ala Gly Phe Ala Gly Asn Ala Gly<br>120                      125                      130                      135 | 576 |
| aag agt gcg atc cag gat cac gcc cgt tcc agt ttc gcc ttc gac gtg<br>Lys Ser Ala Ile Gln Asp His Ala Arg Ser Ser Phe Ala Phe Asp Val<br>                140                      145                      150 | 624 |
| ttg ctg gcg cag gac aag ggc gtc aac gat cgc ggc atc gtc gtg ccg<br>Leu Leu Ala Gln Asp Lys Gly Val Asn Asp Arg Gly Ile Val Val Pro<br>          155                      160                      165 | 672 |
| atg cgc gcg gtc gcc tgg gaa cgc gcc ttc gac gcg cgc aag ctg gtg<br>Met Arg Ala Val Ala Trp Glu Arg Ala Phe Asp Ala Arg Lys Leu Val<br>                170                      175                      180 | 720 |
| cgg ctg cgc gcg ccg ttc gtg cgc ctg gac gtg agc cgc gac cgg gtc<br>Arg Leu Arg Ala Pro Phe Val Arg Leu Asp Val Ser Arg Asp Arg Val<br>185                      190                      195 | 768 |
| gag gcg ggt agc ttg aag gac gac ggc gcg ttc gcg atc gac ccg ctc<br>Glu Ala Gly Ser Leu Lys Asp Asp Gly Ala Phe Ala Ile Asp Pro Leu<br>200                      205                      210                      215 | 816 |
| agc gaa acc ctg cgc gcg ccg gcg ctg acc gcc gcc gac gaa aag agc<br>Ser Glu Thr Leu Arg Ala Pro Ala Leu Thr Ala Ala Asp Glu Lys Ser<br>                220                      225                      230 | 864 |
| acc gac tac ggc ccg gcg ctg tgg gtc gcc tcg ccc tat cac tcc gcg<br>Thr Asp Tyr Gly Pro Ala Leu Trp Val Ala Ser Pro Tyr His Ser Ala<br>          235                      240                      245 | 912 |
| cgc acg tcc tac gac tcg gtc acc atc cac acg atg cag ggt tat tac<br>Arg Thr Ser Tyr Asp Ser Val Thr Ile His Thr Met Gln Gly Tyr Tyr<br>                250                      255                      260 | 960 |
| gcc ggc agc atc tcc tgg ttc cag aac aac ccc agc agc gtc agc gcg<br>Ala Gly Ser Ile Ser Trp Phe Gln Asn Asn Pro Ser Ser Val Ser Ala<br>265                      270                      275 | 1008 |

-continued

```
cat tac ctg atc cgc agt tcc gac ggc cag atc acc cag atg gtg cgc    1056
His Tyr Leu Ile Arg Ser Ser Asp Gly Gln Ile Thr Gln Met Val Arg
280                 285                 290                 295 gag aac cgc gcg gcc cat cac gtc ggc gtg cac aac aag acc acg ctc    1104
Glu Asn Arg Ala Ala His His Val Gly Val His Asn Lys Thr Thr Leu
            300                 305                 310 ggc atc gag cac gaa ggt ttc atc aac aac gcc agc tgg tac acc gcc    1152
Gly Ile Glu His Glu Gly Phe Ile Asn Asn Ala Ser Trp Tyr Thr Ala
        315                 320                 325 gcg atg tac aac gcc tcg gcg gcg ttg acc cgg cac ttc tgc gcg acc    1200
Ala Met Tyr Asn Ala Ser Ala Ala Leu Thr Arg His Phe Cys Ala Thr
    330                 335                 340 tac agc gcg atc agc tgc gcg agc gcg ttc agg ggc ccg gcc ggc agc    1248
Tyr Ser Ala Ile Ser Cys Ala Ser Ala Phe Arg Gly Pro Ala Gly Ser
345                 350                 355 ggc atc aac gtg ctg ccg gcc agc gtc aag gtc aag ggc cac cag cat    1296
Gly Ile Asn Val Leu Pro Ala Ser Val Lys Val Lys Gly His Gln His
360                 365                 370                 375 tac agc agc cag acc cat acc gat ccg ggc atc aac tgg gat tgg gcg    1344
Tyr Ser Ser Gln Thr His Thr Asp Pro Gly Ile Asn Trp Asp Trp Ala
            380                 385                 390 cgt tac tac aac ctg ctc aac ccg ggc aat ccg ccc ggc ggc ggc agc    1392
Arg Tyr Tyr Asn Leu Leu Asn Pro Gly Asn Pro Pro Gly Gly Gly Ser
        395                 400                 405 gtg atc gac agt ttc gaa agc acg gtc ggg cat ttc gat acc ggc ccg    1440
Val Ile Asp Ser Phe Glu Ser Thr Val Gly His Phe Asp Thr Gly Pro
    410                 415                 420 gcg tac tcg ggc agc acc acc ggc atc gcc gcg acg tcg ctg agc gaa    1488
Ala Tyr Ser Gly Ser Thr Thr Gly Ile Ala Ala Thr Ser Leu Ser Glu
425                 430                 435 cgc aac tgc acc acg cgc aag aac ggc gag tgc tcg ctg cgg ctg ttg    1536
Arg Asn Cys Thr Thr Arg Lys Asn Gly Glu Cys Ser Leu Arg Leu Leu
440                 445                 450                 455 ctg aaa gac gac gcg gcc agc gcc ggc gcc tgg gcg gtg agg ctg ttg    1584
Leu Lys Asp Asp Ala Ala Ser Ala Gly Ala Trp Ala Val Arg Leu Leu
            460                 465                 470 tcg ggc agc ggc aat ccg ggc agc aac gcg gcc ttg acc cgc gcc aac    1632
Ser Gly Ser Gly Asn Pro Gly Ser Asn Ala Ala Leu Thr Arg Ala Asn
        475                 480                 485 ggc aag gtc ggc ttc tgg gtc ttc acc ggc gcg acc ggc atg agc gcg    1680
Gly Lys Val Gly Phe Trp Val Phe Thr Gly Ala Thr Gly Met Ser Ala
    490                 495                 500 gcg gtc ggc atc gac gac agc gac ggc acc gag cgt tcg atc agc cgc    1728
Ala Val Gly Ile Asp Asp Ser Asp Gly Thr Glu Arg Ser Ile Ser Arg
505                 510                 515 gcg atc ccg gcc aac acc tgg acc tac ctg gag tgg agc ctg agc gac    1776
Ala Ile Pro Ala Asn Thr Trp Thr Tyr Leu Glu Trp Ser Leu Ser Asp
520                 525                 530                 535 gac gcg cag tgg gat gcg tgg gtc ggc ggc gcc aac ggc gcg atc acc    1824
Asp Ala Gln Trp Asp Ala Trp Val Gly Gly Ala Asn Gly Ala Ile Thr
            540                 545                 550 gcc gcg tcg gtg aag ctc gac gcg gtg tgg ttc tac cgc gat cag acc    1872
Ala Ala Ser Val Lys Leu Asp Ala Val Trp Phe Tyr Arg Asp Gln Thr
        555                 560                 565 tcg ttc gat gtg aat gtg tat gtc gac gat gtg cag gtg aag aac tga    1920
Ser Phe Asp Val Asn Val Tyr Val Asp Asp Val Gln Val Lys Asn
    570                 575                 580
```

<210> SEQ ID NO 107

-continued

```
<211> LENGTH: 639
<212> TYPE: PRT
<213> ORGANISM: Lysobacter capsici

<400> SEQUENCE: 107
```

| | | | | | | | | | | | |
|---|---|---|---|---|---|---|---|---|---|---|---|
| Met | Asn | Glu | Tyr | Ser | Thr | Ala | Arg | Arg | Gly | Val | Val | Thr | Gly | Val | Arg |
| | | -55 | | | | -50 | | | | -45 | |
| Ser | Leu | Ser | Gly | Ser | Leu | Thr | Val | Ala | Val | Leu | Ala | Leu | Ala | Ala | Pro |
| | -40 | | | | -35 | | | | -30 | | |
| Leu | Ala | Ala | Gln | Ala | Gln | Ala | Ala | Pro | Glu | Asp | Arg | Ala | Leu | Ala | Gln |
| -25 | | | | -20 | | | | -15 | | | | -10 |
| His | Leu | Gln | Ile | Glu | Glu | Ser | Leu | Gln | Arg | Val | Asp | Arg | Ala | Leu | Tyr |
| | | | -5 | | | | -1 | 1 | | | 5 |
| Ala | Asp | Tyr | Phe | Arg | Gln | Ala | Tyr | Ala | Arg | Tyr | Pro | Ser | Ile | Pro | Ala |
| | | 10 | | | | 15 | | | | 20 | |
| Gly | Thr | Leu | Glu | Ser | Ile | Ala | Tyr | Val | Met | Ser | Arg | Trp | Gln | Gln | Leu |
| | 25 | | | | 30 | | | | 35 | | |
| Gln | Pro | Gly | Ser | Val | Ala | Ala | Tyr | Gly | Glu | Gln | His | Gln | His | Met | Pro |
| 40 | | | | 45 | | | | 50 | | | | 55 |
| Arg | Ser | Tyr | Gly | Val | Met | Gly | Leu | Tyr | His | Gly | Glu | Gly | Phe | Ala | Asp |
| | | 60 | | | | 65 | | | | 70 |
| Gln | Val | Gly | Glu | Gly | Ala | Arg | Leu | Ile | Gly | Val | Pro | Ala | Ala | Arg | Val |
| | | 75 | | | | 80 | | | | 85 |
| Gln | Arg | Asp | Pro | Leu | Ser | Asn | Ile | Leu | Ala | Ser | Ala | Leu | Leu | Asp |
| | | 90 | | | | 95 | | | | 100 |
| Arg | Glu | Leu | Arg | Ala | Asp | Gly | Ile | Gly | Ala | Lys | Ser | Ala | Val | Glu | Ala |
| | 105 | | | | 110 | | | | 115 | | |
| Thr | Arg | Pro | Ala | Leu | Glu | Arg | Tyr | Ala | Gly | Phe | Ala | Gly | Asn | Ala | Gly |
| 120 | | | | 125 | | | | 130 | | | | 135 |
| Lys | Ser | Ala | Ile | Gln | Asp | His | Ala | Arg | Ser | Ser | Phe | Ala | Phe | Asp | Val |
| | | | 140 | | | | 145 | | | | 150 |
| Leu | Leu | Ala | Gln | Asp | Lys | Gly | Val | Asn | Asp | Arg | Gly | Ile | Val | Val | Pro |
| | | 155 | | | | 160 | | | | 165 |
| Met | Arg | Ala | Val | Ala | Trp | Glu | Arg | Ala | Phe | Asp | Ala | Arg | Lys | Leu | Val |
| | 170 | | | | 175 | | | | 180 | | |
| Arg | Leu | Arg | Ala | Pro | Phe | Val | Arg | Leu | Asp | Val | Ser | Arg | Asp | Arg | Val |
| | 185 | | | | 190 | | | | 195 | | |
| Glu | Ala | Gly | Ser | Leu | Lys | Asp | Asp | Gly | Ala | Phe | Ala | Ile | Asp | Pro | Leu |
| 200 | | | | 205 | | | | 210 | | | | 215 |
| Ser | Glu | Thr | Leu | Arg | Ala | Pro | Ala | Leu | Thr | Ala | Ala | Asp | Glu | Lys | Ser |
| | | | 220 | | | | 225 | | | | 230 |
| Thr | Asp | Tyr | Gly | Pro | Ala | Leu | Trp | Val | Ala | Ser | Pro | Tyr | His | Ser | Ala |
| | | 235 | | | | 240 | | | | 245 |
| Arg | Thr | Ser | Tyr | Asp | Ser | Val | Thr | Ile | His | Thr | Met | Gln | Gly | Tyr | Tyr |
| | | 250 | | | | 255 | | | | 260 |
| Ala | Gly | Ser | Ile | Ser | Trp | Phe | Gln | Asn | Asn | Pro | Ser | Ser | Val | Ser | Ala |
| | 265 | | | | 270 | | | | 275 | | |
| His | Tyr | Leu | Ile | Arg | Ser | Ser | Asp | Gly | Gln | Ile | Thr | Gln | Met | Val | Arg |
| 280 | | | | 285 | | | | 290 | | | | 295 |
| Glu | Asn | Arg | Ala | Ala | His | His | Val | Gly | Val | His | Asn | Lys | Thr | Thr | Leu |
| | | | 300 | | | | 305 | | | | 310 |
| Gly | Ile | Glu | His | Glu | Gly | Phe | Ile | Asn | Asn | Ala | Ser | Trp | Tyr | Thr | Ala |
| | | 315 | | | | 320 | | | | 325 |

```
Ala Met Tyr Asn Ala Ser Ala Ala Leu Thr Arg His Phe Cys Ala Thr
        330                 335                 340

Tyr Ser Ala Ile Ser Cys Ala Ser Ala Phe Arg Gly Pro Ala Gly Ser
        345                 350                 355

Gly Ile Asn Val Leu Pro Ala Ser Val Lys Val Lys Gly His Gln His
360                 365                 370                 375

Tyr Ser Ser Gln Thr His Thr Asp Pro Gly Ile Asn Trp Asp Trp Ala
                380                 385                 390

Arg Tyr Tyr Asn Leu Leu Asn Pro Gly Asn Pro Pro Gly Gly Gly Ser
                395                 400                 405

Val Ile Asp Ser Phe Glu Ser Thr Val Gly His Phe Asp Thr Gly Pro
                410                 415                 420

Ala Tyr Ser Gly Ser Thr Thr Gly Ile Ala Ala Thr Ser Leu Ser Glu
        425                 430                 435

Arg Asn Cys Thr Thr Arg Lys Asn Gly Glu Cys Ser Leu Arg Leu Leu
440                 445                 450                 455

Leu Lys Asp Asp Ala Ala Ser Ala Gly Ala Trp Ala Val Arg Leu Leu
                460                 465                 470

Ser Gly Ser Gly Asn Pro Gly Ser Asn Ala Ala Leu Thr Arg Ala Asn
                475                 480                 485

Gly Lys Val Gly Phe Trp Val Phe Thr Gly Ala Thr Gly Met Ser Ala
        490                 495                 500

Ala Val Gly Ile Asp Asp Ser Asp Gly Thr Glu Arg Ser Ile Ser Arg
        505                 510                 515

Ala Ile Pro Ala Asn Thr Trp Thr Tyr Leu Glu Trp Ser Leu Ser Asp
520                 525                 530                 535

Asp Ala Gln Trp Asp Ala Trp Val Gly Gly Ala Asn Gly Ala Ile Thr
                540                 545                 550

Ala Ala Ser Val Lys Leu Asp Ala Val Trp Phe Tyr Arg Asp Gln Thr
                555                 560                 565

Ser Phe Asp Val Asn Val Tyr Val Asp Asp Val Gln Val Lys Asn
                570                 575                 580

<210> SEQ ID NO 108
<211> LENGTH: 582
<212> TYPE: PRT
<213> ORGANISM: Lysobacter capsici

<400> SEQUENCE: 108

Arg Val Asp Arg Ala Leu Tyr Ala Asp Tyr Phe Arg Gln Ala Tyr Ala
1               5                   10                  15

Arg Tyr Pro Ser Ile Pro Ala Gly Thr Leu Glu Ser Ile Ala Tyr Val
            20                  25                  30

Met Ser Arg Trp Gln Gln Leu Gln Pro Gly Ser Val Ala Ala Tyr Gly
        35                  40                  45

Glu Gln His Gln His Met Pro Arg Ser Tyr Gly Val Met Gly Leu Tyr
    50                  55                  60

His Gly Glu Gly Phe Ala Asp Gln Val Gly Glu Gly Ala Arg Leu Ile
65                  70                  75                  80

Gly Val Pro Ala Ala Arg Val Gln Arg Asp Pro Leu Ser Asn Ile Leu
                85                  90                  95

Ala Ser Ala Ala Leu Leu Asp Arg Glu Leu Arg Ala Asp Gly Ile Gly
            100                 105                 110
```

```
Ala Lys Ser Ala Val Glu Ala Thr Arg Pro Ala Leu Glu Arg Tyr Ala
        115                 120                 125

Gly Phe Ala Gly Asn Ala Gly Lys Ser Ala Ile Gln Asp His Ala Arg
    130                 135                 140

Ser Ser Phe Ala Phe Asp Val Leu Leu Ala Gln Asp Lys Gly Val Asn
145                 150                 155                 160

Asp Arg Gly Ile Val Val Pro Met Arg Ala Val Ala Trp Glu Arg Ala
                165                 170                 175

Phe Asp Ala Arg Lys Leu Val Arg Leu Arg Ala Pro Phe Val Arg Leu
                180                 185                 190

Asp Val Ser Arg Asp Arg Val Glu Ala Gly Ser Leu Lys Asp Asp Gly
            195                 200                 205

Ala Phe Ala Ile Asp Pro Leu Ser Glu Thr Leu Arg Ala Pro Ala Leu
        210                 215                 220

Thr Ala Ala Asp Glu Lys Ser Thr Asp Tyr Gly Pro Ala Leu Trp Val
225                 230                 235                 240

Ala Ser Pro Tyr His Ser Ala Arg Thr Ser Tyr Asp Ser Val Thr Ile
                245                 250                 255

His Thr Met Gln Gly Tyr Tyr Ala Gly Ser Ile Ser Trp Phe Gln Asn
                260                 265                 270

Asn Pro Ser Ser Val Ser Ala His Tyr Leu Ile Arg Ser Ser Asp Gly
            275                 280                 285

Gln Ile Thr Gln Met Val Arg Glu Asn Arg Ala Ala His His Val Gly
        290                 295                 300

Val His Asn Lys Thr Thr Leu Gly Ile Glu His Glu Gly Phe Ile Asn
305                 310                 315                 320

Asn Ala Ser Trp Tyr Thr Ala Met Tyr Asn Ala Ser Ala Ala Leu
                325                 330                 335

Thr Arg His Phe Cys Ala Thr Tyr Ser Ala Ile Ser Cys Ala Ser Ala
                340                 345                 350

Phe Arg Gly Pro Ala Gly Ser Gly Ile Asn Val Leu Pro Ala Ser Val
            355                 360                 365

Lys Val Lys Gly His Gln His Tyr Ser Ser Gln Thr His Thr Asp Pro
        370                 375                 380

Gly Ile Asn Trp Asp Trp Ala Arg Tyr Asn Leu Leu Asn Pro Gly
385                 390                 395                 400

Asn Pro Pro Gly Gly Gly Ser Val Ile Asp Ser Phe Glu Ser Thr Val
                405                 410                 415

Gly His Phe Asp Thr Gly Pro Ala Tyr Ser Gly Ser Thr Thr Gly Ile
                420                 425                 430

Ala Ala Thr Ser Leu Ser Glu Arg Asn Cys Thr Thr Arg Lys Asn Gly
        435                 440                 445

Glu Cys Ser Leu Arg Leu Leu Leu Lys Asp Asp Ala Ala Ser Ala Gly
    450                 455                 460

Ala Trp Ala Val Arg Leu Leu Ser Gly Ser Gly Asn Pro Gly Ser Asn
465                 470                 475                 480

Ala Ala Leu Thr Arg Ala Asn Gly Lys Val Gly Phe Trp Val Phe Thr
                485                 490                 495

Gly Ala Thr Gly Met Ser Ala Ala Val Gly Ile Asp Asp Ser Asp Gly
            500                 505                 510

Thr Glu Arg Ser Ile Ser Arg Ala Ile Pro Ala Asn Thr Trp Thr Tyr
        515                 520                 525
```

```
Leu Glu Trp Ser Leu Ser Asp Asp Ala Gln Trp Asp Ala Trp Val Gly
    530                 535                 540

Gly Ala Asn Gly Ala Ile Thr Ala Ala Ser Val Lys Leu Asp Ala Val
545                 550                 555                 560

Trp Phe Tyr Arg Asp Gln Thr Ser Phe Asp Val Asn Val Tyr Val Asp
                565                 570                 575

Asp Val Gln Val Lys Asn
            580

<210> SEQ ID NO 109
<211> LENGTH: 27
<212> TYPE: PRT
<213> ORGANISM: Artificial
<220> FEATURE:
<223> OTHER INFORMATION: Signal peptide

<400> SEQUENCE: 109

Met Lys Lys Pro Leu Gly Lys Ile Val Ala Ser Thr Ala Leu Leu Ile
1               5                   10                  15

Ser Val Ala Phe Ser Ser Ser Ile Ala Ser Ala
            20                  25

<210> SEQ ID NO 110
<211> LENGTH: 8
<212> TYPE: PRT
<213> ORGANISM: Artificial
<220> FEATURE:
<223> OTHER INFORMATION: His-TAG

<400> SEQUENCE: 110

His His His His His His Pro Arg
1               5

<210> SEQ ID NO 111
<211> LENGTH: 9
<212> TYPE: PRT
<213> ORGANISM: Artificial
<220> FEATURE:
<223> OTHER INFORMATION: Motif
<220> FEATURE:
<221> NAME/KEY: Misc
<222> LOCATION: (2)..(2)
<223> OTHER INFORMATION: Xaa = I(Ile) or V(Val)
<220> FEATURE:
<221> NAME/KEY: Misc
<222> LOCATION: (3)..(3)
<223> OTHER INFORMATION: Xaa = Any natural amino acid
<220> FEATURE:
<221> NAME/KEY: Misc
<222> LOCATION: (4)..(4)
<223> OTHER INFORMATION: Xaa = A(Ala) or G(Gly)
<220> FEATURE:
<221> NAME/KEY: Misc
<222> LOCATION: (5)..(5)
<223> OTHER INFORMATION: Xaa = G(Gly) or A(Ala) or S(Ser)
<220> FEATURE:
<221> NAME/KEY: Misc
<222> LOCATION: (7)..(7)
<223> OTHER INFORMATION: Xaa = A(Ala) or Y(Tyr)
<220> FEATURE:
<221> NAME/KEY: Misc
<222> LOCATION: (8)..(8)
<223> OTHER INFORMATION: Xaa = L(Leu) or V(Val)

<400> SEQUENCE: 111

Asn Xaa Xaa Xaa Xaa Ala Xaa Xaa Leu
1               5
```